United States Patent
Peters et al.

(10) Patent No.: US 9,708,311 B2
(45) Date of Patent: Jul. 18, 2017

(54) BENZIMIDAZOLE DERIVATIVES AS EP4 ANTAGONISTS

(71) Applicant: BAYER PHARMA AKTIENGESELLSCHAFT, Berlin (DE)

(72) Inventors: Olaf Peters, Tabarz (DE); Nico Bräuer, Falkensee (DE); Thorsten Blume, Wuppertal (DE); Antonius Ter Laak, Berlin (DE); Ludwig Zorn, Berlin (DE); Jens Nagel, Daxweiler (DE); Stefan Kaulfuss, Berlin (DE); Gernot Langer, Falkensee (DE); Joachim Kuhnke, Potsdam (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/649,896

(22) PCT Filed: Dec. 3, 2013

(86) PCT No.: PCT/EP2013/075309
§ 371 (c)(1),
(2) Date: Jun. 4, 2015

(87) PCT Pub. No.: WO2014/086739
PCT Pub. Date: Jun. 12, 2014

(65) Prior Publication Data
US 2016/0214977 A1    Jul. 28, 2016

(30) Foreign Application Priority Data
Dec. 6, 2012   (EP) .................................. 12195849

(51) Int. Cl.
| C07D 403/04 | (2006.01) |
| C07D 403/14 | (2006.01) |
| C07D 405/14 | (2006.01) |
| C07D 471/04 | (2006.01) |
| A61K 31/437 | (2006.01) |
| A61K 31/4184 | (2006.01) |
| A61P 5/00 | (2006.01) |
| A61K 31/5377 | (2006.01) |
| A61K 45/06 | (2006.01) |

(52) U.S. Cl.
CPC ........ *C07D 471/04* (2013.01); *A61K 31/4184* (2013.01); *A61K 31/437* (2013.01); *A61K 31/5377* (2013.01); *A61K 45/06* (2013.01); *C07D 403/04* (2013.01); *C07D 403/14* (2013.01); *C07D 405/14* (2013.01)

(58) Field of Classification Search
CPC .. C07D 471/04; C07D 403/04; C07D 403/14; C07D 405/14; A61K 31/4184; A61K 31/437; A61K 31/5377
USPC ........ 514/394, 411; 548/304.4, 304.7, 306.1, 548/440
See application file for complete search history.

(56) References Cited

U.S. PATENT DOCUMENTS

| 2004/0082635 A1 | 4/2004 | Hashimoto et al. |
| 2004/0122046 A1 | 6/2004 | Elliott |
| 2016/0318905 A1* | 11/2016 | Peters ................. A61K 45/06 |

FOREIGN PATENT DOCUMENTS

| EP | 1162196 A1 | 12/2001 |
| EP | 1257280 B1 | 10/2005 |
| EP | 2172447 A1 | 4/2010 |
| WO | 0232422 A2 | 4/2002 |
| WO | 0232900 A2 | 4/2002 |
| WO | 03086371 A2 | 10/2003 |
| WO | 2004/011439 A2 | 2/2004 |
| WO | 2004022572 A1 | 3/2004 |
| WO | 2004/055002 A1 | 7/2004 |
| WO | 2004067524 A1 | 8/2004 |
| WO | 2004087690 A2 | 10/2004 |
| WO | 2005021508 A | 3/2005 |
| WO | 2005105733 A1 | 10/2005 |
| WO | 2005102389 A2 | 11/2005 |
| WO | 2006076009 A2 | 7/2006 |
| WO | 2007121578 A1 | 11/2007 |

(Continued)

OTHER PUBLICATIONS

Ballinger et al., "Critical Role of Prostaglandin E2 Overproduction in Impaired Pulmonary Host Response following Bone Marrow Transplantation," The Journal of Immunology, 2006, 177: 5499-5508.

Chang et al., "Regulation of vascular endothelial cell growth factor expression in mouse mammary tumor cells by the EP2 subtype of the prostaglandin E2 receptor," Prostaglandins & other Lipid Mediators, 2005, 76:48-58.

Chishima F et al, "Increased expression of cyclooxygenase-2 in local lesions of endometriosis patients," Am J Reprod. Immunol, 2002, 48:50-56.

(Continued)

*Primary Examiner* — Irina Neagu
(74) *Attorney, Agent, or Firm* — Nixon & Vanderhye P.C.

(57) ABSTRACT

The present invention relates to novel benzimidazole derivatives of the general formula

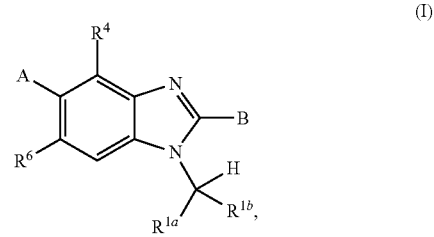

(I)

processes for their preparation and their use for the production of pharmaceutical compositions for the treatment of diseases and indications that are connected with the receptor EP4.

10 Claims, 3 Drawing Sheets

(56) References Cited

FOREIGN PATENT DOCUMENTS

| WO | 2008017164 A1 | 2/2008 |
|---|---|---|
| WO | 2008104055 A1 | 4/2008 |
| WO | 2008107373 A1 | 9/2008 |
| WO | 2009020588 A1 | 2/2009 |
| WO | 2010019796 A1 | 2/2010 |
| WO | 2010117639 A2 | 10/2010 |
| WO | 2010124097 A2 | 10/2010 |
| WO | 2011102149 A1 | 8/2011 |

OTHER PUBLICATIONS

Cimino et al., "Therapeutic Targets in Prostaglandin E2 Signaling for Neurologic Disease," Current Medicinal, Chemistry, 2008, 1863-1869.
Fulton et al., "Targeting Prostaglandin E EP Receptors to Inhibit Metastasis," Cancer Res, 2006, 66(20): 9794-7.
Giudice L C, "Endometriosis," N Engl J Med, 2010, 362: 2389-98.
Hoshino et al., "Involvement of Prostaglandin E2 in Production of Amyloid-Beta Peptides Both in Vitro and in Vivo," J Biol Chem.; 2007, 282(45): 32676-88.
Hull et al., "Prostaglandin EP receptors: Targets for treatment and prevention of colorectal cancer?" Mol Cancer Ther, 2004, 3(8):1031-9.
Imir et al., Aromatase Expression in Uterine Leiomyomata Is Regulated Primarily by Proximal Promoters I.3/II, J Clin Endocrinol Metab, 2007, 92:1979-1982.
Kamiyama et al., "EP2, a receptor for PGE2, regulates tumor angiogenesis through direct effects on endothelial cell motility and survival," Oncogene, 2006, 25:7019-7028.
Kihara et al., "Targeted lipidomics reveals mPGES-1-PGE2 as a therapeutic target for multiple sclerosis," Proc Natl Acad Sci U. S. A, 2009, 106(51): 21807-21812.
Kuwano et al., "Cyclooxygenase 2 is a key enzyme for inflammatory cytokine-induced angiogenesis," FASEB J. 2004, 18: 300-310.
Liu et al., "Prostaglandin E2 mediates proliferation and chloride secretion in ADPKD cystic renal epithelia," Am J Physiol Renal Physiol., Aug. 29, 2012.
Minami et al., Prostaglandin E Receptor Type 4-associated Protein Interacts Directly with NF-kB1 and Attenuates Macrophage Activation, J Biol Chem., Apr. 11, 2008; 283 (15): 9692-703.
Murase et al., "Effect of prostanoid EP4 receptor antagonist, CJ-042,794, in rat models of pain and inflammation," Eur J Pharmacol. Feb. 2, 2008, 580(1-2):116-21.
Palumbo et al., "Time-dependent changes in the brain arachidonic acid cascade during cuprizone-induced myelination and demyelination," Prostaglandins, Leukotrienes and Essential Fatty Acids, 2011, 85: 29-35.
Petraglia F; Reduced pelvic pain in women with endometriosis: efficacy of long-term dienogest treatment; Arch Gynecol Obstet, Jan. 2012, 285(11:167-73.
Sales K J; "Cyclooxygenase enzymes and prostaglandins in pathology of the endometrium," Reproduction, 2003, 126: 559-567.
Sapijanskaite B et al, "Kai Kuriu 2-pakeistu benzimidazolo dariniu sintereze ir savybes," Chemine Technologija 2005, 2:57-62.
Serezani et al., "Prostaglandin E2 Suppresses Bacterial Killing in Alveolar Macrophages by Inhibiting NADPH Oxidase," Am J Respir Cell Mol Biol, 2007, 37: 562-570.
Sheibanie et al., "The Proinflammatory Effect of Prostaglandin E2 in Experimental Inflammatory Bowel Disease Is Mediated through the IL-23-IL-17 Axis,," The Journal of Immunology, 2007, 178: 8138-8147.
Smith et al., 2007, "Cyclooxygenase enzyme expression and E series prostaglandin receptor signalling are enhanced in heavy menstruation," Human Reproduction, 2007, 22(5):1450-1456.
Stratton P et al., "Chronic pelvic pain and endometriosis: translational evidence of the relationship and implications," Human Reproduction Update, 2011, 17(3): 327-346.
Wang et al., "Prostaglandin E2 Alters Human Orbital Fibroblast Shape Through a Mechanism Involving the Generation of Cyclic Adenosine Monopnosphate," J Clin Endocrinol Metab 1995, 80(12): 3553-3560.
Wang et al., "Cyclooxygenase-2: A Potential Target in Breast Cancer," Seminars in Oncology, 2004, 31(1, Suppl 3): 64-73.
Zeilhofer, "Prostanoids in nociception and pain," Biochemical Pharmacology 2007, 73: 165-174.

* cited by examiner

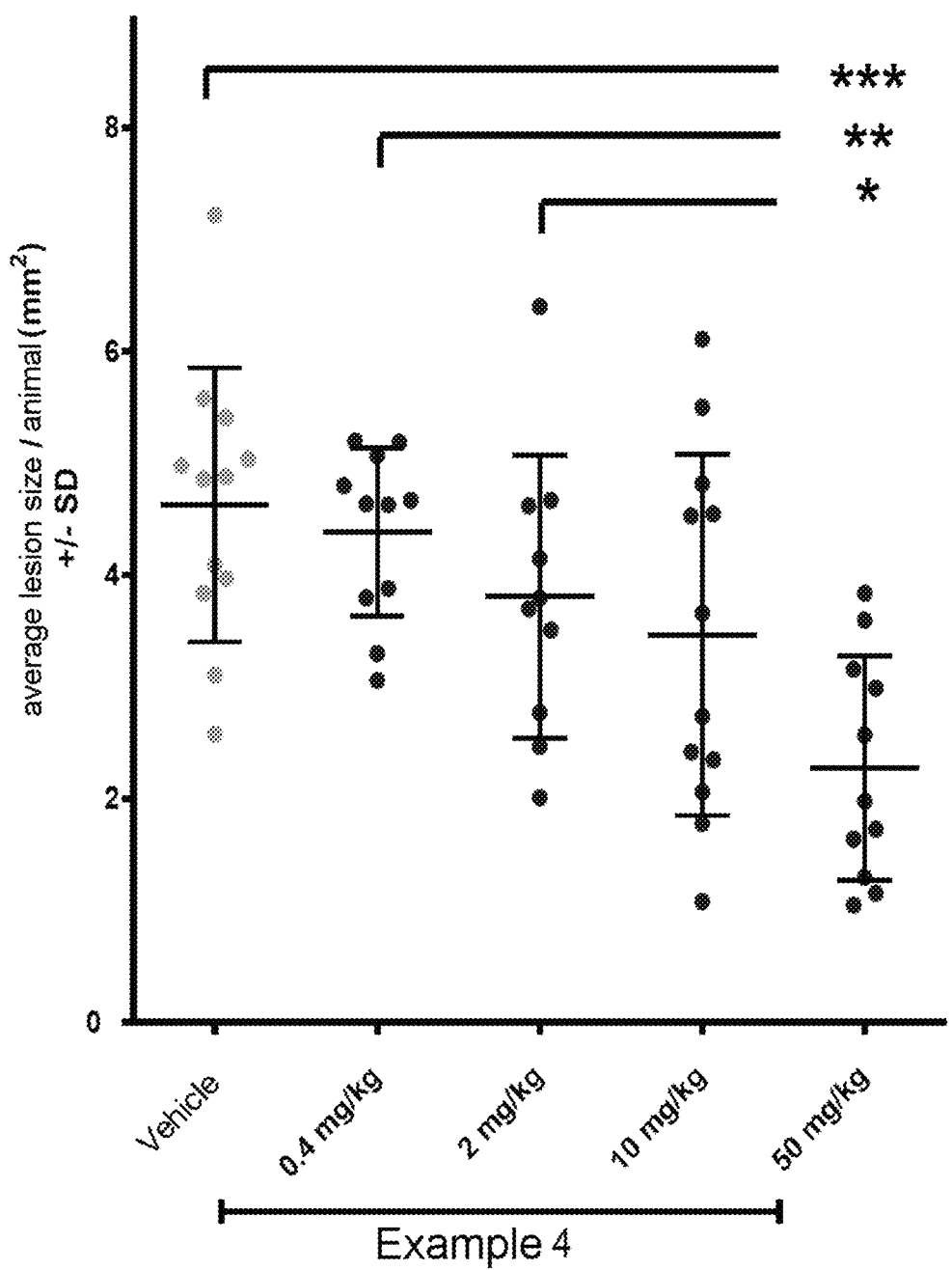
Figure 1 : s.c. experiment

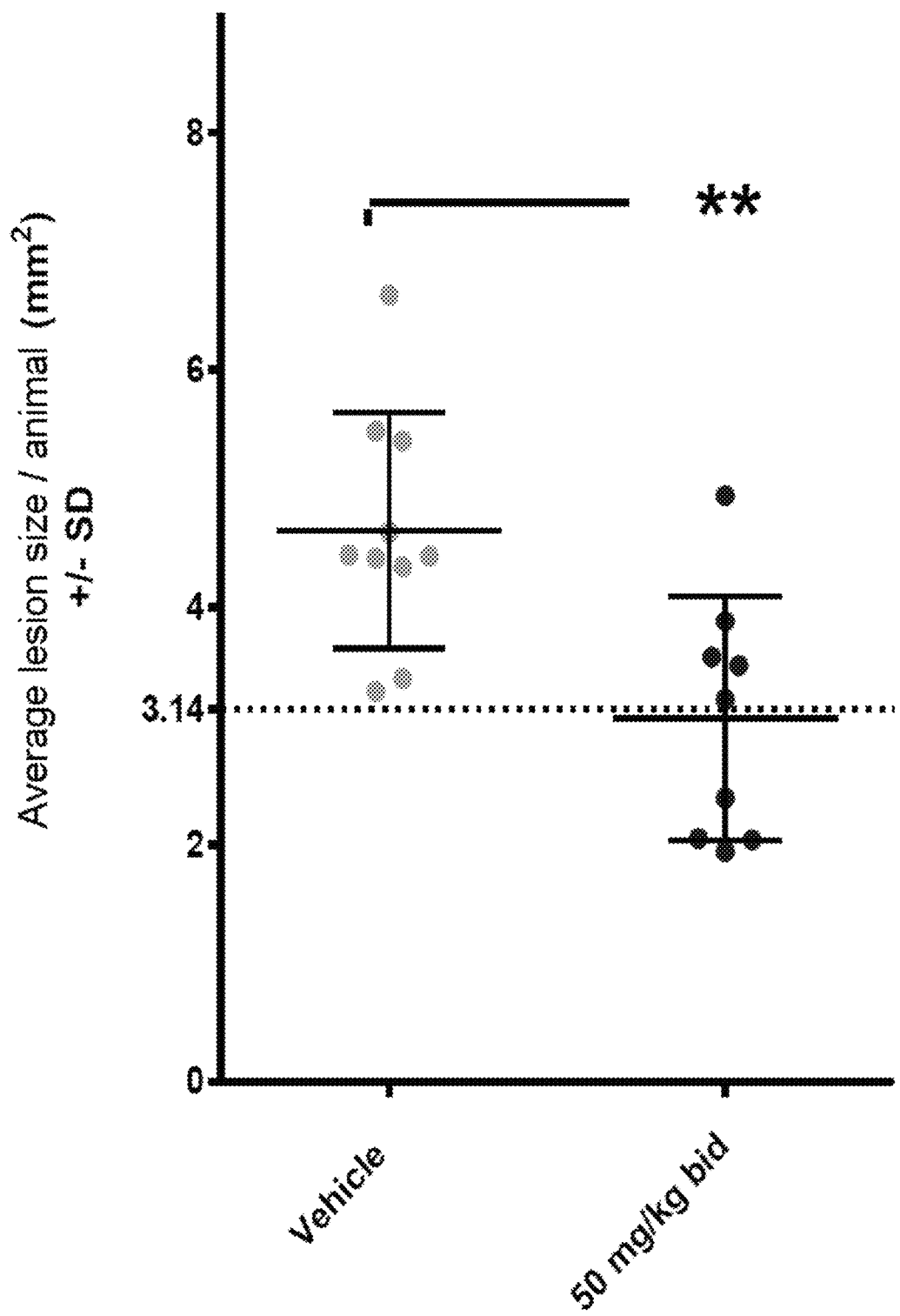
Figure 2 : p.o. experiment

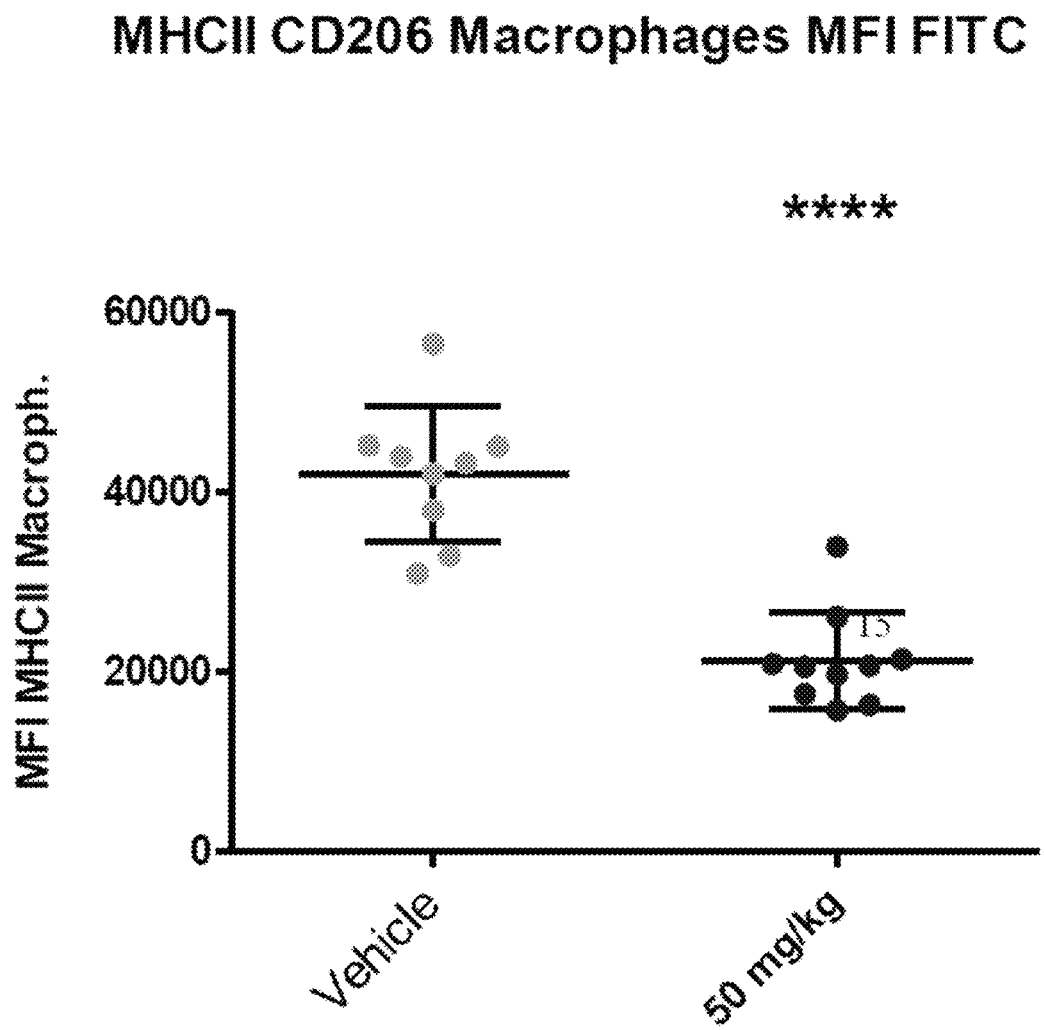
Figure 3 : activation of macrophages

BENZIMIDAZOLE DERIVATIVES AS EP4 ANTAGONISTS This application is a National Stage entry of PCT/EP2013/07539, filed on 3 Dec. 2013, claiming priority from European Patent Application Number 12195849.0, filed on 6 Dec. 2012.

The present invention relates to novel EP4 antagonists and their use for the treatment and/or prophylaxis of diseases, and their use as medicaments and pharmaceutical preparations that contain the novel benzimidazole-5-carboxylic acid derivatives.

The clinical picture of endometriosis has been comprehensively investigated and described, even though the pathogenic mechanisms are still not completely known. Characteristic of endometriosis is a persistent colonization of endometrial tissue outside the uterine cavity, which leads to typical foci. "Endometriotic lesions" are formed, which can be detected in varying distribution and occurrence in the muscular region of the uterus (internal endometriosis, adenomyosis), at various points of the abdominal cavity, e.g. the ligaments, on the parietal peritoneum of the Douglas pouch (peritoneal endometriosis), the intestinal wall, on the ovary ("endometrioma") or rectovaginally (rectovaginal, frequently also deeply infiltrating, endometriosis). The newly established tissue retains key features of the original tissue (uterus, endometrium). Endometriosis has an inflammatory character and often manifests itself by various forms of lower abdominal pain. It is assumed that 10-20% of women of reproductive age are affected by endometriosis. Core symptoms of endometriosis are chronic lower abdominal pain, dysmenorrhoea, dyspareunia, dysuria, bleeding disorders and infertility. The symptoms usually occur in combination.

It is presumed that endometrial tissue that reaches the peritoneal cavity by retrograde menstruation via the oviduct can settle in the peritoneal tissue and causes the lesions observed in endometriosis (Stratton & Berkley, Giudice 2010). These lesions cause progressive local inflammation in the course of the disease and are characterized by up-regulation of $COX_2$ enzyme and increased prostaglandin synthesis (Chishima et al 2002; Sales & Jabbour 2003).

The actions of the prostaglandins are mediated by their G-protein-coupled receptors, which are located in the cell membrane. Of particular interest is prostaglandin E2 (PGE2), which achieves a diversity of cellular actions, by binding to functionally different receptor subtypes, namely EP1, EP2, EP3 and EP4.

The receptor EP4 ($PTGR_4$) is one of the 4 human receptors that are activated by endogenously formed prostaglandin E2 (PGE2). EP4 belongs to the family of membrane-bound G-protein coupled receptors (GPCR) and is mainly provided with a Gs coupling, which after activation leads to an accumulation of the intracellular signal molecule cAMP. The expression of the receptor was detected on peripheral nerve endings of nociceptors, on macrophages and neutrophils. For these cell types, great importance was demonstrated in connection with endometriosis. It is assumed that the local inflammation of the endometriotic lesions makes a significant contribution to the genesis of the pain symptoms observed (Stratton & Berkley 2010; Giudice 2010).

Current therapeutic approaches for the treatment of diagnosed endometriosis are very restricted.

Thus endometriosis can be treated by operative removal of the endometriotic lesions in a laparoscopic intervention. Here, endometrial foci are removed operatively using heat (electrocauterization) or by excision (extirpation). Additionally, in this connection possibly present adhesions can be resolved, endometrial cysts can be removed and in the case of the desire for children the permeability of the oviducts can be checked by means of chromopertubation. The relapse rate after such an intervention, however, is very high (25-30%). Hysterectomy, that is the complete removal of the uterus, exists in such particularly difficult cases as the final therapeutic option.

In the case of particularly severe diseases, sometimes only the removal of both ovaries and of oviducts (bilateral salpingo-oophorectomy, adnexectomy) affords a definitive treatment.

Menstrual pain and prolonged or increased bleeding, which originate from endometriosis in the uterine muscle (adenomyosis uteri), can also be treated successfully by a hysterectomy.

These interventions, however, lead to infertility and a premature menopause with the problems associated therewith, which is why the use must be weighed well against the disadvantages.

Besides invasive surgical interventions, a medicinal therapy can also be taken into consideration. This is frequently used in the case of a large-area, possibly not completely operable attack, but is also employed in the case of mild to moderate disease. In addition to mainly symptomatic pain therapy using non-steroidal anti-inflammatory drugs (NSAID), four substance groups come into consideration in principle for this:

(a) combined oral contraceptives (consisting of oestrogen and gestagen) (OCs)
(b) gestagens
(c) GnRH analogues (GnRH=gonadotropin-releasing hormone) and
(d) Danazol®

The combined oral contraceptives (a) regulate the course of the cycle and reduce the menstrual flow. Their effectiveness in endometriosis patients presumably follows from this. However, patient satisfaction with this form of treatment is low, which is presumably to be attributed to side-effects due to the influencing of the hormone balance and unsatisfactory pain control. In addition, new studies indicate that long-term use of the hormonal active substances appears to be associated with an increased rate of deeply infiltrating endometriosis, a particularly painful form of endometriosis.

The use of OCs in the treatment of endometriosis is also described in the patent literature. Thus EP 1257280 discloses that micronized drospirenone is suitable for the treatment of endometriosis. It is described there in paragraph [0045] that compositions of drospirenone having a low content of oestrogen or else without any oestrogen are suitable, inter alia, for the treatment of endometriosis. This is explained from the gestagenic property of drospirenone. In EP1257280, amounts of 0.5 to 10 mg of drospirenone are described as effective. Nothing is disclosed in this specification about the length of treatment of endometriosis with drospirenone.

In WO2008/107373, mineralocorticoid receptor antagonists are described for the production of a medicament for the treatment of endometriosis. In addition to the use of compounds having pure antimineralocorticoid action, compounds are also proposed there that moreover also show an effect on the progesterone receptor, on the oestrogen receptor, on the glucocorticoid receptor and/or on the androgen receptor. In particular, the compounds disclosed in WO2008/107373, spironolactone and the drospirenone mentioned beforehand, also have a gestagenic action.

The compound eplerenone mentioned in WO2008/107373 shows, as a pure MR antagonist, a relatively weak in vitro potency. MR antagonists are preferred that in in vitro trans activation assays have an at least 10-fold lower $IC_{50}$ compared with eplerenone.

Gestagens (b) are likewise employed in endometriosis. The starting point here is, on the one hand, the suppression of the function of the ovaries and, on the other hand, the induction of the terminal differentiation of the endometrium, decidualization, which finally leads to tissue death.

The gestagens simulate a pregnancy in the body and thus create a changed hormonal situation. Ovulation no longer takes place and the endometrium atrophies. In general, the endometriosis symptoms then subside within from 6 to 8 weeks.

Depot MPA (medroxyprogesterone acetate) and Visanne© (Dienogest) are licensed for endometriosis treatment. A distinct analgesic action of Visanne© occurs only after several weeks of treatment (Petraglia et al 2011). There is no evidence on the generally desired rapid pain alleviation. In the case of MPA, a reduction of the bone mass can already occur after an administration period of 6 months on account of the anti-oestrogenic action of the compound. It should therefore in no case be administered over a longer period of time than 2 years. Under treatment with Visanne, an undesired influencing of the bleeding profile can occur as a side-effect of the gestagenic properties. (specialist info side-effects).

In addition to the hormone cycle, gestagens in general also influence the bleeding profile, with bleeding disorders as a frequent side-effect of gestagens. This also relates to substances that are active on other hormone receptors and simultaneously have a gestagenic activity, such as, for example, spironolactone. As a result of defective angiogenesis (neovascularization, a process that takes place cyclically in the endometrium) during the decidualization of the endometrium, the vessel walls become fragile and "breakthrough bleeding" occurs, which takes place independently of menstrual bleeding and is characteristic of chronic treatment with gestagens.

The gonadotrophin-releasing hormone analogues (GnRH) (c) currently represent the gold standard of the licensed therapeutics against all stages of endometriosis. GnRH analogues block the pituitary gland completely. The menstrual cycle no longer takes place. These substances thus temporarily artificially transpose the body of the woman into the menopause and the endometriosis tissue can therefore also no longer jointly bleed. The tissue becomes hypotrophic.

On account of the side-effect profile, this therapeutic approach, however, is likewise only suitable for short-term use (up to 6 months). Thus GnRH agonists induce postmenopausal symptoms, such as hot flushes (80-90%), sleep disorders (60-90%), vaginal dryness (30%), headaches (20-30%), mood changes (10%) and decrease in bone density with accompanying increased risk of osteoporosis.

Apart from the side-effects mentioned, after ending the treatment the normal cycle sets in again within 2 to 3 months. In over 60% of the women affected, the symptoms of endometriosis then also return, such that a renewed treatment cycle must be considered.

Due to the disadvantages mentioned, GnRH analogues have thus far not gained any wide use in the treatment of endometriosis, even though these have replaced the standard therapy established in the 1970s with Danazol®, a gestagenic androgen, due to the somewhat better side-effect profile.

Danazol® (d) was the first "classical" therapeutic of endometriosis and the gold standard until the 1970s. In the case of relatively long administration, Danazol®, similarly to the male sex hormone testosterone, leads to a masculinization of the woman. The effects known for androgens, such as acne, hyperandrogenism, hirsutism and (irreversible) voice pitch change occur as further side-effects (note specialist info).

Danazol®, like the GnRH agonists, acts on the pituitary gland, which is responsible for the production of hormones that stimulate the ovaries. The production of oestrogens in the ovaries is adjusted in this way.

There is therefore an urgent need for alternative preparations, which allow a non-invasive treatment of endometriosis and which do not have the disadvantages of the prior art.

Up to now, no EP4 antagonist has been licensed as a medicament. However, EP4 antagonists of different structural classes have been described, which differ significantly from the compounds according to the invention in that they do not have their carbazolyl benzimidazole structure. Thus in WO2005/0121508, WO2005102389 and WO2005/105733 (Pfizer), for example, N-benzylarylamides, N-benzylheteroarylamides and [(1H-benzimidazol-1-yl)phenylethyl]aryl- and [(1H-benzimidazol-1-yl)phenylethyl] heteroarylsulphonylcarbamates are described for use in the case of pain, inflammation, osteoarthritis and rheumatoid arthritis. Pfizer also describes in WO2002032422, WO2002032900 and WO2003086371 structures that include generic benzimidazoles, but cannot be substituted in position 2 by a fused tricycle, such as carbazole. Thiophene-N-benzylamides in WO2008017164 and WO2009020588, indole-N-benzylamides in WO2007121578 and N-{[(6,8-dihydro-7H-pyrrolo[3,4-g]quinolin-7-yl)-aryl]
methyl}sulphonylamides in WO2008104055 are addressed for nearly the same indication spectrum by Merck-Frosst. In WO2010019796 (Chemietek), generically very widely polysubstituted heterobicycles are claimed, the typical units of the compounds according to the invention, carbazole and benzimidazole, not occurring in the very few examples and tricyclic substituents such as carbazole also not being addressed generically. In WO2004067524 (Pharmagene Laboratories), furan derivatives for the treatment of headache and migraine are described, in which the furan ring is connected linearly to two further aryl- or heteroaryl units, in each case having six ring atoms.

EP2172447 (Astellas Pharma) claims generically in a very broad manner compounds that can consist of two heterocycles connected directly to one another, of which one, however, must be substituted by an aminocarbonyl group and the amino group must be further substituted by a substituent that carries a carboxyl group or a carboxyl surrogate, for the indications renal insufficiency and diabetic nephropathy.

Compounds are also described that are not EP4 antagonists, but are structurally related to the compounds according to the invention. US2004/0122046 (Pfizer) addresses carbazoles, which are connected directly to a heterocycle via position 3, that can also be benzimidazole, as NPY receptor antagonists for the treatment of obesity. In contrast to the compounds according to the invention, the NH of the benzimidazole unit, however, is mandatorily unsubstituted and the two six-membered rings of the carbazole unit can carry no further substituents. WO03/000254 or EP1162196 (Japan Tobacco) generically claims in a broad manner heterobicycles, which can be connected directly to a heterocycle, as a therapeutic for hepatitis C. If the heterocycle is a benzimidazole, this, in contrast to the compounds according to the invention, must be compulsorily connected directly to a cycloalkyl or cycloalkenyl unit by a bond in position 1. Paratek describes substituted benzimidazoles as anti-infectives in WO2010/124097. However, the benzimidazole, unlike in the compounds according to the invention, compulsorily carries an alkyl group that is substituted terminally by a carboxylic acid or phosphonic acid or sulphonic acid function or its derivatives in position 4; furthermore, heterocycloalkyl, but not heteroaryl, is permitted as a direct cyclic substituent in position 2. Starting from the prior art described, there was therefore no cause to modify the structures of the prior art according to the invention to obtain structures that act antagonistically on the EP4 receptor.

It is the object of the present invention to prepare compounds available in vivo and thus effective and stable, which act as potent and selective antagonists of the receptor EP4, and which are therefore suitable for the treatment and/or prophylaxis of diseases such as, for example, endometriosis.

This object was achieved by the compounds of the general formula I,

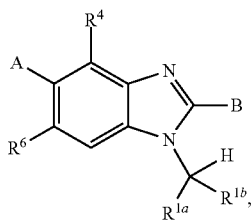

(I)

in which $R^{1a}$, $R^{1b}$ independently of one another represent H, $C_1$-$C_5$-alkyl, $C_2$-$C_5$-alkenyl, $C_2$-$C_5$-alkynyl, $C_3$-$C_6$-cycloalkyl-$(CH_2)_m$, $C_3$-$C_6$-heterocycloalkyl-$(CH_2)_n$, $C_1$-$C_5$-alkoxy-$C_1$-$C_3$-alkyl, $C_3$-$C_6$-cycloalkoxy-$C_1$-$C_3$-alkyl, amino-$C_1$-$C_3$-alkyl, $C_1$-$C_5$-alkylamino-$C_1$-$C_3$-alkyl, $C_1$-$C_5$-dialkylamino-$C_1$-$C_3$-alkyl or cyano, where the optionally present heterocyclic unit is preferably selected from the group consisting of oxetane, tetrahydrofuran, tetrahydropyran, 1,4-dioxane, morpholine, azetidine, pyrrolidine, piperazine and piperidine and where optionally present alkyl, cycloalkyl or heterocycloalkyl radicals can be mono- or polysubstituted, identically or differently by halogen, $C_1$-$C_5$-alkyl, hydroxyl, carboxyl, carboxy-$C_1$-$C_5$-alkyl, $C_1$-$C_5$-alkoxycarbonyl-$C_1$-$C_5$-alkyl or $C_1$-$C_5$-alkylsulphonyl, $R^4$ represents H, F, Cl, $C_1$-$C_2$-alkyl, $C_3$-$C_5$-cycloalkyl, $C_1$-$C_2$-alkoxy or $C_3$-$C_4$-cycloalkylmethyl, where the corresponding alkyl or cycloalkyl unit can be mono- or polysubstituted, identically or differently by halogen or hydroxyl, A represents H, $C_1$-$C_3$-alkyl, Br, 4-6-membered heterocyclyl, formyl, RO—CO$(CH_2)_p$, $R^5$, $R^5$N—CO$(CH_2)_p$, carboxymethoxy, ROSO$_2(CH_2)_p$, $R^5R^{5'}$N—SO$_2(CH_2)_p$, $C_1$-$C_6$-alkylsulphonyl, $C_1$-$C_6$-alkylsulphonimidoyl, $C_3$-$C_6$-cycloalkylsulphonimidoyl or cyano, where R represents H, $C_1$-$C_7$-alkyl, $C_3$-$C_7$-cycloalkyl, phenyl-$(CH_2)_q$ or $C_1$-$C_7$-alkoxy-$C_1$-$C_5$-alkyl and an optionally present heterocyclic unit is preferably selected from the group consisting of pyrazole, imidazole, triazole, tetrazole, oxazole, isoxazoles and oxadiazole and an alkyl unit contained can be mono- or polysubstituted, identically or differently by halogen or hydroxyl and an optionally contained heterocyclic unit or the phenyl can be mono- or polysubstituted by $C_1$-$C_3$-alkyl, trifluoromethyl or hydroxyl, $R^5$, $R^{5'}$ independently of one another represent H, $C_1$-$C_7$-alkyl, $C_1$-$C_7$-alkoxy, $C_1$-$C_7$-alkoxy-$C_2$-$C_5$-alkyl, $C_3$-$C_6$-heterocycloalkyl-$(CH_2)_r$, $C_1$-$C_7$-alkylcarbonyl, $C_3$-$C_7$-cycloalkylcarbonyl, aryl-$(CH_2)_r$-carbonyl, pyridyl-$(CH_2)_r$-carbonyl, $C_1$-$C_7$-alkylsulphonyl, $C_3$-$C_7$-cycloalkylsulphonyl or aryl-$(CH_2)_r$-sulphonyl, where aryl denotes phenyl or naphthyl, or represent pyridyl-$(CH_2)_r$-sulphonyl, and an optionally contained heterocyclic unit is preferably selected from the group consisting of oxetane, tetrahydrofuran, tetrahydropyran, 1,4-dioxane, morpholine, azetidines, pyrrolidine, piperazine and piperidine and where $R^5$ and $R^{5'}$ can optionally be mono- or polysubstituted, identically or differently by $C_1$-$C_2$-alkyl, trifluoromethyl, halogen, $C_1$-$C_5$-alkylamino, $C_1$-$C_5$-dialkylamino, $C_1$-$C_2$-alkoxy, trifluoromethoxy or hydroxyl, or $R^5$, $R^{5'}$ together with the nitrogen atom, to which they are bonded, form a 4-6-membered heterocyclic ring optionally containing a further heteroatom, which is selected from the group consisting of O and N, and which can optionally be mono- or polysubstituted, identically or differently by oxo, hydroxyl, carboxyl, $C_1$-$C_2$-alkyl or $C_1$-$C_2$-alkoxy, m is 0, 1, 2 or 3,
n is 0, 1, 2 or 3,
p is 0, 1 or 2,
q is 1, 2 or 3,
r is 0, 1, 2 or 3, and
B is selected from the following structures,

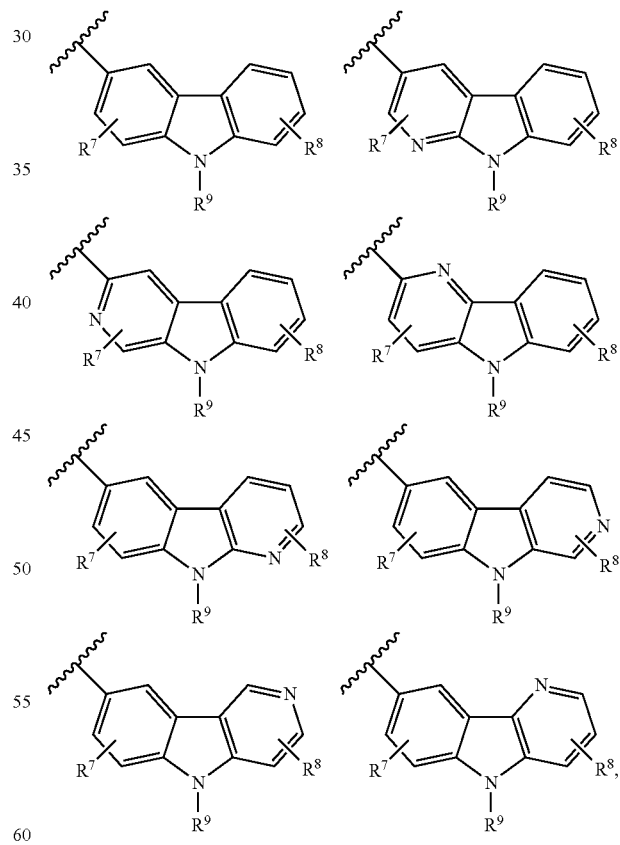

$R^6$ represents H, F, Cl, $CH_3$, $CF_3$, $CH_3O$ or $CF_3O$,
$R^7$, $R^8$ in each case independently of one another represent H, F, Cl, cyano, $SF_5$, $C_1$-$C_3$-alkyl, $C_3$-$C_5$-cycloalkyl, $C_1$-$C_2$-alkoxy or $C_3$-$C_4$-cycloalkylmethyl, where the corresponding alkyl or cycloalkyl unit can be mono- or polyhalogenated, and R⁹ represents $C_1$-$C_5$-alkyl, $C_2$-$C_5$-alkenyl, $C_2$-$C_5$-alkynyl, $C_3$-$C_6$-cycloalkyl-$(CH_2)_n$, $C_3$-$C_6$-heterocycloalkyl-$(CH_2)_n$, or $C_1$-$C_7$-alkoxy-$C_2$-$C_5$-alkyl, where the optionally present heterocyclic unit is selected from the group consisting of oxetane, tetrahydrofuran, tetrahydropyran, morpholine, pyrrolidine and piperidine and where the optionally present alkyl, cycloalkyl or heterocycloalkyl units can be mono- or polysubstituted, identically or differently by halogen, $C_1$-$C_2$-alkyl, $C_1$-$C_2$-alkoxy or carboxyl,
and their isomers, diastereomers, enantiomers, solvates and salts or cyclodextrin clathrates, for the production of medicaments.

Compounds according to the invention are the compounds of the formula (I) and their stereoisomers, tautomers, N-oxides, hydrates, salts, solvates and solvates of the salts, and the compounds and their stereoisomers, tautomers, N-oxides, hydrates, salts, solvates and solvates of the salts comprised by formula (I), subsequently called exemplary embodiments.

In the context of the present invention, preferred salts are physiologically acceptable salts of the compounds according to the invention. Also comprised are salts that are not suitable for pharmaceutical applications themselves, but can be used, for example, for the isolation or purification of the compounds according to the invention.

Physiologically acceptable salts of the compounds according to the invention comprise acid addition salts of mineral acids, carboxylic acids and sulphonic acids, e.g. salts of hydrochloric acid, hydrobromic acid, sulphuric acid, phosphoric acid, methane-sulphonic acid, ethanesulphonic acid, toluenesulphonic acid, benzenesulphonic acid, naphthalenedisulphonic acid, formic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also comprise salts of customary bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

In the context of the invention, solvates are designated as those forms of the compounds according to the invention which form a complex in solid or liquid state by coordination with solvent molecules. Hydrates are a special form of the solvates, in which the coordination takes place with water. In the context of the present invention, hydrates are preferred as solvates.

Depending on their structure, the compounds according to the invention can exist in different stereoisomeric forms, i.e. in the form of configurational isomers or optionally also as conformational isomers (enantiomers and/or diastereomers, including those in atropisomers). The present invention therefore comprises the enantiomers and diastereomers and their respective mixtures. The stereoisomerically uniform constituents can be isolated in a known manner from such mixtures of enantiomers and/or diastereomers; chromatographic processes are preferably used for this purpose, in particular HPLC chromatography on an achiral or chiral phase.

If the compounds according to the invention can occur in tautomeric forms, the present invention comprises all tautomeric forms.

The present invention also comprises all suitable isotopic variants of the compounds according to the invention. An isotopic variant of a compound according to the invention is understood here as meaning a compound in which at least one atom within the compound according to the invention is exchanged for another atom of the same atomic number, but with a different atomic mass than the atomic mass occurring usually or mainly in nature. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Certain isotopic variants of a compound according to the invention, such as in particular those in which one or more radioactive isotopes are incorporated, can be of use, for example for the Investigation of the mechanism of action or of the active substance distribution in the body; on account of the comparatively easy preparability and detectability, in particular compounds labelled with $^3H$ or $^{14}C$ isotopes are suitable for this. Moreover, the incorporation of isotopes, such as, for example, of deuterium, can lead to certain therapeutic advantages as a result of a greater metabolic stability of the compound, such as, for example, a prolongation of the half-life in the body or a reduction in the necessary effective dose; such modifications of the compounds according to the invention can therefore optionally also be a preferred embodiment of the present invention. Isotopic variants of the compounds according to the invention can be prepared according to the processes known to the person skilled in the art, thus, for example, according to the methods described further below and the procedures shown in the exemplary embodiments, by employing corresponding isotopic modifications of the respective reagents and/or starting compounds.

The present invention further relates to all possible crystalline and polymorphic forms of the compounds according to the invention, where the polymorphs can be present, either as individual polymorphs or as a mixture of a number of polymorphs in all concentration ranges.

Moreover, the present invention also comprises prodrugs of the compounds according to the invention. The term "prodrugs" here designates compounds which themselves can be biologically active or inactive, but during their residence time in the body are converted to compounds according to the invention (for example metabolically or hydrolytically).

The compounds according to the invention are novel and have an antagonistic action on the EP4 receptor and serve, inter alia, for the treatment of endometriosis.

In the context of the present invention, the substituents, if not specified otherwise, have the following meaning:

Alkyl stands for a linear or branched, saturated, monovalent hydrocarbon radical having at least 1 and at most 7 carbon atoms ($C_1$-$C_7$-alkyl). An optionally undertaken restriction of the range for the number of carbon atoms can be identified directly from the prefix before 'alkyl', for example $C_1$-$C_3$-alkyl denotes that only alkyl groups having 1, 2 or 3 carbon atoms are allowed. The following may be mentioned by way of example: methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl. The alkyl radicals can optionally be mono- or polysubstituted by fluorine.

Alkenyl and alkynyl designate linear or branched, unsaturated, monovalent hydrocarbon radicals that are derived from the aforementioned alkyl groups in that the radical contains at least two carbon atoms and in that a single bond between two carbon atoms provided with the suitable number of hydrogen atoms is replaced by a double bond or a triple bond. The following may be mentioned by way of example: vinyl, allyl, buten-1-yl for alkenyl and ethynyl, propargyl, pentyn-1-yl for alkynyl. The number of carbon atoms results from the prefix, e.g. $C_2$-$C_5$-alkenyl denotes an alkenyl group having 2 to 5 carbon atoms.

Alkoxy stands for a linear or branched, saturated alkyl ether radical of the formula alkyl-O having at least 1 and at most 7 carbon atoms ($C_1$-$C_7$-alkoxy), such as, for example methoxy, ethoxy, n-propoxy, isopropoxy, n-butoxy, sec-butoxy, isobutoxy, tert-butoxy, pentyloxy, hexyloxy and heptyloxy. The alkoxy radicals can optionally be mono- or polysubstituted by fluorine.

Alkoxyalkyl stands for an alkyl radical substituted by alkoxy, where $C_n$-alkoxy-$C_m$-alkyl denotes that here the alkoxy moiety contains n carbon atoms and the alkyl moiety, via which the radical is bonded, contains m carbon atoms.

Cycloalkoxy stands for a radical $C_3$-$C_6$-cycloalkyl-O, where $C_3$-$C_6$-cycloalkyl has the meaning indicated below.

$C_3$-$C_6$-Cycloalkyl designates monocyclic alkyl radicals having 3 to 6 carbon atoms, where the number of ring atoms can be modified, as then shown in the indices (e.g. $C_4$-$C_5$-cycloalkyl denotes 4 or 5 ring atoms). The following may be mentioned by way of example: cyclopropyl, cyclobutyl, cyclopentyl and cyclohexyl. The cycloalkyl radicals can optionally be mono- or polysubstituted by fluorine.

Cycloalkoxyalkyl stands for an alkyl radical substituted by cycloalkoxy, where $C_n$-cycloalkoxy-$C_m$-alkyl denotes that here the cycloalkoxy moiety contains n carbon atoms and the alkyl moiety, by means of which the radical blinds further, contains m carbon atoms.

Aminoalkyl stands for an alkyl radical substituted by an amino group, where amino-$C_n$-alkyl denotes that the alkyl group contains n carbon atoms.

Alkylamino stands for an amino radical substituted by an alkyl group, where, for example, $C_1$-$C_5$-alkylamino denotes an amino radical substituted by an alkyl group having 1 to 5 carbon atoms. The following may be mentioned by way of example: methylamino, ethylamino, propylamino, isopropylamino, tert-butylamino, pentylamino, hexylamino, N,N-dimethylamino, N,N-diethylamino, N-ethyl-N-methylamino, N-methyl-N-propylamino, N-isopropyl-N-propylamino, N-tert-butyl-N-methylamino, N-ethyl-N-pentylamino and N-hexyl-N-methylamino.

Dialkylamino correspondingly stands for an amino radical substituted by two independently chosen alkyl groups. The following may be mentioned by way of example: N,N-dimethylamino, N,N-diethylamino, N-ethyl-N-methylamino, N-methyl-N-propylamino, N-isopropyl-N-propylamino, N-tert-butyl-N-methylamino, N-ethyl-N-pentylamino and N-hexyl-N-methylamino.

Alkylaminoalkyl or dialkylaminoalkyl stands for an alkyl group that is substituted by an alkylamino group or a dialkylamino group. Thus, for example, $C_1$-$C_5$-dialkylamino-$C_1$-$C_3$-alkyl denotes an alkyl group having 1 to 3 carbon atoms, which is substituted by an amino group, which in turn is substituted by two independently chosen alkyl groups containing 1 to 5 carbon atoms. The following may be mentioned by way of example: N-methylaminomethyl, N-methylamino-ethyl, N-methylamino-propyl, N,N-dimethylaminomethyl, N,N-dimethylamino-ethyl, N,N-dimethylamino-propyl, N,N-diethylamino-methyl, N,N-diethylamino-ethyl, N-ethyl-N-methylamino-methyl, N-methyl-N-propylamino-methyl, N-ethyl-N-methylamino-ethyl, N-methyl-N-propylamino-ethyl.

Carboxyalkyl stands for an alkyl radical substituted by a carboxyl group, where carboxyl-$C_1$-$C_5$-alkyl denotes that the alkyl radical to which the carboxyl group is bonded can contain 1 to 5 carbon atoms. The following may be mentioned by way of example: carboxymethyl, carboxyethyl, carboxypropyl, carboxybutyl and carboxypentyl.

Alkylcarbonyl or cycloalkylcarbonyl or aryl-$(CH_2)_r$-carbonyl or pyridyl-$(CH_2)_r$-carbonyl stands for an alkyl group or cycloalkyl group or aryl group or pyridyl group bonding via a carbonyl group CO.

Aryl-$(CH_2)_r$-sulphonyl or pyridyl-$(CH_2)_r$-sulphonyl stands for a radical aryl-$(CH_2)_r$—$SO_2$ or pyridyl-$(CH_2)_r$—$SO_2$.

Alkoxycarbonylalkyl stands for an alkyl radical substituted by an alkoxycarbonyl group, where $C_1$-$C_5$-alkoxycarbonyl-$C_1$-$C_5$-alkyl denotes that the alkoxy radical can contain one to five carbon atoms and is bonded via its oxygen atom to the carbonyl group, which carbonyl group in turn further binds to the alkyl radical, which independently of the alkoxy radical can contain one to five carbons. The following may be mentioned by way of example: methoxycarbonylmethyl, ethoxycarbonylmethyl, methoxycarbonylethyl, ethoxycarbonyl-ethyl, methoxycarbonylpropyl, ethoxycarbonylpropyl, methoxycarbonylbutyl, ethoxy-carbonylpentyl, propoxycarbonylmethyl, butoxycarbonylmethyl, tert-butoxycarbonyl-methyl, neopentyloxycarbonylmethyl.

Alkylsulphonyl stands for a radical alkyl-$SO_2$, where the alkyl radical can possess one to five carbon atoms.

Alkylsulphonimidoyl or cycloalkylsulphonimidoyl stands for an alkyl or cycloalkyl group, which in each case bonds further via a sulphoximino radical $S(O)(NH)$.

$C_3$-$C_6$-Heterocyclyl or $C_3$-$C_6$-heterocycloalkyl or 3- to 6-membered heterocyclyl designates monocyclic alkyl radicals, which possess 3 to 6 ring atoms, where the number of ring atoms can be modified, as then shown in the indices (e.g. $C_4$-$C_5$-heterocycloalkyl denotes 4 or 5 ring atoms) and which instead of one or more ring carbon atoms contain one or more heteroatoms, such as oxygen, sulphur and/or nitrogen or a hetero group such as —$S(O)$—, —$SO_2$—. The bond valency can be to any desired carbon atom or to a nitrogen atom.

The following may be mentioned by way of example: azetidinyl, pyrrolidinyl, piperidinyl, piperazinyl, 1,4-diazepanyl, morpholinyl, thiomorpholinyl, oxetanyl, tetrahydrofuranyl, tetrahydropyranyl, 1,4-dioxanyl, 2-oxo-oxazolidinyl. The heterocyclyl radicals can optionally be mono- or polysubstituted by fluorine, hydroxyl, methoxy or by oxo.

Halogen is in each case to be understood as meaning fluorine, chlorine or bromine.

A $C_6$-$C_{10}$-membered aryl radical denotes phenyl or naphthyl. This can optionally be monosubstituted by fluorine, chlorine or a methyl group.

A $C_5$-$C_{10}$-heteroaryl radical is to be understood as meaning mono- or bicyclic ring systems, which in each case contain 5-10 ring atoms and which instead of the carbon can contain one or more, identical or different heteroatoms, such as oxygen, sulphur or nitrogen. The bond valency can be to any desired carbon atom or to a nitrogen atom. For example, the following may be mentioned: thienyl, thiazolyl, furyl, pyrrolyl, oxazolyl, imidazolyl, pyrazolyl, isoxazolyl, isothiazolyl, oxadiazolyl, triazolyl, thiadiazolyl, tetrazolyl, pyridyl, pyridazinyl, pyrimidinyl, pyrazinyl, triazinyl, phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, isoquinolinyl, quinolinyl, quinolizinyl, quinazolinyl, quinoxalinyl, cinnolinyl, phthalazinyl, 1,7- or 1,8-naphthyridinyl, pteridinyl. The $C_5$-$C_{10}$-membered heteroaryl radical can optionally be monosubstituted by fluorine, chlorine or a methyl group.

If a basic function is contained, the physiologically tolerable salts of organic and inorganic acids are suitable, such as hydrochloric acid, sulphuric acid, phosphoric acid, citric acid, tartaric acid, inter alia.

Preferred compounds are those of the formula I, where $R^{1a}$, $R^{1b}$ independently of one another represent H, $C_1$-$C_3$-alkyl, $C_2$-$C_3$-alkenyl, $C_2$-$C_3$-alkynyl, $C_3$-$C_6$-cycloalkyl-$(CH_2)_m$, $C_3$-$C_6$-heterocycloalkyl-$(CH_2)_n$, methoxy-$C_1$-$C_2$-alkyl or dimethylaminomethyl, where the optionally present heterocyclic unit is preferably selected from the group consisting of oxetane, tetrahydrofuran, 1,4-dioxane, morpholine and pyrrolidine and where optionally present alkyl, cycloalkyl or heterocycloalkyl units can be identically or differently mono- or polysubstituted, by fluorine, methyl, hydroxyl or methylsulphonyl, $R^4$ represents H, F, Cl, methyl or methoxy, A represents methyl that can be substituted by hydroxyl and/or trifluoromethyl, 4-6-membered heterocyclyl, formyl, RO—CO$(CH_2)_p$, $R^5$, $R^{5'}$N—CO$(CH_2)_p$, carboxymethoxy, HOSO$_2$, $R^5$, $R^{5'}$N—SO$_2$, methylsulphonyl, methylsulphonimidoyl or cyano, R representing H or $C_1$-$C_2$-alkyl and an optionally present heterocyclic unit preferably being selected from the group consisting of triazole, tetrazole and oxadiazole and it being possible for an optionally contained heterocyclic unit to be substituted by hydroxyl, $R^5$, $R^{5'}$ independently of one another represent H, $C_1$-$C_3$-alkyl, $C_1$-$C_2$-alkoxy-ethyl, $C_3$-$C_6$-heterocycloalkylethyl, $C_1$-$C_3$-alkylsulphonyl, cyclopropylsulphonyl or aryl-$(CH_2)_r$-sulphonyl, where aryl denotes phenyl or naphthyl, or represent pyridylmethylsulphonyl or pyridylethylsulphonyl, and an optionally contained heterocyclic unit is preferably selected from the group consisting of morpholine or pyrrolidine and where $R^5$ and $R^{5'}$ can optionally be mono- or polysubstituted, identically or differently, by $C_1$-$C_2$-alkyl, trifluoromethyl, dimethylamino, fluorine, methoxy or trifluoromethoxy, or $R^5$, $R^{5'}$ together with the nitrogen atom, to which they are bonded, form a 4-6-membered alicyclic or heterocyclic ring containing 1 or 2 heteroatoms, which are selected from the group consisting of O and N, and which can optionally be mono- or polysubstituted, identically or differently, by oxo, hydroxyl or carboxyl, m is 0 or 1,
n is 0 or 1,
p is 0 or 1,
r is 0, 1, or 2, and
B is selected from the following structures,

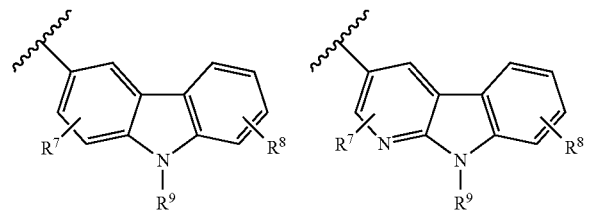

-continued

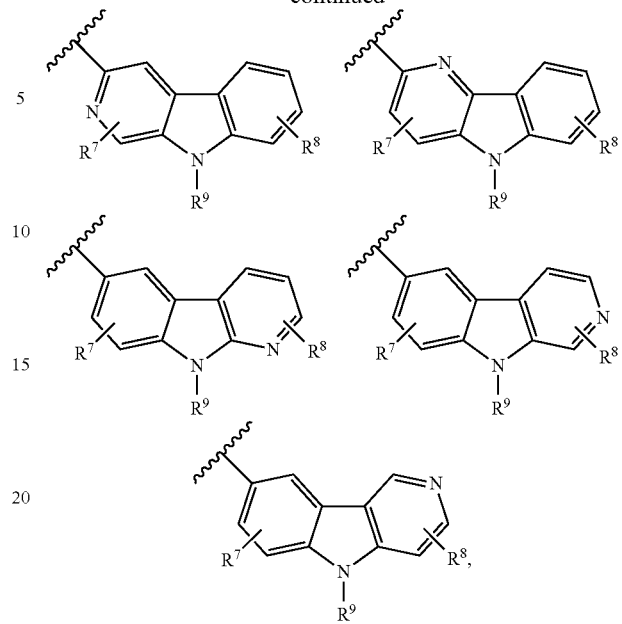

$R^6$ represents H, F, Cl, methyl or methoxy,
$R^7$, $R^8$ in each case independently of one another represent H, F, Cl, methyl or methoxy and
$R^9$ represents $C_1$-$C_3$-alkyl, allyl, propargyl, $C_3$-$C_4$-cycloalkylmethyl, methoxyethyl or carboxymethyl,
and their isomers, diastereomers, enantiomers, solvates and salts or cyclodextrin clathrates.

Compounds of the formula I are preferred, where
$R^{1a}$ represents H or $C_1$-$C_5$-alkyl,
$R^{1b}$ represents H, $C_1$-$C_5$-alkyl, $C_2$-$C_5$-alkenyl, $C_3$-$C_6$-cycloalkyl-$(CH_2)_m$, $C_3$-$C_6$-heterocycloalkyl-$(CH_2)_n$, $C_1$-$C_5$-alkoxy-$C_1$-$C_3$-alkyl or $C_1$-$C_5$-dialkylamino-$C_1$-$C_3$-alkyl, where the optionally present heterocyclic unit is preferably selected from the group consisting of oxetane, tetrahydrofuran, 1,4-dioxane, morpholine and pyrrolidine and where optionally present alkyl- or cycloalkyl radicals can be mono- or polysubstituted, identically or differently, by $C_1$-$C_5$-alkyl, hydroxyl, or $C_1$-$C_5$-alkylsulphonyl,
$R^4$ represents H, F, Cl, $C_1$-$C_2$-alkyl or $C_1$-$C_2$-alkoxy,
A represents $C_1$-$C_3$-alkyl, 5-membered heterocyclyl, RO—CO$(CH_2)_p$, $R^5$, $R^{5'}$N—CO$(CH_2)_p$, $R^5R^{5'}$N—SO$_2$$(CH_2)_p$, or cyano, where R represents H or $C_1$-$C_7$-alkyl and an optionally present heterocyclic unit is preferably selected from the group consisting of triazole, tetrazole and oxadiazole and an alkyl unit contained can be mono- or polysubstituted, by hydroxyl and an optionally contained heterocyclic unit can be monosubstituted by hydroxyl,
$R^5$, $R^{5'}$ independently of one another represent H, $C_1$-$C_7$-alkyl, $C_3$-$C_6$-heterocycloalkyl-$(CH_2)_r$, $C_1$-$C_7$-alkylsulphonyl, $C_3$-$C_7$-cycloalkylsulphonyl or aryl-$(CH_2)_r$-sulphonyl, where aryl denotes phenyl or naphthyl, or represent pyridyl-$(CH_2)_r$-sulphonyl, and an optionally contained heterocyclic unit is preferably selected from the group consisting of morpholine and pyrrolidine and where $R^5$ and $R^{5'}$ can optionally be mono- or polysubstituted, identically or differently, by $C_1$-$C_2$-alkyl, trifluoromethyl, halogen, $C_1$-$C_5$-dialkylamino, $C_1$-$C_2$-alkoxy, or trifluoromethoxy, or
$R^5$, $R^{5'}$ together with the nitrogen atom to which they are bonded, form a 4-6-membered heterocyclic ring optionally having a further heteroatom, which is selected from the group consisting of O, and which can optionally be monosubstituted by oxo or hydroxyl,
m is 0 or 1,
n is 0 or 1,
p is 0,
r is 0, 1 or 2, and
B is selected from the following structures,

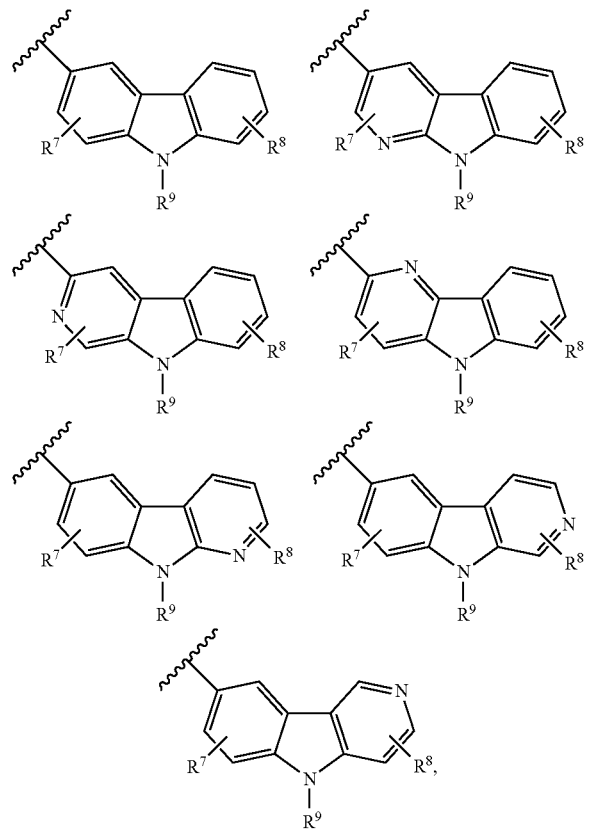

$R^6$ represents H, F, $CH_3$ or $CH_3O$,
$R^7$, $R^8$ in each case independently of one another represent H, F, Cl, $C_1$-$C_3$-alkyl or $C_1$-$C_2$-alkoxy, and
$R^9$ represents $C_1$-$C_5$-alkyl, $C_2$-$C_5$-alkenyl, $C_2$-$C_5$-alkynyl, $C_3$-$C_6$-cycloalkyl-$(CH_2)_n$ or $C_1$-$C_7$-alkoxy-$C_2$-$C_5$-alkyl,
and their isomers, diastereomers, enantiomers, solvates and salts or cyclodextrin clathrates.

Preferred compounds are those of the formula I, where
$R^{1a}$ represents H or methyl,
$R^{1b}$ represents H, $C_1$-$C_2$-alkyl, vinyl, cyclopropyl-$(CH_2)_m$, $C_3$-$C_6$-heterocycloalkyl-$(CH_2)_n$, methoxy-$C_1$-$C_2$-alkyl or (N,N-dimethylamino)-methyl, where the optionally present heterocyclic unit is preferably selected from the group consisting of oxetane, tetrahydrofuran, 1,4-dioxane, morpholine and pyrrolidine and where optionally present alkyl or cycloalkyl radicals can be mono- or polysubstituted, identically or differently, by methyl, hydroxyl, or methylsulphonyl,
$R^4$ represents H, F, Cl, methyl or methoxy,
A represents iso-propyl, 5-membered heterocyclyl, RO—CO$(CH_2)_p$, $R^5$, $R^{5'}$N—CO$(CH_2)_p$, $R^5R^{5'}$N—SO$_2$$(CH_2)_p$, or cyano, where R represents H or $C_1$-$C_2$-alkyl and an optionally present heterocyclic unit is preferably selected from the group consisting of triazole, tetrazole, and oxadiazole and an alkyl unit contained can be monosubstituted by hydroxyl and a heterocyclic unit optionally contained can be monosubstituted by hydroxyl,
$R^5$, $R^{5'}$ independently of one another represent H, $C_1$-$C_2$-alkyl, $C_5$-$C_6$-heterocycloalkyl-$(CH_2)_r$, $C_1$-$C_5$-alkylsulphonyl, cyclopropylsulphonyl or aryl-$(CH_2)_r$-sulphonyl, where aryl denotes phenyl or naphthyl, or represent pyridyl-$(CH_2)_r$-sulphonyl, and a heterocyclic unit optionally contained is preferably selected from the group consisting of morpholine and pyrrolidine and where $R^5$ and $R^{5'}$ can optionally be mono- or polysubstituted, identically or differently, by methyl, trifluoromethyl, Cl, F, N,N-dimethylamino, methoxy, or trifluoromethoxy, or
$R^5$, $R^{5'}$ together with the nitrogen atom, to which they are bonded, form a 4-6-membered heterocyclic ring optionally containing a further heteroatom, which is selected from the group consisting of O, and which can optionally be monosubstituted by oxo or hydroxyl,
m is 0 or 1,
n is 0 or 1,
p is 0,
r is 0, 1 or 2, and
B is selected from the following structures,

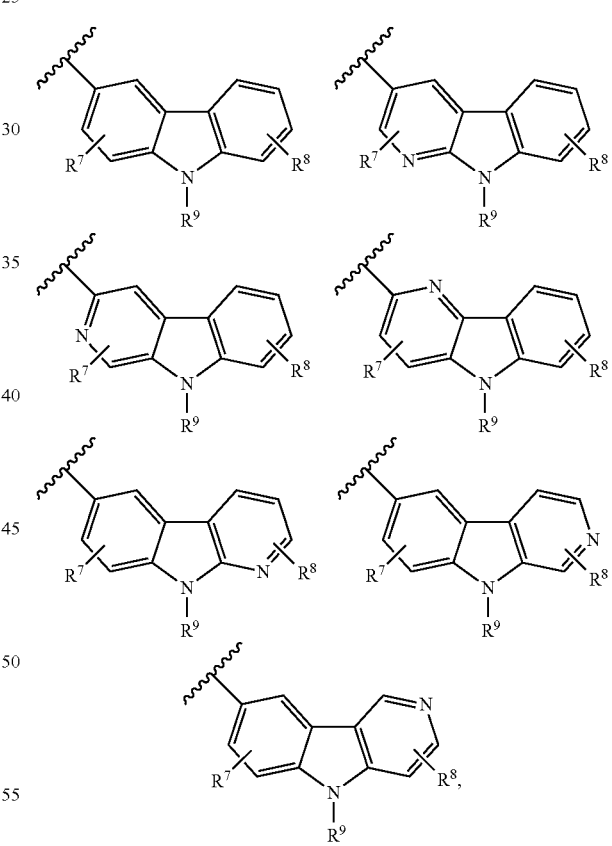

$R^6$ represents H, F, $CH_3$ or $CH_3O$,
$R^7$, $R^8$ in each case independently of one another represent H, F, Cl, methyl or methoxy, and
$R^9$ represents $C_1$-$C_3$-alkyl, allyl, propargyl, $C_3$-$C_4$-cycloalkyl-$(CH_2)_n$ or methoxyethyl,
and their isomers, diastereomers, enantiomers, solvates and salts or cyclodextrin clathrates.

Preferred compounds are those of the formula I, in which $R^{1a}$ represents H, and $R^{1b}$ represents methoxy-$C_1$-$C_2$-alkyl.

Preferred compounds are those of the formula I, in which
$R^{1a}$ represents H, and
$R^{1b}$ represents methoxymethyl.

Preferred compounds are those of the formula I, in which
$R^4$ represents H or $C_1$-$C_2$-alkyl.

Preferred compounds are those of the formula I, in which
$R^4$ represents H.

Preferred compounds are those of the formula I, in which
$R^4$ represents $C_1$-$C_2$-alkyl.

Preferred compounds are those of the formula I, in which
$R^4$ represents methyl.

Preferred compounds are those of the formula I, in which
$R^6$ represents H.

Preferred compounds are those of the formula I, in which
A represents RO—CO($CH_2$)$_p$,
where R represents H or $C_1$-$C_2$-alkyl and p=0.

Preferred compounds are those of the formula I, in which
A represents RO—CO($CH_2$)$_p$,
where R represents H and p=0.

Preferred compounds are those of the formula I, in which
A represents RO—CO($CH_2$)$_p$,
where R represents $C_1$-$C_2$-alkyl and p=0.

Preferred compounds are those of the formula I, in which
A represents RO—CO($CH_2$)$_p$,
where R represents methyl and p=0.

Preferred compounds are those of the formula I, in which
B represents

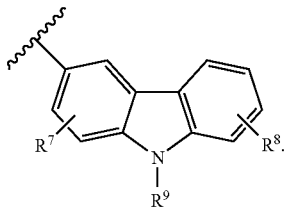

Preferred compounds are those of the formula I, in which
$R^7$, $R^8$ in each case independently of one another, represent H, Cl or methyl.

Preferred compounds are those of the formula I, in which
$R^7$ represents H.

Preferred compounds are those of the formula I, in which
$R^8$ represents H, Cl or methyl.

Preferred compounds are those of the formula I, in which
$R^8$ represents H.

Preferred compounds are those of the formula I, in which
$R^8$ represents Cl.

Preferred compounds are those of the formula I, in which
$R^8$ represents methyl.

Preferred compounds are those of the formula I, in which
$R^9$ represents $C_1$-$C_3$-alkyl.

Preferred compounds are those of the formula I, in which
$R^9$ represents ethyl.

The following compounds according to the present invention are very particularly preferred:
1. Methyl 1-allyl-2-(9-ethyl-9H-carbazol-3-yl)-1H-benzimidazole-5-carboxylate
2. 1-Allyl-2-(9-ethyl-9H-carbazol-3-yl)-1H-benzimidazole-5-carboxylic acid
3. Methyl 2-(9-ethyl-9H-carbazol-3-yl)-1-(2-methoxyethyl)-1H-benzimidazole-5-carboxylate
4. 2-(9-Ethyl-9H-carbazol-3-yl)-1-(2-methoxyethyl)-1H-benzimidazole-5-carboxylic acid
5. Methyl 1-(cyclopropylmethyl)-2-(9-ethyl-9H-carbazol-3-yl)-1H-benzimidazole-5-carboxylate
6. 1-(Cyclopropylmethyl)-2-(9-ethyl-9H-carbazol-3-yl)-1H-benzimidazole-5-carboxylic acid
7. Methyl 4-chloro-1-(cyclopropylmethyl)-2-(9-ethyl-9H-carbazol-3-yl)-1H-benzimidazole-5-carboxylate
8. 4-Chloro-1-(cyclopropylmethyl)-2-(9-ethyl-9H-carbazol-3-yl)-1H-benzimidazole-5-carboxylic acid
9. 1-(Cyclopropylmethyl)-2-(9-ethyl-9H-carbazol-3-yl)-4-methyl-1H-benzimidazole-5-carboxylic acid
10. 2-(9-Ethyl-7-fluoro-9H-carbazol-3-yl)-1-(2-methoxyethyl)-1H-benzimidazole-5-carboxylic acid
11. 2-(9-Ethyl-5-fluoro-9H-carbazol-3-yl)-1-(2-methoxyethyl)-1H-benzimidazole-5-carboxylic acid
12. 2-(9-Ethyl-8-fluoro-9H-carbazol-3-yl)-1-(2-methoxyethyl)-1H-benzimidazole-5-carboxylic acid
13. 1-(Cyclopropylmethyl)-2-[9-(2-methoxyethyl)-9H-carbazol-3-yl]-1H-benzimidazole-5-carboxylic acid
14. 1-(Cyclopropylmethyl)-2-(9-ethyl-9H-pyrido[2,3-b]indol-3-yl)-1H-benzimidazole-5-carboxylic acid
15. 2-(9-Ethyl-9H-carbazol-3-yl)-1-(2-methoxyethyl)-N-(methylsulphonyl)-1H-benzimidazole-5-carboxamide
16. N-(Cyclopropylsulphonyl)-2-(9-ethyl-9H-carbazol-3-yl)-1-(2-methoxyethyl)-1H-benzimidazole-5-carboxamide
17. N-[(3-Chlorophenyl)sulphonyl]-2-(9-ethyl-9H-carbazol-3-yl)-1-(2-methoxyethyl)-1H-benzimidazole-5-carboxamide
18. 2-(9-Ethyl-9H-carbazol-3-yl)-N-(ethylsulphonyl)-1-(2-methoxyethyl)-1H-benzimidazole-5-carboxamide
19. 2-(9-Ethyl-9H-carbazol-3-yl)-1-(2-methoxyethyl)-N-[(4-methoxyphenyl)-sulphonyl]-1H-benzimidazole-5-carboxamide
20. 2-(9-Ethyl-9H-carbazol-3-yl)-1-(2-methoxyethyl)-N-({2-[4-(trifluoromethyl)-phenyl]ethyl}sulphonyl)-1H-benzimidazole-5-carboxamide
21. 1-(Cyclopropylmethyl)-2-(9-ethyl-9H-carbazol-3-yl)-N-(2-methoxyethyl)-1H-benzimidazole-5-carboxamide
22. [1-(Cyclopropylmethyl)-2-(9-ethyl-9H-carbazol-3-yl)-1H-benzimidazol-5-yl](pyrrolidin-1-yl)methanone
23. [1-(Cyclopropylmethyl)-2-(9-ethyl-9H-carbazol-3-yl)-1H-benzimidazol-5-yl](3-hydroxyazetidin-1-yl)methanone
24. 1-(Cyclopropylmethyl)-2-(9-ethyl-9H-carbazol-3-yl)-N-methyl-1H-benzimidazole-5-carboxamide
25. 1-(Cyclopropylmethyl)-2-(9-ethyl-9H-carbazol-3-yl)-N,N-dimethyl-1H-benzimidazole-5-carboxamide
26. 1-(Cyclopropylmethyl)-2-(9-ethyl-9H-carbazol-3-yl)-1H-benzimidazole-5-carboxamide
27. 1-(Cyclopropylmethyl)-2-(9-ethyl-9H-carbazol-3-yl)-N-(2,2,2-trifluoroethyl)-1H-benzimidazole-5-carboxamide
28. 4-{[1-(Cyclopropylmethyl)-2-(9-ethyl-9H-carbazol-3-yl)-1H-benzimidazol-5-yl]carbonyl}piperazin-2-one
29. [1-(Cyclopropylmethyl)-2-(9-ethyl-9H-carbazol-3-yl)-1H-benzimidazol-5-yl](morpholin-4-yl)methanone
30. Azetidine-1-yl[2-(9-ethyl-9H-carbazol-3-yl)-1-(2-methoxyethyl)-1H-benzimidazol-5-yl]methanone
31. 2-(9-Ethyl-9H-carbazol-3-yl)-N,1-bis(2-methoxyethyl)-1H-benzimidazole-5-carboxamide
32. 2-(9-Ethyl-6-methoxy-9H-carbazol-3-yl)-1-(2-methoxyethyl)-1H-benzimidazole-5-carboxylic acid
33. 2-(9-Allyl-9H-carbazol-3-yl)-1-(cyclopropylmethyl)-1H-benzimidazole-5-carboxylic acid
34. 1-(Cyclopropylmethyl)-2-(9-methyl-9H-carbazol-3-yl)-1H-benzimidazole-5-carboxylic acid
35. 1-(Cyclopropylmethyl)-2-[9-(cyclopropylmethyl)-9H-carbazol-3-yl]-1H-benzimidazole-5-carboxylic acid 36. 2-[9-(Cyclopropylmethyl)-9H-carbazol-3-yl]-1-(2-methoxyethyl)-1H-benzimidazole-5-carboxylic acid
37. Ethyl-2-(9-ethyl-9H-carbazol-3-yl)-1-[2-(pyrrolidin-1-yl)ethyl]-1H-benzimidazole-5-carboxylate
38. 2-(9-Ethyl-9H-carbazol-3-yl)-1-[2-(pyrrolidin-1-yl)ethyl]-1H-benzimidazole-5-carboxylic acid
39. N-(tert-Butylsulphonyl)-2-(9-ethyl-9H-carbazol-3-yl)-1-(2-methoxyethyl)-1H-benzimidazole-5-carboxamide
40. 2-(9-Ethyl-9H-carbazol-3-yl)-1-(2-methoxyethyl)-N-[(1-methylcyclopropyl)-sulphonyl]-1H-benzimidazole-5-carboxamide
41. 2-(9-Ethyl-9H-carbazol-3-yl)-1-(2-methoxyethyl)-N-methyl-1H-benzimidazole-5-carboxamide
42. 2-(5-Ethyl-5H-pyrido[3,2-b]indol-2-yl)-1-(2-methoxyethyl)-1H-benzimidazole-5-carboxylic acid
43. 1-(Cyclopropylmethyl)-2-(9-ethyl-6-methoxy-9H-carbazol-3-yl)-1H-benzimidazole-5-carboxylic acid
44. 2-(9-Ethyl-9H-carbazol-3-yl)-1-(2-methoxyethyl)-1H-benzimidazole-5-carbonitrile
45. 9-Ethyl-3-[1-(2-methoxyethyl)-5-(1H-tetrazol-5-yl)-1H-benzimidazole-2-yl]-9H-carbazole
46. 3-[2-(9-Ethyl-9H-carbazol-3-yl)-1-(2-methoxyethyl)-1H-benzimidazol-5-yl]-1,2,4-oxadiazol-5(4H)-one
47. 2-(9-Ethyl-9H-carbazol-3-yl)-1-(2-methoxyethyl)-N-[(3-methylphenyl)sulphonyl]-1H-benzimidazole-5-carboxamide
48. 2-(9-Ethyl-9H-carbazol-3-yl)-1-(2-methoxyethyl)-N-[(4-methylphenyl)sulphonyl]-1H-benzimidazole-5-carboxamide
49. N-[(4-Chlorophenyl)sulphonyl]-2-(9-ethyl-9H-carbazol-3-yl)-1-(2-methoxyethyl)-1H-benzimidazole-5-carboxamide
50. 2-(9-Ethyl-9H-carbazol-3-yl)-1-(2-methoxyethyl)-N-(phenylsulphonyl)-1H-benzimidazole-5-carboxamide
51. 2-(9-Ethyl-9H-carbazol-3-yl)-1-(2-methoxyethyl)-N-(2-naphthylsulphonyl)-1H-benzimidazole-5-carboxamide
52. 2-(9-Ethyl-9H-carbazol-3-yl)-1-(2-methoxyethyl)-N-[(2-methoxyphenyl)-sulphonyl]-1H-benzimidazole-5-carboxamide
53. 2-(9-Ethyl-9H-carbazol-3-yl)-1-(2-methoxyethyl)-N-[(2-methylphenyl)sulphonyl]-1H-benzimidazole-5-carboxamide
54. 2-(9-Ethyl-9H-carbazol-3-yl)-1-(2-methoxyethyl)-N-{[2-(trifluoromethoxy)-phenyl]sulphonyl}-1H-benzimidazole-5-carboxamide
55. N-(Benzylsulphonyl)-2-(9-ethyl-9H-carbazol-3-yl)-1-(2-methoxyethyl)-1H-benzimidazole-5-carboxamide
56. N-{[2-(3-Chlorophenyl)ethyl]sulphonyl}-2-(9-ethyl-9H-carbazol-3-yl)-1-(2-methoxyethyl)-1H-benzimidazole-5-carboxamide
57. 2-(9-Ethyl-9H-carbazol-3-yl)-1-(2-methoxyethyl)-N-{[2-(2-methylphenyl)ethyl]sulphonyl}-1H-benzimidazole-5-carboxamide
58. 2-(9-Ethyl-9H-carbazol-3-yl)-N-[(4-fluorbenzyl)sulphonyl]-1-(2-methoxyethyl)-1H-benzimidazole-5-carboxamide
59. 2-(9-Ethyl-9H-carbazol-3-yl)-1-(2-methoxyethyl)-N-[(2-methoxyethyl)sulphonyl]-1H-benzimidazole-5-carboxamide
60. N-[(2,6-Dichlorbenzyl)sulphonyl]-2-(9-ethyl-9H-carbazol-3-yl)-1-(2-methoxyethyl)-1H-benzimidazole-5-carboxamide
61. N-{[2-(2-Chlorophenyl)ethyl]sulphonyl}-2-(9-ethyl-9H-carbazol-3-yl)-1-(2-methoxyethyl)-1H-benzimidazole-5-carboxamide
62. 2-(9-Ethyl-9H-carbazol-3-yl)-1-(2-methoxyethyl)-N-{[4-(trifluoromethyl)benzyl]sulphonyl}-1H-benzimidazole-5-carboxamide
63. 2-(9-Ethyl-9H-carbazol-3-yl)-1-(2-methoxyethyl)-N-[(5-methylpyridin-2-yl)sulphonyl]-1H-benzimidazole-5-carboxamide
64. N-[(4-Chlorobenzyl)sulphonyl]-2-(9-ethyl-9H-carbazol-3-yl)-1-(2-methoxyethyl)-1H-benzimidazole-5-carboxamide
65. 2-(9-Ethyl-9H-carbazol-3-yl)-1-(2-methoxyethyl)-N-{[2-(trifluoromethoxy)-benzyl]sulphonyl}-1H-benzimidazole-5-carboxamide
66. N-[(2,2-Dimethylpropyl)sulphonyl]-2-(9-ethyl-9H-carbazol-3-yl)-1-(2-methoxyethyl)-1H-benzimidazole-5-carboxamide
67. N-[(2-Chloro-6-methylbenzyl)sulphonyl]-2-(9-ethyl-9H-carbazol-3-yl)-1-(2-methoxyethyl)-1H-benzimidazole-5-carboxamide
68. 2-(9-Ethyl-9H-carbazol-3-yl)-1-(2-methoxyethyl)-N-{[(3-methylpyridin-2-yl)methyl]sulphonyl}-1H-benzimidazole-5-carboxamide
69. 2-(9-Ethyl-9H-carbazol-3-yl)-1-(2-methoxyethyl)-N-{[2-(3-methoxyphenyl)ethyl]sulphonyl}-1H-benzimidazole-5-carboxamide
70. 2-(9-Ethyl-9H-carbazol-3-yl)-1-[2-(morpholin-4-yl)ethyl]-1H-benzimidazole-5-carboxylic acid
71. Ethyl-1-[2-(dimethylamino)ethyl]-2-(9-ethyl-9H-carbazol-3-yl)-1H-benzimidazole-5-carboxylate
72. 1-[2-(Dimethylamino)ethyl]-2-(9-ethyl-9H-carbazol-3-yl)-1H-benzimidazole-5-carboxylic acid
73. 1-[2-(Dimethylamino)ethyl]-2-(9-ethyl-9H-carbazol-3-yl)-N-methyl-1H-benzimidazole-5-carboxamide
74. N-(Cyclopropylsulphonyl)-1-[2-(dimethylamino)ethyl]-2-(9-ethyl-9H-carbazol-3-yl)-1H-benzimidazole-5-carboxamide
75. 1-[2-(Dimethylamino)ethyl]-2-(9-ethyl-9H-carbazol-3-yl)-N-[(4-methylphenyl)sulphonyl]-1H-benzimidazole-5-carboxamide
76. [2-(9-Ethyl-9H-carbazol-3-yl)-1-(2-methoxyethyl)-1H-benzimidazol-5-yl](pyrrolidin-1-yl)methanone
77. 2-(9-Ethyl-9H-carbazol-3-yl)-1-(2-methoxyethyl)-N-(2,2,2-trifluoroethyl)-1H-benzimidazole-5-carboxamide
78. 2-(9-Ethyl-9H-carbazol-3-yl)-1-(2-methoxyethyl)-N-[2-(morpholin-4-yl)ethyl]-1H-benzimidazole-5-carboxamide
79. 1-(Cyclopropylmethyl)-2-(9-ethyl-9H-carbazol-3-yl)-N-[2-(morpholin-4-yl)ethyl]-1H-benzimidazole-5-carboxamide
80. Azetidin-1-yl[1-(cyclopropylmethyl)-2-(9-ethyl-9H-carbazol-3-yl)-1H-benzimidazol-5-yl]methanone
81. [2-(9-Ethyl-9H-carbazol-3-yl)-1-(2-methoxyethyl)-1H-benzimidazol-5-yl](morpholin-4-yl)methanone
82. 2-(9-Ethyl-9H-carbazol-3-yl)-1-(2-methoxyethyl)-1H-benzimidazole-5-carboxamide
83. 2-(9-Ethyl-9H-carbazol-3-yl)-1-(2-methoxyethyl)-N,N-dimethyl-1H-benzimidazole-5-carboxamide
84. 2-(9-Ethyl-9H-carbazol-3-yl)-1-(2-methoxyethyl)-N-methyl-N-(methylsulphonyl)-1H-benzimidazole-5-carboxamide
85. 1-Allyl-2-(9-ethyl-9H-carbazol-3-yl)-N,N-dimethyl-1H-benzimidazole-5-carboxamide
86. N-[2-(Dimethylamino)ethyl]-2-(9-ethyl-9H-carbazol-3-yl)-1-(2-methoxyethyl)-1H-benzimidazole-5-carboxamide
87. 2-(9-Ethyl-9H-carbazol-3-yl)-1-(2-methoxyethyl)-N-[2-(pyrrolidin-1-yl)ethyl]-1H-benzimidazole-5-carboxamide 88. 1-Allyl-2-(9-ethyl-9H-carbazol-3-yl)-N-methyl-1H-benzimidazole-5-carboxamide
89. 1-Allyl-2-(9-ethyl-9H-carbazol-3-yl)-1H-benzimidazole-5-carboxamide
90. 2-(9-Ethyl-9H-carbazol-3-yl)-N, 1-dimethyl-1H-benzimidazole-5-carboxamide
91. 2-(9-Ethyl-9H-carbazol-3-yl)-1-(2-hydroxyethyl)-1H-benzimidazole-5-carboxylic acid
92. Ethyl-2-(9-ethyl-9H-carbazol-3-yl)-1-isopropyl-1H-benzimidazole-5-carboxylate
93. 2-(9-Ethyl-9H-carbazol-3-yl)-1-isopropyl-1H-benzimidazole-5-carboxylic acid
94. 2-(9-Ethyl-9H-carbazol-3-yl)-1-methyl-1H-benzimidazole-5-carboxylic acid
95. Methyl 1-ethyl-2-(9-ethyl-9H-carbazol-3-yl)-1H-benzimidazole-5-carboxylate
96. 2-(9-Allyl-9H-carbazol-3-yl)-1-(2-methoxyethyl)-1H-benzimidazole-5-carboxylic acid
97. Ethyl 1-(2-methoxyethyl)-2-[9-(2-methoxyethyl)-9H-carbazol-3-yl]-H-benzimidazole-5-carboxylate
98. 1-(2-Methoxyethyl)-2-[9-(2-methoxyethyl)-9H-carbazol-3-yl]-1H-benzimidazole-5-carboxylic acid
99. Ethyl 2-(9-ethyl-9H-carbazol-3-yl)-1-(3-methoxypropyl)-1H-benzimidazole-5-carboxylate
100. 2-(9-Ethyl-9H-carbazol-3-yl)-1-(3-methoxypropyl)-1H-benzimidazole-5-carboxylic acid
101. 2-[2-(9-Ethyl-9H-carbazol-3-yl)-1-(2-methoxyethyl)-1H-benzimidazol-5-yl]propan-2-ol
102. 1-(Cyclopropylmethyl)-2-(9-ethyl-9H-carbazol-3-yl)-6-methoxy-1H-benzimidazole-5-carboxylic acid
103. 2-(9-Ethyl-9H-carbazol-3-yl)-6-methoxy-1-(2-methoxyethyl)-1H-benzimidazole-5-carboxylic acid
104. 1-(Cyclopropylmethyl)-2-(9-ethyl-9H-carbazol-3-yl)-4-methoxy-1H-benzimidazole-5-carboxylic acid
105. 2-(9-Ethyl-9H-carbazol-3-yl)-1-(2-methoxyethyl)-4-methyl-1H-benzimidazole-5-carboxylic acid
106. 5-[2-(9-Ethyl-9H-carbazol-3-yl)-1-(2-methoxyethyl)-1H-benzimidazol-5-yl]-1,3,4-oxadiazol-2(3H)-one
107. 1-(Cyclopropylmethyl)-2-(9-ethyl-9H-pyrido[2,3-b]indol-3-yl)-4-methyl-1H-benzimidazole-5-carboxylic acid
108. 1-(Cyclopropylmethyl)-2-(9-ethyl-9H-beta-carbolin-6-yl)-1H-benzimidazole-5-carboxylic acid
109. 1-(Cyclopropylmethyl)-2-(5-ethyl-5H-pyrido[4,3-b]indol-8-yl)-1H-benzimidazole-5-carboxylic acid
110. 1-(Cyclopropylmethyl)-2-(9-ethyl-9H-carbazol-3-yl)-6-methyl-1H-benzimidazole-5-carboxylic acid
111. 2-(9-Ethyl-9H-carbazol-3-yl)-1-(2-methoxyethyl)-6-methyl-1H-benzimidazole-5-carboxylic acid
112. 2-(9-Ethyl-9H-carbazol-3-yl)-6-fluoro-1-(2-methoxyethyl)-1H-benzimidazole-5-carboxylic acid
113. 1-(Cyclopropylmethyl)-2-(9-ethyl-9H-carbazol-3-yl)-6-fluoro-1H-benzimidazole-5-carboxylic acid
114. 2-(9-Ethyl-9H-carbazol-3-yl)-4-fluoro-1-(2-methoxyethyl)-1H-benzimidazole-5-carboxylic acid
115. 1-(Cyclopropylmethyl)-2-(9-ethyl-9H-carbazol-3-yl)-4-fluoro-1H-benzimidazole-5-carboxylic acid
116. 1-(Cyclopropylmethyl)-2-(9-ethyl-9H-pyrido[2,3-b]indol-6-yl)-1H-benzimidazole-5-carboxylic acid
117. 1-(2-Cyclopropylethyl)-2-(9-ethyl-9H-carbazol-3-yl)-1H-benzimidazole-5-carboxylic acid
118. 1-(2-Methoxyethyl)-2-(9-propyl-9H-carbazol-3-yl)-1H-benzimidazole-5-carboxylic acid
119. 1-(2-Methoxyethyl)-2-[9-(prop-2-yn-1-yl)-9H-carbazol-3-yl]-1H-benzimidazole-5-carboxylic acid
120. 1-(Cyclopropylmethyl)-2-(9-propyl-9H-carbazol-3-yl)-1H-benzimidazole-5-carboxylic acid
121. 1-[(2,2-Dimethylcyclopropyl)methyl]-2-(9-ethyl-9H-carbazol-3-yl)-1H-benzimidazole-5-carboxylic acid
122. Ethyl 2-(9-ethyl-9H-carbazol-3-yl)-1-(oxetan-3-ylmethyl)-1H-benzimidazole-5-carboxylate
123. 2-(9-Ethyl-9H-carbazol-3-yl)-1-(oxetan-3-ylmethyl)-1H-benzimidazole-5-carboxylic acid
124. 2-[9-(Cyclobutylmethyl)-9H-carbazol-3-yl]-1-(2-methoxyethyl)-1H-benzimidazole-5-carboxylic acid
125. 2-[9-(Cyclobutylmethyl)-9H-carbazol-3-yl]-1-(cyclopropylmethyl)-1H-benzimidazole-5-carboxylic acid
126. 5-{1-[2-(Dimethylamino)ethyl]-2-(9-ethyl-9H-carbazol-3-yl)-1H-benzimidazol-5-yl}-1,3,4-oxadiazol-2(3H)-one
127. 2-(9-Ethyl-9H-carbazol-3-yl)-1-(2-methoxyethyl)-1H-benzimidazole-5-sulphonamide
128. 9-Ethyl-3-[1-methyl-5-(1H-1,2,3-triazol-1-yl)-1H-benzimidazole-2-yl]-9H-carbazole
129. 2-(9-Ethyl-9H-carbazol-3-yl)-N, 1-dimethyl-1H-benzimidazole-5-sulphonamide
130. 2-(9-Ethyl-9H-carbazol-3-yl)-1-[2-(trifluoromethoxy)ethyl]-1H-benzimidazole-5-carboxylic acid
131. 1-(Cyclopropylmethyl)-2-(9-ethyl-1-methyl-9H-beta-carbolin-3-yl)-1H-benzimidazole-5-carboxylic acid
132. 2-(9-Ethyl-9H-carbazol-3-yl)-1-(oxetan-2-ylmethyl)-1H-benzimidazole-5-carboxylic acid
133. 2-(9-Ethyl-9H-carbazol-3-yl)-1-(tetrahydrofuran-2-ylmethyl)-1H-benzimidazole-5-carboxylic acid
134. 2-(9-Ethyl-9H-carbazol-3-yl)-1-[(2R)-2-hydroxy-3-methoxypropyl]-1H-benzimidazole-5-carboxylic acid
135. 2-(9-Ethyl-9H-carbazol-3-yl)-1-[(2S)-2-hydroxy-3-methoxypropyl]-1H-benzimidazole-5-carboxylic acid
136. 2-(9-Ethyl-9H-carbazol-3-yl)-1-[2-(methylsulphonyl)ethyl]-1H-benzimidazole-5-carboxylic acid
137. 1-(2-Cyclopropyl-2-hydroxyethyl)-2-(9-ethyl-9H-carbazol-3-yl)-1H-benzimidazole-5-carboxylic acid
138. 1-[(2S)-2,3-Dihydroxypropyl]-2-(9-ethyl-9H-carbazol-3-yl)-1H-benzimidazole-5-carboxylic acid
139. 1-(1,4-Dioxan-2-ylmethyl)-2-(9-ethyl-9H-carbazol-3-yl)-1H-benzimidazole-5-carboxylic acid
140. 1-(1,4-Dioxan-2-ylmethyl)-2-(9-ethyl-9H-carbazol-3-yl)-1H-benzimidazole-5-carboxylic acid
141. 2-(9-Ethyl-6-methyl-9H-carbazol-3-yl)-1-(2-methoxyethyl)-4-methyl-1H-benzimidazole-5-carboxylic acid
142. 2-(6-Chloro-9-ethyl-9H-carbazol-3-yl)-1-(2-methoxyethyl)-4-methyl-1H-benzimidazole-5-carboxylic acid
143. 2-(8-Chloro-9-ethyl-9H-carbazol-3-yl)-1-(2-methoxyethyl)-4-methyl-1H-benzimidazole-5-carboxylic acid The present invention relates to the compounds of the formula (I), for the treatment and/or prophylaxis of diseases.

In the preventive endometriosis animal model, it was shown for EP4 antagonists for the first time that when using the compound according to the invention in the said dose range after subcutaneous (FIG. 1) and after oral administration (FIG. 2) a significant reduction of the endometrial lesions and an immunomodulatory action in vivo is to be observed. Thus 2 significant aspects of endometriosis are addressed by the use of the compounds applied for. The immunomodulatory effect was identified by 2 features:

1) the infiltration of neutrophiles in the lesions observed in the control group failed to materialize in the dose groups 10 mg/kg and 50 mg/kg (FIG. 1, s.c. experiment);
2) in a FACS analysis of the peritoneal fluid, which was collected in the course of the dissection, it was possible to detect a significant reduction of macrophage activation in the high-dose group (FIG. 3). The hormonal cycle of the animals remained uninfluenced. No gastrointestinal damage after 28 days' administration was determined in the said dose range. Overall, the histopathological investigation of stomach, small intestine, kidney, liver and heart of the experimental animals after 28 days' treatment produced no abnormalities compared to the organs of the control group.

The compounds of the general formula I according to the invention bind to the EP4 receptor and have antagonistic action.

The subject of the present invention is therefore compounds of the formula (I), which act antagonistically on the EP4 receptor, for the treatment and/or prophylaxis of endometriosis, of uterine leiomyomas, of uterine bleeding disorders, where the bleeding disorders can be severe and long-lasting bleeding, temporally irregular bleeding and pain, of dysmenorrhoea, of cancer, where the cancers can be lung, intestine, breast, skin, prostate, oesophageal cancer and leukaemia, of arteriosclerosis and of polycystic kidney diseases.

Likewise, the present invention relates to the use of a compound according to formula (I) for the production of a medicament for the treatment and/or prophylaxis of diseases. This can be the treatment and/or prophylaxis of endometriosis, of uterine leiomyomas, of uterine bleeding disorders, where the bleeding disorders can be severe and long-lasting bleeding, temporally irregular bleeding and pain, of dysmenorrhoea, of cancer, where the cancers can be lung, intestine, breast, skin, prostate, oesophageal cancer and leukaemia, of arteriosclerosis and of polycystic kidney diseases.

The antagonistic action can be determined by an antagonism test (see Example 3.2.1 of the biological examples). Thus, for example, the compound 4 according to the invention binds to the EP4 receptor with an $IC_{50}$ value of about 6 nM.

Antagonists are understood as meaning those molecules that bind to their corresponding receptors and which inhibit the initiation of the signal transduction pathway/s coupled with the receptor by the naturally occurring ligand(s). Customarily, the antagonists compete with the naturally occurring ligand of the receptor for binding to the receptor. However, other modifications of the receptor by molecules that prevent the signal transduction pathways coupled with the receptor being activated by the naturally occurring ligands are also possible (e.g. non-competitive, steric modifications of the receptor).

Preferentially, the antagonists bind reversibly to their corresponding receptors.

The EP4 antagonist has a preferred affinity for the receptor EP4 compared to any other EP subtype. The antagonism is measured in the presence of the natural agonist (PGE2).

Likewise, the present invention relates on the basis of the antagonistic action on the receptor EP4 to medicaments for the treatment and/or prophylaxis of diseases, amongst which are counted infectious diseases, cancer, cardiovascular diseases, angiogenetic diseases, disorders of uterine contraction, acute and chronic pain, inflammatory diseases, neuroinflammatory diseases, neurodegenerative diseases, autoimmune diseases, immune-dependent diseases/therapies, nephrological diseases, ophthalmological diseases.

Infectious diseases are to be understood as meaning diseases caused by unicellular parasites (e.g. *Klebsiella, Streptococcus*). In the case of infectious diseases, the medicaments can have an immunomodulatory action such that the diseases can be treated prophylactically (reduction of the danger of infection, such as, for example, in bone marrow transplants) or therapeutically. Cancer is to be understood as meaning solid tumours and leukaemias; viral infections are to be understood as meaning, e.g., cytomegalus infections, hepatitis, hepatitis B and C and HIV diseases; cardiovascular diseases are to be understood as meaning ischaemic reperfusion disease, stenoses, arterioscleroses, restenoses, arthritis, Kawasaki syndrome and aneurysms; angiogenetic diseases are to be understood, in addition to endometriosis, as meaning fibrosis and fibroids in the uterus; disorders of uterine contraction are to be understood as meaning, e.g., menstrual complaints; pain is to be understood as meaning, for example, inflammatory hyperalgesia, arthritis, arthrosis, neuropathic pain, gout, visceral pain, backache, headache, migraine, toothache, pain due to sunburn and pain due to burn injuries, inflammatory diseases are to be understood as meaning, for example, inflammatory intestinal diseases; neuroinflammatory and neurodegenerative diseases are to be understood as meaning, e.g., multiple sclerosis, Alzheimer's, Parkinson's, ALS, stroke; immune-dependent diseases/therapies are to be understood as meaning, e.g., transplants, in which immunmodulation increases the therapeutic success; autoimmune diseases are to be understood as meaning, for example, the ophthalmological disease Basedow's disease, and nephrological diseases are to be understood as meaning polycystic kidney diseases, glomerulonephritis.

The compounds according to the invention can be mixed here with the customary pharmaceutical excipients. The EP4 antagonists are formulated in a manner known per se to the person skilled in the art.

Likewise, the present invention relates to the use of a compound according to formula (I) for the production of a medicament.

Likewise, the present invention relates to medicaments that contain the compounds according to the invention, containing suitable formulating substances and excipients.

The therapeutically active dose is dependent on the body weight, administration route, individual behaviour, the type of preparation and time or interval at which administration takes place. A typical dose range for a woman of 70 kg body weight is between 1-500 mg/day, preferably between 5 and 20 mg/day.

A further subject of the present invention relates to medicaments containing at least one compound according to the invention and at least one or more other active substances, in particular for the treatment and/or prophylaxis of endometriosis. Suitable combination active substances that may be mentioned by way of example and preferably are: selective oestrogen receptor modulators (SERMs), oestrogen receptor (ER) antagonists, aromatase inhibitors, 17β-HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen activated protein (MAP) kinase and inhibitors of MAP kinases (Mkk3/6, Mek1/2, Erk1/2), inhibitors of protein kinases B (PKBα/β/γ; Akt1/2/3), inhibitors of phosphoinositide-3 kinase (PI3K), inhibitors of cyclin-dependent kinase (CDK1/2), Inhibitors of the hypoxia-induced signal pathway (HIF1alpha inhibitors, activators of the prolylhydroxylases), histone deacetylase (HDAC) inhibitors, prostaglandin F receptor (FP) (PTGFR) antagonists, neurokinin 1 receptor antagonists, paracetamol, selective COX2 inhibitors and/or non-selective COX1/COX2 inhibitors.

The invention also relates to pharmaceutical preparations that contain at least one compound of the general formula I (or physiologically tolerable addition salts with organic and inorganic acids thereof) and the use of these compounds for the production of medicaments, in particular for the aforementioned indications.

The compounds can be employed for the aforementioned indications, both after oral as well as parenteral administration.

The compounds according to the invention can act systemically and/or locally. For this purpose, they can be administered in a suitable manner, such as e.g. orally, parenterally, pulmonarily, nasally, sublingually, lingually, buccally, rectally, dermally, transdermally, conjunctivally, otically or as an implant or stent.

For these administration routes, the compounds according to the invention can be administered in suitable administration forms.

The dosage of the compounds of the general formula I in these preparations should be 0.01%-20%, in order to achieve an adequate pharmacological action.

The dosage of the active substances can vary, depending on administration route, age and weight of the patient, nature and severity of the disease to be treated and similar factors. The treatment can be carried out by means of individual doses or by a plurality of doses over a relatively long period. The daily dose is 0.5-1000 mg, preferably 50-200 mg, where the dose can be given as an individual dose to be administered once or subdivided into 2 or more daily doses.

As carrier systems, surface-active excipients such as salts of the bile acids or animal or vegetable phospholipids can also be used, but also mixtures thereof and liposomes or their constituents.

The formulations and administration forms described above are likewise the subject of the present invention.

If, in addition to the compound according to the invention according to formula I, further active substances are contained, these can be formulated in a common administration form or optionally also administered as a combination preparation.

For oral administration, administration forms functioning according to the prior art, releasing the compounds to be used according to the invention rapidly and/or in modified form, which contain the compounds according to the invention in crystalline and/or amorphized and/or dissolved form, are suitable, such as, e.g., tablets (non-coated or coated tablets, for example, having enteric or slowly dissolving or insoluble coatings, which control the release of the compound to be used according to the invention), tablets or films/wafers disintegrating rapidly in the oral cavity, films/lyophilizates, capsules (for example, hard or soft gelatine capsules), coated tablets, granules, pellets, powders, emulsions, suspensions, aerosols or solutions.

Parenteral administration can take place circumventing an absorption step (e.g. intravenously, intraarterially, intracardially, intraspinally or intralumbarly) or with inclusion of an absorption (e.g. intramuscularly, subcutaneously, intracutaneously, percutaneously or intraperitoneally). For parenteral administration, suitable administration forms are, inter alia, injection and infusion preparations in the form of solutions, suspensions, emulsions, lyophilizates or sterile powders.

For the other administration routes, e.g., pharmaceutical forms for inhalation (inter alia powder inhalers, nebulizers), nose drops, solutions or sprays, tablets to be administered lingually, sublingually or buccally, films/wafers or capsules, suppositories, ear or eye preparations, tinctures, vaginal capsules and suppositories, tampons, intrauterine pessaries, aqueous suspensions (lotions, shaking mixtures), lipophilic suspensions, crystal suspensions, aqueous and oily injection solutions, depot preparations, ointments, fatty ointments, gels, creams, transdermal therapeutic systems (e.g. patches), milk, pastes, foams, dusting powders, implants, intrauterine spirals, vaginal rings or stents are suitable.

Oral or parenteral administration is preferred, in particular oral and intravenous administration.

The compounds to be used according to the invention can be converted into the administration forms mentioned. This can take place in a manner known per se by mixing with inert, non-toxic, pharmaceutically suitable excipients. These excipients include, inter alia, carrier substances (for example, microcrystalline cellulose, lactose, mannitol), solvents (e.g. liquid polyethylene glycols), emulsifiers and dispersants or wetting agents (for example sodium dodecylsulphate, polyoxysorbitan oleate), binding agents (for example polyvinylpyrrolidone), synthetic and natural polymers (for example albumin), stabilizers (e.g. antioxidants such as, for example, ascorbic acid), colourants (e.g. inorganic pigments such as, for example, iron oxides) and taste and/or odour corrigents.

A further subject of the present invention is medicaments that contain at least one compound according to the invention, customarily together with one or more inert, non-toxic, pharmaceutically suitable excipients, and their use for the previously mentioned purposes.

In the case of oral administration, the amount per day is approximately 0.01 to 100 mg/kg of body weight. The amount of a compound of the general formula I to be administered varies within a wide range and can cover any effective amount. Depending on the state to be treated and the type of administration, the amount of the compound administered can be 0.01-100 mg/kg of body weight per day.

Nevertheless, it can optionally be necessary to deviate from the amounts mentioned, namely, depending on body weight, administration route, individual behaviour towards the active substance, nature of the preparation and time or interval at which administration takes place. Thus, in some cases it can be adequate to manage with less than the aforementioned minimum amount, while in other cases the upper limit mentioned must be exceeded. In the case of the administration of relatively large amounts, it can be advisable to divide these into a number of individual doses over the course of the day.

The percentages in the following tests and examples are, if not stated otherwise, percentages by weight; parts are parts by weight. Solvent ratios, dilution ratios and concentrations of liquid/liquid solutions in each case relate to the volume.

Likewise, a subject of the present invention is the use of the substances according to the invention as EP4 receptor antagonists for the prophylaxis and direct treatment of diseases that are related causally to the EP4 receptor or of diseases that can be treated by influencing the EP4 receptor.

Prostaglandins play an important role in angiogenesis (Sales, Jabbour, 2003, Reproduction 126, 559-567; Kuwano et al., 2004, FASEB J. 18, 300-310; Kamiyama et al., 2006, Oncogene 25, 7019-7028; Chang et al., 2005, Prostaglandins & other Lipid Mediators 76, 48-58).

Prostaglandins play an important role in uterine contraction, contractions that are too strong are responsible for menstrual pains (Sales, Jabbour, 2003, Reproduction 126, 559-567). Prostaglandins and here especially the EP4 and the EP2 receptor have been connected with severe menstrual haemorrhages (Smith et al., 2007 (Human Reproduction, Vol. 22, No. 5 pp. 1450-1456).

The present invention relates to the use of the substances of the general formula I for the prophylaxis and treatment of menstrual complaints and severe menstrual haemorrhages and pain during menstruation.

Fibroids (myomas) are benign tumours in the uterus having a high prevalence rate. A connection to prostaglandin metabolism exists by way of the stimulation of aromatase by a PGE2/cAMP-mediated signal pathway, and by possible other mechanisms (Imir et al., 2007, J Clin Endocrinol Metab 92, 1979-1982).

The present invention relates to the use of the substances of the general formula I for the prophylaxis and treatment of fibroids (myomas).

Growing research results also confirm the importance of the EP receptors in a large number of types of cancer (e.g. breast cancer, colon cancer, lung cancer, prostate cancer, leukaemia, skin cancer), which suggests future possibilities of the use of modulators (antagonists or agonists) of the EP4 receptor for the treatment and prevention (prophylactic and/or adjuvant) of cancer (Fulton et al., 2006, Cancer Res; 66(20): 9794-7; Hull et al., 2004, Mol Cancer Ther; 3(8): 1031-9; Wang et al., 2004, Seminars in Oncology, Vol 31, No 1, Suppl 3: pp 64-73).

The present invention relates to the use of the substances of the general formula I for the treatment and prevention of cancers.

The activation of endothelial cells in the pathogenic process of arteriosclerosis plays an important role. Recent research shows an involvement of the EP4 receptor (Minami et al., 2008, J Biol Chem., April 11; 283(15):9692-703. Epub 2008 Feb. 12).

The present invention relates to the use of the substances of the general formula I for the treatment and prevention of arteriosclerosis.

Recent scientific publications show that in neurodegenerative, neuroinflammatory and ischaemic diseases (Alzheimer's, Parkinson's, ALS, stroke) prostaglandins and the EP4 receptor are important components of the disease process (Hoshino et al., 2007, J Biol Chem.; 282(45): 32676-88; Cimino et al., 2008, Current Medicinal Chemistry, 1863-1869).

Multiple sclerosis is a chronic inflammation of the nervous system. Prostaglandins, especially PGE2 and effects mediated by means of the EP4 receptor are causally associated with the pathological processes in multiple sclerosis (Palumbo et al., 2011, Prostaglandins, Leukotrienes and Essential Fatty Acids 85: 29-35; Kihara et al., 2009, Proc Natl Acad Sci U.S.A., 106, Nr. 51: 21807-21812).

The present invention relates to the use of the substances of the general formula I for the treatment and prevention of neurodegenerative, neuroinflammatory and ischaemic diseases such as, for example, Alzheimer's, Parkinson's, ALS, stroke and the treatment of multiple sclerosis.

Polycystic kidney diseases are likewise connected with the EP4 receptor (Liu et al., 2012, Am J Physiol Renal Physiol. 2012 Aug. 29. [Epub ahead of print.])

The present invention relates to the use of the substances of the general formula I for the treatment and prevention of polycystic kidney diseases.

There are indications that an inflammatory, increased sensitivity to pain can be treated by specifically modulating EP4 receptors. In addition, the EP4 receptor is connected with further types of pain (Zeilhofer, 2007, Biochemical Pharmacology 73; 165-174). Murase et al. (Eur J Pharmacol. 2008 Feb. 2; 580(1-2):116-21) report on a connection between EP4 receptor blockade and a symptomatic relief from the symptoms that occur in osteoarthritis and/or rheumatoid arthritis.

The present invention relates to the use of the substances according to the invention for the treatment and prevention of pain of differing origin such as, for example, inflammatory hyperalgesia or arthritis.

Recent scientific publications indicate a use of EP4 inhibitors for the prevention and/or treatment of infections of the airways. Serezani et al. (Am Respir Cell Mol Biol Vol 37. pp 562-570, 2007) describe that by means of the activation of the EP4 receptor by PGE2, macrophages of the respiratory tract are impaired in their ability to destroy bacteria. Bacterial infections lead to an increased production of prostaglandins, inter alia PGE2, which, by means of this mechanism weakens the body's own defense against bacteria. As shown in this publication, this capability of bacterial control can be restored again by an inactivation of the EP4 receptor (and of the EP2 receptor).

The present invention relates to the use of the substances according to the invention for the prevention and treatment of infectious diseases of the lung.

Inflammatory bowel diseases (e.g. Crohn's disease) are likewise connected with the prostaglandin EP4 receptor (Sheibanie et al., 2007, The Journal of Immunology, 178: 8138-8147).

The present invention relates to the use of the substances according to the invention for the prevention and treatment of inflammatory bowel diseases.

In bone marrow transplants, complications due to infections often occur, an overproduction of PGE2 being connected with a reduced immune defense (Ballinger et al., 2006, The Journal of Immunology, 177: 5499-5508).

The present invention relates to the use of the substances according to the invention for prophylaxis and treatment in connection with bone marrow transplants.

Basedow's disease (in English called "Graves' disease") is an autoimmune disease of the thyroid, in which the clinical picture can also comprise pathological changes in the eye (endocrine ophthalmopathy; prominence of the eyeballs (exophthalmos). In this connection, immigrating lymphocytes activate existing fibroblasts, which leads, inter alia, to an accumulation of mucopolysaccharides. Possible consequences are impairments of vision up to blindness. Investigations show that interleukin-6 has a decisive importance for the pathological mechanisms and acts by means of PGE2 (Wang et al., 1995, J Clin Endocrinol Metab 80: 3553-3560).

The present invention relates to the use of the substances according to the invention for prophylaxis and treatment in the case of ophthalmopathy in connection with Basedow's disease (Graves' Disease) or other pathological diseases of the eye.

The natural ligand (agonist) of the EP4 receptor is PGE2, the synthesis of which is mediated by means of cyclooxygenases (COX) enzymes (COX-1, COX-2). These enzymes are usually involved in the syndromes, indications and their origin mentioned by means of an increased expression and activity. Therefore in the case of all administration possibilities mentioned a combination of a COX inhibitor (COX-2 and/or COX-1) is possible, with the aim a) of achieving a higher and more effective pharmacological efficacy than with one class of substance and b) of making possible a low dose of one of the two or both substance classes, which leads to a reduction of possible side effects and better tolerability.

The present invention therefore also relates to medicaments containing a compound of the general formula (I) in combination with a COX inhibitor for the treatment of diseases (combination preparations). COX inhibitors that may be mentioned are, for example the non-selective COX inhibitors such as aspirin, naproxen, indomethacin, ibuprofen or the selective COX inhibitors meloxicam, ketoprofen, piroxicam, tenoxicam, nimesulide, mefanemic acid, ketoralac, celecoxib (4-[5-(4-methylphenyl)-3-(trifluoromethyl)-1H-pyrazol-1-yl]benzenesulphonamide), parecoxib (N-[4-(5-methyl-3-phenyl-4-isoxazolyl)phenyl]-sulphonylpropionamide), rofecoxib (4-(4-mesylphenyl)-3-phenylfuran-2(5H)-one), valdecoxib (4-[5-methyl-3-phenyl-4-isoxazoyl]benzenesulphonamide), NS-398 (N-methyl-2-cyclohexanoxy-4-nitrobenzenesulphonamide), lumiracoxib [2-(2'-chloro-6'-fluorphenyl)-amino-5-methylbenzeneacetic acid], ceracoxib and etoricoxib.

These combination preparations can be employed for the treatment of the following diseases: infectious diseases, cancer, cardiac/circulatory diseases, angiogenetic diseases, disorders of uterine contraction, pain, inflammatory diseases, neuroinflammatory diseases, neurodegenerative diseases, autoimmune diseases, immune-dependent diseases/therapies, nephrological diseases, ophthalmological diseases.

The alternative reaction schemes are shown below, according to which the compounds according to the invention can be prepared, in each case depending on the availability of the starting materials. For all schemes, exemplary embodiments show the reaction procedure in detail.

The radicals R, $R^{1a}$, $R^{1b}$, $R^4$, $R^5$, $R^{5'}$, $R^6$, $R^7$, $R^8$, $R^9$, A and B listed in the schemes 1-7 have the meanings listed in the claim and serve for illustration of the synthesis, without the scope of the claimed compounds being restricted to these examples.

Thus, for example, benzimidazoles of the general structure IV or XII can be prepared by reaction of substituted o-phenylenediamines of the general formula II or XI with aldehydes of the formula III, XXIV or XXI. This can be achieved, for example, by heating the components II and III in the presence of acids and an oxidizing agent. The compounds IV and XII thus generated can then be substituted on the nitrogen atoms of the imidazole according to processes known in the literature, preferably using alkyl halides, oxiranes or other nucleophiles (Scheme 1, Scheme 3). In this synthesis variant the isomers Va and Vb or else XIIa and XIIb usually result, which can be separated from one another by customary methods. Customary methods are separation processes such as, for example crystallization, chromatography on silica gel or else separations by means of high pressure or high performance liquid chromatography.

Carboxylic acids of the formula VI can be reacted with an amine by processes known to the person skilled in the art to give the compounds according to the invention of the general formula I (Scheme 1-4, general formula VII).

The reaction to give amides of the formula VII takes place, for example, by converting a carboxylic acid of the formula VI with isobutyl chloroformate in the presence of a tertiary amine, for example triethylamine, into a mixed anhydride, which reacts with an alkali metal salt of the corresponding amine in an inert solvent or solvent mixture, for example tetrahydrofuran, N,N-dimethylformamide, dimethoxyethane at temperatures between −30° C. and +60° C. to give the target compounds of the formula I.

It is likewise possible to activate a carboxylic acid VI with reagents such as, for example, dicyclohexylcarbodiimide (DCC), 1-(3-dimethylaminopropyl)-3-ethylcarbodiimide (EDCI), N-hydroxybenzotriazole (HOBT), N-[(dimethylamino)-(3H-[1,2,3]triazolo[4,5-b]pyridin-3-yloxy)methylidene]-N-methylmethanaminium hexafluoro-phosphate (HATU). For example, the reaction with HATU takes place in an inert solvent, for example N,N-dimethylformamide, dimethyl sulphoxide, in presence of the corresponding amine and of a tertiary amine, for example triethylamine, diisopropylethylamine at temperatures between −30° C. and +60° C.

It is likewise possible to convert a carboxylic acid of the formula VI with an inorganic acid chloride, for example phosphorus pentachloride, phosphorus trichloride, thionyl chloride, into the corresponding carbonyl chloride and subsequently in pyridine or an inert solvent, such as, for example N,N-dimethylformamide in the presence of the appropriate amine and of a tertiary amine, for example triethylamine at temperatures between −30° C. and +60° C., into the target compounds of the general formula I.

The compounds of the general formula I according to the invention can likewise be obtained from amines of the general formula XXXII by reaction with carboxylic acids, carbonyl chlorides or carboxylic acid anhydrides.

The compounds of the general formula I according to the invention can likewise be obtained from bromoimidazoles of the general formula XIII (XIIIa and/or XIIIb) under palladium(0) catalysis by reaction with an appropriate alcohol or amine and carbon monoxide (CO) or a carbon monoxide source, such as, e.g., molybdenum hexacarbonyl in a suitable solvent or solvent mixture, for example 1,4-dioxane/water or tetrahydrofuran, addition of a base such as, for example, sodium carbonate or 1,8-diazabicyclo(5.4.0)undec-7-ene (DBU) and of a catalyst/ligand mixture, for example palladium(II) acetate or trans-bis(acetato)bis[o-(di-o-tolylphosphino)benzyl]-dipalladium(II)/tri-tert-butyl phosphinotetrafluoroborate at temperatures between 80° C. and 160° C. (optionally with microwave irradiation between 80-200 watt), and in the case of the use of carbon monoxide at a CO pressure of 5-15 bar (Scheme 3, Scheme 4).

This method is not restricted to methyl esters, i.e. to the use of methanol, but is also extendable to other esters. Thus, the corresponding ethyl esters can be synthesized in this manner, for example, by use of ethanol instead of methanol.

The carboxylic acids of the general formula VI can be obtained, for example, from esters of the formula Va by saponification of the ester in a suitable solvent or solvent mixture, for example methanol, ethanol, tetrahydrofuran, water with addition of an aqueous solution of an alkali metal hydroxide, for example, sodium hydroxide, lithium hydroxide, at temperatures between 20° C. and 60° C. (Scheme 1-4).

The compounds of the general formula XXIV can be prepared, for example, from the corresponding anilines XX, by cyclizing XX according to methods known to the person skilled in the art to give formula XXII and subsequently oxidizing to XXIII. The compounds XXIII thus generated can be alkylated on the nitrogen of the carbazole according to methods known in the literature (Scheme 5) and can then be employed in reactions in which the benzimidazoles of the formula I according to the invention are prepared.

Scheme 1
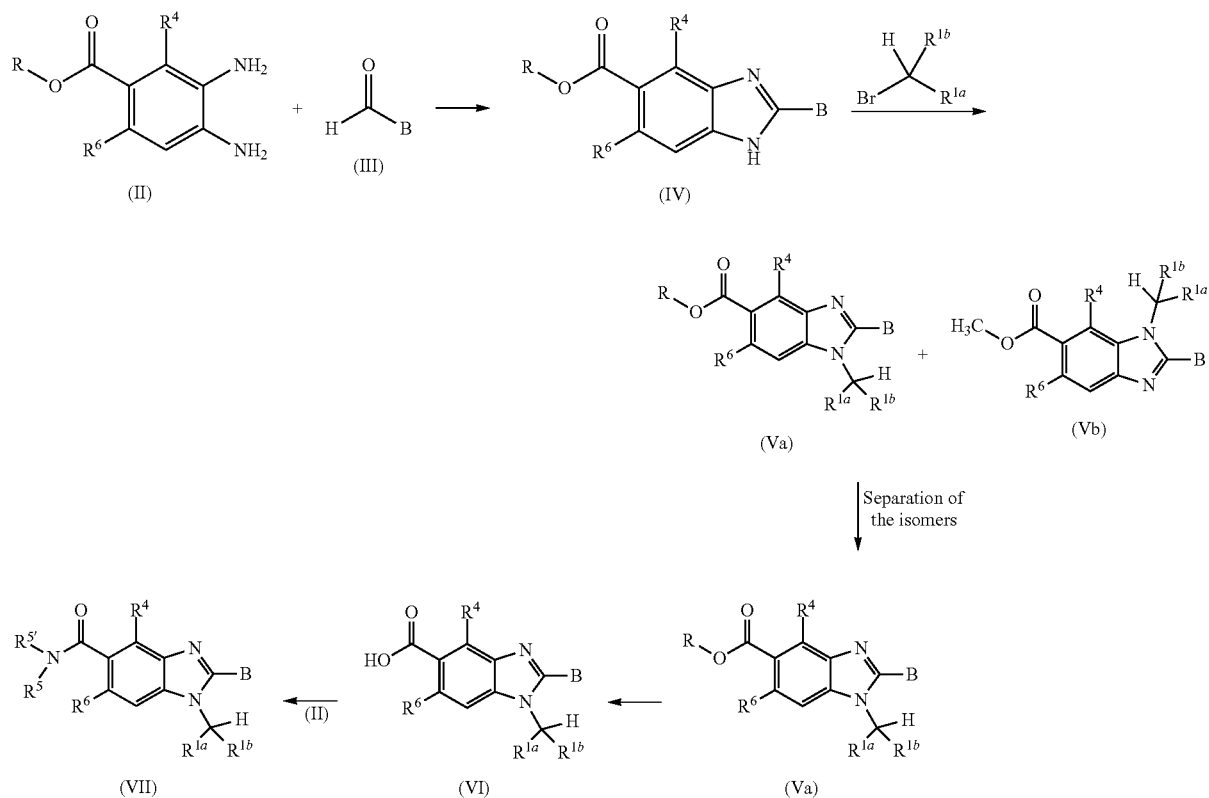
Scheme 2
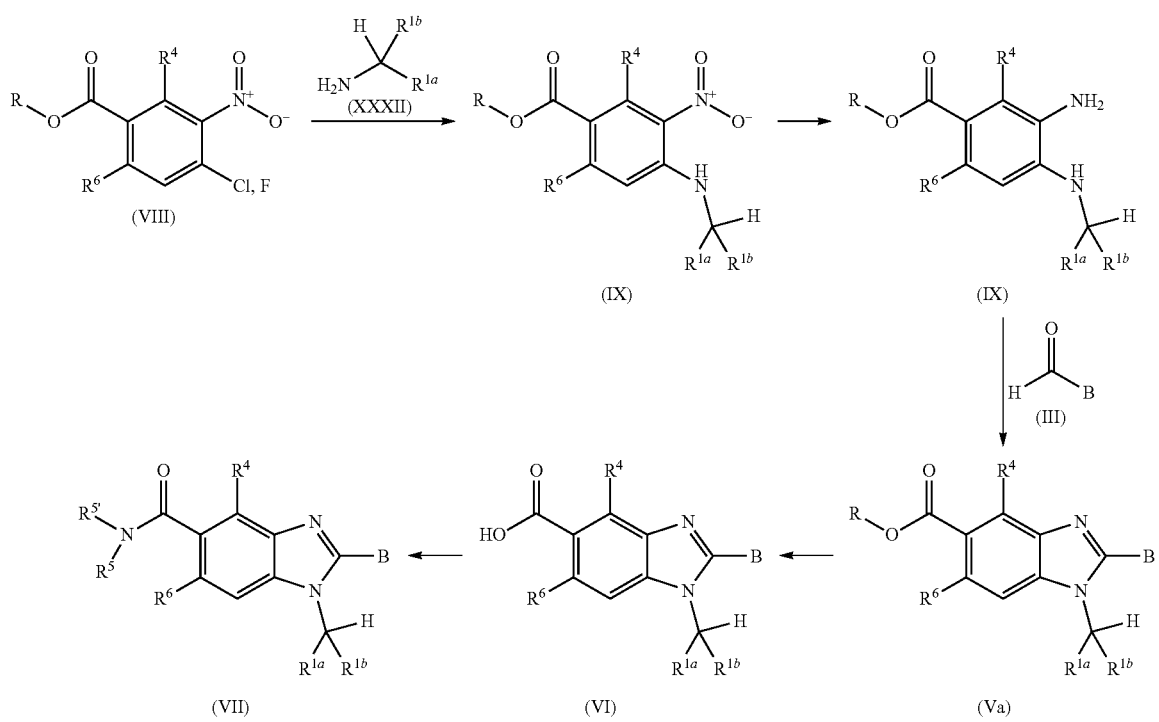

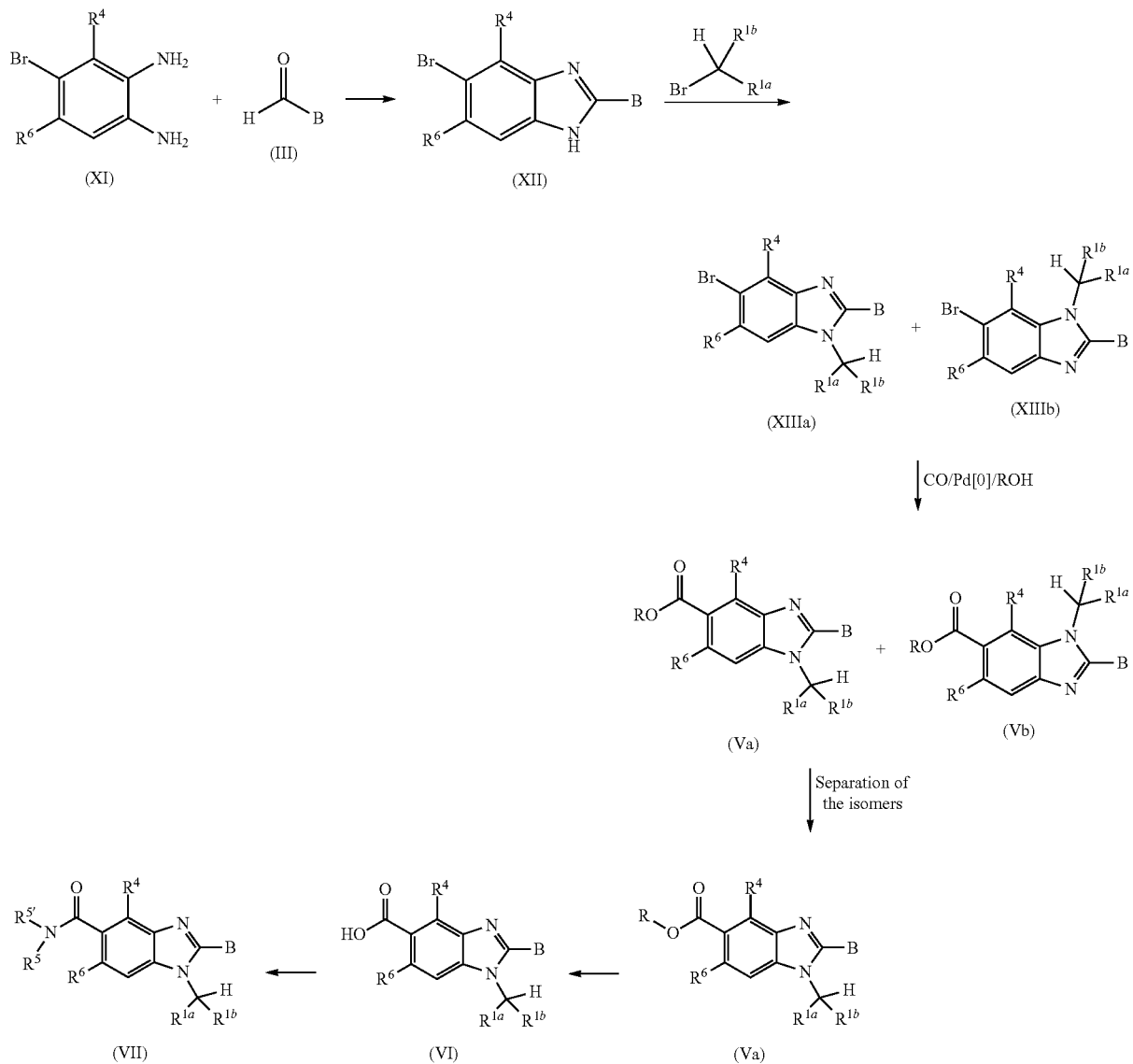
Scheme 3
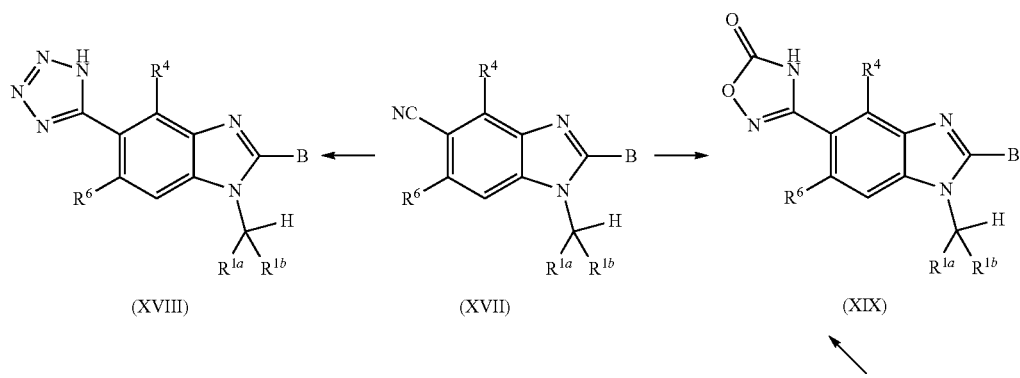
Scheme 4

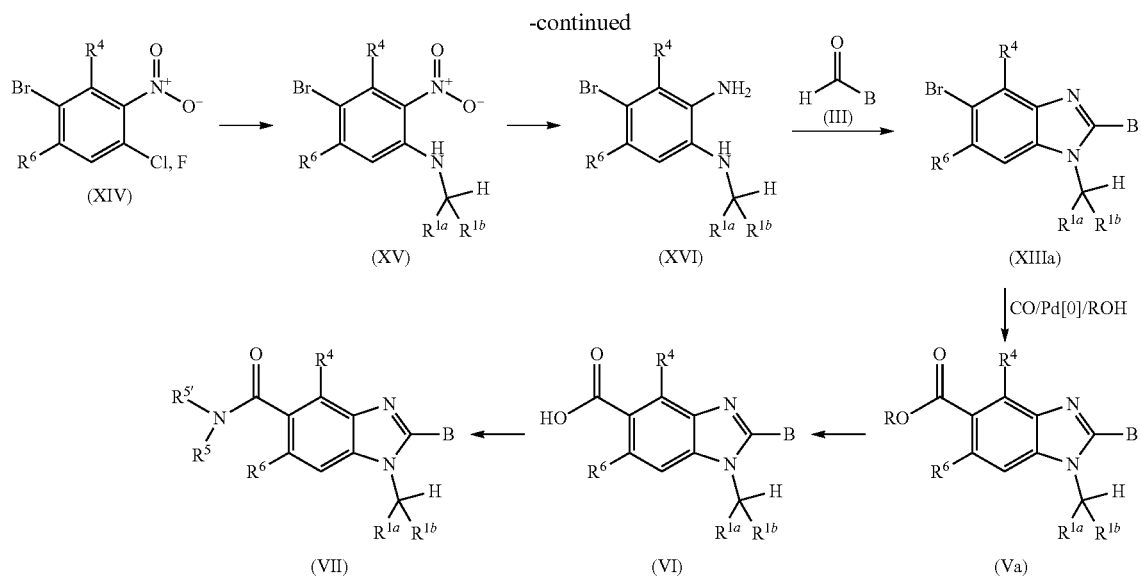
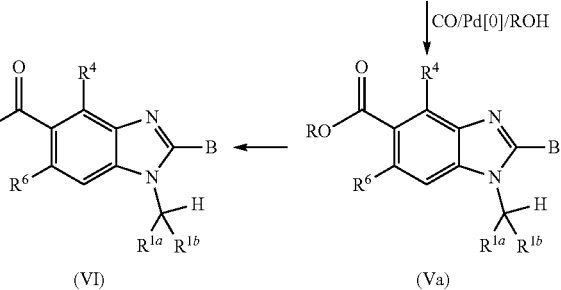
Scheme 5
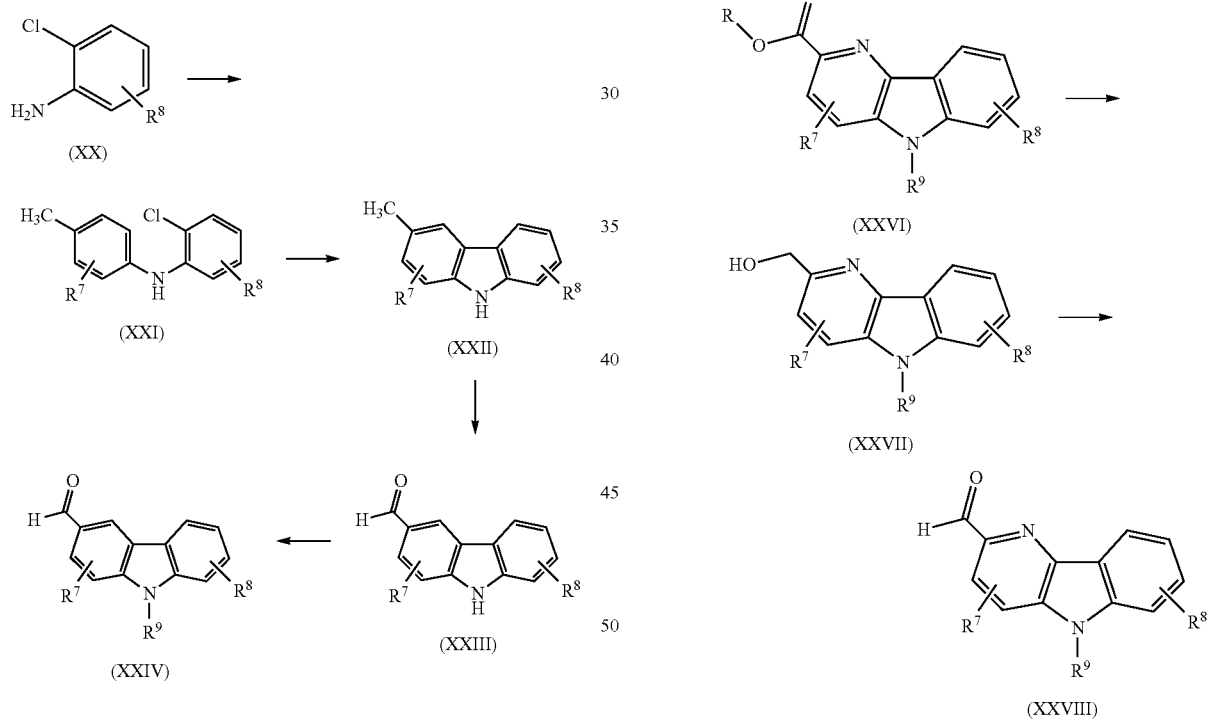
Scheme 6
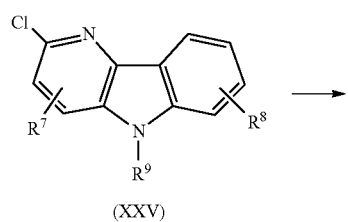
Scheme 7
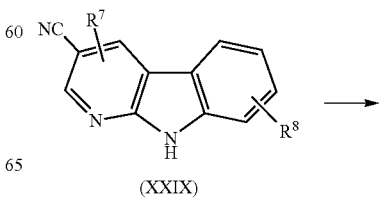

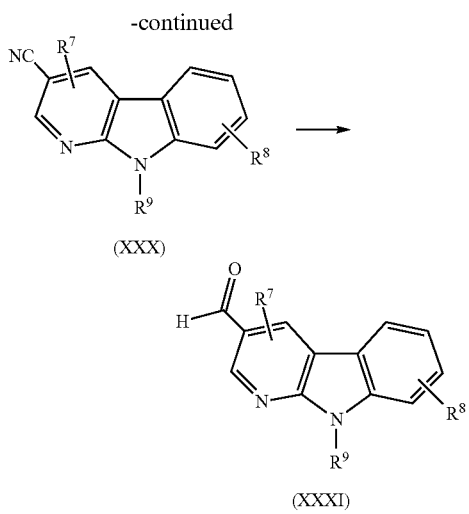

Preparation of the compounds according to the invention

The following examples illustrate the preparation of the compounds of the general formula (I) according to the invention, without the scope of the claimed compounds being restricted to these examples.

The compounds of the general formula (I) according to the invention can be prepared and characterized as described below.

Abbreviations
CO carbon monoxide
DBU 1,8-diazabicyclo[5.4.0]undec-7-ene
DCM dichloromethane
DMF N,N-dimethylformamide
DMSO dimethyl sulphoxide
h hour(s)
HPLC high-pressure, high-performance liquid chromatography
konz. concentrated
M molar
min minute(s)
N normal
NMR nuclear magnetic resonance spectroscopy
RT room temperature
tert tertiary
THF tetrahydrofuran NMR peak shapes are indicated such as they appear in the spectrum, possible effects of higher order were not taken into consideration.

EXPERIMENTAL SECTION

Intermediate 1

Methyl 2-(9-ethyl-9H-carbazol-3-yl)-1H-benzimidazole-5-carboxylate

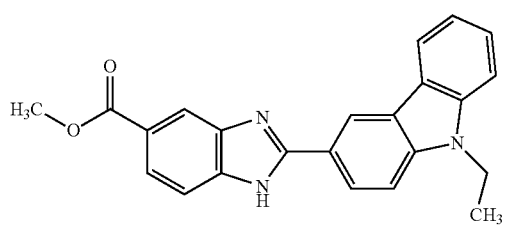 [SMILES: CCn1c2ccccc2c2cc(-c3nc4cc(C(=O)OC)ccc4[nH]3)ccc21]

25.7 g (135 mmol) of sodium disulphite were dissolved in 60 ml of water and treated with a solution of 14.8 g (66 mmol) of 9-ethyl-9H-carbazole-3-carbaldehyde in 135 ml of THF. 20 g (120 mmol) of methyl 3,4-diaminobenzoate in 90 ml THF were then added and the mixture was heated to reflux for 3 h and stirred for 15 h with cooling to RT. 150 ml of saturated sodium hydrogencarbonate solution were added to the reaction mixture, it was extracted several times with dichloromethane, and the collected organic phases were dried using sodium sulphate and evaporated to dryness. The residue was taken up in a little dichloromethane and brought to crystallization. 20.56 g (84%) of the title compound were thus obtained.

$^1$H-NMR (300 MHz, DMSO-d6), δ [ppm]=1.33 (t, 3H), 3.85 (s, 3H), 4.48 (q, 2H), 7.26 (t, 1H), 7.49 (t, 1H), 7.59-7.70 (m, 2H), 7.74-7.87 (m, 2H), 8.11-8.34 (m, 3H), 8.97 (d, 1H), 12.60-13.70 (1H).

Intermediate 2

Ethyl 4-[(2-methoxyethyl)amino]-3-nitrobenzoate

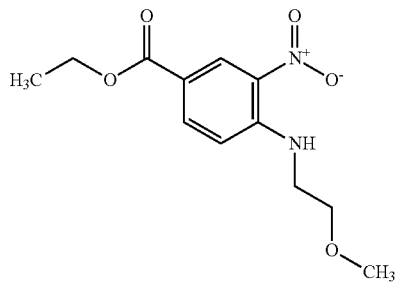 [SMILES: CCOC(=O)c1ccc(NCCOC)c([N+](=O)[O-])c1]

40.0 g (0.17 mol) of ethyl-4-chloro-3-nitrobenzoate were added to 200 ml of DMSO, 20.9 g (0.28 mol) of 2-methoxyethanamine were added, and the mixture was heated for 6 h at 60° C. and then cooled to RT overnight. The reaction mixture was poured onto 200 ml of saturated sodium hydrogencarbonate solution, and the resulting precipitate was filtered off and washed with 100 ml water. The precipitate was dried. 45.5 g (78%) of the title compound were thus obtained.

$^1$H-NMR (300 MHz, DMSO-d6), δ [ppm]=1.31 (t, 3H), 3.31-3.32 (m, 1H), 3.57-3.62 (m, 4H), 4.29 (q, 2H), 7.19 (d, 1H), 7.97 (dd, 1H), 8.50-8.56 (m, 1H), 8.61 (d, 1H).

Intermediate 3

4-[(2-Methoxyethyl)amino]-3-nitrobenzoic acid

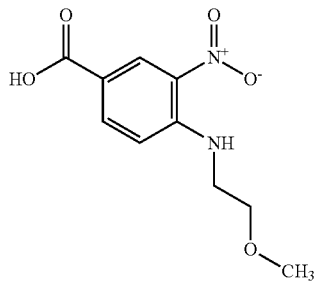 [SMILES: COCCNc1ccc(C(=O)O)cc1[N+](=O)[O-]]

26.0 g (0.097 mol) of ethyl 4-[(2-methoxyethyl)amino]-3-nitrobenzoate were added to 100 ml of ethanol, treated with 55 ml of 2M sodium hydroxide solution and heated to reflux for 1 h. After cooling, 75 ml of 2M hydrochloric acid were added and the mixture was extracted five times with dichloromethane. The organic phases collected were dried over sodium sulphate, filtered and concentrated. 21.8 g (93%) of the title compound were thus obtained.

$^1$H-NMR (300 MHz, DMSO-d6), δ [ppm]=3.31 (s, 3H), 3.57-3.61 (4H), 7.17 (d, 1H), 7.96 (dd, 1H), 8.47-8.53 (br. s., 1H), 8.61 (d, 1H), 12.40-13.30 (1H).

Intermediate 4

3-Amino-4-[(2-methoxyethyl)amino]benzoic acid

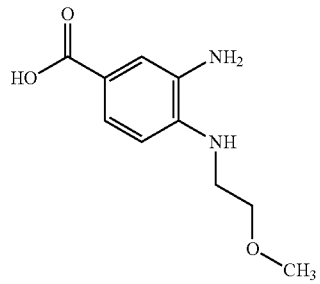

21.8 g (0.09 mol) of 4-[(2-methoxyethyl)amino]-3-nitrobenzoic acid were dissolved in 500 ml of ethanol, treated with 2.5 g of palladium/carbon (10%) and stirred at RT for 4 h with introduction of hydrogen. Then 2.5 g of palladium/carbon (10%) were added once again and hydrogen was introduced for a further 2 h. The catalyst was filtered off and the solution was concentrated. 19.0 g (82%) of the title compound were thus obtained.

$^1$H-NMR (400 MHz, DMSO-d6), δ [ppm]=3.23-3.31 (m, 5H), 3.41-3.48 (m, 2H), 5.35-5.65 (1H), 5.70-6.20 (2H), 6.15 (d, 1H), 6.70 (s, 1H), 7.16 (d, 1H), 11.40-12.50 (1H).

Intermediate 5

3-Amino-4-[(cyclopropylmethyl)amino]benzoic acid

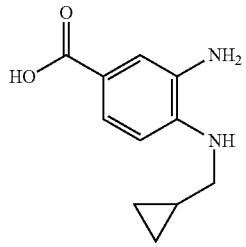 [SMILES: Nc1cc(C(=O)O)ccc1NCC1CC1]

In analogy to Intermediate 4, 3-amino-4-[(cyclopropylmethyl)amino]benzoic acid was obtained from ethyl 4-chloro-3-nitrobenzoate and 1-cyclopropylmethanamine in three stages.

$^1$H-NMR (300 MHz, DMSO-d6), δ [ppm]=0.21-0.27 (m, 2H), 0.46-0.53 (m, 2H), 1.05-1.15 (m, 1H), 2.98 (d, 2H), 5.00-5.80 (3H), 6.47 (d, 1H), 7.22-7.28 (m, 2H), 11.10-12.35 (1H).

Intermediate 6

4-Bromo-3-chloro-N-(cyclopropylmethyl)-2-nitroaniline

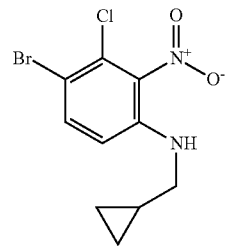 [SMILES: O=[N+]([O-])c1c(NCC2CC2)ccc(Br)c1Cl]

650 mg (2.59 mmol) of 4-bromo-3-chloro-2-nitroaniline were added to 5 ml of trifluoroacetic acid, cooled to −15° C., treated in portions with 822 mg (3.88 mmol) of sodium triacetoxyborohydride and stirred at −15° C. for 10 min. 272 mg (3.88 mmol) of cyclopropanecarbaldehyde in 5 ml of dichloromethane were then added and stirred for a further 30 min at −15° C. Subsequently, the reaction mixture was poured onto cold saturated sodium hydrogencarbonate solution and extracted three times with dichloromethane. The organic phases were filtered and concentrated. In this way, 720 mg (87%) of the title compound were obtained.

$^1$H-NMR (400 MHz, DMSO-d6), δ [ppm]=0.19-0.23 (m, 2H), 0.41-0.46 (m, 2H), 1.00-1.09 (m, 1H), 3.03 (t, 2H), 6.48 (t, 1H), 6.92 (d, 1H), 7.64 (d, 1H).

Intermediate 7

4-Bromo-3-chloro-N1-(cyclopropylmethyl)benzene-1,2-diamine

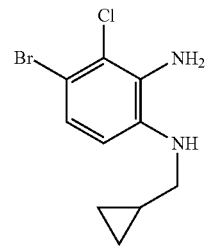 [SMILES: Nc1c(NCC2CC2)ccc(Br)c1Cl]

720 mg (2.36 mmol) of 4-bromo-3-chloro-N-(cyclopropylmethyl)-2-nitroaniline were added to 30 ml ethanol, treated with 2.13 g (9.43 mmol) of tin(II) chloride dihydrate and subsequently stirred at 70° C. for 3 h. The reaction mixture was then concentrated almost to dryness, treated slowly with saturated sodium hydrogencarbonate solution and extracted three times with dichloromethane. The combined organic phases were filtered and subsequently concentrated.

$^1$H-NMR (400 MHz, DMSO-d6), δ [ppm]=0.19-0.24 (m, 2H), 0.46-0.52 (m, 2H), 1.04-1.10 (m, 1H), 2.89 (dd, 2H), 4.98-5.05 (m, 1H), 5.12 (s, 2H), 6.32 (d, 1H), 6.80 (d, 1H).

Intermediate 8

3-[5-Bromo-4-chloro-1-(cyclopropylmethyl)-1H-benzimidazol-2-yl]-9-ethyl-9H-carbazole

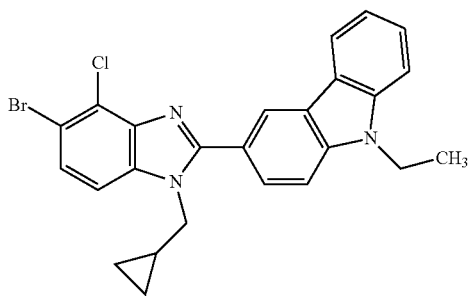 [SMILES: CCn1c2ccccc2c2cc(-c3nc4c(Cl)c(Br)ccc4n3CC3CC3)ccc21]

486 mg (2.56 mmol) of sodium disulphite were added to 3 ml of water, stirred at RT for 5 min and then treated with a solution of 253 mg (1.14 mmol) of 9-ethyl-9H-carbazole-3-carbaldehyde in 1 ml of THF. 470 mg (1.71 mmol) of 4-bromo-3-chloro-N1-(cyclopropyl-methyl)benzene-1,2-diamine in 3 ml of THF were then added, stirred for 10 min at RT and subsequently heated to reflux for 30 min. The reaction mixture was added to saturated sodium hydrogencarbonate solution and extracted three times with ethyl acetate. The organic phases were concentrated and the residue purified by chromatography on silica gel (hexane/ethyl acetate 1:0->4:6). 720 mg (79%) of the title compound were thus obtained.

$^1$H-NMR (300 MHz, DMSO-d6), δ [ppm]=0.10-0.18 (m, 2H), 0.30-0.39 (m, 2H), 0.95-1.10 (m, 1H), 1.37 (t, 3H), 4.36 (d, 2H), 4.53 (q, 2H), 7.27 (t, 1H), 7.49-7.56 (m, 1H), 7.60 (d, 1H), 7.67-7.76 (m, 2H), 7.79-7.84 (m, 1H), 7.87-7.92 (m, 1H), 8.32 (d, 1H), 8.64 (d, 1H).

Intermediate 9

Methyl 3-amino-4-[(cyclopropylmethyl)amino]-2-methylbenzoate

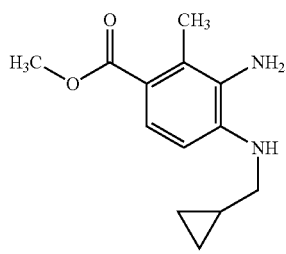 [SMILES: COC(=O)c1ccc(NCC2CC2)c(N)c1C]

1.0 g (5.2 mmol) of 4-acetamido-2-methylbenzoic acid was added to 5 ml of concentrated sulphuric acid and a mixture of 0.22 ml of concentrated nitric acid and 0.50 ml of concentrated sulphuric acid was subsequently added dropwise at 0° C. The reaction mixture was warmed to RT and left overnight at RT. The mixture was then added to ice water and the resulting precipitate was filtered off. 1.47 g of 4-amino-2-methyl-3-nitrobenzoic acid were thus obtained as a crude product. 0.96 g (4.9 mmol) of crude 4-amino-2-methyl-3-nitrobenzoic acid were added to 40 ml of methanol, treated with 2.4 ml of concentrated sulphuric acid and heated to reflux for 18 h. After cooling to RT, the deposited precipitate (methyl 4-amino-2-methyl-3-nitrobenzoate, 228 mg, 22%) was filtered off and employed without further purification in the next stage.

220 mg (1.05 mmol) of crude methyl 4-amino-2-methyl-3-nitrobenzoate in 1.1 ml of trifluoroacetic acid were cooled to −15° C. and treated in portions with 333 mg (1.57 mmol) of sodium triacetoxyborohydride. After 10 min, 73 mg (1.05 mmol) of cyclopropanecarbaldehyde in 2.2 ml of dichloromethane were added dropwise and the reaction mixture was poured after a further 5 min onto cooled, saturated sodium hydrogencarbonate solution. Subsequently, the mixture was extracted three times with dichloromethane, the organic phases were dried with sodium sulphate, filtered and the filtrate was concentrated.

The residue thus obtained (240 mg) was taken up in methanol and hydrogenated under normal pressure on palladium (10% strength on carbon). The catalyst was filtered off and the filtrate was concentrated. 190 mg (79%) of the title compound were thus obtained, which was employed without further purification in the next stage.

Intermediate 10

7-Fluoro-3-methyl-9H-carbazole

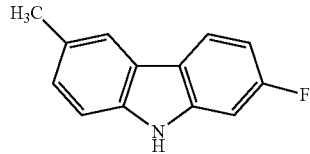

A mixture of 2.0 g (11.7 mmol) of 1-bromo-4-methylbenzene, 1.7 g (11.7 mmol) of 2-chloro-5-fluoroaniline, 5.6 g (58.5 mmol) of sodium tert.-butylate, 131 mg (0.59 mmol) of palladium(II) acetate and 237 mg (0.82 mmol) of tri-tert.-butylphosphonium tetrafluoroborate were taken up in 15 ml of toluene and heated for 3 h in a microwave at 160° C. After cooling, the mixture was acidified to pH 2 with 1M hydrochloric acid, extracted three times with dichloromethane and the combined organic phases were concentrated. The residue was purified by chromatography on silica gel (hexane/ethyl acetate 10:1). 465 mg (20%) of the title compound were thus obtained.

$^1$H-NMR (400 MHz, chloroform-d), δ [ppm]=2.53 (s, 3H), 6.92-6.99 (m, 1H), 7.08 (dd, 1H), 7.20-7.25 (m, 1H), 7.28-7.35 (m, 2H), 7.82 (s, 1H), 7.92-7.98 (m, 1H).

Intermediate 11

7-Fluoro-9H-carbazole-3-carbaldehyde

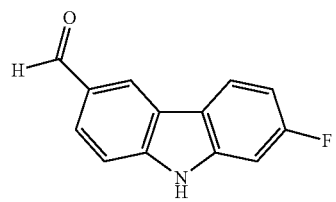 [SMILES: O=Cc1ccc2[nH]c3cc(F)ccc3c2c1]

421 mg (2.11 mmol) of 7-fluoro-3-methyl-9H-carbazole were added to 5.5 ml of methanol/water (10/1), 2.0 g (8.90 mmol) of 2,3-dichloro-5,6-dicyano-1,4-benzoquinone were added thereto and the mixture was stirred at RT for 1.5 h. The reaction mixture was filtered over Celite, the filtrate was concentrated and the residue was purified by chromatography on silica gel (dichloromethane). 263 mg (58%) of the title compound were thus obtained.

$^1$H-NMR (300 MHz, chloroform-d), δ [ppm]=7.03 (td, 1H), 7.12-7.19 (m, 1H), 7.49 (d, 1H), 7.93 (dd, 1H), 8.02 (d, 1H), 8.52 (s, 1H), 9.60 (br. s., 1H), 10.06 (s, 1H).

Intermediate 12

9-Ethyl-7-fluoro-9H-carbazole-3-carbaldehyde

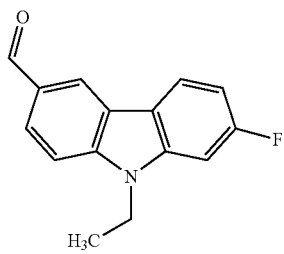 [SMILES: CCn1c2ccc(C=O)cc2c2ccc(F)cc21]

Under argon, 65 mg (1.36 mmol) of sodium hydride (60% strength mineral oil dispersion) were washed twice with 1 ml each of toluene and treated at 0° C. with a solution of 263 mg (1.23 mmol) of 7-fluoro-9H-carbazole-3-carbaldehyde in 4 ml of DMF. 231 mg (1.48 mmol) of iodethane were then added and the mixture was stirred at 50° for 17 h. After cooling, the reaction mixture was treated with 2 ml of water, stirred for 30 min and extracted three times with ethyl acetate. The organic phases were dried using sodium sulphate and concentrated. 300 mg (100%) of the title compound were thus obtained as a crude product.

Intermediate 13

9-Ethyl-5-fluoro-9H-carbazole-3-carbaldehyde

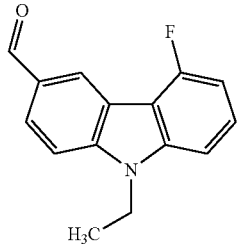 [SMILES: CCn1c2ccc(C=O)cc2c2c(F)cccc21]

Starting from 1-bromo-4-methylbenzene and 2-chloro-3-fluoroaniline, 9-ethyl-5-fluoro-9H-carbazole-3-carbaldehyde, which was employed as a crude product, was obtained over three stages in analogy to the intermediates 10-12.

Intermediate 14

9-Ethyl-8-fluoro-9H-carbazole-3-carbaldehyde

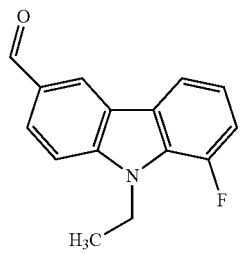 [SMILES: CCn1c2ccc(C=O)cc2c2cccc(F)c21]

Starting from 1-bromo-4-methylbenzene and 2-chloro-6-fluoroaniline, 9-ethyl-8-fluoro-9H-carbazole-3-carbaldehyde, which was employed as a crude product, was obtained over three stages in analogy to the intermediates 10-12.

Intermediate 15

9-(2-Methoxyethyl)-9H-carbazole-3-carbaldehyde

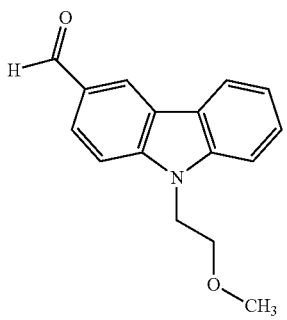 [SMILES: COCCn1c2ccccc2c2cc(C=O)ccc21]

In analogy to Intermediate 12, 9-(2-methoxyethyl)-9H-carbazole-3-carbaldehyde, which was employed without further purification in the next stage, was obtained from 9H-carbazole-3-carbaldehyde and 1-bromo-2-methoxyethane.

$^1$H-NMR (400 MHz, chloroform-d), δ [ppm]=3.30 (s, 3H), 3.81 (t, 2H), 4.53 (t, 2H), 7.31-7.38 (m, 1H), 7.45-7.60 (m, 3H), 8.02 (dd, 1H), 8.16 (d, 1H), 8.62 (d, 1H), 10.11 (s, 1H).

Intermediate 16

9-Ethyl-6-methoxy-9H-carbazole-3-carbaldehyde

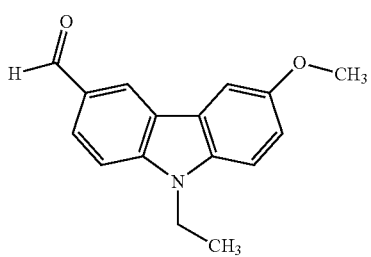 [SMILES: CCn1c2ccc(C=O)cc2c2cc(OC)ccc21]

1.3 g (5.78 mmol) of 6-methoxy-9H-carbazole-3-carbaldehyde were dissolved in 78 ml DMF, then 4.7 g (14.43 mmol) of caesium carbonate and 900 mg (5.78 mmol) of iodethane were added and the mixture was stirred at 65° C. for 1 h. After cooling, the reaction mixture was filtered and the filtrate was concentrated. In this way, 1.3 g (89%) of the title compound were obtained.

$^1$H-NMR (300 MHz, DMSO-d6), δ [ppm]=1.32 (t, 3H), 3.88 (s, 3H), 4.47 (q, 2H), 7.16 (dd, 1H), 7.62 (d, 1H), 7.73 (d, 1H), 7.93-7.98 (m, 2H), 8.76 (d, 1H), 10.03 (s, 1H).

Intermediate 17

9-Allyl-9H-carbazole-3-carbaldehyde

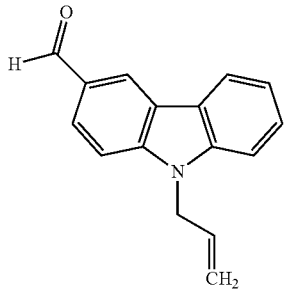 [SMILES: C=CCn1c2ccccc2c2cc(C=O)ccc21]

In analogy to Intermediate 16, 9-allyl-9H-carbazole-3-carbaldehyde was obtained from 9H-carbazole-3-carbaldehyde and allyl bromide.

$^1$H-NMR (300 MHz, DMSO-d6), δ [ppm]=4.97 (dd, 1H), 5.09-5.17 (m, 3H), 5.94-6.09 (m, 1H), 7.28-7.35 (m, 1H), 7.53 (td, 1H), 7.64-7.69 (m, 1H), 7.75 (d, 1H), 7.99 (dd, 1H), 8.31 (d, 1H), 8.78 (d, 1H), 10.07 (s, 1H).

Intermediate 18

2-Chloro-5-ethyl-5H-pyrido[3,2-b]indole

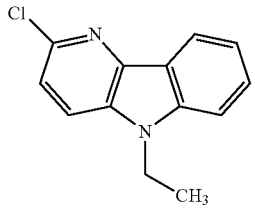 [SMILES: CCn1c2ccccc2c2nc(Cl)ccc21]

2-Chloro-5-ethyl-5H-pyrido[3,2-b]indole was prepared starting from 1-(1-ethyl-1H-indol-3-yl)ethanone analogously to the synthesis described for 2-chloro-5-methyl-5H-pyrido[3,2-b]indole in WO 2004/046143, $^1$H-NMR (400 MHz, DMSO-d6), δ [ppm]=1.30-1.34 (m, 3H), 4.50 (q, 2H), 7.29-7.34 (m, 1H), 7.52 (d, 1H), 7.61 (m, 1H), 7.75 (d, 1H), 8.16-8.21 (m, 2H).

Intermediate 19

Methyl 5-ethyl-5H-pyrido[3,2-b]indole-2-carboxylate

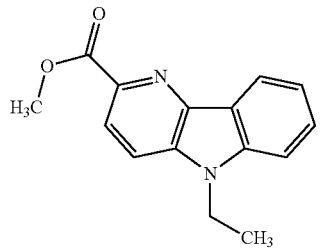 [SMILES: CCn1c2ccccc2c2nc(C(=O)OC)ccc21]

1.5 g (6.5 mmol) of 2-chloro-5-ethyl-5H-pyrido[3,2-b]indole were dissolved in 30 ml of methanol, treated with 1.06 g (1.3 mmol) of bis(triphenylphosphine)palladium(II) chloride and 2.5 g (26.0 mmol) of potassium acetate, and stirred under carbon monoxide, at 12 bar and 100° C., for 23 h in an autoclave. After cooling to RT, the mixture was filtered, the filtrate was concentrated in vacuo and the residue thus obtained was purified by chromatography on silica gel (hexane/ethyl acetate 7:3). 1.0 g (61%) of the title compound was thus obtained.

$^1$H-NMR (300 MHz, DMSO-d6), δ [ppm]=1.35 (t, 3H), 3.94 (s, 3H), 4.53 (q, 2H), 7.37 (t, 1H), 7.66 (m, 1H), 7.76-7.81 (m, 1H), 8.19 (d, 2H), 8.29 (d, 1H).

Intermediate 20

5-Ethyl-5H-pyrido[3,2-b]indole-2-carbaldehyde

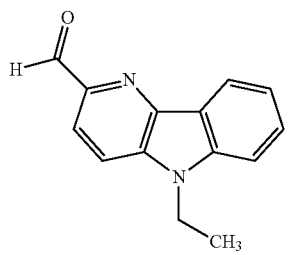 [SMILES: CCn1c2ccccc2c2nc(C=O)ccc21]

200 mg (0.79 mmol) of methyl 5-ethyl-5H-pyrido[3,2-b]indole-2-carboxylate were dissolved in 4.5 ml of toluene under argon, treated at 0° C. with 2.4 ml of diisobutylaluminium hydride solution (1.0 M in toluene), warmed to RT and stirred at RT for 2 h. 1.5 ml of ethanol, 1.5 ml of ethanol/water (1:1) and 1.5 ml of water were then added in succession and the mixture was acidified with 1N sulphuric acid to pH=3. It was then extracted three times with ethyl acetate, and the collected organic phases were dried using sodium sulphate, filtered and concentrated. In this way, 162 mg (77%) of (5-ethyl-5H-pyrido[3,2-b]indol-2-yl)methanol were obtained as a crude product, which was employed in the next synthesis stage without further purification. 100 mg (0.44 mmol) of crude (5-ethyl-5H-pyrido[3,2-b]indol-2-yl)methanol were dissolved in 3.2 ml of dichloromethane, treated at RT with 50 mg (0.23 mmol) of pyridinium chlorochromate and the mixture was stirred at this temperature for 1 h. It was then filtered and the filtrate was concentrated in vacuo. In this way, 54 mg (54%) of the title compound were obtained.

¹H-NMR (400 MHz, DMSO-d6), δ [ppm]=1.36 (t, 3H), 4.56 (d, 2H), 7.69 (t, 1H), 7.75-7.85 (m, 2H), 8.08 (d, 1H), 8.25 (d, 1H), 8.34 (d, 1H), 10.14 (s, 1H).

Intermediate 21

9-Ethyl-9H-pyrido[2,3-b]indole-3-carbonitrile

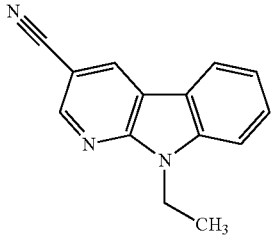 [SMILES: CCn1c2ccccc2c2cc(C#N)cnc21]

5.99 g (18.37 mmol) of caesium carbonate and 1.15 g (7.35 mmol) of iodethane were added to 1.42 g (7.35 mmol) 9H-pyrido[2,3-b]indole-3-carbonitrile in 14 ml of DMF and the mixture was stirred at 65° C. for 1.5 h. After cooling, the mixture was filtered, the filtrate was concentrated and the residue was purified by chromatography on silica gel (hexane/ethyl acetate 7:3). In this way, 261 mg (16%) of the title compound were obtained.

¹H-NMR (400 MHz, chloroform-d), δ [ppm]=1.50 (t, 3H), 4.58 (q, 2H), 7.39 (t, 1H), 7.53-7.57 (m, 1H), 7.60-7.66 (m, 1H), 8.12 (d, 1H), 8.55 (d, 1H), 8.76 (d, 1H).

Intermediate 22

9-Ethyl-9H-pyrido[2,3-b]indole-3-carbaldehyde

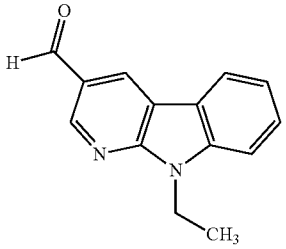 [SMILES: CCn1c2ccccc2c2cc(C=O)cnc21]

1.4 ml (1.70 mmol) of diisobutylaluminium hydride in toluene (25% solution) were added dropwise at 0° C. under argon to a solution of 250 mg (1.13 mmol) of 9-ethyl-9H-pyrido[2,3-b]indole-3-carbonitrile in 15 ml of toluene and stirred for 1 h. The mixture was then added to methanol, acidified with 1M sulphuric acid, then neutralized with saturated sodium hydrogencarbonate solution and extracted three times with ethyl acetate. The organic phases collected were dried with sodium sulphate, filtered and concentrated. In this way, 160 mg (63%) of the title compound were obtained.

¹H-NMR (400 MHz, DMSO-d6), δ [ppm]=1.39 (t, 3H), 4.59 (q, 2H), 7.35-7.41 (m, 1H), 7.59-7.65 (m, 1H), 7.79 (d, 1H), 8.37 (d, 1H), 9.03 (s, 2H), 10.15 (s, 1H).

Intermediate 23

Ethyl 3-amino-4-{[2-(pyrrolidin-1-yl)ethyl]amino}benzoate

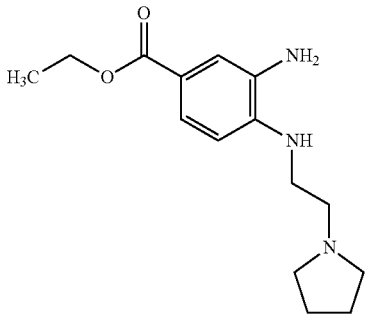 [SMILES: CCOC(=O)c1ccc(NCCN2CCCC2)c(N)c1]

In analogy to Intermediate 2, 1.2 g (88%) of ethyl 3-nitro-4-{[2-(pyrrolidin-1-yl)ethyl]amino}benzoate, which was employed in the next stage without further purification, were first prepared from 1.0 g (4.4 mmol) of ethyl 4-chloro-3-nitrobenzoate and 0.8 g (7.0 mmol) of 2-(pyrrolidine-1-yl)ethanamine.

The crude material of the last stage (1.2 g) was then hydrogenated with hydrogen on palladium analogously to Intermediate 4. The crude material of the title compound thus prepared amounted to 1.14 g (97%) and was employed in the next stage without further purification.

Intermediate 24

Ethyl 3-amino-4-[(cyclopropylmethyl)amino]benzoate

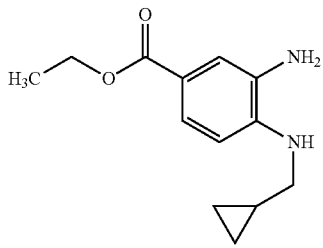 [SMILES: CCOC(=O)c1ccc(NCC2CC2)c(N)c1]

In analogy to the preparation of Intermediate 2, ethyl 4-[(cyclopropylmethyl)amino]-3-nitrobenzoate, which was then reacted with hydrogen on palladium analogously to the preparation of Intermediate 4 to give the title compound, was first prepared from ethyl 4-chloro-3-nitrobenzoate and 1-cyclopropylmethanamine.

Ethyl 4-[(cyclopropylmethyl)amino]-3-nitrobenzoate
¹H-NMR (400 MHz, DMSO-d6): δ [ppm]=0.30-0.36 (m, 2H), 0.50-0.56 (m, 2H), 1.12-1.24 (m, 1H), 1.31 (t, 3H), 3.27-3.32 (m, 2H), 4.29 (q, 2H), 7.17 (d, 1H), 7.97 (dd, 1H), 8.56 (t, 1H), 8.62 (d, 1H).

Ethyl 3-amino-4-[(cyclopropylmethyl)amino]benzoate
¹H-NMR (400 MHz, DMSO-d6): δ [ppm]=0.20-0.27 (m, 2H), 0.46-0.53 (m, 2H), 1.04-1.15 (m, 1H), 1.26 (t, 3H), 2.95-3.01 (m, 2H), 4.18 (q, 2H), 4.77 (s, 2H), 5.26 (t, 1H), 6.43 (d, 1H), 7.15-7.22 (m, 2H).

Intermediate 25

4-Bromo-N1-(2-methoxyethyl)benzene-1,2-diamine

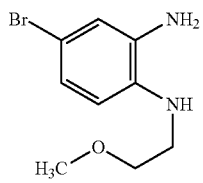

In analogy to the preparation of Intermediate 2, 4-bromo-N-(2-methoxyethyl)-2-nitroaniline, which was then reacted with hydrogen on Raney nickel analogously to the preparation of Intermediate 4 to give the title compound, was first prepared from 4-bromo-1-fluoro-2-nitrobenzene and 2-methoxy ethanamine.

$^1$H-NMR (400 MHz, DMSO-d6): δ [ppm]=3.26-3.33 (m, 5H), 3.48-3.54 (m, 2H), 3.55-3.61 (m, 2H), 7.10 (d, 1H), 7.66 (dd, 1H), 8.16 (d, 1H), 8.20 (br. s., 1H).

Intermediate 26

3-[5-Bromo-1-(2-methoxyethyl)-1H-benzimidazol-2-yl]-9-ethyl-9H-carbazole

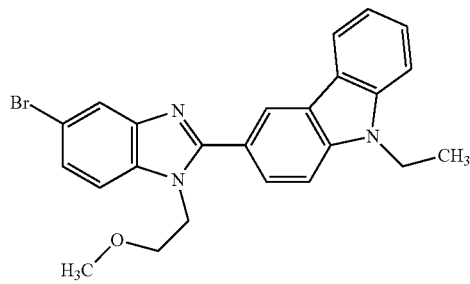 [SMILES: CCn1c2ccccc2c2cc(-c3nc4cc(Br)ccc4n3CCOC)ccc21]

In analogy to the preparation von Intermediate 8, 1.1 g (68%) of the title compound was obtained from 0.87 g (3.5 mmol) of 4-bromo-N1-(2-methoxyethyl)benzene-1,2-diamine and 0.53 g (2.4 mmol) of 9-ethyl-9H-carbazole-3-carbaldehyde.

$^1$H-NMR (300 MHz, DMSO-d6), δ [ppm]=1.37 (t, 3H), 3.14 (s, 3H), 3.71 (t, 2H), 4.47-4.59 (m, 4H), 7.27 (t, 1H), 7.42 (dd, 1H), 7.48-7.57 (m, 1H), 7.66-7.72 (m, 2H), 7.79 (d, 1H), 7.86-7.96 (m, 2H), 8.26 (d, 1H), 8.66 (d, 1H).

Intermediate 27

Ethyl 3-amino-4-{[2-(morpholin-4-yl)ethyl]amino}benzoate

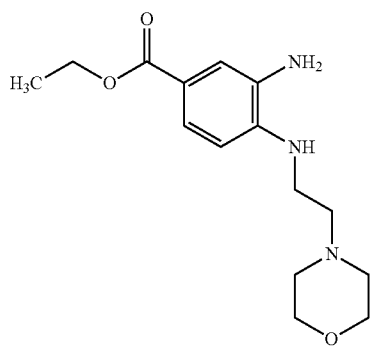 [SMILES: CCOC(=O)c1ccc(NCCN2CCOCC2)c(N)c1]

In analogy to Intermediate 2, 1.27 g (90%) of ethyl 3-amino-4-{[2-(morpholin-4-yl)ethyl]amino}benzoate, which was employed without further purification in the next stage, were first prepared from 1.0 g (4.4 mmol) of ethyl 4-chloro-3-nitrobenzoate and 0.91 g (7.0 mmol) 2-(morpholin-4-yl)ethanamine.

The crude material of the last stage (1.27 g) was then hydrogenated with hydrogen on palladium analogously to Intermediate 4. The crude material of the title compound thus prepared amounted to 1.19 g (90%) and was employed without further purification in the next stage.

Intermediate 28

Ethyl 3-amino-4-(isopropylamino)benzoate

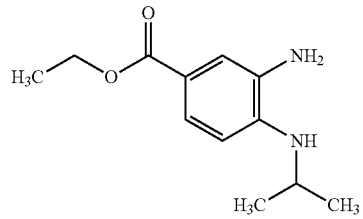 [SMILES: CCOC(=O)c1ccc(NC(C)C)c(N)c1]

In analogy to the preparation of Intermediate 2, ethyl 4-(isopropylamino)-3-nitrobenzoate, which was then reacted with hydrogen on palladium analogously to the preparation of Intermediate 4 to give the title compound, was first prepared from ethyl 4-chloro-3-nitrobenzoate and propan-2-amine.

$^1$H-NMR (400 MHz, DMSO-d6): δ [ppm]=1.18 (d, 6H), 1.26 (t, 3H), 3.65 (s, 1H), 4.18 (q, 2H), 4.80-5.30 (br., 3H), 6.46 (d, 1H), 7.17-7.25 (m, 2H).

Intermediate 29

Ethyl 3-amino-4-[(2-methoxyethyl)amino]benzoate

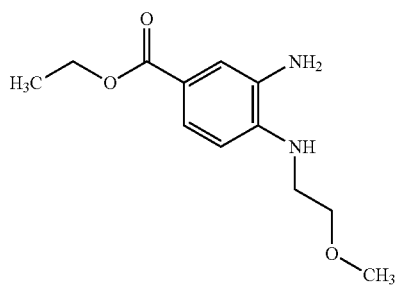 [SMILES: CCOC(=O)c1ccc(NCCOC)c(N)c1]

Ethyl 3-amino-4-[(2-methoxyethyl)amino]benzoate was prepared from ethyl 4-[(2-methoxyethyl)amino]-3-nitrobenzoate by reduction with hydrogen on palladium analogously to Intermediate 4.

$^1$H-NMR (400 MHz, DMSO-d6), δ [ppm]=1.25 (t, 3H), 3.25-3.31 (m, 5H), 3.42-3.47 (m, 2H), 4.13-4.20 (m, 2H), 6.02 (br. s., 1H), 6.17 (d, 1H), 6.71 (d, 1H), 7.18 (dd, 1H), NH2 not specified.

Intermediate 30

Ethyl 3-amino-4-[(3-methoxypropyl)amino]benzoate

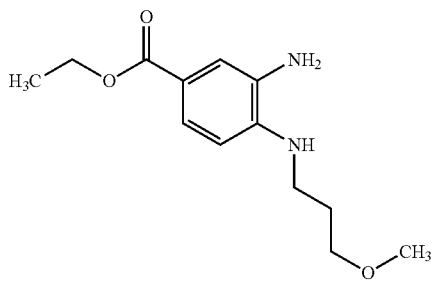 [SMILES: CCOC(=O)c1ccc(NCCCOC)c(N)c1]

In analogy to Intermediate 2, 1.20 g (88%) of ethyl 4-[(3-methoxypropyl)amino]-3-nitrobenzoate, which was then hydrogenated with hydrogen on palladium analogously to Intermediate 4, were first prepared from 1.0 g (4.4 mmol) of ethyl 4-chloro-3-nitrobenzoate and 0.62 g (7.0 mmol) of 3-methoxypropan-1-amine. The crude material of the title compound thus prepared amounted to 1.15 g (93%).

Ethyl 4-[(3-methoxypropyl)amino]-3-nitrobenzoate $^1$H-NMR (300 MHz, DMSO-d6): δ [ppm]=1.26-1.38 (m, 3H), 1.88 (quin, 2H), 3.27 (s, 3H), 3.42-3.50 (m, 4H), 4.29 (q, 2H), 7.13 (d, 1H), 7.94-8.01 (m, 1H), 8.62 (d, 1H), 8.70 (t, 1H).

Ethyl 3-amino-4-[(3-methoxypropyl)amino]benzoate $^1$H-NMR (400 MHz, DMSO-d6): δ [ppm]=1.26 (t, 3H), 1.82 (quin, 2H), 3.13-3.18 (m, 2H), 3.25 (s, 3H), 3.43 (t, 2H), 4.19 (q, 2H), 6.45 (d, 1H), 7.20 (d, 1H), 7.24 (dd, 1H), NH and NH2 not specified.

Intermediate 31

3-(5-Bromo-6-methoxy-1H-benzimidazol-2-yl)-9-ethyl-9H-carbazole

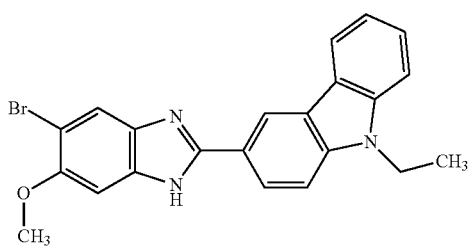 [SMILES: CCn1c2ccccc2c2cc(-c3nc4cc(Br)c(OC)cc4[nH]3)ccc21]

4.81 g (19.5 mmol) of 4-bromo-5-methoxy-2-nitroaniline were dissolved in a mixture of 58 ml of ethanol and 39 ml of water, subsequently treated with 1.2 ml of acetic acid and 5.44 g (97.3 mmol) of iron powder and then heated to reflux for 2 h. After cooling to RT, the mixture was filtered through Celite, washed with ethyl acetate and the filtrate was concentrated to dryness in vacuo. The crude product (4-bromo-5-methoxybenzene-1,2-diamine, 4.92 g) thus obtained was employed without further purification in the next stage.

12.92 g (68.0 mmol) of sodium disulphite were added to 15 ml water, stirred at RT for 5 min and then treated with a solution of 5.06 g (22.7 mmol) of 9-ethyl-9H-carbazole-3-carbaldehyde in 15 ml of THF. 4.92 g (22.7 mmol) of 4-bromo-5-methoxybenzene-1,2-diamine in 15 ml of THF were then added, and the mixture was stirred at RT for 10 min and subsequently heated to reflux for 30 min. After cooling auf RT, the reaction mixture was added to saturated sodium hydrogencarbonate solution and extracted several times with ethyl acetate. The organic phases were concentrated and the residue was purified by chromatography on silica gel. 5.87 g (57%) of the title compound were thus obtained.

$^1$H-NMR (400 MHz, DMSO-d6), δ [ppm]=1.36 (t, 3H), 3.91 (s, 3H), 4.50 (d, 2H), 7.12-7.41 (m, 2H), 7.49-7.54 (m, 1H), 7.64-7.88 (m, 3H), 8.20-8.27 (m, 2H), 8.91 (d, 1H), 12.73-13.00 (br, 1H).

Intermediate 32

3-(5-Bromo-4-fluoro-1H-benzimidazol-2-yl)-9-ethyl-9H-carbazole

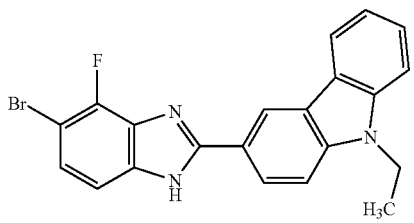 [SMILES: CCn1c2ccccc2c2cc(-c3nc4c(F)c(Br)ccc4[nH]3)ccc21]

In analogy to Example 31, starting from 4-bromo-3-fluoro-2-nitroaniline, first 4-bromo-3-fluorobenzene-1,2-diamine was prepared, which was subsequently reacted with 9-ethyl-9H-carbazole-3-carbaldehyde to give 3-(5-bromo-4-fluoro-1H-benzimidazol-2-yl)-9-ethyl-9H-carbazole.

$^1$H-NMR (400 MHz, DMSO-d6): δ [ppm]=1.36 (t, 3H), 4.51 (q, 2H), 7.26-7.32 (m, 1H), 7.33-7.43 (m, 2H), 7.53 (td, 1H), 7.68 (d, 1H), 7.81 (d, 1H), 8.23-8.34 (m, 2H), 9.01 (s., 1H), 13.31 (br. s., 1H).

Intermediate 33

3-(5-Bromo-6-fluoro-1H-benzimidazole-2-yl)-9-ethyl-9H-carbazole

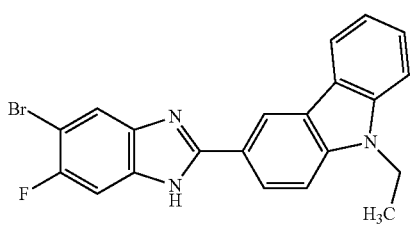 [SMILES: CCn1c2ccccc2c2cc(-c3nc4cc(Br)c(F)cc4[nH]3)ccc21]

In analogy to Example 31, starting from 4-bromo-5-fluoro-2-nitroaniline, first 4-bromo-5-fluorobenzene-1,2-diamine was prepared. This was subsequently reacted with 9-ethyl-9H-carbazole-3-carbaldehyde to give 3-(5-bromo-6-fluoro-1H-benzimidazol-2-yl)-9-ethyl-9H-carbazole and employed directly in further stages.

Intermediate 34

Methyl 3-amino-4-[(2-methoxyethyl)amino]-2-methylbenzoate

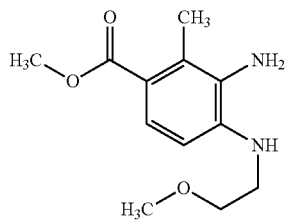

27.5 g (0.12 mol) of a mixture of methyl 4-chloro-2-methyl-5-nitrobenzoate and methyl 4-chloro-2-methyl-3-nitrobenzoate, prepared according to M. Baumgarth et al., J. Med. Chem. 1997, 40, 2017-2034, were added to 50 ml DMSO, treated with 31 ml (0.36 mol) of 2-methoxyethanamine and stirred at 80° C. for 25 h. The mixture was then treated with water, extracted several times with DCM and the collected organic phases were evaporated. The residue was separated by chromatography on silica gel (hexane/DCM 1:0→0:1). In this way, 9.3 g (29%) of methyl 4-[(2-methoxyethyl)amino]-2-methyl-3-nitrobenzoate and 15.5 g (49%) of methyl 4-[(2-methoxyethyl)amino]-2-methyl-5-nitrobenzoate were obtained.

Methyl 4-[(2-methoxyethyl)amino]-2-methyl-3-nitrobenzoate $^1$H-NMR (400 MHz, DMSO-d6), δ [ppm]=2.37 (s, 3H), 3.26 (s, 3H), 3.36 (q, 2H), 3.47 (t, 2H), 3.77 (s, 3H), 6.42 (t, 1H), 6.86 (d, 1H), 7.83 (d, 1H).

Methyl 4-[(2-methoxyethyl)amino]-2-methyl-5-nitrobenzoate $^1$H-NMR (400 MHz, DMSO-d6), δ [ppm]=2.55 (s, 3H), 3.32 (s, 3H), 3.56-3.62 (m, 4H), 3.79 (s, 3H), 6.99 (s, 1H), 8.39-8.44 (m, 1H), 8.64 (s, 1H).

3.33 g (12.4 mmol) of methyl 4-[(2-methoxyethyl)amino]-2-methyl-3-nitrobenzoate were dissolved in 80 ml of THF/methanol (1:1) and hydrogenated under normal pressure on palladium (10% strength on carbon). The catalyst was filtered off and the filtrate was concentrated. 2.85 g (92%) of crude methyl 3-amino-4-[(2-methoxyethyl)amino]-2-methylbenzoate were thus obtained, which was employed in following stages without further purification.

$^1$H-NMR (400 MHz, DMSO-d6), δ [ppm]=2.31 (s, 3H), 3.25-3.31 (m, 5H), 3.53 (t, 2H), 3.70 (s, 3H), 4.44 (br, 2H), 5.20 (t, 1H), 6.37 (d, 1H), 7.18 (d, 1H).

Intermediate 35 and Intermediate 36

6-Chloro-9-ethyl-9H-carbazole-3-carbaldehyde and 8-chloro-9-ethyl-9H-carbazole-3-carbaldehyde

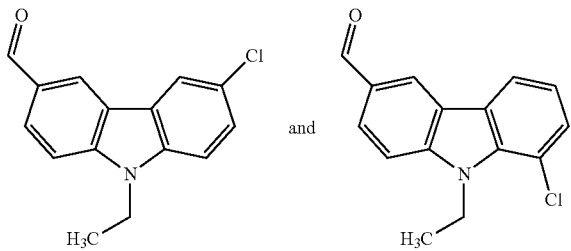 [SMILES: CCn1c2ccc(Cl)cc2c2cc(C=O)ccc21 ; CCn1c2ccc(C=O)cc2c2cccc(Cl)c21]

15.0 g (67.2 mmol) of 9-ethyl-9H-carbazole-3-carbaldehyde and 9.9 g (73.9 mmol) of N-chlorosuccinimide (NCS) were added to 228 ml of acetonitrile and stirred at RT for 24 h. The reaction mixture was then evaporated, and the residue was taken up in 340 ml DCM and subsequently treated with 300 ml of n-hexane. The precipitate was filtered off, the filtrate was evaporated to dryness and the evaporation residue was purified by chromatography on silica gel (hexane/ethyl acetate 8:2->7:3). 11.4 g (66%) of 6-chloro-9-ethyl-9H-carbazole-3-carbaldehyde and 4.8 g (25%) of 8-chloro-9-ethyl-9H-carbazole-3-carbaldehyde were thus obtained.

6-Chloro-9-ethyl-9H-carbazole-3-carbaldehyde $^1$H-NMR (600 MHz, DMSO-d6), δ [ppm]=1.33 (t, 3H), 4.51 (q, 2H), 7.55 (dd, 1H), 7.69-7.87 (m, 2H), 8.02 (dd, 1H), 8.42 (d, 1H), 8.81 (d, 1H), 10.05 (s, 1H).

8-Chloro-9-ethyl-9H-carbazole-3-carbaldehyde $^1$H-NMR (400 MHz, DMSO-d6), δ [ppm]=1.40 (t, 3H), 4.83 (q, 2H), 7.29 (t, 1H), 7.56 (dd, 1H), 7.85 (d, 1H), 8.05 (dd, 1H), 8.31 (dd, 1H), 8.80 (d, 1H), 10.08 (s, 1H).

Example 1

Methyl 1-allyl-2-(9-ethyl-9H-carbazol-3-yl)-1H-benzimidazole-5-carboxylate

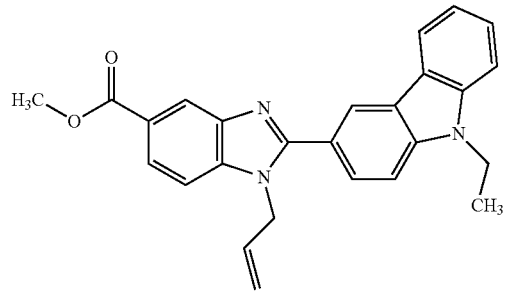 [SMILES: C=CCn1c(-c2ccc3c(c2)c2ccccc2n3CC)nc2cc(C(=O)OC)ccc21]

179 mg (4.45 mmol) of sodium hydride (60% strength mineral oil dispersion) were first added to a solution of 1.5 g (4.1 mmol) of methyl 2-(9-ethyl-9H-carbazol-3-yl)-1H-benzimidazole-5-carboxylate in 50 ml of DMF under argon, subsequently stirred at RT for 30 min and then treated with 0.42 ml (4.87 mmol) of allyl bromide. After 30 h, 50 ml of saturated sodium hydrogencarbonate solution were added and the mixture was extracted several times with dichloromethane. The collected organic phases were washed with water, dried using sodium sulphate and concentrated. The residue was first purified by chromatography on silica gel (hexane/ethyl acetate 7:3) and the crude product (1.46 g) thus obtained was separated by means of preparative HPLC. In this way, 613 mg (37%) of methyl 1-allyl-2-(9-ethyl-9H-carbazol-3-yl)-1H-benzimidazole-5-carboxylate and 457 mg (28%) of methyl 1-allyl-2-(9-ethyl-9H-carbazol-3-yl)-1H-benzimidazole-6-carboxylate were obtained.

Methyl 1-allyl-2-(9-ethyl-9H-carbazol-3-yl)-1H-benzimidazole-5-carboxylate $^1$H-NMR (300 MHz, chloroform-d), δ [ppm]=1.48 (t, 3H), 3.97 (s, 3H), 4.43 (q, 2H), 4.89-4.98 (m, 2H), 5.19 (d, 1H), 5.42 (d, 1H), 6.17 (ddt, 1H), 7.27-7.32 (m, 1H), 7.39 (d, 1H), 7.43-7.57 (m, 3H), 7.88 (dd, 1H), 8.04 (dd, 1H), 8.12 (d, 1H), 8.56 (dd, 2H).

Methyl 1-allyl-2-(9-ethyl-9H-carbazol-3-yl)-1H-benzimidazole-6-carboxylate

¹H-NMR (300 MHz, chloroform-d), δ [ppm]=1.49 (3H), 3.97 (3H), 4.44 (2H), 4.92-5.02 (2H), 5.21 (1H), 5.44 (1H), 6.12-6.29 (1H), 7.28-7.32 (1H), 7.44-7.59 (3H), 7.83-7.95 (2H), 8.05 (1H), 8.13 (2H), 8.58 (1H).

Example 2

1-Allyl-2-(9-ethyl-9H-carbazol-3-yl)-1H-benzimidazole-5-carboxylic acid

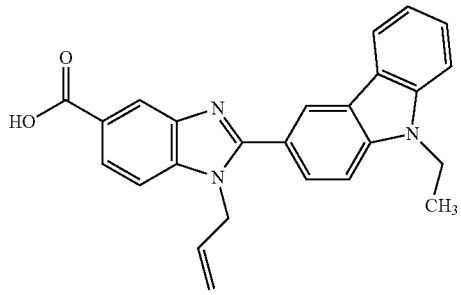 [SMILES: C=CCn1c(-c2ccc3c(c2)c2ccccc2n3CC)nc2cc(C(=O)O)ccc21]

575 mg (1.40 mmol) of methyl 1-allyl-2-(9-ethyl-9H-carbazol-3-yl)-1H-benzimidazole-5-carboxylate were dissolved in a mixture of 7.5 ml of ethanol and 3 ml of dichloromethane, treated with 11.2 ml of 1.0 M sodium hydroxide solution and heated to 80° C. for 20 h. After cooling to RT, the mixture was acidified to pH 2 with 1 M hydrochloric acid, extracted several times with ethyl acetate and the combined organic phases were concentrated to dryness. 389 mg (70%) of the title compound were thus obtained.

¹H-NMR (400 MHz, DMSO-d₆): d [ppm]=1.38 (t, 3H), 4.57 (q, 2H), 5.12-5.42 (m, 3H), 5.35 (d, 1H), 6.13-6.28 (m, 1H), 7.33 (t, 1H), 7.58 (td, 1H), 7.76 (d, 1H), 7.91-7.97 (m, 3H), 8.11 (dd, 1H), 8.26 (d, 1H), 8.35 (d, 1H), 8.74 (s, 1H), 12.60-14.10 (1H).

Example 3

Methyl 2-(9-ethyl-9H-carbazol-3-yl)-1-(2-methoxyethyl)-1H-benzimidazole-5-carboxylate

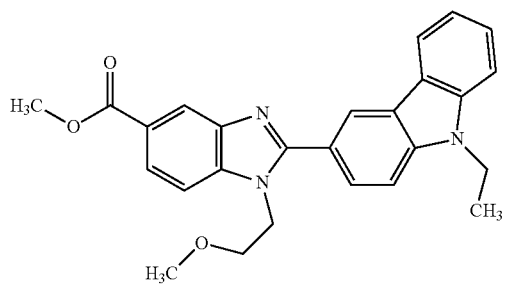 [SMILES: CCn1c2ccccc2c2cc(-c3nc4cc(C(=O)OC)ccc4n3CCOC)ccc21]

In analogy to Example 1, 721 mg (21%) of the title compound and 761 mg (22%) of the isomeric methyl 2-(9-ethyl-9H-carbazol-3-yl)-1-(2-methoxyethyl)-1H-benzimidazole-6-carboxylate were obtained from 3.0 g (8.12 mmol) of methyl 2-(9-ethyl-9H-carbazol-3-yl)-1H-benzimidazole-5-carboxylate and 1.15 ml (12.18 mmol) of 2-bromoethyl methyl ether.

Methyl 2-(9-ethyl-9H-carbazol-3-yl)-1-(2-methoxyethyl)-1H-benzimidazole-5-carboxylate ¹H-NMR (300 MHz, chloroform-d), δ [ppm]=1.50 (t, 3H), 3.33 (s, 3H), 3.84 (t, 2H), 3.98 (s, 3H), 4.45 (q, 2H), 4.53 (t, 2H), 7.29-7.34 (m, 1H), 7.46-7.59 (m, 4H), 7.92 (dd, 1H), 8.06 (dd, 1H), 8.15 (d, 1H), 8.56 (d, 1H), 8.62 (d, 1H).

Methyl 2-(9-ethyl-9H-carbazol-3-yl)-1-(2-methoxyethyl)-1H-benzimidazole-6-carboxylate ¹H-NMR (300 MHz, chloroform-d), δ [ppm]=1.50 (3H), 3.34 (3H), 3.88 (2H), 3.99 (3H), 4.44 (2H), 4.56 (2H), 7.28-7.33 (1H), 7.45-7.58 (3H), 7.85 (1H), 7.97 (1H), 8.04 (1H), 8.14 (1H), 8.24 (1H), 8.67 (1H)

Example 4

2-(9-Ethyl-9H-carbazol-3-yl)-1-(2-methoxyethyl)-1H-benzimidazole-5-carboxylic acid

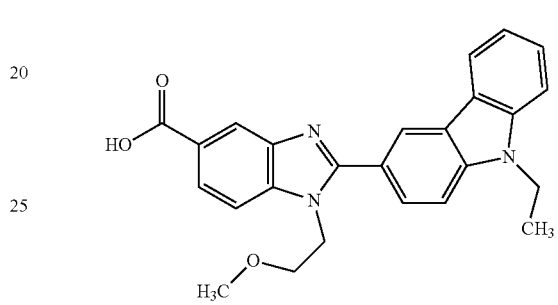

Variant A

In analogy to Example 2, 93 mg (14%) of the title compound were obtained from 685 mg (1.60 mmol) of methyl 2-(9-ethyl-9H-carbazol-3-yl)-1-(2-methoxyethyl)-1H-benzimidazole-5-carboxylate.

¹H-NMR (400 MHz, DMSO-d6), δ [ppm]=1.38 (t, 3H), 3.14 (s, 3H), 3.73 (t, 2H), 4.53 (q, 2H), 4.59 (t, 2H), 7.27 (t, 1H), 7.49-7.56 (m, 1H), 7.69 (d, 1H), 7.79 (t, 2H), 7.88-7.97 (m, 2H), 8.24-8.30 (m, 2H), 8.68 (d, 1H), 12.40-13.00 (1H).

Example 4

Variant B 2-(9-Ethyl-9H-carbazol-3-yl)-1-(2-methoxyethyl)-1H-benzimidazole-5-carboxylic acid

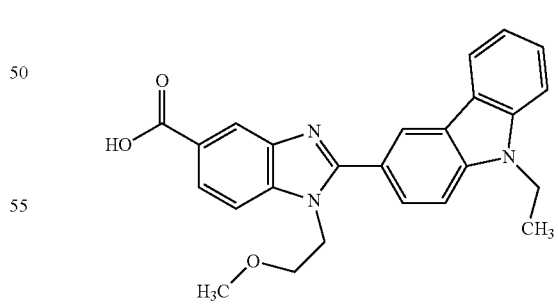

4.78 g (25.19 mmol) of sodium disulphite were added to 11 ml water and then treated with a solution of 2.5 g (11.20 mmol) of 9-ethyl-9H-carbazole-3-carbaldehyde in 25 ml of THF. 3.53 g (16.80 mmol) of 3-amino-4-[(2-methoxyethyl)amino]benzoic acid in 10 ml of THF were then added, and the mixture was stirred at RT for 10 min and subsequently heated to reflux for 2.5 h. After cooling, the reaction mixture was treated with 7.5 ml of water, acidified to pH 2 with 1M hydrochloric acid and extracted three times with dichloromethane. The collected organic phases were washed with water, dried with sodium sulphate and concentrated to dryness. After digestion of the evaporation residue with ethyl acetate, 3.99 g (86%) of the title compound were obtained.

¹H-NMR (400 MHz, DMSO-d6), δ [ppm]=1.38 (t, 3H), 3.14 (s, 3H), 3.73 (t, 2H), 4.53 (q, 2H), 4.59 (t, 2H), 7.27 (t, 1H), 7.49-7.56 (m, 1H), 7.69 (d, 1H), 7.79 (t, 2H), 7.88-7.97 (m, 2H), 8.24-8.30 (m, 2H), 8.68 (d, 1H), 12.40-13.00 (1H).

Example 5

Methyl 1-(cyclopropylmethyl)-2-(9-ethyl-9H-carbazol-3-yl)-1H-benzimidazole-5-carboxylate

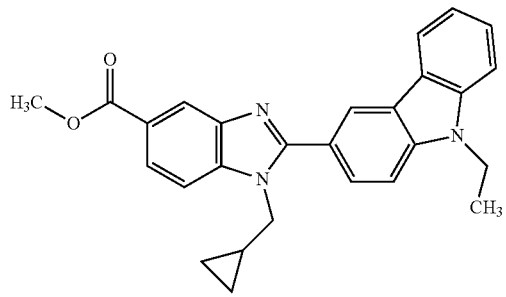 [SMILES: CCn1c2ccccc2c2cc(-c3nc4cc(C(=O)OC)ccc4n3CC3CC3)ccc21]

In analogy to Example 1, 7.04 g (30%) of the title compound and 5.96 g (25%) of the isomeric methyl 1-(cyclopropylmethyl)-2-(9-ethyl-9H-carbazol-3-yl)-1H-benzimidazole-6-carboxylate were obtained from 20.4 g (8.12 mmol) of methyl 2-(9-ethyl-9H-carbazol-3-yl)-1H-benzimidazole-5-carboxylate and 6.5 ml (66.3 mmol) of (bromomethyl)-cyclopropane.

Methyl 1-(cyclopropylmethyl)-2-(9-ethyl-9H-carbazol-3-yl)-1H-benzimidazole-5-carboxylate ¹H-NMR (300 MHz, DMSO-d6), δ [ppm]=0.11-0.21 (m, 2H), 0.31-0.42 (m, 2H), 1.00-1.12 (m, 1H), 1.38 (t, 3H), 3.90 (s, 3H), 4.38 (d, 2H), 4.53 (q, 2H), 7.27 (t, 1H), 7.48-7.59 (m, 1H), 7.69 (d, 1H), 7.77-7.97 (m, 4H), 8.24-8.34 (m, 2H), 8.64 (d, 1H).

Methyl 1-(cyclopropylmethyl)-2-(9-ethyl-9H-carbazol-3-yl)-1H-benzimidazole-6-carboxylate ¹H-NMR (300 MHz, DMSO-d6), δ [ppm]=0.16 (q, 2H), 0.31-0.42 (m, 2H), 0.99-1.13 (m, 1H), 1.38 (t, 3H), 3.91 (s, 3H), 4.45 (d, 2H), 4.53 (q, 2H), 7.27 (t, 1H), 7.53 (t, 1H), 7.69 (d, 1H), 7.75-7.85 (m, 2H), 7.87-7.95 (m, 2H), 8.28-8.37 (m, 2H), 8.66 (d, 1H).

Example 6

1-(Cyclopropylmethyl)-2-(9-ethyl-9H-carbazol-3-yl)-1H-benzimidazole-5-carboxylic acid

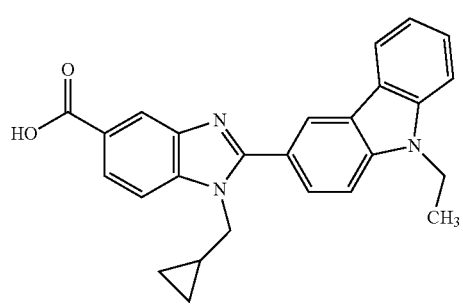 [SMILES: CCn1c2ccccc2c2cc(-c3nc4cc(C(=O)O)ccc4n3CC3CC3)ccc21]

In analogy to Example 4/Variant A, 4.99 g (73%) of the title compound were obtained from 7.04 g (16.62 mmol) of methyl 1-(cyclopropylmethyl)-2-(9-ethyl-9H-carbazol-3-yl)-1H-benzimidazole-5-carboxylate.

¹H-NMR (300 MHz, DMSO-d6), δ [ppm]=0.14-0.22 (m, 2H), 0.33-0.43 (m, 2H), 1.02-1.14 (m, 1H), 1.38 (t, 3H), 4.40 (d, 2H), 4.54 (q, 2H), 7.28 (t, 1H), 7.49-7.58 (m, 1H), 7.70 (d, 1H), 7.80-7.99 (m, 4H), 8.26-8.35 (m, 2H), 8.66 (d, 1H), 12.50-13.20 (1H).

Example 7

Methyl 4-chloro-1-(cyclopropylmethyl)-2-(9-ethyl-9H-carbazol-3-yl)-1H-benzimidazole-5-carboxylate

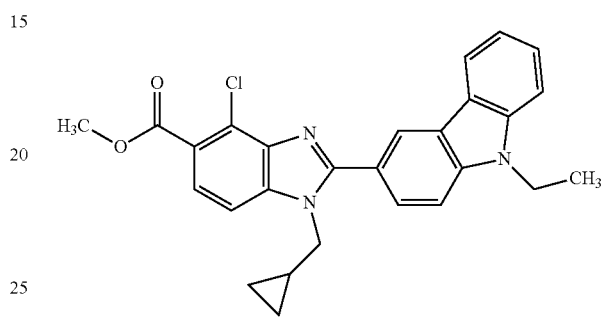

200 mg (0.38 mmol) of (3-[5-bromo-4-chloro-1-(cyclopropylmethyl)-1H-benzimidazole-2-yl]-9-ethyl-9H-carbazole were dissolved in 11 ml of methanol/DMSO (10:1), treated with 108 mg of bis(triphenylphosphine)palladium(II) chloride and 130 µl of triethylamine, and stirred in an autoclave under carbon monoxide, at 12.5 bar and 100° C., for 48 h. Subsequently, the reaction mixture was cooled, concentrated, treated with water and the precipitated solid was filtered off. The residue thus obtained was purified by chromatography on silica gel (hexane/ethyl acetate 7:3). 123 mg (68%) of the title compound were thus obtained.

¹H-NMR (400 MHz, DMSO-d6), δ [ppm]=0.16 (q, 2H), 0.33-0.39 (m, 2H), 0.99-1.10 (m, 1H), 1.38 (t, 3H), 3.91 (s, 3H), 4.39 (d, 2H), 4.54 (q, 2H), 7.27 (t, 1H), 7.51-7.56 (m, 1H), 7.70 (d, 1H), 7.78-7.85 (m, 3H), 7.89-7.93 (m, 1H), 8.32 (d, 1H), 8.65 (d, 1H).

Example 8

4-Chloro-1-(cyclopropylmethyl)-2-(9-ethyl-9H-carbazol-3-yl)-1H-benzimidazole-5-carboxylic acid

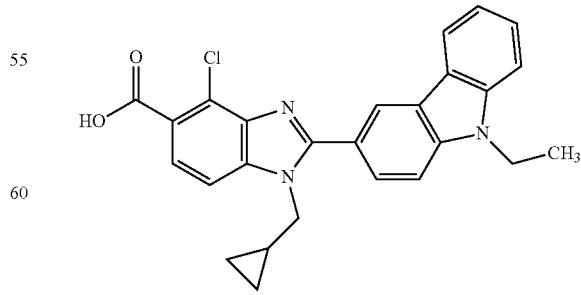

115 mg (0.25 mmol) of methyl 4-chloro-1-(cyclopropylmethyl)-2-(9-ethyl-9H-carbazol-3-yl)-1H-benzimidazole-5- carboxylate were initially introduced in 2.5 ml of methanol, then treated with 0.3 ml of 2M sodium hydroxide solution and heated to reflux for 1.5 h. After cooling, the mixture was acidified to pH 3 with 2M hydrochloric acid and extracted three times with dichloromethane. The organic phase was filtered, concentrated and the crude product thus obtained was purified by means of HPLC. 88 mg (75%) of the title compound were obtained.

$^1$H-NMR (300 MHz, DMSO-d6), δ [ppm]=0.15 (q, 2H), 0.31-0.40 (m, 2H), 0.97-1.11 (m, 1H), 1.38 (t, 3H), 4.38 (d, 2H), 4.54 (q, 2H), 7.27 (t, 1H), 7.53 (t, 1H), 7.70 (d, 1H), 7.76-7.85 (m, 3H), 7.89 (d, 1H), 8.33 (d, 1H), 8.65 (d, 1H), 12.95-13.20 (1H).

Example 9

1-(Cyclopropylmethyl)-2-(9-ethyl-9H-carbazol-3-yl)-4-methyl-1H-benzimidazole-5-carboxylic acid

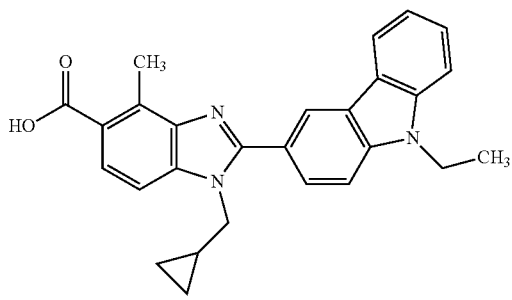

800 mg (3.41 mmol) of methyl 3-amino-4-[(cyclopropylmethyl)amino]-2-methylbenzoate and 381 mg (1.71 mmol) of 9-ethyl-9H-carbazole-3-carbaldehyde were added to 32 ml of glacial acetic acid and heated to reflux for 1 h with supply of air. After cooling, the mixture was concentrated and the crude methyl 1-(cyclopropylmethyl)-2-(9-ethyl-9H-carbazol-3-yl)-4-methyl-1H-benzimidazole-5-carboxylate (1.4 g) thus obtained was employed in the next stage without further purification.

1.4 g (3.2 mmol) of crude methyl 1-(cyclopropylmethyl)-2-(9-ethyl-9H-carbazol-3-yl)-4-methyl-1H-benzimidazole-5-carboxylate were initially introduced in 9 ml of methanol, then treated with 4.3 ml of 2M sodium hydroxide solution and heated to reflux for 5 h. After cooling, the mixture was acidified to pH 3 with acetic acid and the precipitated product was separated off and purified by means of preparative HPLC. 227 mg (17%) of the title compound were obtained.

$^1$H-NMR (400 MHz, DMSO-d6), δ [ppm]=0.10-0.16 (m, 2H), 0.30-0.39 (m, 2H), 1.00-1.08 (m, 1H), 1.38 (t, 3H), 2.89 (s, 3H), 4.32 (d, 2H), 4.53 (q, 2H), 7.26 (t, 1H), 7.48-7.59 (m, 2H), 7.69 (d, 1H), 7.77-7.90 (m, 3H), 8.31 (d, 1H), 8.60 (d, 1H), 12.2-13.10 (1H).

Example 10

2-(9-Ethyl-7-fluoro-9H-carbazol-3-yl)-1-(2-methoxyethyl)-1H-benzimidazole-5-carboxylic acid

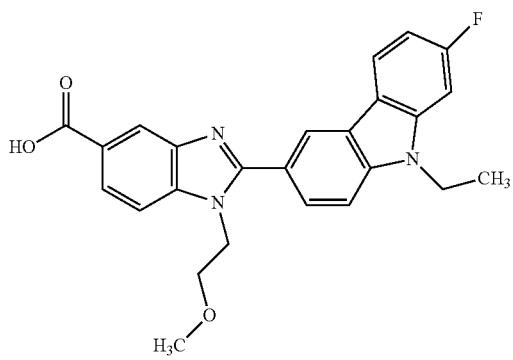 [SMILES: CCn1c2ccc(-c3nc4cc(C(=O)O)ccc4n3CCOC)cc2c2ccc(F)cc21]

177 mg (2.25 mmol) of sodium disulphite were added to 0.5 ml water and then treated with a solution of 100 mg (0.41 mmol) of 9-ethyl-8-fluoro-9H-carbazole-3-carbaldehyde in 1.0 ml of THF. 131 mg (0.62 mmol) of 3-amino-4-[(2-methoxyethyl)amino]benzoic acid in 0.5 ml of THF were then added, and the mixture was stirred at RT for 10 min and subsequently heated to reflux for 1 h. The reaction mixture was treated with 5 ml of water, acidified to pH 2 with 1M hydrochloric acid and the deposited precipitate was filtered off and dried. After purification by means of HPLC, 68 mg (38%) of the title compound were obtained.

$^1$H-NMR (500 MHz, DMSO-d6), δ [ppm]=1.36 (t, 3H), 3.13 (s, 3H), 3.71 (t, 2H), 4.47-4.61 (m, 4H), 7.07-7.12 (m, 1H), 7.60 (dd, 1H), 7.79 (t, 2H), 7.89-7.95 (m, 2H), 8.26-8.31 (m, 2H), 8.66 (d, 1H), 12.65-12.80 (1H).

Example 11

2-(9-Ethyl-5-fluoro-9H-carbazol-3-yl)-1-(2-methoxyethyl)-1H-benzimidazole-5-carboxylic acid

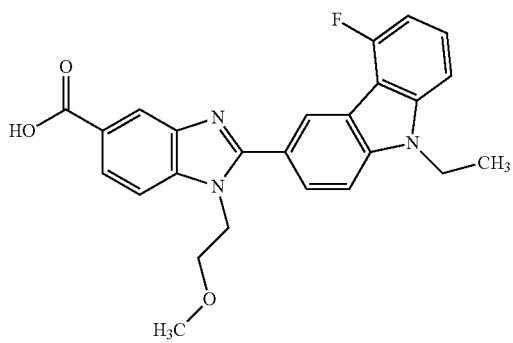 [SMILES: CCn1c2ccc(-c3nc4cc(C(=O)O)ccc4n3CCOC)cc2c2c(F)cccc21]

177 mg (2.25 mmol) of sodium disulphite were added to 0.5 ml water and then treated with a solution of 100 mg (0.41 mmol) of 9-ethyl-5-fluoro-9H-carbazole-3-carbaldehyde in 1.0 ml of THF. 131 mg (0.62 mmol) of 3-amino-4-[(2-methoxyethyl)amino]benzoic acid in 0.5 ml of THF were then added, and the mixture was stirred at RT for 10 min and subsequently heated to reflux for 1 h. The reaction mixture was treated with 5 ml of water, acidified to pH 2 with 1M hydrochloric acid and the deposited precipitate was filtered off and dried. After purification by means of HPLC, 32 mg (18%) of the title compound were obtained.

$^1$H-NMR (500 MHz, DMSO-d6), δ [ppm]=1.38 (t, 3H), 3.18 (s, 3H), 3.78 (t, 2H), 4.53-4.61 (m, 4H), 7.08 (dd, 1H), 7.50-7.58 (m, 2H), 7.78 (d, 1H), 7.85-7.94 (m, 2H), 8.02 (dd, 1H), 8.28 (d, 1H), 8.64 (d, 1H), 12.72 (s, 1H).

Example 12

2-(9-Ethyl-8-fluoro-9H-carbazol-3-yl)-1-(2-methoxyethyl)-1H-benzimidazole-5-carboxylic acid

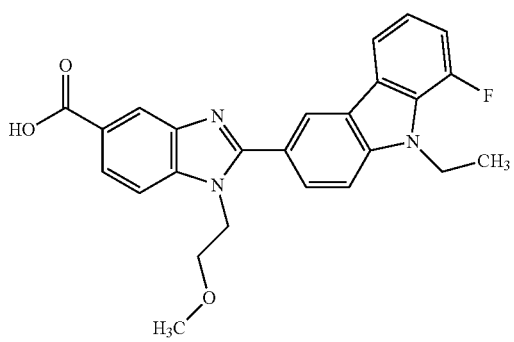 [SMILES: CCn1c2ccc(-c3nc4cc(C(=O)O)ccc4n3CCOC)cc2c2cccc(F)c21]

177 mg (2.25 mmol) of sodium disulphite were added to 0.5 ml of water and then treated with a solution of 100 mg (0.41 mmol) of 9-ethyl-8-fluoro-9H-carbazole-3-carbaldehyde in 1.0 ml of THF. 131 mg (0.62 mmol) 3-amino-4-[(2-methoxyethyl)-amino]benzoic acid in 0.5 ml THF were then added, the mixture was stirred at RT for 10 min and subsequently heated to reflux for 1 h. The reaction mixture was treated with 5 ml of water, acidified to pH 2 with 1M hydrochloric acid and the precipitate deposited was filtered off and dried. After purification by means of HPLC, 51 mg (28%) of the title compound were obtained.

$^1$H-NMR (500 MHz, DMSO-d6), δ [ppm]=1.42 (t, 3H), 3.14 (s, 3H), 3.72 (t, 2H), 4.55-4.66 (m, 4H), 7.21-7.26 (m, 1H), 7.36 (dd, 1H), 7.79 (d, 1H), 7.84-7.94 (m, 2H), 8.00 (dd, 1H), 8.12 (d, 1H), 8.27 (d, 1H), 8.71 (d, 1H), 12.60-12.90 (1H).

Example 13

1-(Cyclopropylmethyl)-2-[9-(2-methoxyethyl)-9H-carbazol-3-yl]-1H-benzimidazole-5-carboxylic acid

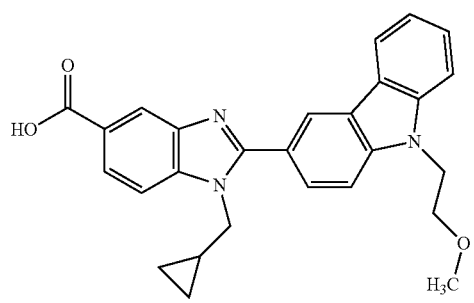 [SMILES: COCCn1c2ccccc2c2cc(-c3nc4cc(C(=O)O)ccc4n3CC3CC3)ccc21]

In analogy to Example 9, 19 mg (19%) of the title compound were obtained from 67 mg (0.27 mmol) of 9-(2-methoxyethyl)-9H-carbazole-3-carbaldehyde and 109 mg (0.53 mmol) of 3-amino-4-[(cyclopropylmethyl)amino]benzoic acid.

$^1$H-NMR (300 MHz, chloroform-d), δ [ppm]=0.17-0.26 (m, 2H), 0.50-0.59 (m, 2H), 1.15-1.30 (m, 1H), 3.34 (s, 3H), 3.85 (t, 2H), 4.28 (d, 2H), 4.57 (t, 2H), 7.28-7.34 (m, 1H), 7.51-7.64 (m, 4H), 7.85 (dd, 1H), 8.11-8.18 (m, 2H), 8.51 (d, 1H), 8.68 (d, 1H), 12.35-12.85 (1H).

Example 14

1-(Cyclopropylmethyl)-2-(9-ethyl-9H-pyrido[2,3-b]indol-3-yl)-1H-benzimidazole-5-carboxylic acid

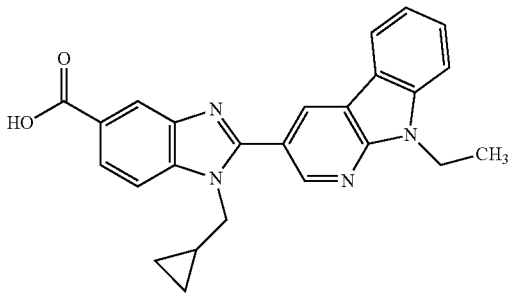

48 mg (0.21 mmol) of 9-ethyl-9H-pyrido[2,3-b]indole-3-carbaldehyde and 88 mg (0.43 mmol) of 3-amino-4-[(cyclopropylmethyl)amino]benzoic acid were added to 4 ml of glacial acetic acid and heated to reflux for 1 h with supply of air. After cooling, the mixture was concentrated and purified by means of preparative HPLC. In this way, 24 mg (25%) of the title compound were obtained.

$^1$H-NMR (300 MHz, DMSO-d6), δ [ppm]=0.18 (q, 2H), 0.34-0.41 (m, 2H), 1.02-1.12 (1H), 1.42 (t, 3H), 4.39 (d, 2H), 4.61 (q, 2H), 7.35 (t, 1H), 7.61 (t, 1H), 7.79 (d, 1H), 7.83-7.88 (m, 1H), 7.94 (dd, 1H), 8.30 (d, 1H), 8.37 (d, 1H), 8.91 (d, 1H), 9.04 (d, 1H), 12.40-12.85 (1H).

Example 15

2-(9-Ethyl-9H-carbazol-3-yl)-1-(2-methoxyethyl)-N-(methylsulphonyl)-1H-benzimidazole-5-carboxamide

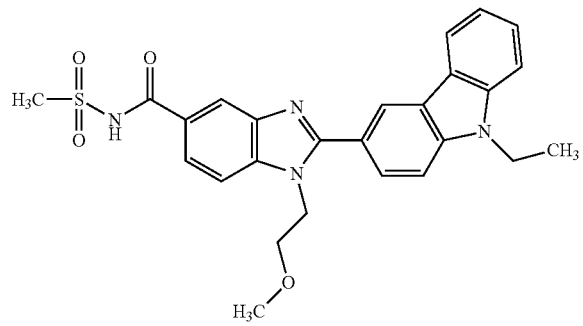 [SMILES: CCn1c2ccccc2c2cc(-c3nc4cc(C(=O)NS(C)(=O)=O)ccc4n3CCOC)ccc21]

100 mg (0.24 mmol) of 2-(9-ethyl-9H-carbazol-3-yl)-1-(2-methoxyethyl)-1H-benzimidazole-5-carboxylic acid were heated to reflux for 2 h in a mixture of 0.11 ml (1.45 mmol) of thionyl chloride and 4 ml of toluene and subsequently concentrated. The residue was taken up in 4 ml of dichloromethane and added dropwise at 0° C. to a mixture of 16 mg (0.36 mmol) of sodium hydride (60% strength mineral oil dispersion) and 104 mg (1.08 mmol) of methanesulphonamide in 2 ml of DMF. After warming to RT, it was cautiously acidified to pH 3 with 1M hydrochloric acid and then extracted with dichloromethane. The organic phase was concentrated and the residue was purified by means of preparative HPLC. In this way, 25 mg (21%) of the title compound were obtained.

$^1$H-NMR (400 MHz, DMSO-d6), δ [ppm]=1.38 (t, 3H), 3.13 (s, 3H), 3.39 (s, 3H), 3.72 (t, 2H), 4.50-4.63 (m, 4H), 7.27 (t, 1H), 7.53 (t, 1H), 7.69 (d, 1H), 7.81 (dd, 2H), 7.88-7.99 (m, 2H), 8.24-8.36 (m, 2H), 8.68 (s, 1H), 12.09 (br. s., 1H).

Example 16

N-(Cyclopropylsulphonyl)-2-(9-ethyl-9H-carbazol-3-yl)-1-(2-methoxyethyl)-1H-benzimidazole-5-carboxamide

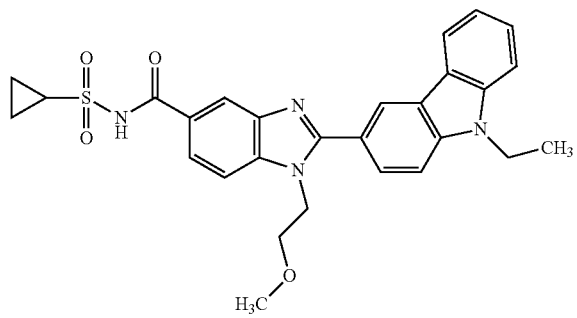 [SMILES: CCn1c2ccccc2c2cc(-c3nc4cc(C(=O)NS(=O)(=O)C5CC5)ccc4n3CCOC)ccc21]

In analogy to Example 15, 200 mg (51%) of the title compound were obtained from 300 mg (0.73 mmol) of 2-(9-ethyl-9H-carbazol-3-yl)-1-(2-methoxyethyl)-1H-benzimidazole-5-carboxylic acid.

$^1$H-NMR (400 MHz, DMSO-d6), δ [ppm]=1.11-1.22 (m, 4H), 1.38 (t, 3H), 3.13 (s, 3H), 3.16-3.23 (m, 1H), 3.72 (t, 2H), 4.54 (q, 2H), 4.60 (t, 2H), 7.27 (t, 1H), 7.50-7.56 (m, 1H), 7.69 (d, 1H), 7.79-7.85 (m, 2H), 7.89-7.97 (m, 2H), 8.28 (d, 1H), 8.33 (d, 1H), 8.69 (d, 1H), 12.03 (br. s., 1H).

Example 17

N-[(3-Chlorophenyl)sulphonyl]-2-(9-ethyl-9H-carbazol-3-yl)-1-(2-methoxyethyl)-1H-benzimidazole-5-carboxamide

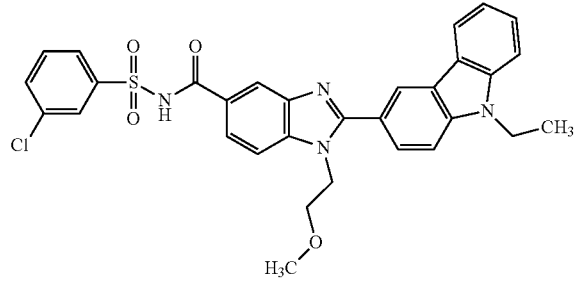 [SMILES: CCn1c2ccccc2c2cc(-c3nc4cc(C(=O)NS(=O)(=O)c5cccc(Cl)c5)ccc4n3CCOC)ccc21]

In analogy to Example 15, 10 mg (9%) of the title compound were obtained from 80 mg (0.19 mmol) of 2-(9-ethyl-9H-carbazol-3-yl)-1-(2-methoxyethyl)-1H-benzimidazole-5-carboxylic acid.

$^1$H-NMR (400 MHz, DMSO-d6), δ [ppm]=1.38 (t, 3H), 3.12 (s, 3H), 3.71 (t, 2H), 4.54 (q, 2H), 4.60 (t, 2H), 7.28 (t, 1H), 7.51-7.56 (m, 1H), 7.66-7.72 (m, 2H), 7.77-7.89 (m, 4H), 7.93-8.02 (m, 3H), 8.26-8.30 (m, 2H), 8.69 (s, 1H), 12.45-13.00 (1H).

Example 18

2-(9-Ethyl-9H-carbazol-3-yl)-N-(ethylsulphonyl)-1-(2-methoxyethyl)-1H-benzimidazole-5-carboxamide

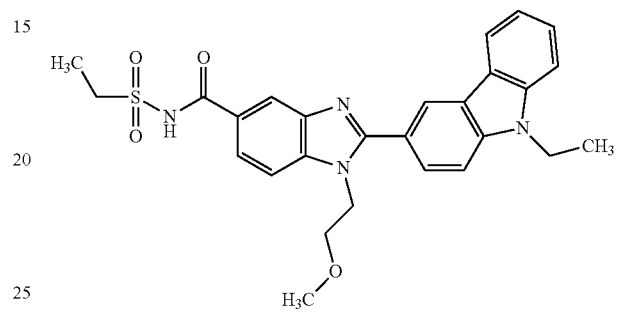

In analogy to Example 15, 45 mg (44%) of the title compound were obtained from 80 mg (0.19 mmol) of 2-(9-ethyl-9H-carbazol-3-yl)-1-(2-methoxyethyl)-1H-benzimidazole-5-carboxylic acid.

$^1$H-NMR (400 MHz, DMSO-d6), δ [ppm]=1.29 (t, 3H), 1.38 (t, 3H), 3.13 (s, 3H), 3.56 (q, 2H), 3.72 (t, 2H), 4.54 (q, 2H), 4.60 (t, 2H), 7.25-7.30 (m, 1H), 7.50-7.56 (m, 1H), 7.69 (d, 1H), 7.79-7.85 (m, 2H), 7.89-7.97 (m, 2H), 8.28 (d, 1H), 8.35 (d, 1H), 8.68 (d, 1H), 11.98 (br. s., 1H).

Example 19

2-(9-Ethyl-9H-carbazol-3-yl)-1-(2-methoxyethyl)-N-[(4-methoxyphenyl)sulphonyl]-1H-benzimidazole-5-carboxamide

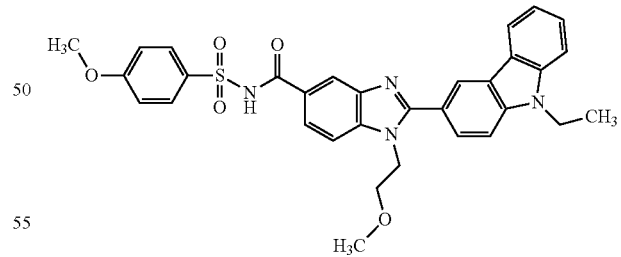

In analogy to Example 15, 45 mg (38%) of the title compound were obtained from 80 mg (0.19 mmol) of 2-(9-ethyl-9H-carbazol-3-yl)-1-(2-methoxyethyl)-1H-benzimidazole-5-carboxylic acid.

$^1$H-NMR (400 MHz, DMSO-d6), δ [ppm]=1.37 (t, 3H), 3.11 (s, 3H), 3.69 (t, 2H), 3.86 (s, 3H), 4.48-4.62 (m, 4H), 7.17 (d, 2H), 7.27 (t, 1H), 7.50-7.55 (m, 1H), 7.69 (d, 1H), 7.76-7.83 (m, 3H), 7.91-8.01 (m, 3H), 8.24-8.29 (m, 2H), 8.67 (d, 1H), 12.33 (br. s., 1H).

Example 20

2-(9-Ethyl-9H-carbazol-3-yl)-1-(2-methoxyethyl)-N-({2-[4-(trifluoromethyl)phenyl]ethyl}-sulphonyl)-1H-benzimidazole-5-carboxamide

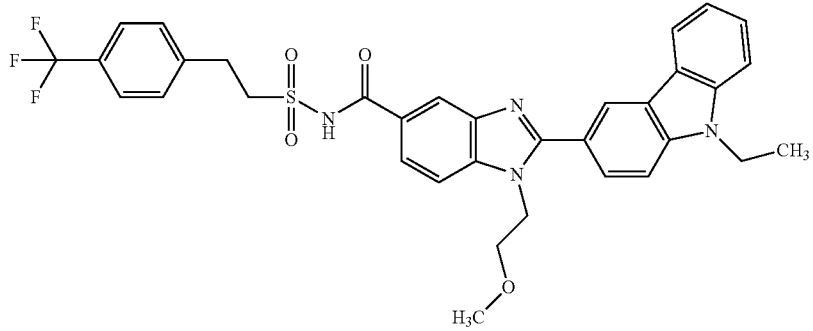 [SMILES: CCn1c2ccccc2c2cc(-c3nc4cc(C(=O)NS(=O)(=O)CCc5ccc(C(F)(F)F)cc5)ccc4n3CCOC)ccc21]

In analogy to Example 15, 70 mg (53%) of the title compound were obtained from 80 mg (0.19 mmol) of 2-(9-ethyl-9H-carbazol-3-yl)-1-(2-methoxyethyl)-1H-benzimidazole-5-carboxylic acid ¹H-NMR (400 MHz, DMSO-d6), δ [ppm]=1.38 (t, 3H), 3.14 (s, 3H), 3.19 (t, 2H), 3.72 (t, 2H), 3.95 (t, 2H), 4.54 (q, 2H), 4.60 (t, 2H), 7.28 (t, 1H), 7.50-7.56 (m, 3H), 7.60-7.64 (m, 2H), 7.70 (d, 1H), 7.78-7.86 (m, 3H), 7.95 (dd, 1H), 8.25-8.31 (m, 2H), 8.69 (d, 1H), 11.90-12.20 (1H).

Example 21

1-(Cyclopropylmethyl)-2-(9-ethyl-9H-carbazol-3-yl)-N-(2-methoxyethyl)-1H-benzimidazole-5-carboxamide 100 mg (0.24 mmol) of 1-(cyclopropylmethyl)-2-(9-ethyl-9H-carbazol-3-yl)-1H-benzimidazole-5-carboxylic acid, 70 mg (0.37 mmol) of 1-(3-dimethylaminopropyl)-3-ethylcarbodiimide hydrochloride (EDCI), 56 mg (0.37 mmol) of 1-hydroxyl-1H-benzotriazole (HOBT hydrate), 221 mg (1.71 mmol) of N,N-diisopropylethylamine and 92 mg (1.22 mmol) of 2-methoxyethanamine in 4.6 ml DMF were added in succession and stirred at RT for 3 h. The reaction mixture was then concentrated, digested with DMSO, filtered and the filtrate was separated by means of preparative HPLC. In this way, 65 mg (56%) of the title compound were obtained.

¹H-NMR (300 MHz, DMSO-d6), δ [ppm]=0.16 (q, 2H), 0.32-0.40 (m, 2H), 1.05 (d, 1H), 1.38 (t, 3H), 3.30 (s, 3H), 3.46-3.52 (m, 4H), 4.36 (d, 2H), 4.53 (q, 2H), 7.27 (t, 1H), 7.49-7.57 (m, 1H), 7.69 (d, 1H), 7.74-7.91 (m, 4H), 8.24 (d, 1H), 8.30 (d, 1H), 8.48-8.55 (m, 1H), 8.62 (d, 1H).

Example 22

[1-(Cyclopropylmethyl)-2-(9-ethyl-9H-carbazol-3-yl)-1H-benzimidazol-5-yl](pyrrolidin-1-yl)methanone

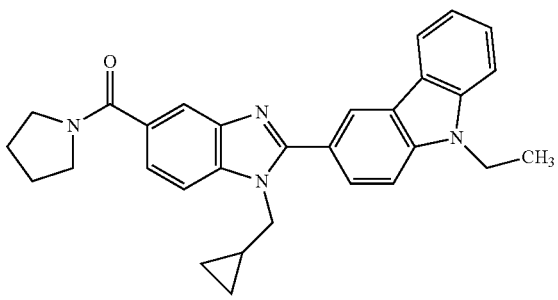 [SMILES: CCn1c2ccccc2c2cc(-c3nc4cc(C(=O)N5CCCC5)ccc4n3CC3CC3)ccc21]

In analogy to Example 21, 50 mg (44%) of the title compound were obtained from 100 mg (0.24 mmol) of 1-(cyclopropylmethyl)-2-(9-ethyl-9H-carbazol-3-yl)-1H-benzimidazole-5-carboxylic acid and 86 mg (1.22 mmol) of pyrrolidine.

¹H-NMR (300 MHz, DMSO-d6), δ [ppm]=0.16 (q, 2H), 0.33-0.42 (m, 2H), 1.01-1.14 (m, 1H), 1.38 (t, 3H), 1.87 (d, 4H), 3.47-3.56 (m, 4H), 4.35 (d, 2H), 4.53 (q, 2H), 7.26 (t, 1H), 7.44-7.56 (m, 2H), 7.66-7.91 (m, 5H), 8.30 (d, 1H), 8.62 (d, 1H).

Example 23

[1-(Cyclopropylmethyl)-2-(9-ethyl-9H-carbazol-3-yl)-1H-benzimidazol-5-yl](3-hydroxyazetidin-1-yl)methanone

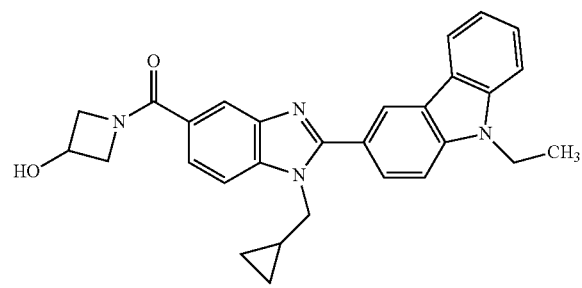 [SMILES: CCn1c2ccccc2c2cc(-c3nc4cc(C(=O)N5CC(O)C5)ccc4n3CC3CC3)ccc21]

In analogy to Example 21, 65 mg (54%) of the title compound were obtained from 100 mg (0.24 mmol) of 1-(cyclopropylmethyl)-2-(9-ethyl-9H-carbazol-3-yl)-1H-benzimidazole-5-carboxylic acid and 40 mg (1.22 mmol) of 3-hydroxyazetidine hydrochloride.

$^1$H-NMR (400 MHz, DMSO-d6), δ [ppm]=0.16-0.22 (m, 2H), 0.36-0.43 (m, 2H), 1.05-1.14 (m, 1H), 1.38 (t, 3H), 3.85 (br. s., 1H), 4.11 (br. s., 1H), 4.30 (br. s., 1H), 4.40 (d, 2H), 4.50-4.60 (m, 4H), 5.55-5.95 (1H), 7.28 (t, 1H), 7.51-7.57 (m, 1H), 7.63-7.73 (m, 2H), 7.82-7.96 (m, 4H), 8.30 (d, 1H), 8.66 (d, 1H).

Example 24

1-(Cyclopropylmethyl)-2-(9-ethyl-9H-carbazol-3-yl)-N-methyl-1H-benzimidazole-5-carboxamide

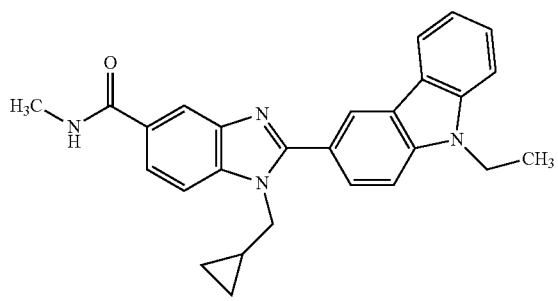 [SMILES: CCn1c2ccccc2c2cc(-c3nc4cc(C(=O)NC)ccc4n3CC3CC3)ccc21]

In analogy to Example 21, 60 mg (58%) of the title compound were obtained from 100 mg (0.24 mmol) of 1-(cyclopropylmethyl)-2-(9-ethyl-9H-carbazol-3-yl)-1H-benzimidazole-5-carboxylic acid and methylamine.

$^1$H-NMR (400 MHz, DMSO-d6), δ [ppm]=0.13-0.18 (m, 2H), 0.33-0.39 (m, 2H), 1.01-1.12 (m, 1H), 1.38 (t, 3H), 2.84 (d, 3H), 4.35 (d, 2H), 4.53 (q, 2H), 7.24-7.29 (m, 1H), 7.53 (td, 1H), 7.69 (d, 1H), 7.75-7.90 (m, 4H), 8.21 (d, 1H), 8.30 (d, 1H), 8.43 (q, 1H), 8.62 (d, 1H).

Example 25

1-(Cyclopropylmethyl)-2-(9-ethyl-9H-carbazol-3-yl)-N,N-dimethyl-1H-benzimidazole-5-carboxamide

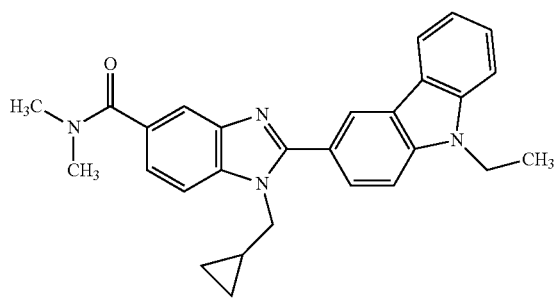 [SMILES: CCn1c2ccccc2c2cc(-c3nc4cc(C(=O)N(C)C)ccc4n3CC3CC3)ccc21]

In analogy to Example 21, 55 mg (51%) of the title compound were obtained from 100 mg (0.24 mmol) of 1-(cyclopropylmethyl)-2-(9-ethyl-9H-carbazol-3-yl)-1H-benzimidazole-5-carboxylic acid and dimethylamine.

$^1$H-NMR (400 MHz, DMSO-d6), δ [ppm]=0.17 (q, 2H), 0.34-0.42 (m, 2H), 1.02-1.14 (m, 1H), 1.38 (t, 3H), 3.02 (s, 6H), 4.35 (d, 2H), 4.53 (q, 2H), 7.26 (t, 1H), 7.34 (dd, 1H), 7.52 (t, 1H), 7.66-7.83 (m, 4H), 7.86-7.90 (m, 1H), 8.30 (d, 1H), 8.62 (d, 1H).

Example 26

1-(Cyclopropylmethyl)-2-(9-ethyl-9H-carbazol-3-yl)-1H-benzimidazole-5-carboxamide

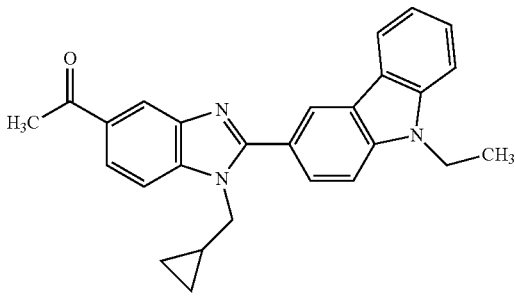 [SMILES: CCn1c2ccccc2c2cc(-c3nc4cc(C(C)=O)ccc4n3CC3CC3)ccc21]

In analogy to Example 21, 70 mg (69%) of the title compound were obtained from 100 mg (0.24 mmol) of 1-(cyclopropylmethyl)-2-(9-ethyl-9H-carbazol-3-yl)-1H-benzimidazole-5-carboxylic acid and 65 mg (1.22 mmol) of ammonium chloride.

$^1$H-NMR (400 MHz, DMSO-d6), δ [ppm]=0.13-0.19 (m, 2H), 0.33-0.40 (m, 2H), 1.00-1.12 (m, 1H), 1.38 (t, 3H), 4.36 (d, 2H), 4.53 (q, 2H), 7.23-7.29 (m, 2H), 7.50-7.55 (m, 1H), 7.69 (d, 1H), 7.74-7.83 (m, 2H), 7.84-7.91 (m, 2H), 7.99 (br. s., 1H), 8.25-8.33 (m, 2H), 8.62 (d, 1H).

Example 27

1-(Cyclopropylmethyl)-2-(9-ethyl-9H-carbazol-3-yl)-N-(2,2,2-trifluoroethyl)-1H-benzimidazole-5-carboxamide

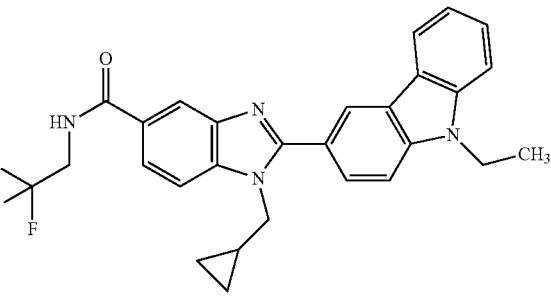

In analogy to Example 21, 100 mg (83%) of the title compound were obtained from 100 mg (0.24 mmol) of 1-(cyclopropylmethyl)-2-(9-ethyl-9H-carbazol-3-yl)-1H-benzimidazole-5-carboxylic acid and 121 mg (1.22 mmol) of 2,2,2-trifluoroethanamine.

$^1$H-NMR (300 MHz, DMSO-d6), δ [ppm]=0.12-0.20 (m, 2H), 0.31-0.40 (m, 2H), 0.99-1.12 (m, 1H), 1.38 (t, 3H), 4.06-4.21 (m, 2H), 4.37 (d, 2H), 4.54 (q, 2H), 7.27 (t, 1H), 7.48-7.57 (m, 1H), 7.69 (d, 1H), 7.78-7.92 (m, 4H), 8.27-8.33 (m, 2H), 8.63 (d, 1H), 9.08 (t, 1H).

Example 28

4-{[1-(Cyclopropylmethyl)-2-(9-ethyl-9H-carbazol-3-yl)-1H-benzimidazol-5-yl]carbonyl}-piperazin-2-one

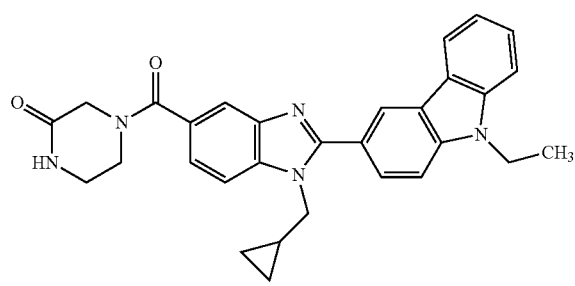 [SMILES: CCn1c2ccccc2c2cc(-c3nc4cc(C(=O)N5CCNC(=O)C5)ccc4n3CC3CC3)ccc21]

In analogy to Example 21, 45 mg (37%) of the title compound were obtained from 100 mg (0.24 mmol) of 1-(cyclopropylmethyl)-2-(9-ethyl-9H-carbazol-3-yl)-1H-benzimidazole-5-carboxylic acid and 122 mg (1.22 mmol) of piperazine-2-one.

$^1$H-NMR (300 MHz, DMSO-d6), δ [ppm]=0.17 (q, 2H), 0.33-0.42 (m, 2H), 1.03-1.13 (m, 1H), 1.38 (t, 3H), 3.20-3.30 (m, 1H), 3.60-3.80 (m, 2H), 4.10 (s, 2H), 4.37 (d, 2H), 4.53 (q, 2H), 7.27 (t, 1H), 7.38 (dd, 1H), 7.53 (t, 1H), 7.69 (d, 1H), 7.76-7.84 (m, 3H), 7.86-7.92 (m, 1H), 8.13 (d, 1H), 8.30 (d, 1H), 8.63 (d, 1H).

Example 29

[1-(Cyclopropylmethyl)-2-(9-ethyl-9H-carbazol-3-yl)-1H-benzimidazol-5-yl](morpholin-4-yl)methanone

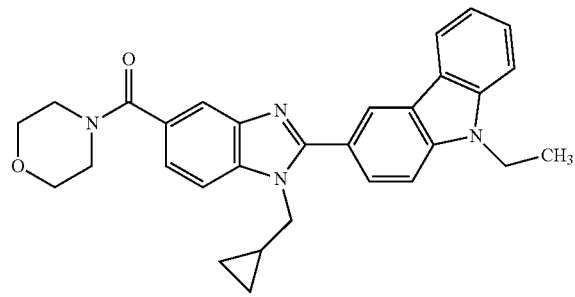 [SMILES: CCn1c2ccccc2c2cc(-c3nc4cc(C(=O)N5CCOCC5)ccc4n3CC3CC3)ccc21]

In analogy to Example 21, 70 mg (60%) of the title compound were obtained from 100 mg (0.24 mmol) of 1-(cyclopropylmethyl)-2-(9-ethyl-9H-carbazol-3-yl)-1H-benzimidazole-5-carboxylic acid and 106 mg (1.22 mmol) of morpholine.

$^1$H-NMR (300 MHz, DMSO-d6), δ [ppm]=0.13-0.20 (m, 2H), 0.33-0.41 (m, 2H), 1.01-1.15 (m, 1H), 1.38 (t, 3H), 3.49-3.71 (m, 8H), 4.36 (d, 2H), 4.53 (q, 2H), 7.27 (t, 1H), 7.35 (dd, 1H), 7.49-7.57 (m, 1H), 7.69 (d, 1H), 7.73 (d, 1H), 7.76-7.83 (m, 2H), 7.85-7.91 (m, 1H), 8.30 (d, 1H), 8.62 (d, 1H).

Example 30

Azetidin-1-yl[2-(9-ethyl-9H-carbazol-3-yl)-1-(2-methoxyethyl)-1H-benzimidazol-5-yl]methanone

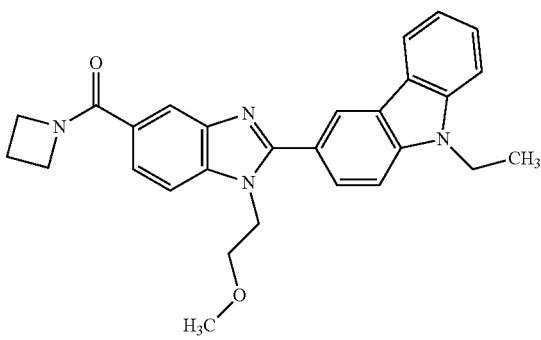 [SMILES: CCn1c2ccccc2c2cc(-c3nc4cc(C(=O)N5CCC5)ccc4n3CCOC)ccc21]

In analogy to Example 21, 33 mg (28%) of the title compound were obtained from 100 mg (0.24 mmol) of 2-(9-ethyl-9H-carbazol-3-yl)-1-(2-methoxyethyl)-1H-benzimidazole-5-carboxylic acid and 69 mg (1.22 mmol) of azetidine.

$^1$H-NMR (300 MHz, DMSO-d6), δ [ppm]=1.37 (t, 3H), 2.29 (2H), 3.15 (s, 3H), 3.73 (t, 2H), 4.09 (br., 2H), 4.40 (br., 2H), 4.48-4.61 (m, 4H), 7.27 (t, 1H), 7.49-7.61 (m, 2H), 7.66-7.83 (m, 3H), 7.90-7.97 (m, 2H), 8.27 (d, 1H), 8.68 (d, 1H).

Example 31

2-(9-Ethyl-9H-carbazol-3-yl)-N,1-bis(2-methoxyethyl)-1H-benzimidazole-5-carboxamide

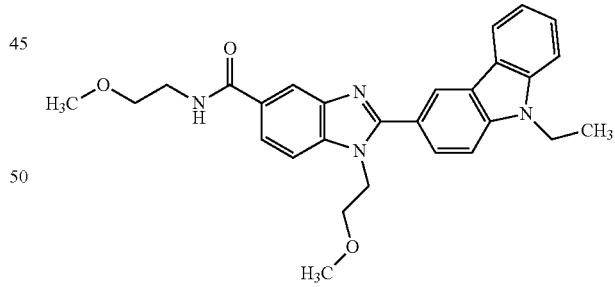

In analogy to Example 21, 33 mg (29%) of the title compound were obtained from 100 mg (0.24 mmol) of 2-(9-ethyl-9H-carbazol-3-yl)-1-(2-methoxyethyl)-1H-benzimidazole-5-carboxylic acid and 91 mg (1.21 mmol) of 2-methoxyethanamine.

$^1$H-NMR (300 MHz, DMSO-d6), δ [ppm]=1.38 (t, 3H), 3.14 (s, 3H), 3.30 (s, 3H), 3.44-3.54 (m, 4H), 3.72 (t, 2H), 4.48-4.61 (m, 4H), 7.27 (t, 1H), 7.49-7.56 (m, 1H), 7.66-7.86 (m, 4H), 7.94 (dd, 1H), 8.21-8.30 (m, 2H), 8.48-8.55 (m, 1H), 8.67 (d, 1H).

Example 32

2-(9-Ethyl-6-methoxy-9H-carbazol-3-yl)-1-(2-methoxyethyl)-1H-benzimidazole-5-carboxylic acid

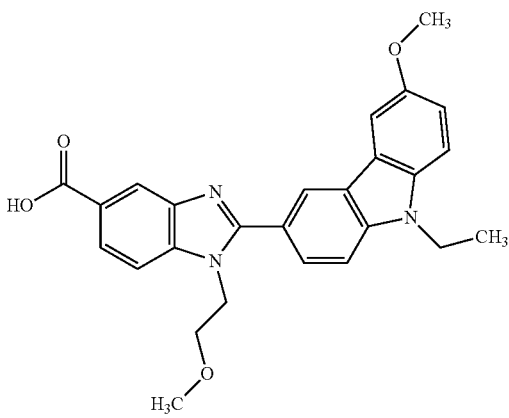 [SMILES: CCn1c2ccc(OC)cc2c2cc(-c3nc4cc(C(=O)O)ccc4n3CCOC)ccc21]

84 mg (0.44 mmol) of sodium disulphite were added to 1 ml water, stirred at RT for 5 min and then treated with a solution of 50 mg (0.20 mmol) of 9-ethyl-6-methoxy-9H-carbazole-3-carbaldehyde in 1 ml of THF. 62 mg (0.30 mmol) of 3-amino-4-[(2-methoxy-ethyl)amino]benzoic acid in 1 ml of THF were then added, and the mixture was stirred at RT for 10 min and subsequently heated to reflux for 1 h. The reaction mixture was added to saturated sodium hydrogencarbonate solution and extracted three times with ethyl acetate. The organic phases were concentrated and the residue was purified by means of HPLC. 20 mg (14%) of the title compound were thus obtained.

$^1$H-NMR (300 MHz, DMSO-d6), δ [ppm]=1.35 (t, 3H), 3.13 (s, 3H), 3.72 (t, 2H), 3.87 (s, 3H), 4.49 (d, 2H), 4.60 (br., 2H), 7.15 (dd, 1H), 7.59 (d, 1H), 7.76 (m, 2H), 7.84-7.97 (m, 3H), 8.26 (s, 1H), 8.67 (s, 1H), 12.00-13.30 (1H).

Example 33

2-(9-Allyl-9H-carbazol-3-yl)-1-(cyclopropylmethyl)-1H-benzimidazole-5-carboxylic acid

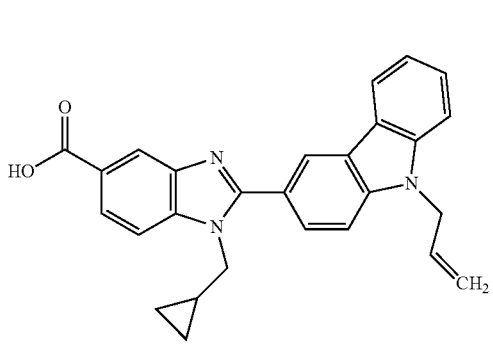 [SMILES: C=CCn1c2ccccc2c2cc(-c3nc4cc(C(=O)O)ccc4n3CC3CC3)ccc21]

In analogy to Example 9, 19 mg (18%) of the title compound were obtained from 57 mg (0.24 mmol) of 9-allyl-9H-carbazole-3-carbaldehyde and 100 mg (0.49 mmol) of 3-amino-4-[(cyclopropylmethyl)amino]benzoic acid.

$^1$H-NMR (300 MHz, chloroform-d), δ [ppm]=0.18-0.27 (m, 2H), 0.50-0.60 (m, 2H), 1.23 (t, 1H), 4.29 (d, 2H), 5.00 (d, 2H), 5.12 (dd, 1H), 5.24 (dd, 1H), 6.06 (ddt, 1H), 7.28-7.35 (m, 1H), 7.43-7.48 (m, 1H), 7.50-7.58 (m, 3H), 7.84 (dd, 1H), 8.12-8.19 (m, 2H), 8.54 (d, 1H), 8.69 (d, 1H), COOH not stated.

Example 34

1-(Cyclopropylmethyl)-2-(9-methyl-9H-carbazol-3-yl)-1H-benzimidazole-5-carboxylic acid

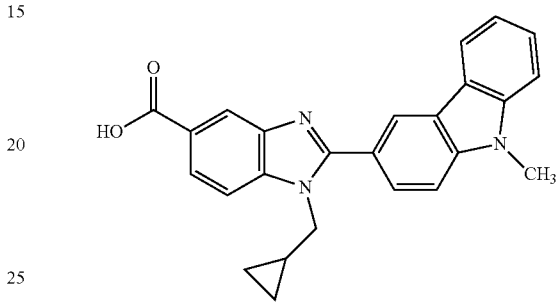

In analogy to Example 32, 55 mg (28%) of the title compound were obtained from 101 mg (0.49 mmol) of 9-methyl-9H-carbazole-3-carbaldehyde and 150 mg (0.73 mmol) of 3-amino-4-[(cyclopropylmethyl)amino]benzoic acid.

$^1$H-NMR (300 MHz, DMSO-d6), δ [ppm]=0.13 (q, 2H), 0.31-0.39 (m, 2H), 0.97-1.12 (m, 1H), 3.97 (s, 3H), 4.37 (d, 2H), 7.27 (t, 1H), 7.51-7.58 (m, 1H), 7.68 (d, 1H), 7.77-7.84 (m, 2H), 7.87-7.94 (m, 2H), 8.25-8.34 (m, 2H), 8.64 (d, 1H), 12.35-13.00 (1H).

Example 35

1-(Cyclopropylmethyl)-2-[9-(cyclopropylmethyl)-9H-carbazol-3-yl]-1H-benzimidazole-5-carboxylic acid

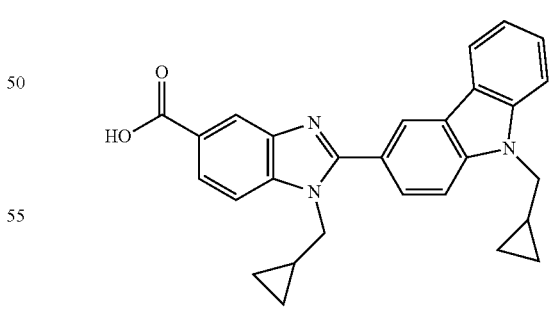

In analogy to Example 9, 14 mg (13%) of the title compound were obtained from 60 mg (0.24 mmol) of 9-(cyclopropylmethyl)-9H-carbazole-3-carbaldehyde and 100 mg (0.49 mmol) of 3-amino-4-[(cyclopropylmethyl) amino]benzoic acid.

$^1$H-NMR (300 MHz, chloroform-d), δ [ppm]=0.19-0.27 (m, 2H), 0.38-0.66 (m, 6H), 1.17-1.30 (m, 1H), 1.31-1.47

(m, 1H), 4.23-4.35 (m, 4H), 7.27-7.34 (m, 1H), 7.40-7.61 (m, 4H), 7.86 (dd, 1H), 8.08-8.19 (m, 2H), 8.53 (d, 1H), 8.70 (s, 1H), COOH not stated.

Example 36

2-[9-(Cyclopropylmethyl)-9H-carbazol-3-yl]-1-(2-methoxyethyl)-1H-benzimidazole-5-carboxylic acid

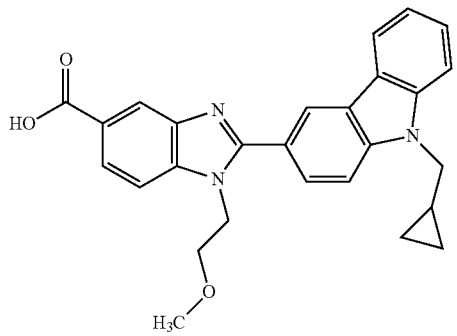 [SMILES: COCCn1c(-c2ccc3c(c2)c2ccccc2n3CC2CC2)nc2cc(C(=O)O)ccc21]

In analogy to Example 9, 6 mg (6%) of the title compound were obtained from 59 mg (0.24 mmol) of 9-(cyclopropylmethyl)-9H-carbazole-3-carbaldehyde and 100 mg (0.48 mmol) of 3-amino-4-[(2-methoxyethyl)amino]benzoic acid.

$^1$H-NMR (300 MHz, chloroform-d), δ [ppm]=0.42-0.49 (m, 2H), 0.56-0.65 (m, 2H), 1.33-1.45 (m, 1H), 3.34 (s, 3H), 3.85 (t, 2H), 4.32 (d, 2H), 4.55 (t, 2H), 7.27-7.34 (m, 3H), 7.47-7.62 (m, 4H), 7.94 (dd, 1H), 8.10-8.19 (m, 1H), 8.61-8.71 (m, 1H), COOH not stated.

Example 37

Ethyl 2-(9-ethyl-9H-carbazol-3-yl)-1-[2-(pyrrolidin-1-yl)ethyl]-1H-benzimidazole-5-carboxylate

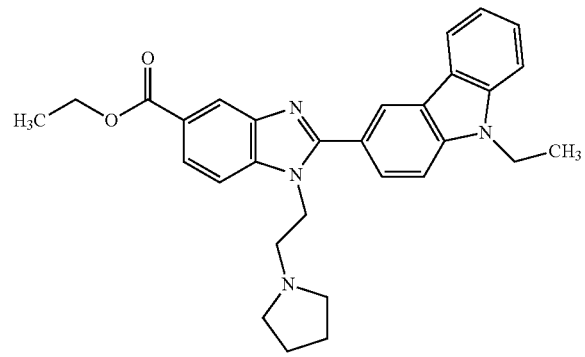 [SMILES: CCOC(=O)c1ccc2c(c1)nc(-c1ccc3c(c1)c1ccccc1n3CC)n2CCN1CCCC1]

In analogy to Example 4/Variant B, 1.6 g (87%) of the title compound were obtained from 569 mg (2.55 mmol) of 9-ethyl-9H-carbazole-3-carbaldehyde and 1.14 g (3.8 mmol) of crude ethyl 3-amino-4-{[2-(pyrrolidin-1-yl)ethyl]amino}benzoate.

$^1$H-NMR (400 MHz, DMSO-d6): δ [ppm]=1.33 (t, 6H), 1.46 (t, 4H), 2.20 (br. s., 4H), 2.75 (t, 2H), 4.32 (q, 2H), 4.47-4.54 (m, 4H), 7.23 (t, 1H), 7.49 (t, 1H), 7.66 (d, 1H), 7.73-7.80 (m, 2H), 7.89 (ddd, 2H), 8.21-8.26 (m, 2H), 8.62 (d, 1H).

Example 38

2-(9-Ethyl-9H-carbazol-3-yl)-1-[2-(pyrrolidin-1-yl)ethyl]-1H-benzimidazole-5-carboxylic acid

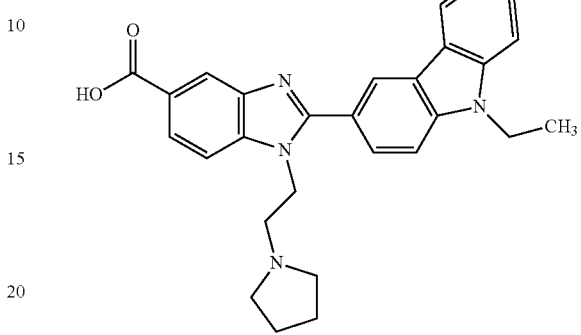

In analogy to Example 2, 0.59 g (42%) of the title compound were obtained from 1.5 g (3.1 mmol) of ethyl 2-(9-ethyl-9H-carbazol-3-yl)-1-[2-(pyrrolidin-1-yl)ethyl]-1H-benzimidazole-5-carboxylate by hydrolysis with sodium hydroxide solution.

$^1$H-NMR (400 MHz, DMSO-d6), δ [ppm]=1.37 (t, 3H), 1.47-1.54 (m, 4H), 2.25 (br., 4H), 2.79 (t, 2H), 4.48-4.58 (m, 4H), 7.27 (t, 1H), 7.49-7.56 (m, 1H), 7.69 (d, 1H), 7.76 (d, 1H), 7.81 (d, 1H), 7.89-7.96 (m, 2H), 8.24-8.30 (m, 2H), 8.66 (d, 1H), 12.20-13.30 (br., 1H).

Example 39

N-(tert-Butylsulphonyl)-2-(9-ethyl-9H-carbazol-3-yl)-1-(2-methoxyethyl)-1H-benzimidazole-5-carboxamide

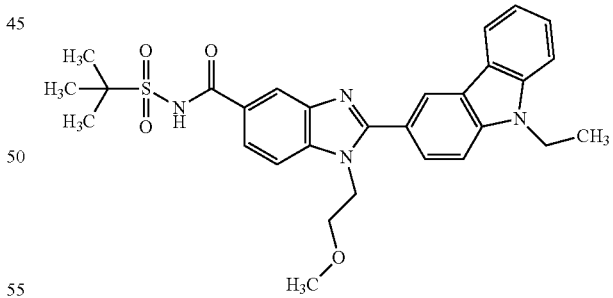

In analogy to Example 21, 72 mg (55%) of the title compound were obtained from 100 mg (0.24 mmol) of 2-(9-ethyl-9H-carbazol-3-yl)-1-(2-methoxyethyl)-1H-benzimidazole-5-carboxylic acid and 149 mg (1.09 mmol) of 2-methylpropane-2-sulphonamide.

$^1$H-NMR (400 MHz, DMSO-d6), δ [ppm]=1.38 (t, 3H), 1.44 (s, 9H), 3.13 (s, 3H), 3.72 (t, 2H), 4.53 (q, 2H), 4.60 (t, 2H), 7.25-7.30 (m, 1H), 7.50-7.56 (m, 1H), 7.69 (d, 1H), 7.78-7.88 (m, 3H), 7.95 (dd, 1H), 8.25-8.31 (m, 2H), 8.68 (d, 1H), 11.52 (br. s., 1H).

Example 40

2-(9-Ethyl-9H-carbazol-3-yl)-1-(2-methoxyethyl)-N-[(1-methylcyclopropyl)sulphonyl]-1H-benzimidazole-5-carboxamide

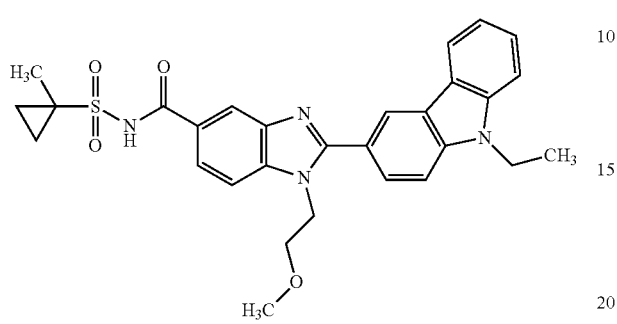

In analogy to Example 21, 46 mg (35%) of the title compound were obtained from 100 mg (0.24 mmol) of 2-(9-ethyl-9H-carbazol-3-yl)-1-(2-methoxyethyl)-1H-benzimidazole-5-carboxylic acid and 147 mg (1.09 mmol) of 1-methylcyclopropane-sulphonamide.

$^1$H-NMR (400 MHz, DMSO-d6), δ [ppm]=0.98-1.03 (m, 2H), 1.38 (t, 3H), 1.50-1.55 (m, 5H), 3.13 (s, 3H), 3.72 (t, 2H), 4.54 (q, 2H), 4.60 (t, 2H), 7.27 (t, 1H), 7.53 (t, 1H), 7.69 (d, 1H), 7.79-7.84 (dd, 2H), 7.88-7.92 (m, 1H), 7.95 (dd, 1H), 8.28 (d, 1H), 8.34 (d, 1H), 8.68 (d, 1H), 11.84 (br. s., 1H).

Example 41

2-(9-Ethyl-9H-carbazol-3-yl)-1-(2-methoxyethyl)-N-methyl-1H-benzimidazole-5-carboxamide

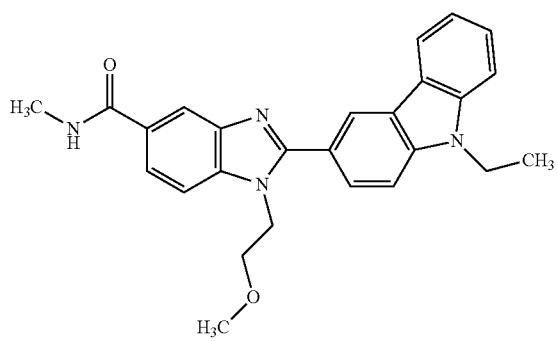 [SMILES: CCn1c2ccccc2c2cc(-c3nc4cc(C(=O)NC)ccc4n3CCOC)ccc21]

In analogy to Example 21, 10 mg (10%) of the title compound were obtained from 100 mg (0.24 mmol) of 2-(9-ethyl-9H-carbazol-3-yl)-1-(2-methoxyethyl)-1H-benzimidazole-5-carboxylic acid and 38 mg (1.3 mmol) of methylamine hydrochloride.

$^1$H-NMR (300 MHz, DMSO-d6), δ [ppm]=1.38 (t, 3H), 2.84 (d, 3H), 3.14 (s, 3H), 3.73 (t, 2H), 4.49-4.60 (m, 4H), 7.27 (t, 1H), 7.49-7.56 (m, 1H), 7.66-7.84 (m, 4H), 7.94 (dd, 1H), 8.20 (d, 1H), 8.27 (d, 1H), 8.43 (d, 1H), 8.67 (d, 1H).

Example 42

2-(5-Ethyl-5H-pyrido[3,2-b]indol-2-yl)-1-(2-methoxyethyl)-1H-benzimidazole-5-carboxylic acid

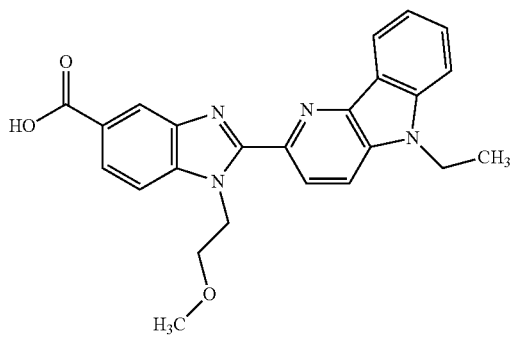 [SMILES: CCn1c2ccccc2c2nc(-c3nc4cc(C(=O)O)ccc4n3CCOC)ccc21]

In analogy to Example 14, 9 mg (9%) title compound were obtained from 50 mg (0.22 mmol) of 5-ethyl-5H-pyrido[3,2-b]indole-2-carbaldehyde and 141 mg (0.67 mmol) of 3-amino-4-[(2-methoxyethyl)amino]benzoic acid.

$^1$H-NMR (300 MHz, DMSO-d6), δ [ppm]=1.39 (t, 3H), 3.21 (s, 3H), 3.99 (t, 2H), 4.57 (q, 2H), 5.19 (t, 2H), 7.39 (t, 1H), 7.62-7.69 (m, 1H), 7.79 (s, 2H), 7.90-7.95 (m, 1H), 8.26-8.33 (m, 3H), 8.51 (d, 1H), 12.65-12.82 (br., 1H).

Example 43

1-(Cyclopropylmethyl)-2-(9-ethyl-6-methoxy-9H-carbazol-3-yl)-1H-benzimidazole-5-carboxylic acid

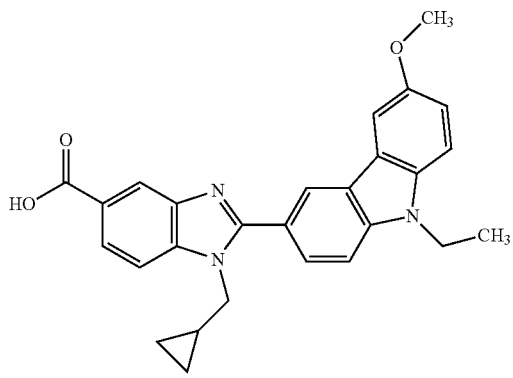 [SMILES: CCn1c2ccc(OC)cc2c2cc(-c3nc4cc(C(=O)O)ccc4n3CC3CC3)ccc21]

67 mg (0.30 mmol) of ethyl-3-amino-4-[(cyclopropylmethyl)amino]benzoate and 38 mg (0.15 mmol) of 9-ethyl-6-methoxy-9H-carbazole-3-carbaldehyde were added in 1.4 ml glacial acetic acid and heated to reflux for 1 h with supply of air. The reaction mixture was then added to saturated sodium chloride solution, and the resulting precipitate was first separated off (40 mg) and then purified by means of preparative HPLC. In this way, 13 mg (9%) of the title compound were obtained.

$^1$H-NMR (300 MHz, DMSO-d6), δ [ppm]=0.15 (q, 2H), 0.30-0.39 (m, 2H), 0.99-1.10 (m, 1H), 1.35 (t, 3H), 3.86 (s, 3H), 4.39 (d, 2H), 4.44-4.55 (m, 2H), 7.15 (dd, 1H), 7.60 (d, 1H), 7.73-7.78 (m, 1H), 7.80-7.94 (m, 4H), 8.27 (s, 1H), 8.64 (s, 1H), 12.77 (br. s., 1H).

Example 44

2-(9-Ethyl-9H-carbazol-3-yl)-1-(2-methoxyethyl)-1H-benzimidazole-5-carbonitrile

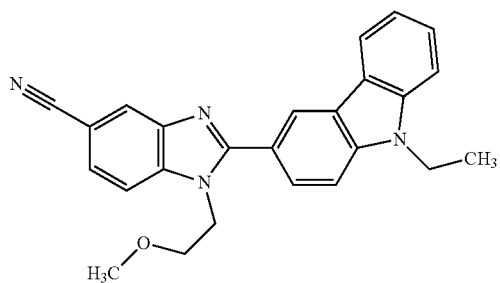 [SMILES: CCn1c2ccccc2c2cc(-c3nc4cc(C#N)ccc4n3CCOC)ccc21]

A mixture of 500 mg (1.1 mmol) of 3-[5-bromo-1-(2-methoxyethyl)-1H-benzimidazol-2-yl]-9-ethyl-9H-carbazole, 124 mg (1.1 mmol) of zinc cyanide and 64 mg (0.06 mmol) of tetrakis(triphenylphosphine)palladium(0) in 10 ml of DMF were stirred under argon for 16 h at 80° C. After cooling, water was added to the reaction mixture and it was extracted with ethyl acetate. The organic phase was washed with saturated sodium chloride solution, concentrated and the residue obtained was chromatographed on silica gel (hexane/ethyl acetate 1:0->2:3). 350 mg (80%) of the title compound were thus obtained.

$^1$H-NMR (300 MHz, DMSO-d6): δ [ppm]=1.37 (t, 3H), 3.13 (s, 3H), 3.71 (t, 2H), 4.53 (d, 2H), 4.62 (t, 2H), 7.27 (t, 1H), 7.49-7.56 (m, 1H), 7.69 (dt, 2H), 7.81 (d, 1H), 7.89-7.98 (m, 2H), 8.21-8.30 (m, 2H), 8.69 (d, 1H).

Example 45

9-Ethyl-3-[1-(2-methoxyethyl)-5-(1H-tetrazol-5-yl)-1H-benzimidazol-2-yl]-9H-carbazole

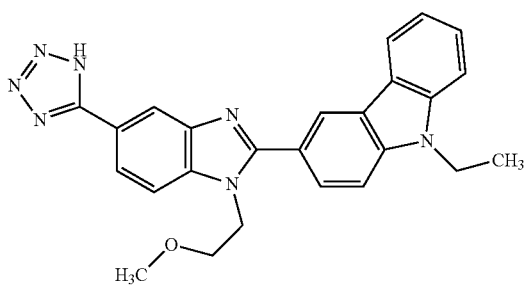 [SMILES: CCn1c2ccccc2c2cc(-c3nc4cc(-c5nnn[nH]5)ccc4n3CCOC)ccc21]

A mixture of 25 mg (0.11 mmol) of 2-(9-ethyl-9H-carbazol-3-yl)-1-(2-methoxyethyl)-1H-benzimidazole-5-carbonitrile, 89 mg (1.4 mmol) of sodium azide and 73 mg (1.4 mmol) of ammonium chloride in 1.5 ml DMF was heated in a microwave to 150° C. for 3 h (maximum irradiation 30 watt). After cooling, the reaction mixture was filtered and the filtrate was purified by means of preparative HPLC. 11 mg (20%) of the title compound were thus obtained.

$^1$H-NMR (300 MHz, DMSO-d6): δ [ppm]=1.37 (t, 3H), 3.15 (s, 3H), 3.75 (t, 2H), 4.48-4.65 (m, 4H), 7.27 (t, 1H), 7.53 (t, 1H), 7.69 (d, 1H), 7.81 (d, 1H), 7.89-8.03 (m, 3H), 8.28 (d, 1H), 8.36 (s, 1H), 8.71 (s, 1H), NH not stated.

Example 46

3-[2-(9-Ethyl-9H-carbazol-3-yl)-1-(2-methoxyethyl)-1H-benzimidazol-5-yl]-1,2,4-oxadiazol-5(4H)-one

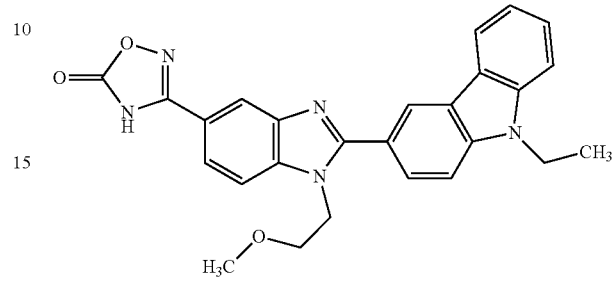

A mixture of 100 mg (0.25 mmol) of 2-(9-ethyl-9H-carbazol-3-yl)-1-(2-methoxyethyl)-1H-benzimidazole-5-carbonitrile, 106 mg (1.52 mmol) of hydroxylammonium chloride and 0.25 ml (1.77 mmol) of triethylamine was heated to reflux in 4 ml ethanol for 2.5 h and then concentrated in vacuo. The residue was subsequently taken up in 10 ml of DMF, 0.03 ml (0.33 mmol) of ethyl chlorocarbonate and 0.09 ml of triethylamine were added and the mixture was heated to 95° C. for 11.5 h. After cooling, it was treated with water and ethyl acetate and the precipitate deposited was filtered off. The organic phase was concentrated and purified by means of preparative HPLC. In this way, 30 mg (24%) of the title compound were obtained.

$^1$H-NMR (300 MHz, DMSO-d6), δ [ppm]=1.37 (t, 3H), 3.14 (s, 3H), 3.73 (t, 2H), 4.48-4.63 (m, 4H), 7.27 (t, 1H), 7.53 (t, 1H), 7.69 (d, 1H), 7.73-7.83 (m, 2H), 7.86-7.90 (m, 1H), 7.96 (dd, 1H), 8.14 (d, 1H), 8.28 (d, 1H), 8.70 (d, 1H), 12.20-13.00 (1H).

Example 47

2-(9-Ethyl-9H-carbazol-3-yl)-1-(2-methoxyethyl)-N-[(3-methylphenyl)sulphonyl]-1H-benzimidazole-5-carboxamide

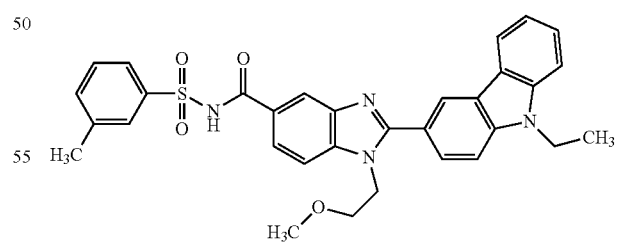

In analogy to Example 15, 80 mg (70%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.37 (t, 3H), 2.43 (s, 3H), 3.11 (s, 3H), 3.69 (t, 2H), 4.49-4.61 (m, 4H), 7.27 (t, 1H), 7.50-7.56 (m, 3H), 7.69 (d, 1H), 7.77-7.86 (m, 5H), 7.94 (dd, 1H), 8.25-8.30 (m, 2H), 8.67 (d, 1H), 12.30-12.55 (br. s., 1H).

Example 48

2-(9-Ethyl-9H-carbazol-3-yl)-1-(2-methoxyethyl)-N-[(4-methylphenyl)sulphonyl]-1H-benzimidazole-5-carboxamide

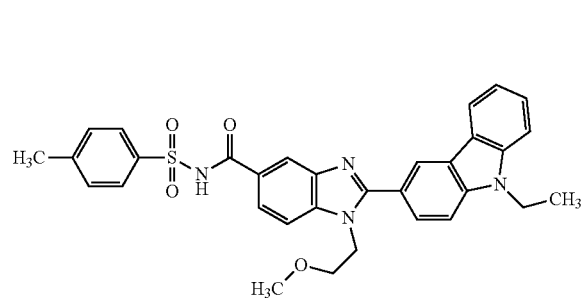 [SMILES: CCn1c2ccccc2c2cc(-c3nc4cc(C(=O)NS(=O)(=O)c5ccc(C)cc5)ccc4n3CCOC)ccc21]

In analogy to Example 15, 60 mg (54%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.37 (t, 3H), 2.41 (s, 3H), 3.11 (s, 3H), 3.69 (t, 2H), 4.49-4.61 (m, 4H), 7.27 (t, 1H), 7.46 (d, 2H), 7.49-7.56 (m, 1H), 7.69 (d, 1H), 7.76-7.83 (m, 3H), 7.90-7.96 (m, 3H), 8.25-8.29 (m, 2H), 8.67 (d, 1H), 12.31-12.52 (br. s., 1H).

Example 49

N-[(4-Chlorophenyl)sulphonyl]-2-(9-ethyl-9H-carbazol-3-yl)-1-(2-methoxyethyl)-1H-benzimidazole-5-carboxamide

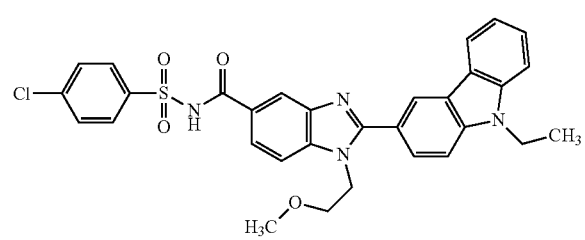 [SMILES: CCn1c2ccccc2c2cc(-c3nc4cc(C(=O)NS(=O)(=O)c5ccc(Cl)cc5)ccc4n3CCOC)ccc21]

In analogy to Example 15, 20 mg (17%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.37 (t, 3H), 3.11 (s, 3H), 3.70 (t, 2H), 4.49-4.63 (m, 4H), 7.27 (t, 1H), 7.50-7.56 (m, 1H), 7.67-7.76 (m, 3H), 7.79-7.86 (m, 3H), 7.94 (dd, 1H), 8.04 (d, 2H), 8.25-8.30 (m, 2H), 8.68 (d, 1H), 12.37-12.90 (br. s., 1H).

Example 50

2-(9-Ethyl-9H-carbazol-3-yl)-1-(2-methoxyethyl)-N-(phenylsulphonyl)-1H-benzimidazole-5-carboxamide

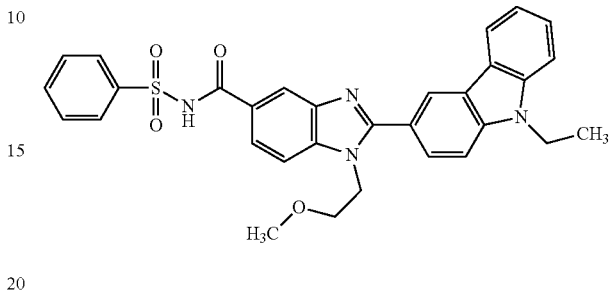

In analogy to Example 15, 40 mg (37%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.37 (t, 3H), 3.11 (s, 3H), 3.69 (t, 2H), 4.49-4.61 (m, 4H), 7.27 (t, 1H), 7.50-7.56 (m, 1H), 7.63-7.76 (m, 4H), 7.77-7.84 (m, 3H), 7.94 (dd, 1H), 8.02-8.07 (m, 2H), 8.25-8.30 (m, 2H), 8.67 (d, 1H), 12.37-12.60 (br. s., 1H).

Example 51

2-(9-Ethyl-9H-carbazol-3-yl)-1-(2-methoxyethyl)-N-(2-naphthylsulphonyl)-1H-benzimidazole-5-carboxamide

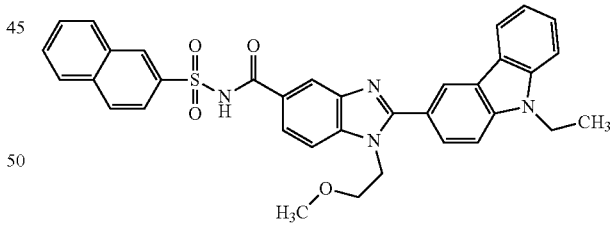

In analogy to Example 15, 50 mg (41%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.37 (t, 3H), 3.10 (s, 3H), 3.69 (t, 2H), 4.49-4.61 (m, 4H), 7.27 (t, 1H), 7.52 (t, 1H), 7.66-7.84 (m, 6H), 7.93 (dd, 1H), 8.02 (dd, 1H), 8.07 (d, 1H), 8.17 (d, 1H), 8.24-8.31 (m, 3H), 8.67 (d, 1H), 8.72 (s, 1H), 12.45-12.77 (br. s., 1H).

Example 52

2-(9-Ethyl-9H-carbazol-3-yl)-1-(2-methoxyethyl)-N-[(2-methoxyphenyl)sulphonyl]-1H-benzimidazole-5-carboxamide

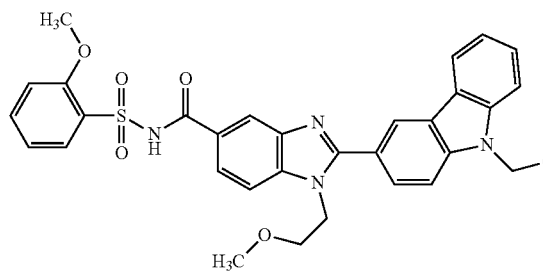

In analogy to Example 15, 60 mg (51%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.12 (s, 3H), 3.70 (t, 2H), 3.88 (s, 3H), 4.49-4.61 (m, 4H), 7.18 (t, 1H), 7.22-7.30 (m, 2H), 7.53 (t, 1H), 7.65-7.71 (m, 2H), 7.76-7.85 (m, 3H), 7.94 (td, 2H), 8.27 (d, 1H), 8.34 (s, 1H), 8.67 (s, 1H), 12.40 (br. s., 1H).

Example 53

2-(9-Ethyl-9H-carbazol-3-yl)-1-(2-methoxyethyl)-N-[(2-methylphenyl)sulphonyl]-1H-benzimidazole-5-carboxamide

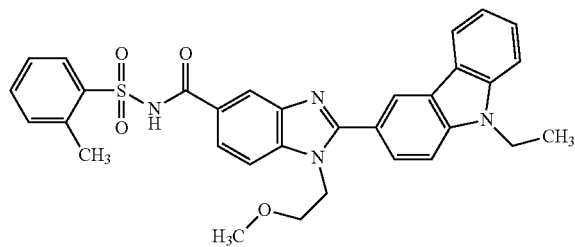 [SMILES: CCn1c2ccccc2c2cc(-c3nc4cc(C(=O)NS(=O)(=O)c5ccccc5C)ccc4n3CCOC)ccc21]

In analogy to Example 15, 32 mg (32%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.37 (t, 3H), 2.66 (s, 3H), 3.12 (s, 3H), 3.70 (t, 2H), 4.49-4.63 (m, 4H), 7.24-7.30 (m, 1H), 7.39-7.63 (m, 4H), 7.69 (d, 1H), 7.77-7.87 (m, 3H), 7.94 (dd, 1H), 8.09 (d, 1H), 8.27 (d, 1H), 8.33 (s, 1H), 8.68 (s, 1H), 12.47-12.81 (br. s., 1H).

Example 54

2-(9-Ethyl-9H-carbazol-3-yl)-1-(2-methoxyethyl)-N-{[2-(trifluoromethoxy)phenyl]-sulphonyl}-1H-benzimidazole-5-carboxamide

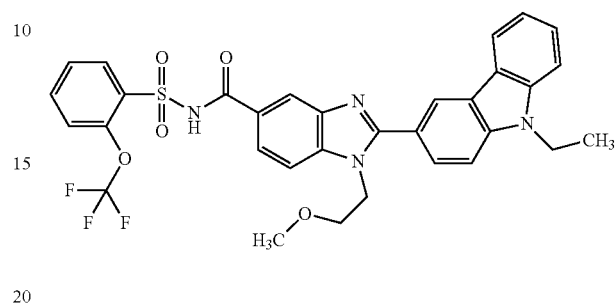

In analogy to Example 15, 15 mg (12%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.13 (s, 3H), 3.72 (t, 2H), 4.50-4.64 (m, 4H), 7.28 (t, 1H), 7.50-7.67 (m, 3H), 7.70 (d, 1H), 7.79-7.91 (m, 4H), 7.96 (d, 1H), 8.17 (d, 1H), 8.27 (d, 1H), 8.34 (s, 1H), 8.70 (s, 1H), 12.73-13.17 (br. s., 1H).

Example 55

N-(Benzylsulphonyl)-2-(9-ethyl-9H-carbazol-3-yl)-1-(2-methoxyethyl)-1H-benzimidazole-5-carboxamide

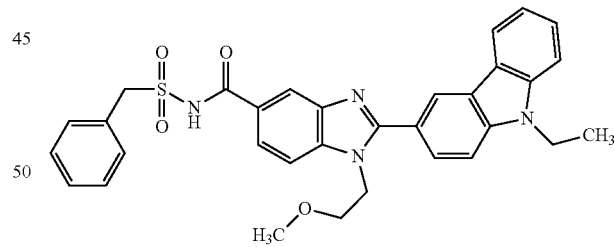

In analogy to Example 15, 50 mg (43%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.14 (s, 3H), 3.72 (t, 2H), 4.50-4.63 (m, 4H), 4.90 (s, 2H), 7.27 (t, 1H), 7.33-7.41 (m, 5H), 7.50-7.56 (m, 1H), 7.69 (d, 1H), 7.82 (dd, 2H), 7.88-7.97 (m, 2H), 8.25-8.31 (m, 2H), 8.68 (d, 1H), 11.89-12.02 (br. s., 1H).

Example 56

N-{[2-(3-Chlorophenyl)ethyl]sulphonyl}-2-(9-ethyl-9H-carbazol-3-yl)-1-(2-methoxyethyl)-1H-benzimidazole-5-carboxamide

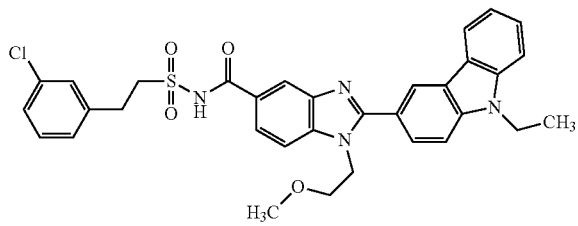 [SMILES: CCn1c2ccccc2c2cc(-c3nc4cc(C(=O)NS(=O)(=O)CCc5cccc(Cl)c5)ccc4n3CCOC)ccc21]

In analogy to Example 15, 25 mg (21%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.08-3.15 (m, 5H), 3.72 (t, 2H), 3.87-3.94 (m, 2H), 4.50-4.64 (m, 4H), 7.22-7.34 (m, 4H), 7.41 (s, 1H), 7.53 (t, 1H), 7.70 (d, 1H), 7.79-7.85 (m, 2H), 7.85-7.90 (m, 1H), 7.95 (dd, 1H), 8.26-8.33 (m, 2H), 8.69 (d, 1H), 11.97-12.18 (br. s., 1H).

Example 57

2-(9-Ethyl-9H-carbazol-3-yl)-1-(2-methoxyethyl)-N-{[2-(2-methylphenyl)ethyl]sulphonyl}-1H-benzimidazole-5-carboxamide

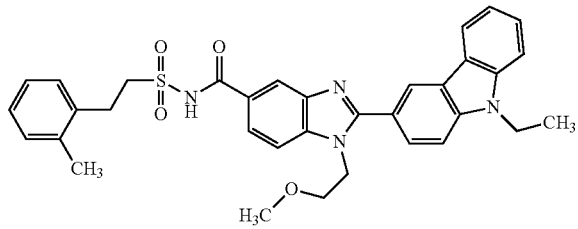 [SMILES: CCn1c2ccccc2c2cc(-c3nc4cc(C(=O)NS(=O)(=O)CCc5ccccc5C)ccc4n3CCOC)ccc21]

In analogy to Example 15, 50 mg (42%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 2.26 (s, 3H), 3.03-3.09 (m, 2H), 3.14 (s, 3H), 3.72 (t, 2H), 3.76-3.82 (m, 2H), 4.54 (q, 2H), 4.61 (t, 2H), 7.10-7.18 (m, 3H), 7.19-7.24 (m, 1H), 7.28 (t, 1H), 7.53 (t, 1H), 7.70 (d, 1H), 7.83 (t, 2H), 7.88-7.92 (m, 1H), 7.95 (dd, 1H), 8.28 (d, 1H), 8.34 (d, 1H), 8.69 (s, 1H), 12.04-12.23 (br. s., 1H).

Example 58

2-(9-Ethyl-9H-carbazol-3-yl)-N-[(4-fluorobenzyl)sulphonyl]-1-(2-methoxyethyl)-1H-benzimidazole-5-carboxamide

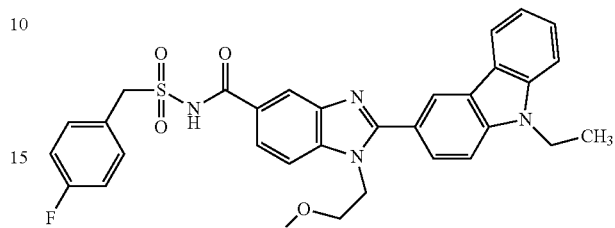

In analogy to Example 15, 60 mg (51%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.14 (s, 3H), 3.72 (t, 2H), 4.53 (q, 2H), 4.60 (t, 2H), 4.91 (s, 2H), 7.19-7.31 (m, 3H), 7.38-7.44 (m, 2H), 7.50-7.56 (m, 1H), 7.69 (d, 1H), 7.82 (dd, 2H), 7.88-7.97 (m, 2H), 8.25-8.31 (m, 2H), 8.68 (d, 1H), 11.89-12.06 (br. s., 1H).

Example 59

2-(9-Ethyl-9H-carbazol-3-yl)-1-(2-methoxyethyl)-N-[(2-methoxyethyl)sulphonyl]-1H-benzimidazole-5-carboxamide

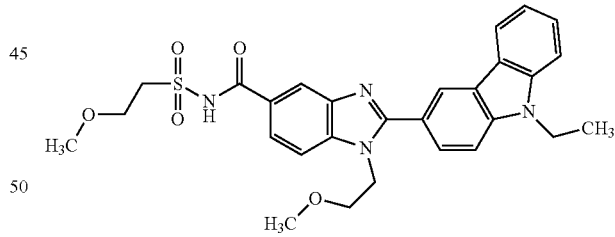

In analogy to Example 15, 70 mg (66%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.14 (s, 3H), 3.22 (s, 3H), 3.72 (t, 2H), 3.75-3.85 (m, 4H), 4.54 (q, 2H), 4.60 (t, 2H), 7.27 (t, 1H), 7.53 (t, 1H), 7.69 (d, 1H), 7.79-7.84 (m, 2H), 7.87-7.91 (m, 1H), 7.95 (dd, 1H), 8.28 (d, 1H), 8.33 (d, 1H), 8.68 (d, 1H), 11.97-12.18 (br. s., 1H).

Example 60

N-[(2,6-Dichlorbenzyl)sulphonyl]-2-(9-ethyl-9H-carbazol-3-yl)-1-(2-methoxyethyl)-1H-benzimidazole-5-carboxamide

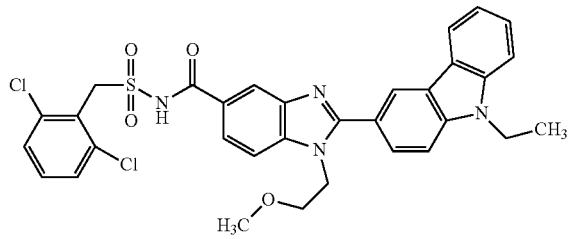 [SMILES: CCn1c2ccccc2c2cc(-c3nc4cc(C(=O)NS(=O)(=O)Cc5c(Cl)cccc5Cl)ccc4n3CCOC)ccc21]

In analogy to Example 15, 40 mg (66%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.15 (s, 3H), 3.73 (t, 2H), 4.50-4.63 (m, 4H), 5.22 (s, 2H), 7.28 (t, 1H), 7.41-7.47 (m, 1H), 7.50-7.59 (m, 3H), 7.70 (d, 1H), 7.79-7.85 (m, 2H), 7.89-7.97 (m, 2H), 8.28 (d, 1H), 8.32 (d, 1H), 8.69 (d, 1H), 12.22-12.43 (br. s., 1H).

Example 61

N-{[2-(2-Chlorophenyl)ethyl]sulphonyl}-2-(9-ethyl-9H-carbazol-3-yl)-1-(2-methoxyethyl)-1H-benzimidazole-5-carboxamide

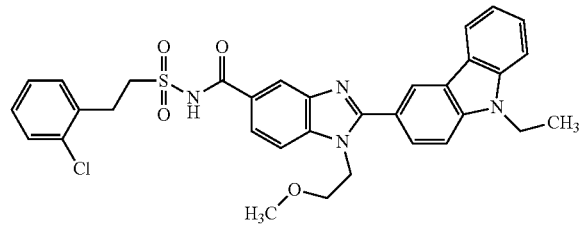 [SMILES: CCn1c2ccccc2c2cc(-c3nc4cc(C(=O)NS(=O)(=O)CCc5ccccc5Cl)ccc4n3CCOC)ccc21]

In analogy to Example 15, 60 mg (48%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.14 (s, 3H), 3.17-3.23 (m, 2H), 3.72 (t, 2H), 3.81-3.88 (m, 2H), 4.54 (q, 2H), 4.61 (t, 2H), 7.23-7.32 (m, 3H), 7.40-7.48 (m, 2H), 7.50-7.56 (m, 1H), 7.69 (d, 1H), 7.79-7.85 (m, 2H), 7.86-7.91 (m, 1H), 7.95 (dd, 1H), 8.28 (d, 1H), 8.32 (d, 1H), 8.69 (d, 1H), 12.08-12.23 (br. s., 1H).

Example 62

2-(9-Ethyl-9H-carbazol-3-yl)-1-(2-methoxyethyl)-N-{[4-(trifluoromethyl)benzyl]sulphonyl}-1H-benzimidazole-5-carboxamide

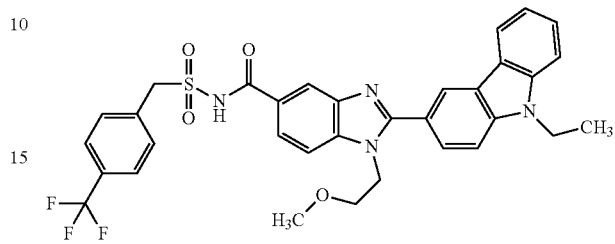

In analogy to Example 15, 40 mg (32%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.14 (s, 3H), 3.72 (t, 2H), 4.54 (q, 2H), 4.61 (t, 2H), 5.05 (s, 2H), 7.28 (t, 1H), 7.53 (t, 1H), 7.60 (d, 2H), 7.70 (d, 1H), 7.76-7.86 (m, 4H), 7.89-7.97 (m, 2H), 8.26-8.31 (m, 2H), 8.68 (d, 1H), 11.93-12.14 (br. s., 1H).

Example 63

2-(9-Ethyl-9H-carbazol-3-yl)-1-(2-methoxyethyl)-N-[(5-methylpyridin-2-yl)sulphonyl]-1H-benzimidazole-5-carboxamide

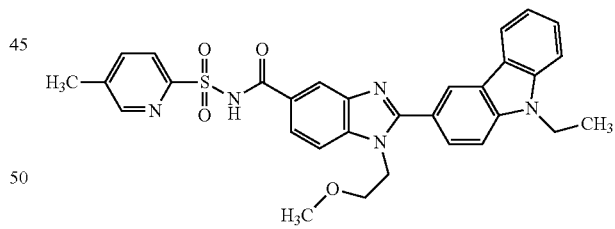

In analogy to Example 15, 32 mg (32%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.37 (t, 3H), 2.42 (s, 3H), 3.12 (s, 3H), 3.70 (t, 2H), 4.48-4.63 (m, 4H), 7.27 (t, 1H), 7.49-7.57 (m, 1H), 7.69 (d, 1H), 7.77-7.86 (m, 3H), 7.91-8.00 (m, 2H), 8.06-8.11 (m, 1H), 8.28 (d, 1H), 8.32 (s, 1H), 8.57 (s, 1H), 8.69 (d, 1H), 12.53-12.92 (br. s., 1H).

Example 64

N-[(4-Chlorobenzyl)sulphonyl]-2-(9-ethyl-9H-carbazol-3-yl)-1-(2-methoxyethyl)-1H-benzimidazole-5-carboxamide

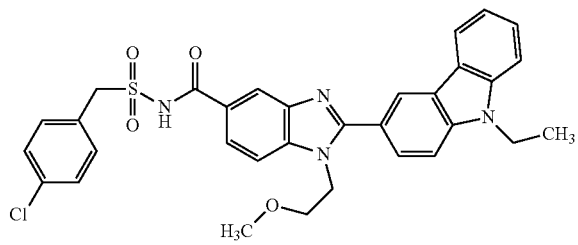 [SMILES: CCn1c2ccccc2c2cc(-c3nc4cc(C(=O)NS(=O)(=O)Cc5ccc(Cl)cc5)ccc4n3CCOC)ccc21]

In analogy to Example 15, 55 mg (52%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.37 (t, 3H), 3.14 (s, 3H), 3.72 (t, 2H), 4.49-4.65 (m, 4H), 4.93 (s, 2H), 7.28 (t, 1H), 7.36-7.41 (m, 2H), 7.44-7.49 (m, 2H), 7.53 (t, 1H), 7.70 (d, 1H), 7.79-7.98 (m, 4H), 8.25-8.31 (m, 2H), 8.69 (d, 1H), 11.87-12.14 (br. s., 1H).

Example 65

2-(9-Ethyl-9H-carbazol-3-yl)-1-(2-methoxyethyl)-N-{[2-(trifluoromethoxy)benzyl]-sulphonyl}-1H-benzimidazole-5-carboxamide

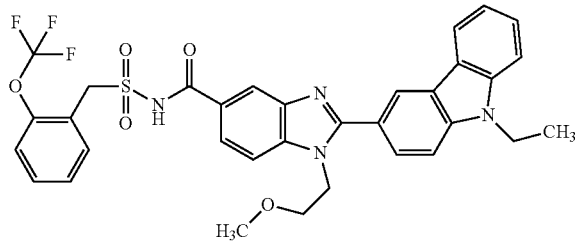 [SMILES: CCn1c2ccccc2c2cc(-c3nc4cc(C(=O)NS(=O)(=O)Cc5ccccc5OC(F)(F)F)ccc4n3CCOC)ccc21]

In analogy to Example 15, 10 mg (9%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.38 (t, 3H), 3.14 (s, 3H), 3.72 (t, 2H), 4.49-4.63 (m, 4H), 5.02 (s, 2H), 7.27 (t, 1H), 7.37-7.47 (m, 2H), 7.49-7.57 (m, 2H), 7.58-7.63 (m, 1H), 7.70 (d, 1H), 7.79-7.86 (m, 2H), 7.88-7.98 (m, 2H), 8.25-8.31 (m, 2H), 8.68 (s, 1H), 12.04-12.20 (br. s., 1H).

Example 66

N-[(2,2-Dimethylpropyl)sulphonyl]-2-(9-ethyl-9H-carbazol-3-yl)-1-(2-methoxyethyl)-1H-benzimidazole-5-carboxamide

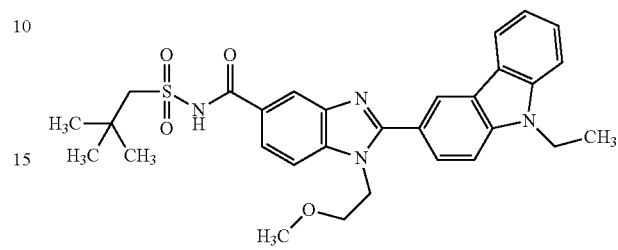

In analogy to Example 15, 30 mg (22%) of the title compound were obtained from 100 mg (0.24 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.15 (s, 9H), 1.37 (t, 3H), 3.12-3.14 (m, 3H), 3.57 (s, 2H), 3.72 (t, 2H), 4.54 (q, 2H), 4.60 (t, 2H), 7.25-7.30 (m, 1H), 7.53 (td, 1H), 7.70 (d, 1H), 7.80-7.86 (m, 2H), 7.89-7.92 (m, 1H), 7.95 (dd, 1H), 8.28 (d, 1H), 8.34 (d, 1H), 8.69 (d, 1H), 12.05 (br. s., 1H).

Example 67

N-[(2-Chloro-6-methylbenzyl)sulphonyl]-2-(9-ethyl-9H-carbazol-3-yl)-1-(2-methoxy-ethyl)-1H-benzimidazole-5-carboxamide

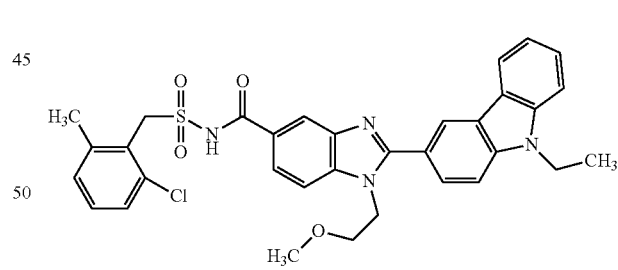

In analogy to Example 15, 20 mg (18%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.38 (t, 3H), 2.53 (s, 3H), 3.15 (s, 3H), 3.73 (t, 2H), 4.49-4.65 (m, 4H), 5.16 (s, 2H), 7.24-7.39 (m, 4H), 7.53 (t, 1H), 7.70 (d, 1H), 7.79-7.88 (m, 2H), 7.91-7.99 (m, 2H), 8.28 (d, 1H), 8.35 (s, 1H), 8.70 (s, 1H), 12.22-12.43 (br. s., 1H).

Example 68

2-(9-Ethyl-9H-carbazol-3-yl)-1-(2-methoxyethyl)-N-{[(3-methylpyridin-2-yl)methyl]-sulphonyl}-1H-benzimidazole-5-carboxamide

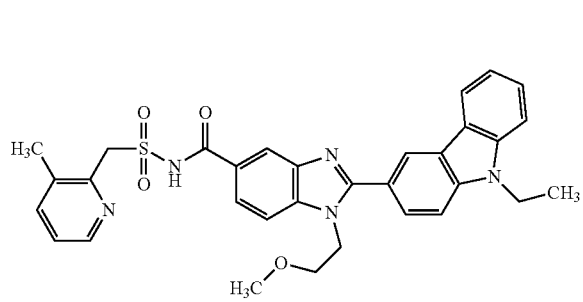 [SMILES: CCn1c2ccccc2c2cc(-c3nc4cc(C(=O)NS(=O)(=O)Cc5ncccc5C)ccc4n3CCOC)ccc21]

In analogy to Example 15, 20 mg (20%) of the title compound were obtained from 70 mg (0.17 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 2.49 (s, 3H), 3.15 (s, 3H), 3.70-3.75 (m, 2H), 4.49-4.63 (m, 4H), 5.06 (s, 2H), 7.24-7.31 (m, 2H), 7.50-7.56 (m, 1H), 7.66-7.77 (m, 2H), 7.78-7.85 (m, 2H), 7.88-7.92 (m, 1H), 7.93-7.98 (m, 1H), 8.24-8.34 (m, 3H), 8.67-8.70 (m, 1H), 11.84-12.11 (br. s., 1H).

Example 69

2-(9-Ethyl-9H-carbazol-3-yl)-1-(2-methoxyethyl)-N-{[2-(3-methoxyphenyl)ethyl]-sulphonyl}-1H-benzimidazole-5-carboxamide

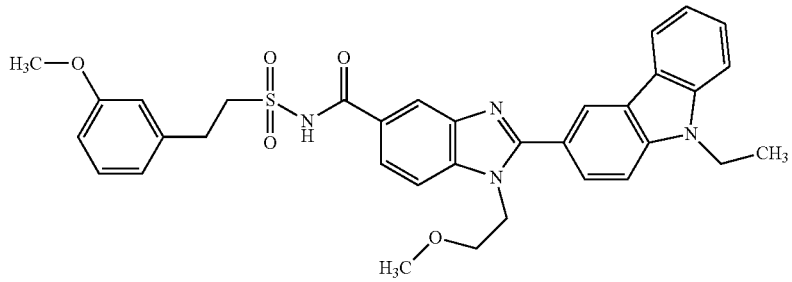 [SMILES: CCn1c2ccccc2c2cc(-c3nc4cc(C(=O)NS(=O)(=O)CCc5cccc(OC)c5)ccc4n3CCOC)ccc21]

In analogy to Example 15, 30 mg (25%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (400 MHz, DMSO-d6), δ [ppm]=1.38 (t, 3H), 3.03-3.08 (m, 2H), 3.13 (s, 3H), 3.70-3.74 (m, 5H), 3.84-3.91 (m, 2H), 4.54 (q, 2H), 4.61 (t, 2H), 6.75 (dd, 1H), 6.82-6.89 (m, 2H), 7.20 (t, 1H), 7.27 (t, 1H), 7.53 (t, 1H), 7.69 (d, 1H), 7.80-7.85 (m, 2H), 7.86-7.90 (m, 1H), 7.95 (dd, 1H), 8.28 (d, 1H), 8.32 (d, 1H), 8.69 (d, 1H), 12.07 (br. s., 1H).

Example 70

2-(9-Ethyl-9H-carbazol-3-yl)-1-[2-(morpholin-4-yl)ethyl]-1H-benzimidazole-5-carboxylic acid

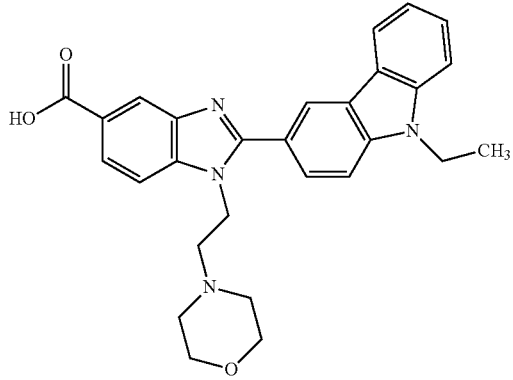 [SMILES: CCn1c2ccccc2c2cc(-c3nc4cc(C(=O)O)ccc4n3CCN3CCOCC3)ccc21]

In analogy to Example 37, 1.85 g (76%) of ethyl 2-(9-ethyl-9H-carbazol-3-yl)-1-[2-(morpholin-4-yl)ethyl]-1H-benzimidazole-5-carboxylate were first obtained as a crude product from 1.19 g (4.06 mmol) of crude ethyl 3-amino-4-{[2-(morpholin-4-yl)ethyl]amino}benzoate and 0.82 g (3.77 mmol) of 9-ethyl-9H-carbazole-3-carbaldehyde. By hydrolysis of 1.75 g of this crude product with sodium hydroxide solution, 0.93 g (56%) of the title compound were obtained.

$^1$H-NMR (300 MHz, DMSO-d6), δ [ppm]=1.37 (t, 3H), 2.16-2.23 (m, 4H), 2.65 (t, 2H), 3.29-3.36 (m, 4H), 4.54 (d, 4H), 7.24-7.30 (m, 1H), 7.53 (t, 1H), 7.67-7.84 (m, 3H), 7.89-7.97 (m, 2H), 8.26-8.32 (m, 2H), 8.64 (s, 1H), 12.57-12.90 (br., 1H).

Example 71

Ethyl-1-[2-(dimethylamino)ethyl]-2-(9-ethyl-9H-carbazol-3-yl)-1H-benzimidazole-5-carboxylate

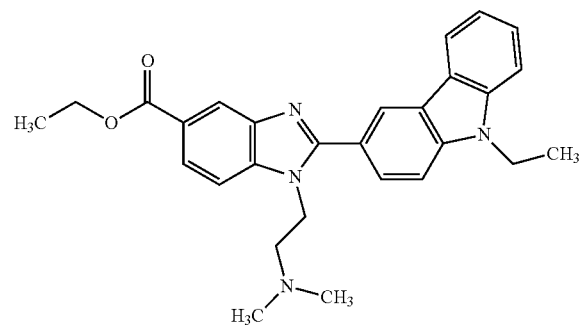 [SMILES: CCOC(=O)c1ccc2c(c1)nc(-c1ccc3c(c1)c1ccccc1n3CC)n2CCN(C)C]

In analogy to the preparation of ethyl 3-amino-4-{[2-(pyrrolidin-1-yl)ethyl]amino}-benzoate, firstly ethyl 3-amino-4-{[2-(dimethylamino)ethyl]amino}benzoate was prepared from ethyl 4-chloro-3-nitrobenzoate and N,N-dimethylethane-1,2-diamine, which was reacted without further purification with 9-ethyl-9H-carbazole-3-carbaldehyde analogously to Example 4/Variant B to give the title compound.

¹H-NMR (500 MHz, DMSO-d6), δ [ppm]=1.35-1.40 (m, 6H), 2.03 (s, 6H), 2.59-2.65 (m, 2H), 4.36 (q, 2H), 4.49-4.57 (m, 4H), 7.27 (t, 1H), 7.50-7.55 (m, 1H), 7.68 (d, 1H), 7.80 (dd, 2H), 7.92 (ddd, 2H), 8.26-8.31 (m, 2H), 8.65 (d, 1H).

Example 72

1-[2-(Dimethylamino)ethyl]-2-(9-ethyl-9H-carbazol-3-yl)-1H-benzimidazole-5-carboxylic acid

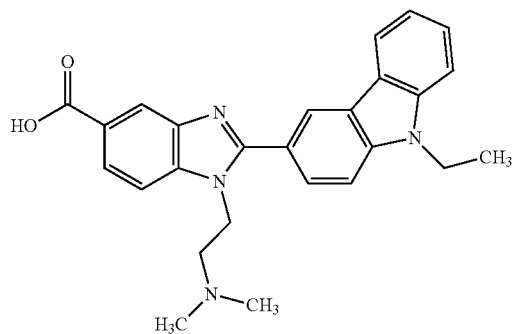 [SMILES: CCn1c2ccccc2c2cc(-c3nc4cc(C(=O)O)ccc4n3CCN(C)C)ccc21]

In analogy to Example 2, 1.42 g (85%) of the title compound were obtained from 1.7 g (3.74 mmol) of ethyl 1-[2-(dimethylamino)ethyl]-2-(9-ethyl-9H-carbazol-3-yl)-1H-benzimidazole-5-carboxylate by hydrolysis with sodium hydroxide solution.

¹H-NMR (400 MHz, DMSO-d6), δ [ppm]=1.38 (t, 3H), 2.03 (s, 6H), 2.62 (t, 2H), 4.47-4.57 (m, 4H), 7.27 (t, 1H), 7.50-7.56 (m, 1H), 7.69 (d, 1H), 7.76 (d, 1H), 7.81 (d, 1H), 7.89-7.94 (m, 2H), 8.25-8.31 (m, 2H), 8.66 (d, 1H), 12.54-12.87 (br., 1H).

Example 73

1-[2-(Dimethylamino)ethyl]-2-(9-ethyl-9H-carbazol-3-yl)-N-methyl-1H-benzimidazole-5-carboxamide

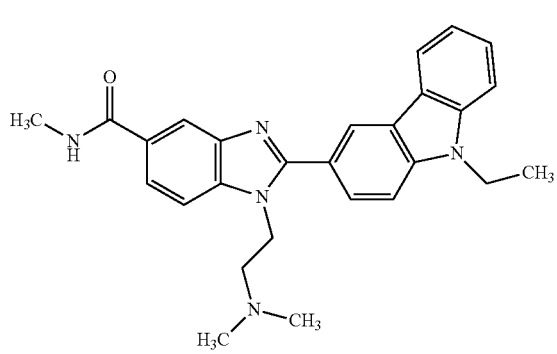 [SMILES: CCn1c2ccccc2c2cc(-c3nc4cc(C(=O)NC)ccc4n3CCN(C)C)ccc21]

In analogy to Example 21, 72 mg (66%) of the title compound were obtained from 100 mg (0.23 mmol) of 1-[2-(dimethylamino)ethyl]-2-(9-ethyl-9H-carbazol-3-yl)-1H-benzimidazole-5-carboxylic acid.

¹H-NMR (300 MHz, DMSO-d6), δ [ppm]=1.37 (t, 3H), 2.04 (s, 6H), 2.62 (t, 2H), 2.83 (d, 3H), 4.45-4.58 (m, 4H), 7.27 (t, 1H), 7.53 (t, 1H), 7.67-7.75 (m, 2H), 7.79-7.84 (m, 2H), 7.89-7.94 (m, 1H), 8.20 (d, 1H), 8.29 (d, 1H), 8.45 (d, 1H), 8.65 (d, 1H).

Example 74

N-(Cyclopropylsulphonyl)-1-[2-(dimethylamino)ethyl]-2-(9-ethyl-9H-carbazol-3-yl)-1H-benzimidazole-5-carboxamide

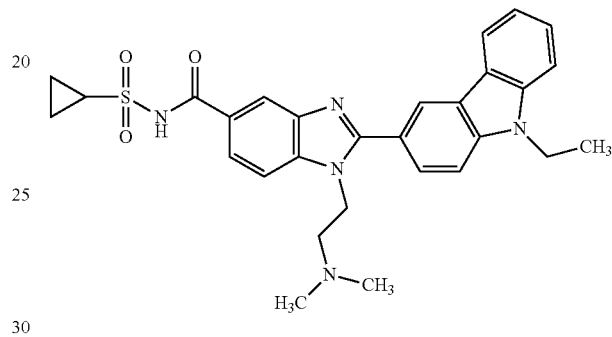

In analogy to Example 15, 2.6 mg (2%) of the title compound were obtained from 100 mg (0.23 mmol) of 1-[2-(dimethylamino)ethyl]-2-(9-ethyl-9H-carbazol-3-yl)-1H-benzimidazole-5-carboxylic acid and 127 mg (1.1 mmol) of cyclopropanesulphonamide.

¹H-NMR (400 MHz, DMSO-d6), δ [ppm]=0.96-1.03 (m, 2H), 1.04-1.12 (m, 2H), 1.38 (t, 3H), 2.10-2.17 (m, 6H), 2.72-2.80 (m, 2H), 3.09-3.17 (m, 1H), 4.50-4.58 (m, 4H), 7.27 (t, 1H), 7.50-7.56 (m, 1H), 7.69 (d, 1H), 7.75 (d, 1H), 7.82 (d, 1H), 7.93 (td, 2H), 8.28-8.32 (m, 2H), 8.65 (d, 1H), 11.36-11.93 (br., 1H).

Example 75

1-[2-(Dimethylamino)ethyl]-2-(9-ethyl-9H-carbazol-3-yl)-N-[(4-methylphenyl)sulphonyl]-1H-benzimidazole-5-carboxamide

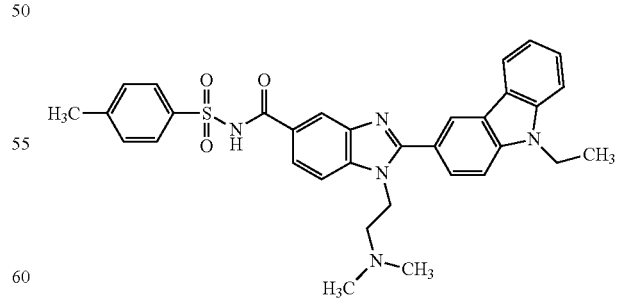

In analogy to Example 15, 5 mg (7%) of the title compound were obtained from 50 mg (0.12 mmol) of 1-[2-(dimethylamino)ethyl]-2-(9-ethyl-9H-carbazol-3-yl)-1H-benzimidazole-5-carboxylic acid and the appropriate sulphonamide.

¹H-NMR (300 MHz, DMSO-d6), δ [ppm]=1.37 (t, 3H), 2.34-2.43 (m, 8H), 2.54 (s, 3H), 4.49-4.66 (m, 4H), 7.23-7.38 (m, 4H), 7.53 (t, 1H), 7.71 (t, 2H), 7.79-7.93 (m, 4H), 8.26 (d, 1H), 8.32 (d, 1H), 8.63 (d, 1H), 10.99-11.97 (br., 1H).

Example 76

[2-(9-Ethyl-9H-carbazol-3-yl)-1-(2-methoxyethyl)-1H-benzimidazol-5-yl](pyrrolidin-1-yl)-methanone

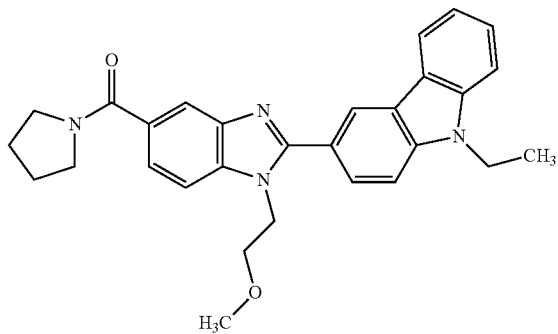 [SMILES: CCn1c2ccccc2c2cc(-c3nc4cc(C(=O)N5CCCC5)ccc4n3CCOC)ccc21]

In analogy to Example 21, 20 mg (17%) of the title compound were obtained from 100 mg (0.24 mmol) of 2-(9-ethyl-9H-carbazol-3-yl)-1-(2-methoxyethyl)-1H-benzimidazole-5-carboxylic acid and 86 mg (1.21 mmol) of pyrrolidine.

¹H-NMR (300 MHz, DMSO-d6), δ [ppm]=1.38 (t, 3H), 1.79-1.95 (m, 4H), 3.16 (s, 3H), 3.51 (d, 4H), 3.74 (t, 2H), 4.49-4.60 (m, 4H), 7.24-7.29 (m, 1H), 7.46 (dd, 1H), 7.52 (td, 1H), 7.69 (d, 1H), 7.73 (d, 1H), 7.80 (d, 1H), 7.84 (d, 1H), 7.94 (dd, 1H), 8.27 (d, 1H), 8.67 (d, 1H).

Example 77

2-(9-Ethyl-9H-carbazol-3-yl)-1-(2-methoxyethyl)-N-(2,2,2-trifluoroethyl)-1H-benzimidazole-5-carboxamide

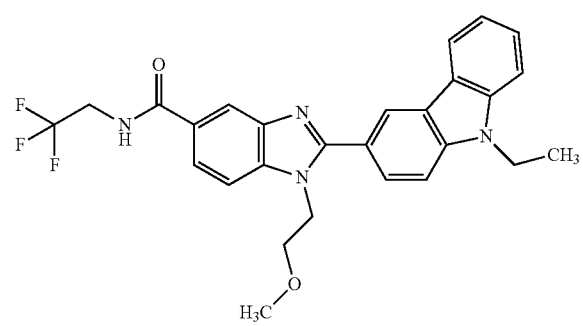 [SMILES: CCn1c2ccccc2c2cc(-c3nc4cc(C(=O)NCC(F)(F)F)ccc4n3CCOC)ccc21]

In analogy to Example 21, 45 mg (37%) of the title compound were obtained from 100 mg (0.24 mmol) of 2-(9-ethyl-9H-carbazol-3-yl)-1-(2-methoxyethyl)-1H-benzimidazole-5-carboxylic acid and 120 mg (1.21 mmol) of 2,2,2-trifluoroethanamine.

¹H-NMR (300 MHz, DMSO-d6), δ [ppm]=1.37 (t, 3H), 3.14 (s, 3H), 3.72 (t, 2H), 4.07-4.21 (m, 2H), 4.48-4.63 (m, 4H), 7.27 (t, 1H), 7.49-7.56 (m, 1H), 7.69 (d, 1H), 7.77-7.83 (m, 2H), 7.85-7.90 (m, 1H), 7.95 (dd, 1H), 8.25-8.30 (m, 2H), 8.68 (d, 1H), 9.10 (t, 1H).

Example 78

2-(9-Ethyl-9H-carbazol-3-yl)-1-(2-methoxyethyl)-N-[2-(morpholin-4-yl)ethyl]-1H-benzimidazole-5-carboxamide

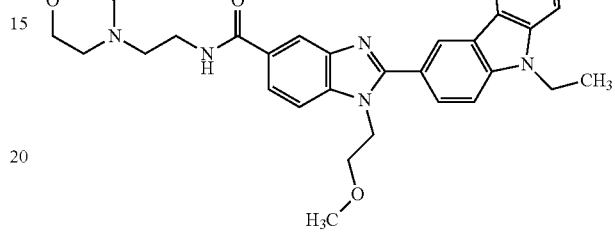

In analogy to Example 21, 50 mg (39%) of the title compound were obtained from 100 mg (0.24 mmol) of 2-(9-ethyl-9H-carbazol-3-yl)-1-(2-methoxyethyl)-1H-benzimidazole-5-carboxylic acid and 157 mg (1.21 mmol) of 2-(morpholin-4-yl)ethanamine.

¹H-NMR (300 MHz, DMSO-d6), δ [ppm]=1.38 (t, 3H), 2.42-2.54 (m, 6H), 3.14 (s, 3H), 3.44 (q, 2H), 3.57-3.62 (m, 4H), 3.72 (t, 2H), 4.48-4.61 (m, 4H), 7.27 (t, 1H), 7.49-7.56 (m, 1H), 7.67-7.84 (m, 4H), 7.94 (dd, 1H), 8.21 (d, 1H), 8.27 (d, 1H), 8.40 (t, 1H), 8.67 (d, 1H).

Example 79

1-(Cyclopropylmethyl)-2-(9-ethyl-9H-carbazol-3-yl)-N-[2-(morpholin-4-yl)ethyl]-1H-benzimidazole-5-carboxamide

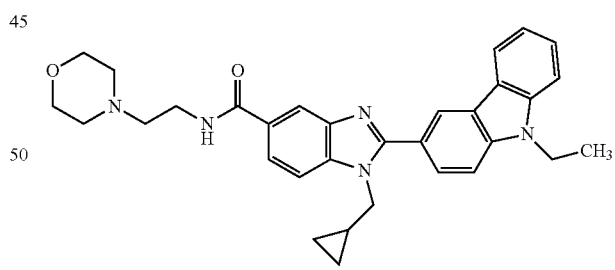

In analogy to Example 21, 85 mg (65%) of the title compound were obtained from 100 mg (0.24 mmol) of 1-(cyclopropylmethyl)-2-(9-ethyl-9H-carbazol-3-yl)-1H-benzimidazole-5-carboxylic acid and 159 mg (1.21 mmol) of 2-(morpholin-4-yl)ethanamine.

¹H-NMR (300 MHz, DMSO-d6), δ [ppm]=0.13-0.18 (m, 2H), 0.32-0.40 (m, 2H), 1.00-1.11 (m, 1H), 1.38 (t, 3H), 2.42-2.54 (m, 6H), 3.44 (q, 2H), 3.56-3.62 (m, 4H), 4.36 (d, 2H), 4.53 (q, 2H), 7.26 (t, 1H), 7.49-7.56 (m, 1H), 7.69 (d, 1H), 7.75-7.91 (m, 4H), 8.22 (s, 1H), 8.30 (d, 1H), 8.41 (t, 1H), 8.62 (d, 1H).

Example 80

Azetidin-1-yl[1-(cyclopropylmethyl)-2-(9-ethyl-9H-carbazol-3-yl)-1H-benzimidazol-5-yl]-methanone

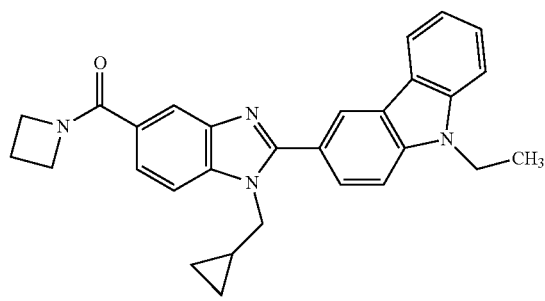 [SMILES: CCn1c2ccccc2c2cc(-c3nc4cc(C(=O)N5CCC5)ccc4n3CC3CC3)ccc21]

In analogy to Example 21, 55 mg (50%) of the title compound were obtained from 100 mg (0.24 mmol) of 1-(cyclopropylmethyl)-2-(9-ethyl-9H-carbazol-3-yl)-1H-benzimidazole-5-carboxylic acid and 70 mg (1.22 mmol) of azetidine.

$^1$H-NMR (300 MHz, DMSO-d6), δ [ppm]=0.12-0.20 (m, 2H), 0.33-0.42 (m, 2H), 1.01-1.13 (m, 1H), 1.38 (t, 3H), 2.29 (quin, 2H), 4.09 (br. s., 2H), 4.32-4.45 (m, 4H), 4.53 (q, 2H), 7.26 (t, 1H), 7.49-7.56 (m, 1H), 7.59 (dd, 1H), 7.69 (d, 1H), 7.75-7.94 (m, 4H), 8.30 (d, 1H), 8.62 (d, 1H).

Example 81

[2-(9-Ethyl-9H-carbazol-3-yl)-1-(2-methoxyethyl)-1H-benzimidazol-5-yl](morpholin-4-yl)-methanone

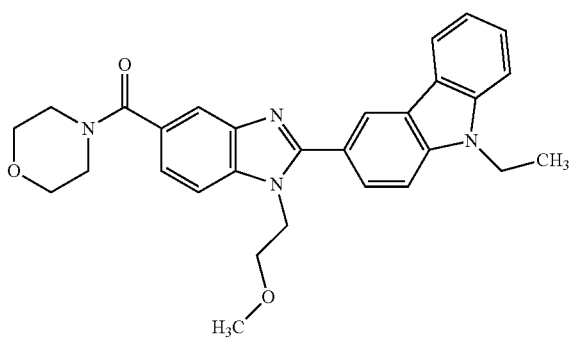 [SMILES: CCn1c2ccccc2c2cc(-c3nc4cc(C(=O)N5CCOCC5)ccc4n3CCOC)ccc21]

In analogy to Example 21, 35 mg (29%) of the title compound were obtained from 100 mg (0.24 mmol) of 2-(9-ethyl-9H-carbazol-3-yl)-1-(2-methoxyethyl)-1H-benzimidazole-5-carboxylic acid and 105 mg (1.21 mmol) of morpholine.

$^1$H-NMR (400 MHz, DMSO-d6), δ [ppm]=1.38 (t, 3H), 3.16 (s, 3H), 3.50-3.68 (m, 8H), 3.74 (t, 2H), 4.49-4.59 (m, 4H), 7.24-7.29 (m, 1H), 7.34 (dd, 1H), 7.53 (td, 1H), 7.67-7.82 (m, 4H), 7.94 (dd, 1H), 8.27 (d, 1H), 8.67 (d, 1H).

Example 82

2-(9-Ethyl-9H-carbazol-3-yl)-1-(2-methoxyethyl)-1H-benzimidazole-5-carboxamide

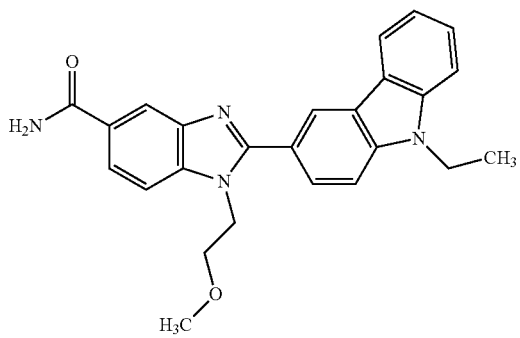 [SMILES: CCn1c2ccccc2c2cc(-c3nc4cc(C(N)=O)ccc4n3CCOC)ccc21]

In analogy to Example 21, 30 mg (29%) of the title compound were obtained from 100 mg (0.24 mmol) of 2-(9-ethyl-9H-carbazol-3-yl)-1-(2-methoxyethyl)-1H-benzimidazole-5-carboxylic acid and 65 mg (1.21 mmol) of ammonium chloride.

$^1$H-NMR (300 MHz, DMSO-d6), δ [ppm]=1.38 (t, 3H), 3.14 (s, 3H), 3.73 (t, 2H), 4.48-4.62 (m, 4H), 7.27 (t, 2H), 7.48-7.56 (m, 1H), 7.65-7.89 (m, 4H), 7.91-8.03 (m, 2H), 8.24-8.29 (m, 2H), 8.67 (d, 1H).

Example 83

2-(9-Ethyl-9H-carbazol-3-yl)-1-(2-methoxyethyl)-N,N-dimethyl-1H-benzimidazole-5-carboxamide In analogy to Example 21, 45 mg (42%) of the title compound were obtained from 100 mg (0.24 mmol) of 2-(9-ethyl-9H-carbazol-3-yl)-1-(2-methoxyethyl)-1H-benzimidazole-5-carboxylic acid and 55 mg (1.21 mmol) of dimethylamine.

$^1$H-NMR (300 MHz, DMSO-d6), δ [ppm]=1.38 (t, 3H), 3.02 (s, 6H), 3.16 (s, 3H), 3.74 (t, 2H), 4.48-4.61 (m, 4H), 7.23-7.35 (m, 2H), 7.49-7.56 (m, 1H), 7.66-7.83 (m, 4H), 7.94 (dd, 1H), 8.27 (d, 1H), 8.67 (d, 1H).

Example 84

2-(9-Ethyl-9H-carbazol-3-yl)-1-(2-methoxyethyl)-N-methyl-N-(methylsulphonyl)-1H-benzimidazole-5-carboxamide

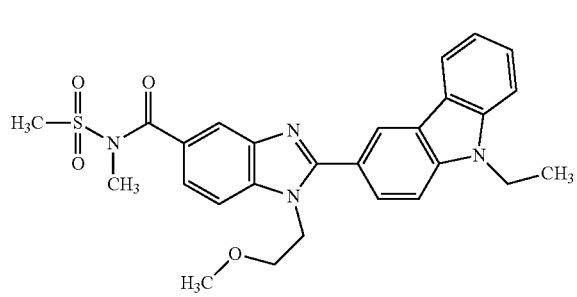 [SMILES: CCn1c2ccccc2c2cc(-c3nc4cc(C(=O)N(C)S(C)(=O)=O)ccc4n3CCOC)ccc21]

In analogy to Example 15, 30 mg (31%) of the title compound were obtained from 80 mg (0.19 mmol) of 2-(9-ethyl-9H-carbazol-3-yl)-1-(2-methoxyethyl)-1H-benzimidazole-5-carboxylic acid and the appropriate sulphonamide.

$^1$H-NMR (300 MHz, DMSO-d6), δ [ppm]=1.37 (t, 3H), 3.02 (s, 6H), 3.16 (s, 3H), 3.74 (t, 2H), 4.48-4.61 (m, 4H), 7.23-7.36 (m, 2H), 7.52 (t, 1H), 7.65-7.83 (m, 4H), 7.95 (dd, 1H), 8.27 (d, 1H), 8.68 (d, 1H).

Example 85

1-Allyl-2-(9-ethyl-9H-carbazol-3-yl)-N,N-dimethyl-1H-benzimidazole-5-carboxamide

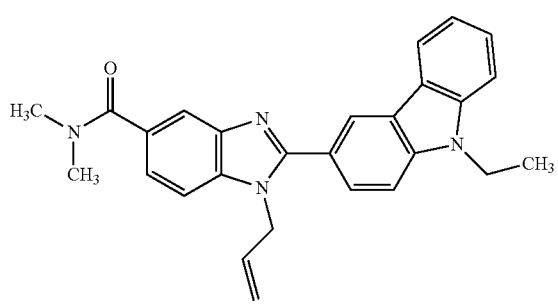 [SMILES: C=CCn1c(-c2ccc3c(c2)c2ccccc2n3CC)nc2cc(C(=O)N(C)C)ccc21]

1-Allyl-2-(9-ethyl-9H-carbazol-3-yl)-N,N-dimethyl-1H-benzimidazole-5-carboxamide was prepared from 1-allyl-2-(9-ethyl-9H-carbazol-3-yl)-1H-benzimidazole-5-carboxylic acid using N-[(1H-benzimidazol-1-yloxy)(dimethylamino)methylene]-N-methylmethanaminium tetrafluoroborate (TBTU) and dimethylamine in analogy to Example 21.

Example 86

N-[2-(Dimethylamino)ethyl]-2-(9-ethyl-9H-carbazol-3-yl)-1-(2-methoxyethyl)-1H-benzimidazole-5-carboxamide

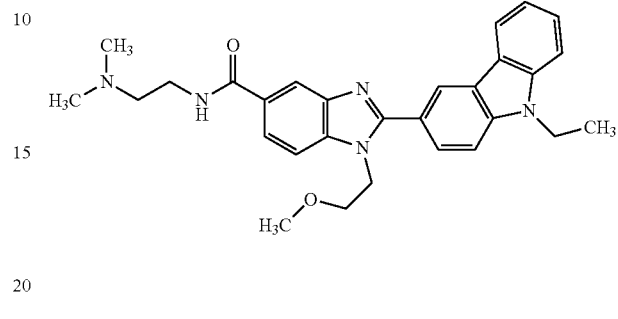

In analogy to Example 21, 7 mg (6%) of the title compound were obtained from 100 mg (0.24 mmol) of 2-(9-ethyl-9H-carbazol-3-yl)-1-(2-methoxyethyl)-1H-benzimidazole-5-carboxylic acid and 107 mg (1.21 mmol) of N,N-dimethylethane-1,2-diamine.

$^1$H-NMR (300 MHz, DMSO-d6), δ [ppm]=1.38 (t, 3H), 2.25-2.29 (m, 1H), 3.17 (s, 3H), 3.27-3.40 (m, 10H), 3.75 (t, 2H), 4.48-4.60 (m, 4H), 7.21-7.30 (m, 2H), 7.49-7.56 (m, 1H), 7.61 (d, 1H), 7.66-7.82 (m, 3H), 7.94 (dd, 1H), 8.27 (d, 1H), 8.67 (d, 1H).

Example 87

2-(9-Ethyl-9H-carbazol-3-yl)-1-(2-methoxyethyl)-N-[2-(pyrrolidin-1-yl)ethyl]-1H-benzimidazole-5-carboxamide

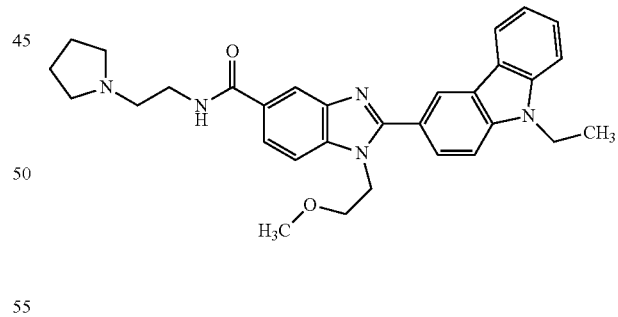

In analogy to Example 21, 51 mg (39%) of the title compound were obtained from 100 mg (0.24 mmol) of 2-(9-ethyl-9H-carbazol-3-yl)-1-(2-methoxyethyl)-1H-benzimidazole-5-carboxylic acid and 138 mg (1.21 mmol) of 2-(pyrrolidine-1-yl)ethanamine.

$^1$H-NMR (300 MHz, DMSO-d6), δ [ppm]=1.37 (t, 3H), 1.69 (t, 4H), 2.46-2.56 (m, 4H), 2.61 (t, 2H), 3.14 (s, 3H), 3.42 (q, 2H), 3.72 (t, 2H), 4.49-4.60 (m, 4H), 7.27 (t, 1H), 7.48-7.56 (m, 1H), 7.66-7.85 (m, 4H), 7.94 (dd, 1H), 8.22 (d, 1H), 8.27 (d, 1H), 8.45 (t, 1H), 8.67 (d, 1H).

Example 88

1-Allyl-2-(9-ethyl-9H-carbazol-3-yl)-N-methyl-1H-benzimidazole-5-carboxamide

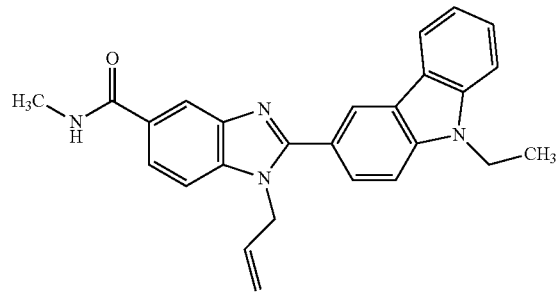 [SMILES: C=CCn1c(-c2ccc3c(c2)c2ccccc2n3CC)nc2cc(C(=O)NC)ccc21]

In analogy to Example 21, 29 mg (28%) of the title compound were obtained from 101 mg (0.25 mmol) of 2-(9-ethyl-9H-carbazol-3-yl)-1-(2-methoxyethyl)-1H-benzimidazole-5-carboxylic acid and methylammonium hydrochloride.

$^1$H-NMR (400 MHz, DMSO-d6), δ [ppm]=1.37 (t, 3H), 2.83 (d, 3H), 4.53 (q, 2H), 4.93-5.06 (m, 3H), 5.26 (dd, 1H), 6.10-6.21 (m, 1H), 7.25-7.29 (m, 1H), 7.50-7.55 (m, 1H), 7.60 (d, 1H), 7.69 (d, 1H), 7.79-7.83 (m, 2H), 7.85-7.90 (m, 1H), 8.22 (d, 1H), 8.26 (d, 1H), 8.45 (q, 1H), 8.61 (d, 1H).

Example 89

1-Allyl-2-(9-ethyl-9H-carbazol-3-yl)-1H-benzimidazole-5-carboxamide

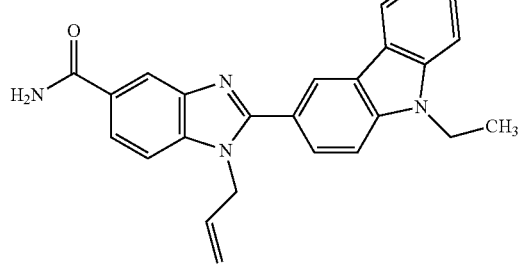

In analogy to Example 21, the title compound was prepared from 2-(9-ethyl-9H-carbazol-3-yl)-1-(2-methoxyethyl)-1H-benzimidazole-5-carboxylic acid and concentrated aqueous ammonium hydroxide solution (21 mg, 14%).

$^1$H-NMR (600 MHz, DMSO-d6), δ [ppm]=1.37 (t, 3H), 4.53 (q, 2H), 4.94-5.06 (m, 3H), 5.26 (dd, 1H), 6.11-6.19 (m, 1H), 7.27 (t, 2H), 7.51-7.55 (m, 1H), 7.58 (d, 1H), 7.69 (d, 1H), 7.81 (d, 1H), 7.86 (ddd, 2H), 7.99 (br. s., 1H), 8.26 (d, 1H), 8.28 (d, 1H), 8.61 (d, 1H).

Example 90

2-(9-Ethyl-9H-carbazol-3-yl)-N,1-dimethyl-1H-benzimidazole-5-carboxamide

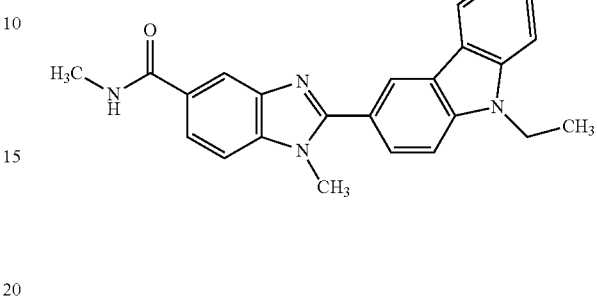

In analogy to Example 21, 106 mg (21%) of the title compound were obtained from 500 mg (1.35 mmol) of 2-(9-ethyl-9H-carbazol-3-yl)-1-methyl-1H-benzimidazole-5-carboxylic acid and 110 mg (1.62 mmol) of methylamine hydrochloride.

$^1$H-NMR (600 MHz, DMSO-d6), δ [ppm]=1.38 (t, 3H), 2.85 (d, 3H), 4.02 (s, 3H), 4.54 (q, 2H), 7.26-7.29 (m, 1H), 7.51-7.55 (m, 1H), 7.68-7.73 (m, 2H), 7.78 (dd, 1H), 7.82 (d, 1H), 7.97-8.00 (m, 1H), 8.16 (d, 1H), 8.33 (d, 1H), 8.45 (q, 1H), 8.71 (d, 1H).

Example 91

2-(9-Ethyl-9H-carbazol-3-yl)-1-(2-hydroxyethyl)-1H-benzimidazole-5-carboxylic acid

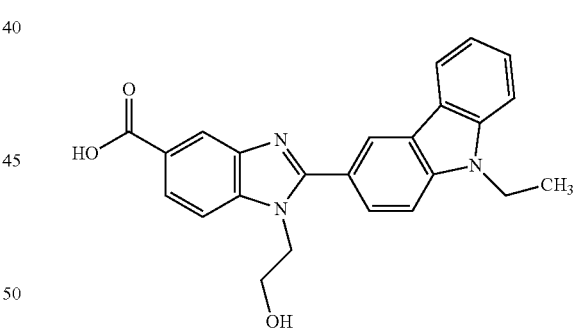

220 mg (0.53 mmol) of 2-(9-ethyl-9H-carbazol-3-yl)-1-(2-methoxyethyl)-1H-benzimidazole-5-carboxylic acid were added at 0° C. to 10 ml of dichloromethane (DCM), treated through a septum with a solution of 5.33 ml (5.33 mmol) of boron tribromide in n-heptane (1M) and stirred at 0° C. for 8 h. Excess reagent was decomposed with methanol, the mixture was concentrated in vacuo and the residue was purified by chromatography on silica gel (DCM/methanol 1:0->4:1) and by means of preparative HPLC. 100 mg (47%) of the title compound were thus obtained.

$^1$H-NMR (300 MHz, DMSO-d6), δ [ppm]=1.38 (t, 3H), 3.82 (t, 2H), 4.42-4.59 (m, 4H), 5.40-5.70 (1H), 7.27 (t, 1H), 7.48-7.57 (m, 1H), 7.66-7.83 (m, 3H), 7.91 (dd, 1H), 8.00 (dd, 1H), 8.22-8.31 (m, 2H), 8.72 (d, 1H), 11.80-12.60 (1H).

Example 92

Ethyl 2-(9-ethyl-9H-carbazol-3-yl)-1-isopropyl-1H-benzimidazole-5-carboxylate

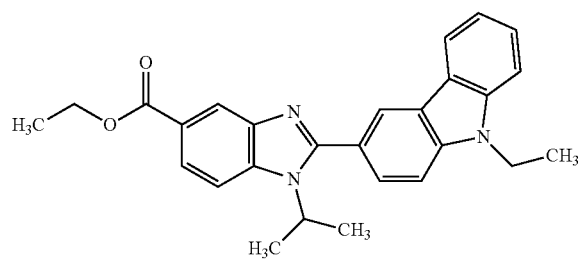 [SMILES: CCOC(=O)c1ccc2c(c1)nc(-c1ccc3c(c1)c1ccccc1n3CC)n2C(C)C]

In analogy to Example 37, 127 mg (68%) of the title compound were prepared from 90 mg (0.41 mmol) of ethyl 3-amino-4-(isopropylamino)benzoate and 60 mg (0.27 mmol) of 9-ethyl-9H-carbazole-3-carbaldehyde.

$^1$H-NMR (300 MHz, DMSO-d6), δ [ppm]=1.33-1.41 (m, 6H), 1.64 (d, 6H), 4.36 (q, 2H), 4.49-4.58 (m, 2H), 4.88 (quin, 1H), 7.23-7.30 (m, 1H), 7.50-7.56 (m, 1H), 7.67-7.76 (m, 2H), 7.80-7.85 (m, 1H), 7.87-7.91 (m, 1H), 7.94-7.99 (m, 1H), 8.27-8.32 (m, 2H), 8.51 (d, 1H).

Example 93

2-(9-Ethyl-9H-carbazol-3-yl)-1-isopropyl-1H-benzimidazole-5-carboxylic acid

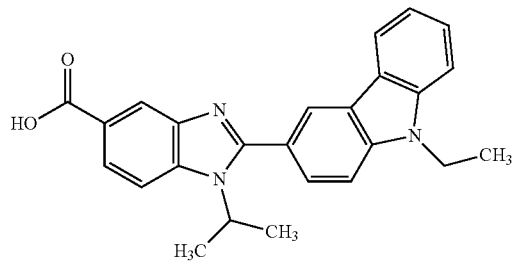 [SMILES: CCn1c2ccccc2c2cc(-c3nc4cc(C(=O)O)ccc4n3C(C)C)ccc21]

The title compound (34 mg, 33%) was obtained by hydrolysis of ethyl 2-(9-ethyl-9H-carbazol-3-yl)-1-isopropyl-1H-benzimidazole-5-carboxylate with sodium hydroxide solution.

$^1$H-NMR (300 MHz, DMSO-d6), δ [ppm]=1.39 (t, 3H), 1.74 (d, 6H), 4.58 (q, 2H), 5.01 (quin, 1H), 7.33 (t, 1H), 7.59 (t, 1H), 7.76 (d, 1H), 7.85-7.92 (m, 1H), 7.95-8.01 (m, 1H), 8.08-8.14 (m, 1H), 8.26-8.33 (m, 2H), 8.36 (s, 1H), 8.67 (s, 1H), 12.86-13.64 (br., 1H).

Example 94

2-(9-Ethyl-9H-carbazol-3-yl)-1-methyl-1H-benzimidazole-5-carboxylic acid

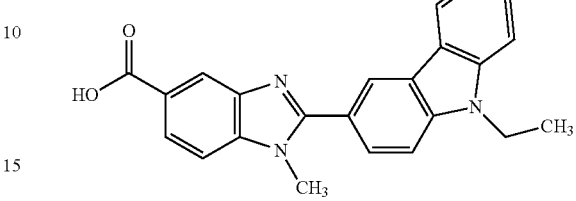

In analogy to Example 38, the title compound (9 mg, 10%) was obtained by hydrolysis of ethyl 2-(9-ethyl-9H-carbazol-3-yl)-1-methyl-1H-benzimidazole-5-carboxylate with sodium hydroxide solution.

$^1$H-NMR (400 MHz, DMSO-d6), δ [ppm]=1.38 (t, 3H), 4.01 (s, 3H), 4.54 (q, 2H), 7.27 (t, 1H), 7.49-7.56 (m, 1H), 7.66-7.72 (m, 2H), 7.81 (d, 1H), 7.93 (dd, 1H), 7.98 (dd, 1H), 8.27 (s, 1H), 8.32 (d, 1H), 8.70 (d, 1H), COOH not stated.

Example 95

Methyl 1-ethyl-2-(9-ethyl-9H-carbazol-3-yl)-1H-benzimidazole-5-carboxylate

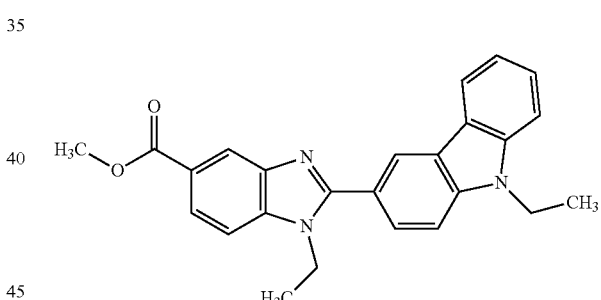

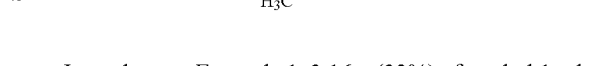

In analogy to Example 1, 3.16 g (32%) of methyl 1-ethyl-2-(9-ethyl-9H-carbazol-3-yl)-1H-benzimidazole-5-carboxylate and 2.99 g (30%) of isomeric methyl 1-ethyl-2-(9-ethyl-9H-carbazol-3-yl)-1H-benzimidazole-6-carboxylate were obtained from 9.22 g (25.0 mmol) of methyl 2-(9-ethyl-9H-carbazol-3-yl)-1H-benzimidazole-5-carboxylate and 11.68 g (74.9 mmol) of ethyl iodide.

Methyl 1-ethyl-2-(9-ethyl-9H-carbazol-3-yl)-1H-benzimidazole-5-carboxylate $^1$H-NMR (400 MHz, DMSO-d6), δ [ppm]=1.37 (td, 6H), 3.90 (s, 3H), 4.45 (q, 2H), 4.53 (q, 2H), 7.24-7.29 (m, 1H), 7.53 (td, 1H), 7.69 (d, 1H), 7.78-7.83 (m, 2H), 7.86-7.90 (m, 1H), 7.94 (dd, 1H), 8.28-8.33 (m, 2H), 8.61 (d, 1H).

Methyl 1-ethyl-2-(9-ethyl-9H-carbazol-3-yl)-1H-benzimidazole-6-carboxylate $^1$H-NMR (400 MHz, DMSO-d6), δ [ppm]=1.38 (t, 6H), 3.91 (s, 3H), 4.48-4.57 (m, 4H), 7.24-7.30 (m, 1H), 7.53 (td, 1H), 7.69 (d, 1H), 7.78 (d, 1H), 7.81-7.84 (m, 1H), 7.87-7.93 (m, 2H), 8.27-8.33 (m, 2H), 8.63 (d, 1H).

Example 96

2-(9-Allyl-9H-carbazol-3-yl)-1-(2-methoxyethyl)-1H-benzimidazole-5-carboxylic acid

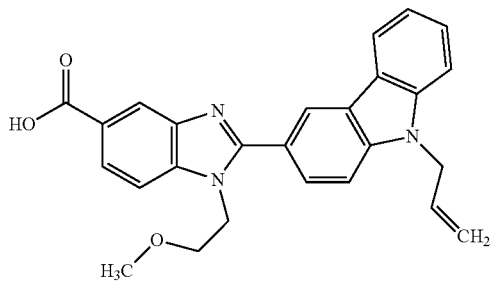 [SMILES: C=CCn1c2ccccc2c2cc(-c3nc4cc(C(=O)O)ccc4n3CCOC)ccc21]

In analogy to Example 14, 3 mg (3%) of the title compound were obtained from 56 mg (0.24 mmol) of 9-allyl-9H-carbazole-3-carbaldehyde and 100 mg (0.48 mmol) of 3-amino-4-[(2-methoxyethyl)amino]benzoic acid.

$^1$H-NMR (300 MHz, chloroform-d), δ [ppm]=3.34 (s, 3H), 3.85 (t, 2H), 4.55 (t, 2H), 5.00 (d, 2H), 5.11 (d, 1H), 5.24 (d, 1H), 5.98-6.13 (m, 1H), 7.28-7.35 (m, 1H), 7.43-7.47 (m, 1H), 7.50-7.60 (m, 3H), 7.93 (dd, 1H), 8.10-8.19 (m, 2H), 8.63-8.68 (m, 2H), COOH not stated.

Example 97

Ethyl 1-(2-methoxyethyl)-2-[9-(2-methoxyethyl)-9H-carbazol-3-yl]-1H-benzimidazole-5-carboxylate

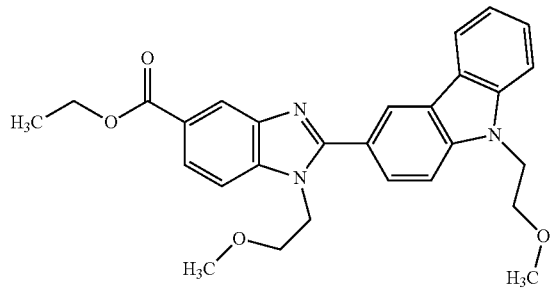 [SMILES: CCOC(=O)c1ccc2c(c1)nc(-c1ccc3c(c1)c1ccccc1n3CCOC)n2CCOC]

In analogy to Example 14, 30 mg (24%) of the title compound were obtained from 32 mg (0.13 mmol) of 9-allyl-9H-carbazole-3-carbaldehyde and 60 mg (0.25 mmol) of ethyl 3-amino-4-[(2-methoxyethyl)amino]benzoate.

$^1$H-NMR (300 MHz, DMSO-d6): δ [ppm]=1.37 (t, 3H), 3.11-3.15 (m, 3H), 3.21 (s, 3H), 3.75 (dt, 4H), 4.36 (q, 2H), 4.62 (dt, 4H), 7.27 (t, 1H), 7.48-7.55 (m, 1H), 7.69 (d, 1H), 7.78-7.84 (m, 2H), 7.89-7.96 (m, 2H), 8.23-8.30 (m, 2H), 8.67 (d, 1H).

Example 98

1-(2-Methoxyethyl)-2-[9-(2-methoxyethyl)-9H-carbazol-3-yl]-1H-benzimidazole-5-carboxylic acid

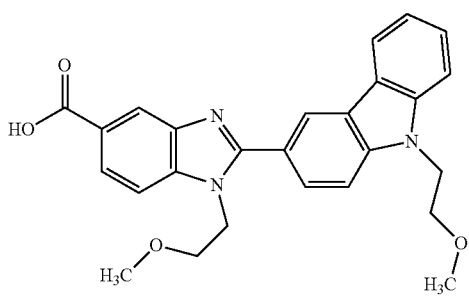 [SMILES: COCCn1c(-c2ccc3c(c2)c2ccccc2n3CCOC)nc2cc(C(=O)O)ccc21]

In analogy to Example 38, the title compound (18 mg, 61%) was obtained by hydrolysis of 30 mg of ethyl 1-(2-methoxyethyl)-2-[9-(2-methoxyethyl)-9H-carbazol-3-yl]-1H-benzimidazole-5-carboxylate with sodium hydroxide solution.

$^1$H-NMR (400 MHz, DMSO-d6): δ [ppm]=3.14 (s, 3H), 3.21 (s, 3H), 3.73 (t, 2H), 3.77 (t, 2H), 4.59 (t, 2H), 4.65 (t, 2H), 7.23-7.32 (m, 1H), 7.51 (t, 1H), 7.69 (d, 1H), 7.80 (dd, 2H), 7.89-7.97 (m, 2H), 8.23-8.30 (m, 2H), 8.67 (d, 1H), 12.74 (br. s., 1H).

Example 99

Ethyl 2-(9-ethyl-9H-carbazol-3-yl)-1-(3-methoxypropyl)-1H-benzimidazole-5-carboxylate

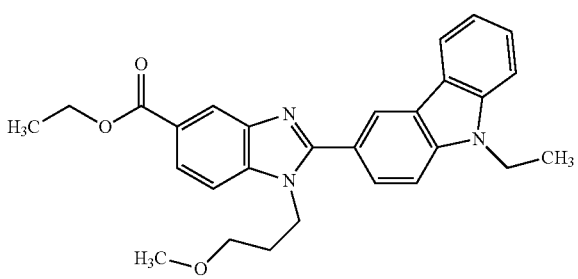 [SMILES: CCOC(=O)c1ccc2c(c1)nc(-c1ccc3c(c1)c1ccccc1n3CC)n2CCCOC]

In analogy to Example 14, the title compound (100 mg, 51%) was obtained from 100 mg (0.40 mmol) of ethyl-3-amino-4-[(2-methoxyethyl)amino]benzoate and 60 mg (0.26 mmol) of 9-ethyl-9H-carbazole-3-carbaldehyde.

$^1$H-NMR (300 MHz, DMSO-d6), δ [ppm]=1.37 (t, 6H), 1.93-2.04 (m, 2H), 3.05 (s, 3H), 3.22 (t, 2H), 4.36 (q, 2H), 4.48-4.60 (m, 4H), 7.28 (t, 1H), 7.49-7.57 (m, 1H), 7.70 (d, 1H), 7.77-7.85 (m, 2H), 7.94 (td, 2H), 8.26-8.32 (m, 2H), 8.64 (d, 1H).

Example 100

2-(9-Ethyl-9H-carbazol-3-yl)-1-(3-methoxypropyl)-1H-benzimidazole-5-carboxylic acid

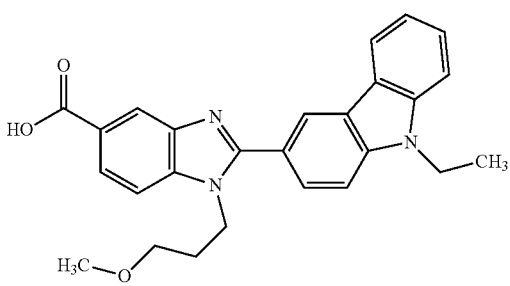 [SMILES: CCn1c2ccccc2c2cc(-c3nc4cc(C(=O)O)ccc4n3CCCOC)ccc21]

The title compound (7 mg, 2%) was obtained by hydrolysis of 394 mg (0.89 mmol) of ethyl 2-(9-ethyl-9H-carbazol-3-yl)-1-(3-methoxypropyl)-1H-benzimidazole-5-carboxylate with sodium hydroxide solution.

$^1$H-NMR (500 MHz, DMSO-d6), δ [ppm]=1.38 (t, 3H), 1.96-2.03 (m, 2H), 3.08 (s, 3H), 3.23-3.27 (m, 2H), 4.50-4.58 (m, 4H), 7.27 (t, 1H), 7.53 (td, 1H), 7.69 (d, 1H), 7.73 (d, 1H), 7.81 (d, 1H), 7.88 (dd, 1H), 7.93 (dd, 1H), 8.25 (d, 1H), 8.29 (d, 1H), 8.64 (d, 1H), COOH not stated.

Example 101

2-[2-(9-Ethyl-9H-carbazol-3-yl)-1-(2-methoxyethyl)-1H-benzimidazol-5-yl]propan-2-ol

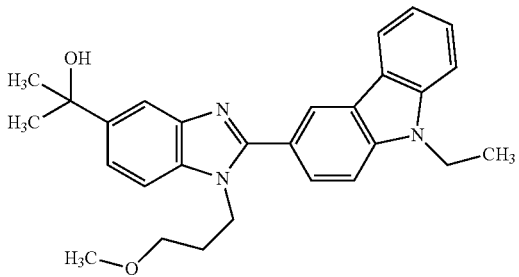 [SMILES: CCn1c2ccccc2c2cc(-c3nc4cc(C(C)(C)O)ccc4n3CCCOC)ccc21]

70 mg (0.16 mmol) of methyl 2-(9-ethyl-9H-carbazol-3-yl)-1-(2-methoxyethyl)-1H-benzimidazole-5-carboxylate were dissolved in 5 ml of tetrahydrofuran (THF) and treated at RT with 1.0 ml (1.0 mmol) of a solution of methylmagnesium bromide in THF (1M). The reaction mixture was poured onto 10 ml of saturated ammonium chloride solution and extracted three times with ethyl acetate. The collected organic phases were concentrated in vacuo and purified by means of preparative HPLC. In this way, 37 mg (52%) of the title compound were obtained.

$^1$H-NMR (500 MHz, DMSO-d6), δ [ppm]=1.37 (t, 3H), 1.52 (s, 6H), 3.16 (s, 3H), 3.73 (t, 2H), 4.48-4.55 (m, 4H), 5.02 (s, 1H), 7.24-7.28 (m, 1H), 7.41 (dd, 1H), 7.52 (ddd, 1H), 7.57 (d, 1H), 7.67 (d, 1H), 7.76-7.79 (m, 2H), 7.92 (dd, 1H), 8.26 (d, 1H), 8.64 (d, 1H).

Example 102

1-(Cyclopropylmethyl)-2-(9-ethyl-9H-carbazol-3-yl)-6-methoxy-1H-benzimidazole-5-carboxylic acid

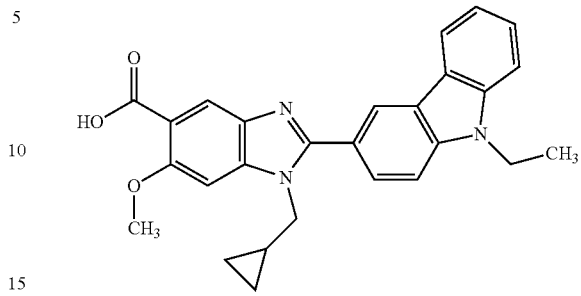

1.57 g (3.74 mmol) of 3-(5-bromo-6-methoxy-1H-benzimidazol-2-yl)-9-ethyl-9H-carbazole were added to 24 ml DMF, treated with 1.01 g (7.47 mmol) of (bromomethyl)cyclopropane and 4.87 g (14.94 mmol) of caesium carbonate and stirred at 60° C. for 2.5 h. After cooling to RT, water was added, the mixture was extracted three times with ethyl acetate, and the organic phases were washed with saturated sodium chloride solution, dried with sodium sulphate and concentrated in vacuo.

The crude product (2.0 g) thus obtained was taken up in 20 ml of THF, 1.67 g of molybdenum hexacarbonyl, 124 mg (0.42 mmol) of tri-tert-butylphosphine tetrafluoroborate, 325 mg (0.42 mmol) of trans-bis(acetato)bis[o-(di-o-tolylphosphino)benzyl]dipalladium(II), 1.54 ml (37.9 mmol) of methanol and 1.89 ml (12.65 mmol) 1,8-diazabicyclo(5.4.0)undec-7-ene were added and it was heated to 125° C. in the microwave for 25 min (irradiation 100 W, 6 bar). After cooling, the reaction mixture was treated with water, extracted with dichloromethane and the organic phase was subsequently concentrated in vacuo.

The residue (1.18 g) was taken up in 48 ml methanol, treated with 205 mg (5.15 mmol) of sodium hydroxide and stirred at 40° C. for 24 h. The mixture was neutralized with 2M hydrochloric acid, and the deposited precipitate was separated off, dried and purified by means of preparative HPLC. In this way, 358 mg of the title compound were obtained.

$^1$H-NMR (400 MHz, DMSO-d6), δ [ppm]=0.10-0.20 (m, 2H), 0.29-0.40 (m, 2H), 1.04 (d, 1H), 1.39 (t, 3H), 3.93 (s, 3H), 4.35 (d, 2H), 4.53 (q, 2H), 7.26 (t, 1H), 7.39 (s, 1H), 7.48-7.56 (m, 1H), 7.67 (d, 1H), 7.73-7.80 (m, 1H), 7.81-7.89 (m, 1H), 7.97 (s, 1H), 8.25-8.33 (m, 1H), 8.58 (d, 1H), 12.25-12.39 (1H).

Example 103

2-(9-Ethyl-9H-carbazol-3-yl)-6-methoxy-1-(2-methoxyethyl)-1H-benzimidazole-5-carboxylic acid

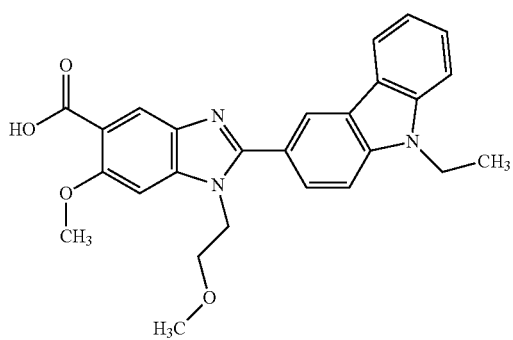 [SMILES: CCn1c2ccccc2c2cc(-c3nc4cc(C(=O)O)c(OC)cc4n3CCOC)ccc21]

The title compound was obtained in analogy to Example 102 starting from 3-(5-bromo-6-methoxy-1H-benzimidazol-2-yl)-9-ethyl-9H-carbazole and 2-bromoethyl methyl ether.

¹H-NMR (400 MHz, DMSO-d6): δ [ppm]=1.38 (t, 3H), 3.15 (s, 3H), 3.71 (t, 2H), 3.84 (s, 3H), 4.47-4.55 (m, 4H), 7.15 (s, 1H), 7.22-7.29 (m, 1H), 7.47-7.53 (m, 1H), 7.60 (s, 1H), 7.66 (d, 1H), 7.75 (d, 1H), 7.89 (dd, 1H), 8.25 (d, 1H), 8.61 (d, 1H), COOH not stated.

Example 104

1-(Cyclopropylmethyl)-2-(9-ethyl-9H-carbazol-3-yl)-4-methoxy-1H-benzimidazole-5-carboxylic acid

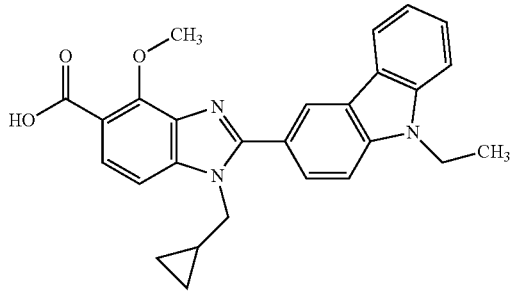 [SMILES: CCn1c2ccccc2c2cc(-c3nc4c(OC)c(C(=O)O)ccc4n3CC3CC3)ccc21]

In analogy to Intermediate 31, 3-(5-bromo-4-methoxy-1H-benzimidazol-2-yl)-9-ethyl-9H-carbazole was first prepared starting from 4-bromo-3-methoxy-2-nitroaniline and 9-ethyl-9H-carbazole-3-carbaldehyde, which was then reacted analogously to Example 102 to give the title compound.

¹H-NMR (400 MHz, DMSO-d6), δ [ppm]=0.14 (q, 2H), 0.33-0.39 (m, 2H), 1.00-1.09 (m, 1H), 1.38 (t, 3H), 4.29-4.33 (m, 2H), 4.34 (s, 3H), 4.53 (q, 2H), 7.26 (t, 1H), 7.43 (d, 1H), 7.49-7.56 (m, 1H), 7.61-7.72 (m, 2H), 7.77-7.83 (m, 1H), 7.85-7.90 (m, 1H), 8.30 (d, 1H), 8.61 (d, 1H), 12.34 (br. s., 1H).

Example 105

2-(9-Ethyl-9H-carbazol-3-yl)-1-(2-methoxyethyl)-4-methyl-1H-benzimidazole-5-carboxylic acid

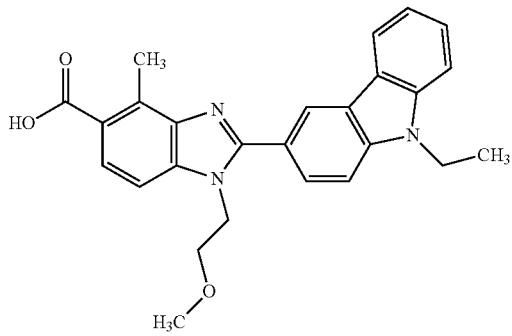 [SMILES: CCn1c2ccccc2c2cc(-c3nc4c(C)c(C(=O)O)ccc4n3CCOC)ccc21]

2-(9-Ethyl-9H-carbazol-3-yl)-1-(2-methoxyethyl)-4-methyl-1H-benzimidazole-5-carboxylic acid was prepared in analogy to Example 9, starting from 4-acetamido-2-methylbenzoic acid.

¹H-NMR (400 MHz, DMSO-d6), δ [ppm]=1.39 (t, 3H), 2.90 (s, 3H), 3.14 (s, 3H), 3.70 (t, 2H), 4.46-4.58 (m, 4H), 7.26 (t, 1H), 7.47-7.57 (m, 2H), 7.67 (d, 1H), 7.78 (d, 1H), 7.84 (d, 1H), 7.92 (dd, 1H), 8.19-8.32 (m, 1H), 8.64 (d, 1H), 12.30-12.70 (1H).

Example 106

5-[2-(9-Ethyl-9H-carbazol-3-yl)-1-(2-methoxyethyl)-1H-benzimidazol-5-yl]-1,3,4-oxadiazol-2(3H)-one

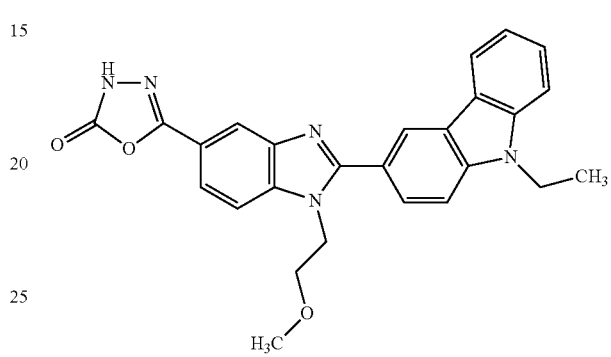

250 mg (0.61 mmol) of 2-(9-ethyl-9H-carbazol-3-yl)-1-(2-methoxyethyl)-1H-benzimidazole-5-carboxylic acid were added to 10 ml THF, treated with 147 mg (0.91 mmol) of 1,1'-carbonyldiimidazole and 36 mg (0.30 mmol) of 4-dimethylaminopyridine and stirred at 60° C. for 1.5 h. After cooling to RT, 0.10 ml (2.12 mmol) of hydrazine hydrate were added, stirred at RT for 2 h and the mixture was then concentrated in vacuo. Subsequently, it was taken up in 10 ml DMF, treated with 303 mg (1.87 mmol) of 1,1'-carbonyldiimidazole in 10 ml of THF and left at RT for 72 h. The mixture was once again concentrated and purified by means of preparative HPLC. In this way, 200 mg of the title compound were obtained.

¹H-NMR (300 MHz, DMSO-d6), δ [ppm]=1.38 (t, 3H), 3.15 (s, 3H), 3.73 (t, 2H), 4.48-4.63 (m, 4H), 7.27 (t, 1H), 7.53 (t, 1H), 7.65-7.89 (m, 4H), 7.96 (dd, 1H), 8.06 (d, 1H), 8.27 (d, 1H), 8.69 (d, 1H), 12.47 (br. s., 1H).

Example 107

1-(Cyclopropylmethyl)-2-(9-ethyl-9H-pyrido[2,3-b]indol-3-yl)-4-methyl-1H-benzimidazole-5-carboxylic acid

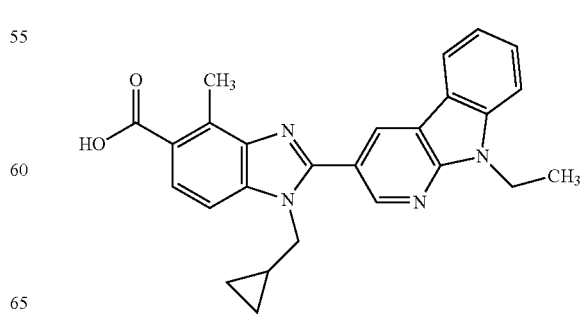

In analogy to Example 9, methyl 1-(cyclopropylmethyl)-2-(9-ethyl-9H-pyrido[2,3-b]indol-3-yl)-4-methyl-1H-benzimidazole-5-carboxylate was first prepared from methyl 3-amino-4-[(cyclopropylmethyl)amino]-2-methylbenzoate and 9-ethyl-9H-pyrido[2,3-b]indole-3-carbaldehyde, which was subsequently hydrolysed with sodium hydroxide solution.

¹H-NMR (300 MHz, DMSO-d6): δ [ppm]=0.16 (q, 2H), 0.32-0.41 (m, 2H), 0.95-1.05 (m, 1H), 1.42 (t, 3H), 2.90 (s, 3H), 4.34 (d, 2H), 4.61 (q, 2H), 7.35 (t, 1H), 7.58-7.66 (m, 2H), 7.78 (d, 1H), 7.87 (d, 1H), 8.38 (d, 1H), 8.89 (d, 1H), 9.01 (d, 1H), COOH not stated.

Example 108

1-(Cyclopropylmethyl)-2-(9-ethyl-9H-beta-carbolin-6-yl)-1H-benzimidazole-5-carboxylic acid

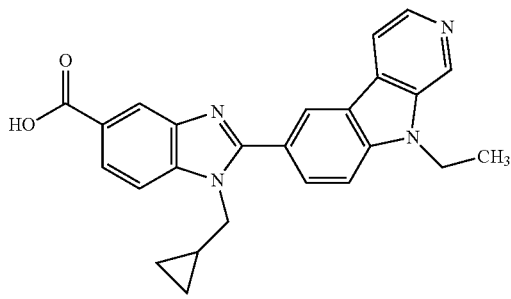

In analogy to Example 38, the title compound (20 mg, 79%) was obtained after hydrolysis of the corresponding ethyl ester (27 mg, 0.1 mmol).

¹H-NMR (300 MHz, DMSO-d6), δ [ppm]=0.16 (q, 2H), 0.32-0.40 (m, 2H), 0.95-1.08 (m, 1H), 1.43 (t, 3H), 4.38 (d, 2H), 4.64 (q, 2H), 7.79-7.85 (m, 1H), 7.89-7.97 (m, 2H), 8.03-8.08 (m, 1H), 8.26-8.32 (m, 2H), 8.46 (d, 1H), 8.78 (d, 1H), 9.15 (s, 1H), COOH not stated.

Example 109

1-(Cyclopropylmethyl)-2-(5-ethyl-5H-pyrido[4,3-b]indol-8-yl)-1H-benzimidazole-5-carboxylic acid

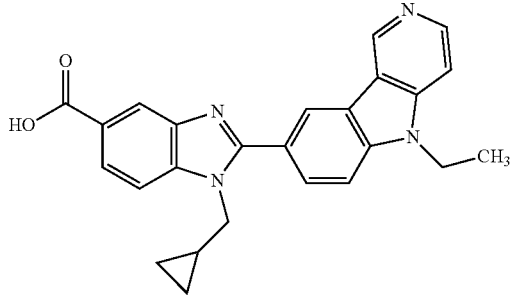 [SMILES: CCn1c2ccncc2c2cc(-c3nc4cc(C(=O)O)ccc4n3CC3CC3)ccc21]

In analogy to Example 38, the title compound (25 mg) was obtained after hydrolysis of the corresponding ethyl ester (27 mg, 0.1 mmol).

¹H-NMR (300 MHz, DMSO-d6), δ [ppm]=0.15 (q, 2H), 0.32-0.40 (m, 2H), 0.95-1.08 (m, 1H), 1.39 (t, 3H), 4.39 (d, 2H), 4.56 (q, 2H), 7.73 (d, 1H), 7.81-7.87 (m, 1H), 7.89-8.02 (m, 3H), 8.28 (d, 1H), 8.55 (d, 1H), 8.77 (d, 1H), 9.50 (s, 1H), COOH not stated.

Example 110

1-(Cyclopropylmethyl)-2-(9-ethyl-9H-carbazol-3-yl)-6-methyl-1H-benzimidazole-5-carboxylic acid

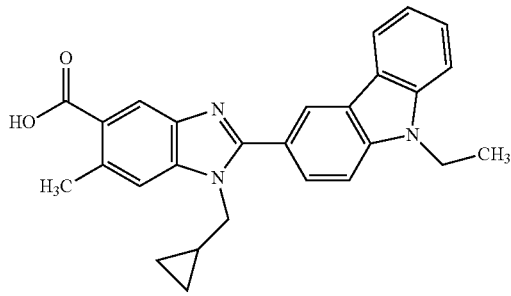 [SMILES: CCn1c2ccccc2c2cc(-c3nc4cc(C(=O)O)c(C)cc4n3CC3CC3)ccc21]

1-(Cyclopropylmethyl)-2-(9-ethyl-9H-carbazol-3-yl)-6-methyl-1H-benzimidazole-5-carboxylic acid was prepared in analogy to Example 9.

¹H-NMR (300 MHz, DMSO-d6), δ [ppm]=0.13 (q, 2H), 0.31-0.40 (m, 2H), 1.00-1.09 (m, 1H), 1.38 (t, 3H), 2.70 (s, 3H), 4.33 (d, 2H), 4.53 (q, 2H), 7.26 (t, 1H), 7.49-7.56 (m, 1H), 7.63 (s, 1H), 7.69 (d, 1H), 7.77-7.82 (m, 1H), 7.84-7.90 (m, 1H), 8.20 (s, 1H), 8.30 (d, 1H), 8.62 (d, 1H), 12.56 (br., s, 1H).

Example 111

2-(9-Ethyl-9H-carbazol-3-yl)-1-(2-methoxyethyl)-6-methyl-1H-benzimidazole-5-carboxylic acid

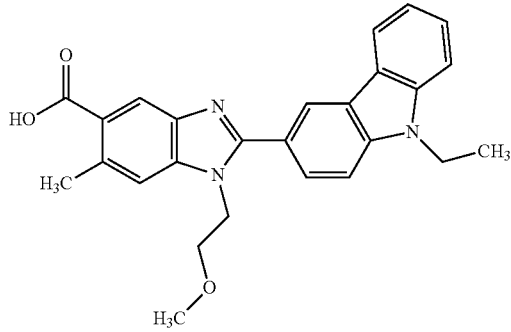 [SMILES: CCn1c2ccccc2c2cc(-c3nc4cc(C(=O)O)c(C)cc4n3CCOC)ccc21]

2-(9-Ethyl-9H-carbazol-3-yl)-1-(2-methoxyethyl)-6-methyl-1H-benzimidazole-5-carboxylic acid was prepared in analogy to Example 9.

¹H-NMR (300 MHz, DMSO-d6), δ [ppm]=1.37 (t, 3H), 2.70 (s, 3H), 3.14 (s, 3H), 3.72 (t, 2H), 4.50-4.58 (m, 4H), 7.27 (t, 1H), 7.52 (t, 1H), 7.61 (s, 1H), 7.69 (d, 1H), 7.80 (d, 1H), 7.94 (dd, 1H), 8.20 (s, 1H), 8.27 (d, 1H), 8.68 (d, 1H), 12.58 (br., s, 1H).

Example 112

1-(Cyclopropylmethyl)-2-(9-ethyl-9H-carbazol-3-yl)-6-fluoro-1H-benzimidazole-5-carboxylic acid

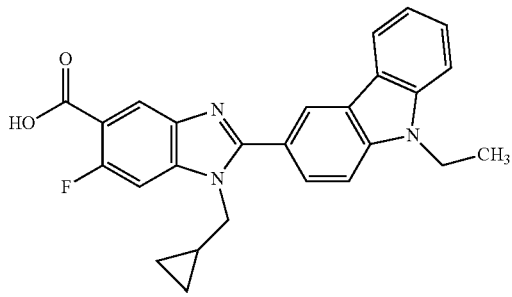 [SMILES: CCn1c2ccccc2c2cc(-c3nc4cc(C(=O)O)c(F)cc4n3CC3CC3)ccc21]

In analogy to Example 102, the title compound was obtained starting from 3-(5-bromo-6-fluoro-1H-benzimidazol-2-yl)-9-ethyl-9H-carbazole and (bromomethyl)cyclopropane.

$^1$H-NMR (400 MHz, DMSO-d6), δ [ppm]=0.15 (q, 2H), 0.31-0.38 (m, 2H), 0.98-1.07 (m, 1H), 1.38 (t, 3H), 4.34 (d, 2H), 4.52 (q, 2H), 7.26 (t, 1H), 7.48-7.55 (m, 1H), 7.64-7.75 (m, 2H), 7.77-7.82 (m, 1H), 7.85-7.90 (m, 1H), 8.15 (d, 1H), 8.29 (d, 1H), 8.62 (d, 1H), 12.20-13.40 (1H).

Example 113

2-(9-Ethyl-9H-carbazol-3-yl)-6-fluoro-1-(2-methoxyethyl)-1H-benzimidazole-5-carboxylic acid

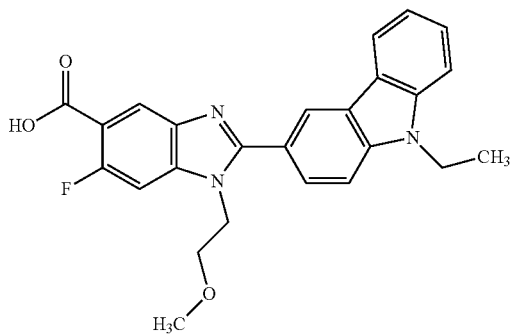 [SMILES: CCn1c2ccccc2c2cc(-c3nc4cc(C(=O)O)c(F)cc4n3CCOC)ccc21]

In analogy to Example 102, the title compound was obtained starting from 3-(5-bromo-6-fluoro-1H-benzimidazol-2-yl)-9-ethyl-9H-carbazole and 2-bromoethyl methyl ether.

$^1$H-NMR (400 MHz, DMSO-d6), δ [ppm]=1.38 (t, 3H), 3.14 (s, 3H), 3.69 (t, 2H), 4.49-4.58 (m, 4H), 7.27 (t, 1H), 7.50-7.56 (m, 1H), 7.66-7.71 (m, 2H), 7.79 (d, 1H), 7.93 (dd, 1H), 8.14 (d, 1H), 8.26 (d, 1H), 8.66 (d, 1H), 12.60-13.40 (1H).

Example 114

2-(9-Ethyl-9H-carbazol-3-yl)-4-fluoro-1-(2-methoxyethyl)-1H-benzimidazole-5-carboxylic acid

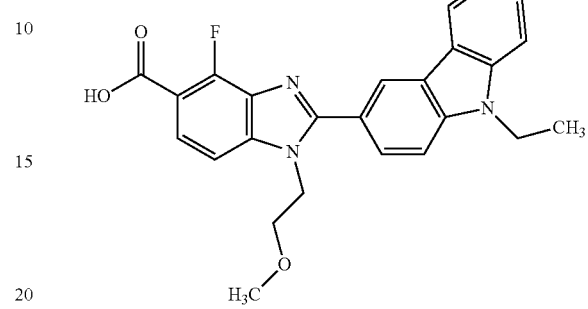

In analogy to Example 102, the title compound (432 mg) was obtained starting from g (49.0 mmol) of 3-(5-bromo-4-fluoro-1H-benzimidazol-2-yl)-9-ethyl-9H-carbazole and 13.6 g (98 mmol) of (2-bromoethyl)methyl ether.

$^1$H-NMR (300 MHz, DMSO-d6), δ [ppm]=1H-NMR (300 MHz, DMSO-d6): δ [ppm]=1.38 (t, 3H), 3.13 (s, 3H), 3.71 (t, 2H), 4.48-4.64 (m, 4H), 7.27 (t, 1H), 7.49-7.57 (m, 1H), 7.61 (d, 1H), 7.69 (d, 1H), 7.74-7.85 (m, 2H), 7.96 (dd, 1H), 8.28 (d, 1H), 8.70 (d, 1H), 12.97 (br. s., 1H).

Example 115

1-(Cyclopropylmethyl)-2-(9-ethyl-9H-carbazol-3-yl)-4-fluoro-1H-benzimidazole-5-carboxylic acid

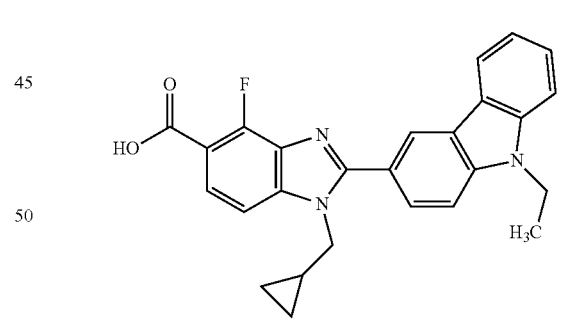

In analogy to Example 102, the title compound (15 mg) was obtained starting from 3.26 g (8.0 mmol) of 3-(5-bromo-4-fluoro-1H-benzimidazol-2-yl)-9-ethyl-9H-carbazole and 1.45 g (16.0 mmol) (bromomethyl)cyclopropane.

$^1$H-NMR (400 MHz, chloroform-d): δ [ppm]=0.17-0.24 (m, 2H), 0.51-0.59 (m, 2H), 1.20 (d, 1H), 1.51 (t, 3H), 4.27 (d, 2H), 4.46 (q, 2H), 7.28-7.35 (m, 2H), 7.47-7.51 (m, 1H), 7.52-7.58 (m, 2H), 7.85 (dd, 1H), 7.97-8.02 (m, 1H), 8.16 (d, 1H), 8.52 (s, 1H), COOH not stated.

Example 116

1-(Cyclopropylmethyl)-2-(9-ethyl-9H-pyrido[2,3-b]indol-6-yl)-1H-benzimidazole-5-carboxylic acid

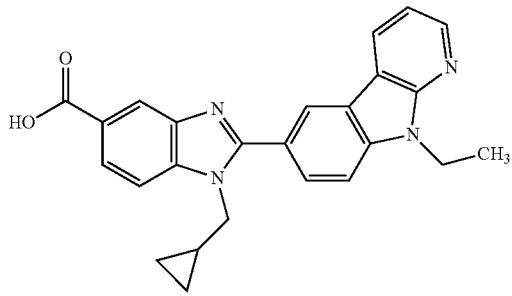 [SMILES: CCn1c2ccc(-c3nc4cc(C(=O)O)ccc4n3CC3CC3)cc2c2cccnc21]

In analogy to Example 38, the title compound (20 mg, 59%) was obtained after hydrolysis of the corresponding ethyl ester (35 mg, 0.1 mmol).

$^1$H-NMR (400 MHz, DMSO-d6), δ [ppm]=0.13-0.19 (m, 2H), 0.33-0.39 (m, 2H), 1.02-1.11 (m, 1H), 1.42 (t, 3H), 4.37 (d, 2H), 4.61 (q, 2H), 7.32 (dd, 1H), 7.77 (d, 1H), 7.88-7.99 (m, 3H), 8.26 (d, 1H), 8.55 (dd, 1H), 8.68-8.73 (m, 2H), COOH not stated.

Example 117

1-(2-Cyclopropylethyl)-2-(9-ethyl-9H-carbazol-3-yl)-1H-benzimidazole-5-carboxylic acid

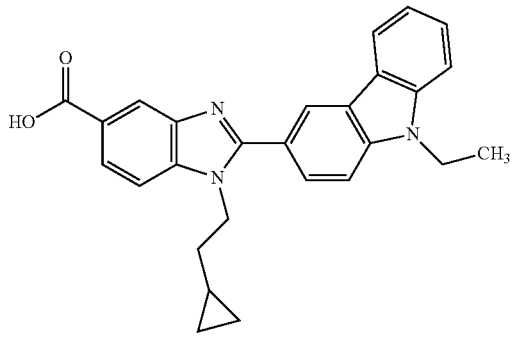 [SMILES: CCn1c2ccccc2c2cc(-c3nc4cc(C(=O)O)ccc4n3CCC3CC3)ccc21]

First, starting from ethyl 4-chloro-3-nitrobenzoate and 2-cyclopropylethanamine, analogously to the synthesis of Intermediate 2, ethyl 3-amino-4-{[2-cyclopropylethyl]-amino}benzoate was prepared, which was reacted with 9-ethyl-9H-carbazole-3-carbaldehyde and hydrolysed in analogy to Example 9.

$^1$H-NMR (400 MHz, DMSO-d6): δ [ppm]=−0.18- −0.13 (m, 2H), 0.18-0.24 (m, 2H), 0.47 (d, 1H), 1.38 (t, 3H), 1.63 (q, 2H), 4.50-4.58 (m, 4H), 7.28 (t, 1H), 7.54 (t, 1H), 7.70 (d, 1H), 7.80-7.86 (m, 2H), 7.88-7.97 (m, 2H), 8.26-8.33 (m, 2H), 8.64 (s, 1H).

Example 118

1-(2-Methoxyethyl)-2-(9-propyl-9H-carbazol-3-yl)-1H-benzimidazole-5-carboxylic acid

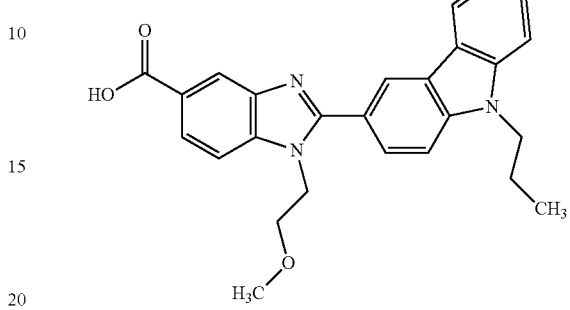

First, from 9H-carbazole-3-carbaldehyde and 3-bromopropane, analogously to the synthesis of Intermediate 16, 9-propyl-9H-carbazole-3-carbaldehyde was prepared, which was then reacted with ethyl 3-amino-4-[(2-methoxyethyl)amino]benzoate in analogy to Example 9 and subsequently hydrolysed.

1H-NMR (400 MHz, chloroform-d): δ [ppm]=1.03 (t, 3H), 1.94-2.03 (m, 2H), 3.34 (s, 3H), 3.85 (t, 2H), 4.36 (t, 2H), 4.55 (t, 2H), 7.28-7.32 (m, 1H), 7.46-7.58 (m, 4H), 7.94 (dd, 1H), 8.09-8.17 (m, 2H), 8.62-8.68 (m, 2H), COOH not stated.

Example 119

1-(2-Methoxyethyl)-2-[9-(prop-2-yn-1-yl)-9H-carbazol-3-yl]-1H-benzimidazole-5-carboxylic acid

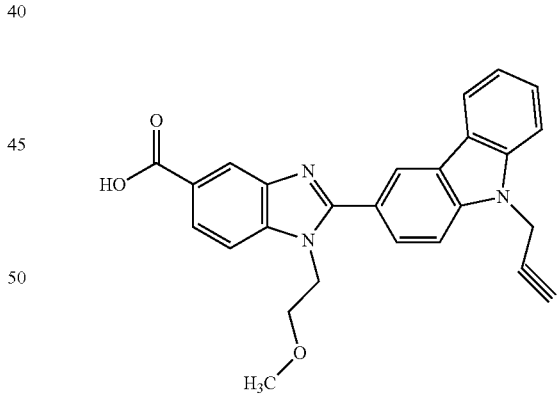

First, from 9H-carbazole-3-carbaldehyde and 3-bromopropyne, analogously to the synthesis of Intermediate 16, 9-(prop-2-yn-1-yl)-9H-carbazole-3-carbaldehyde was prepared, which was then reacted with ethyl 3-amino-4-[(2-methoxyethyl)amino]-benzoate and subsequently hydrolysed in analogy to Example 9.

$^1$H-NMR (400 MHz, chloroform-d): δ [ppm]=2.31-2.35 (m, 1H), 3.33 (s, 3H), 3.84 (t, 2H), 4.54 (t, 2H), 5.12 (d, 2H), 7.34 (ddd, 1H), 7.53-7.58 (m, 3H), 7.65 (d, 1H), 7.97 (dd, 1H), 8.10-8.17 (m, 2H), 8.64-8.68 (m, 2H), COOH not stated.

Example 120

1-(Cyclopropylmethyl)-2-(9-propyl-9H-carbazol-3-yl)-1H-benzimidazole-5-carboxylic acid

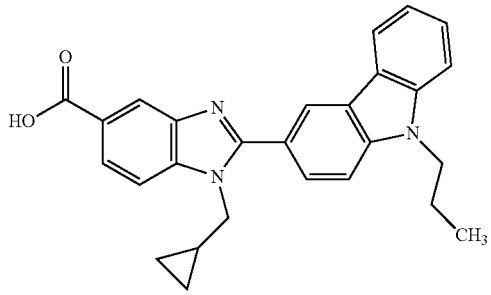 [SMILES: CCCn1c2ccccc2c2cc(-c3nc4cc(C(=O)O)ccc4n3CC3CC3)ccc21]

First, from 9H-carbazole-3-carbaldehyde and 3-bromopropane, analogously to the synthesis of Intermediate 16, 9-propyl-9H-carbazole-3-carbaldehyde was prepared, which was then reacted with ethyl 3-amino-4-[(cyclopropylmethyl)amino]benzoate and subsequently hydrolysed in analogy to Example 9.

$^1$H-NMR (300 MHz, chloroform-d): δ [ppm]=0.18-0.25 (m, 2H), 0.49-0.58 (m, 2H), 1.03 (t, 3H), 1.16-1.28 (m, 1H), 1.99 (m, 2H), 4.29 (d, 2H), 4.36 (t, 2H), 7.28-7.33 (m, 1H), 7.46-7.59 (m, 4H), 7.85 (dd, 1H), 8.14 (t, 2H), 8.52 (s, 1H), 8.67 (s, 1H), COOH not stated.

Example 121

1-[(2,2-Dimethylcyclopropyl)methyl]-2-(9-ethyl-9H-carbazol-3-yl)-1H-benzimidazole-5-carboxylic acid

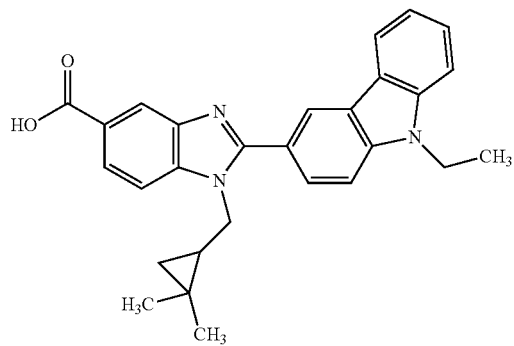 [SMILES: CCn1c2ccccc2c2cc(-c3nc4cc(C(=O)O)ccc4n3CC3CC3(C)C)ccc21]

First, starting from ethyl 4-chloro-3-nitrobenzoate and 1-(2,2-dimethylcycloprop-1-yl)-methanamine, analogously to the synthesis of Intermediate 2, ethyl 3-amino-4-{[(2,2-dimethylcyclopropyl)methyl]amino}benzoate was prepared, which was reacted with 9-ethyl-9H-carbazole-3-carbaldehyde and hydrolysed in analogy to Example 9.

$^1$H-NMR (300 MHz, DMSO-d6): δ [ppm]=0.51 (dd, 2H), 0.70 (d, 1H), 0.85 (d, 6H), 1.37 (t, 3H), 4.26-4.66 (m, 4H), 7.27 (t, 1H), 7.52 (t, 1H), 7.69 (d, 1H), 7.76-7.84 (m, 2H), 7.87-7.95 (m, 2H), 8.25-8.34 (m, 2H), 8.64 (d, 1H).

Example 122

Ethyl 2-(9-ethyl-9H-carbazol-3-yl)-1-(oxetan-3-ylmethyl)-1H-benzimidazole-5-carboxylate

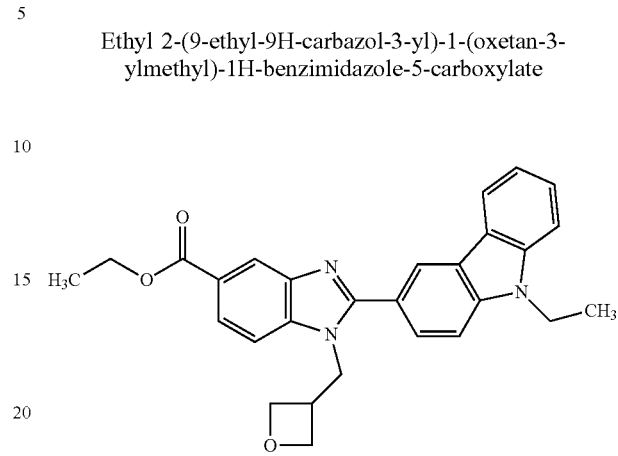

First, starting from ethyl 4-chloro-3-nitrobenzoate and oxetane-3-ylmethanamine, analogously to the synthesis of Intermediate 2, ethyl 3-amino-4-{[oxetan-3-ylmethyl]amino}benzoate was prepared, which was reacted with 9-ethyl-9H-carbazole-3-carbaldehyde in analogy to Example 9.

$^1$H-NMR (300 MHz, DMSO-d6): δ [ppm]=1.38 (q, 6H), 4.01-4.10 (m, 2H), 4.31-4.44 (m, 4H), 4.54 (q, 2H), 4.86 (d, 2H), 7.28 (t, 1H), 7.50-7.58 (m, 1H), 7.70 (d, 1H), 7.80-7.97 (m, 4H), 8.27-8.33 (m, 2H), 8.62 (d, 1H).

Example 123

2-(9-Ethyl-9H-carbazol-3-yl)-1-(oxetan-3-ylmethyl)-1H-benzimidazole-5-carboxylic acid

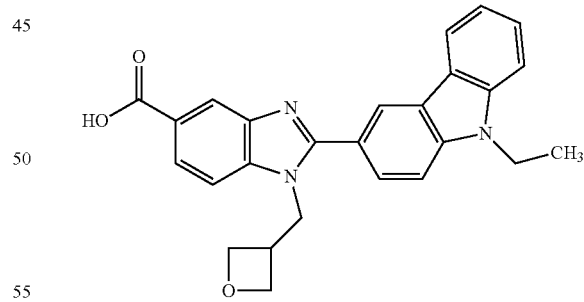

Analogously to Example 2, the title compound was obtained from ethyl 2-(9-ethyl-9H-carbazol-3-yl)-1-(oxetan-3-ylmethyl)-1H-benzimidazole-5-carboxylate.

$^1$H-NMR (300 MHz, DMSO-d6): δ [ppm]=1.39 (t, 3H), 3.22-3.39 (m, 1H), 4.08 (t, 2H), 4.42 (dd, 2H), 4.57 (q, 2H), 4.95 (d, 2H), 7.27-7.35 (m, 1H), 7.56 (t, 1H), 7.74 (d, 1H), 7.88-7.98 (m, 2H), 8.04 (s, 2H), 8.26-8.35 (m, 2H), 8.71 (s, 1H).

Example 124

2-[9-(Cyclobutylmethyl)-9H-carbazol-3-yl]-1-(2-methoxyethyl)-1H-benzimidazole-5-carboxylic acid

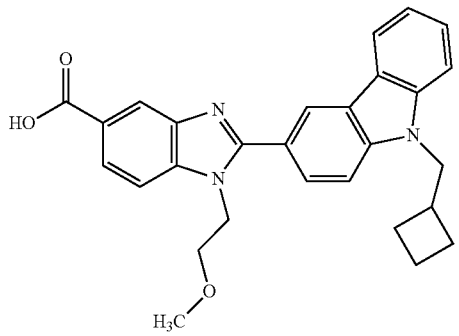 [SMILES: COCCn1c(-c2ccc3c(c2)c2ccccc2n3CC2CCC2)nc2cc(C(=O)O)ccc21]

First, from 9H-carbazole-3-carbaldehyde and 1-cyclobutylmethanamine, analogously to the synthesis of Intermediate 16, 9-(cyclobutylmethyl)-9H-carbazole-3-carbaldehyde was prepared, which was then reacted in analogy to Example 9 with ethyl 3-amino-4-[(2-methoxyethyl)amino]benzoate and subsequently hydrolysed.

$^1$H-NMR (400 MHz, chloroform-d): δ [ppm]=1.89-1.95 (m, 4H), 2.03-2.12 (m, 2H), 2.97-3.06 (m, 1H), 3.34 (s, 3H), 3.85 (t, 2H), 4.40 (d, 2H), 4.54 (t, 2H), 7.28-7.32 (m, 1H), 7.48-7.61 (m, 4H), 7.93 (dd, 1H), 8.10-8.16 (m, 2H), 8.61-8.67 (m, 2H), COOH not stated.

Example 125

2-[9-(Cyclobutylmethyl)-9H-carbazol-3-yl]-1-(cyclopropylmethyl)-1H-benzimidazole-5-carboxylic acid

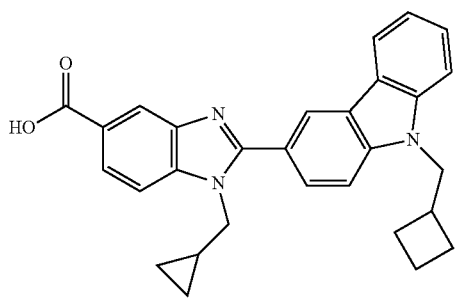 [SMILES: O=C(O)c1ccc2c(c1)nc(-c1ccc3c(c1)c1ccccc1n3CC1CCC1)n2CC1CC1]

First, from 9H-carbazole-3-carbaldehyde and 1-cyclobutylmethanamine, analogously to the synthesis of Intermediate 16, 9-(cyclobutylmethyl)-9H-carbazole-3-carbaldehyde was prepared, which was then reacted with ethyl 3-amino-4-[(cyclopropylmethyl)amino]-benzoate and subsequently hydrolysed in analogy to Example 9.

$^1$H-NMR (400 MHz, chloroform-d): δ [ppm]=0.19-0.25 (m, 2H), 0.51-0.58 (m, 2H), 1.17-1.29 (m, 1H), 1.88-1.97 (m, 4H), 2.03-2.13 (m, 2H), 3.01 (quin, 1H), 4.29 (d, 2H), 4.40 (d, 2H), 7.28-7.32 (m, 1H), 7.48-7.61 (m, 4H), 7.85 (dd, 1H), 8.11-8.17 (m, 2H), 8.51 (d, 1H), 8.68 (s, 1H), COOH not stated.

Example 126

5-{1-[2-(Dimethylamino)ethyl]-2-(9-ethyl-9H-carbazol-3-yl)-1H-benzimidazol-5-yl}-1,3,4-oxadiazol-2(3H)-one

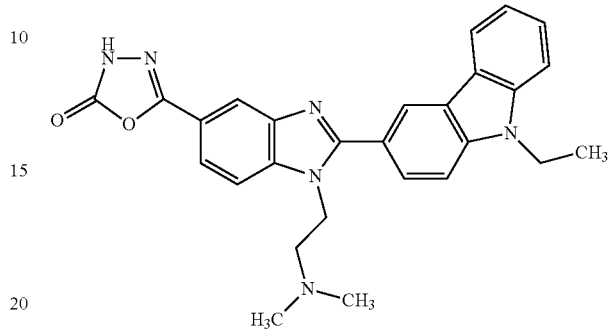

In analogy to Example 106, the title compound (53 mg) was prepared from 100 mg (0.23 mmol) of 1-[2-(dimethylamino)ethyl]-2-(9-ethyl-9H-carbazol-3-yl)-1H-benzimidazole-5-carboxylic acid.

$^1$H-NMR (300 MHz, DMSO-d6), δ [ppm]=1.37 (t, 3H), 2.02 (s, 6H), 2.57-2.65 (m, 2H), 4.47-4.60 (m, 4H), 7.27 (t, 1H), 7.53 (t, 1H), 7.67-7.78 (m, 2H), 7.79-7.89 (m, 2H), 7.93 (d, 1H), 8.05 (s, 1H), 8.29 (d, 1H), 8.67 (s, 1H), NH not stated.

Example 127

2-(9-Ethyl-9H-carbazol-3-yl)-1-(2-methoxyethyl)-1H-benzimidazole-5-sulphonamide

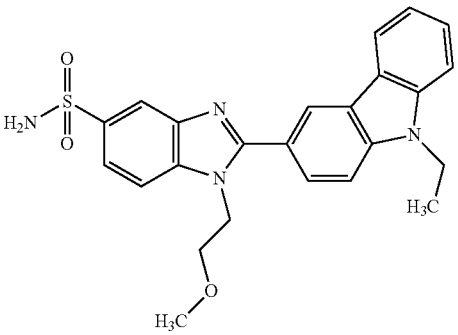 [SMILES: CCn1c2ccccc2c2cc(-c3nc4cc(S(N)(=O)=O)ccc4n3CCOC)ccc21]

In analogy to Example 4/Variant B, the title compound (50 mg, 27%) was prepared from 61 mg (0.27 mmol) of 9H-carbazole-3-carbaldehyde and 100 mg (0.41 mmol) of 3-amino-4-[(2-methoxyethyl)amino]benzenesulphonamide.

$^1$H-NMR (400 MHz, DMSO-d6), δ [ppm]=1.38 (t, 3H), 3.14 (s, 3H), 3.72 (t, 2H), 4.53 (q, 2H), 4.61 (t, 2H), 7.24-7.32 (m, 3H), 7.53 (td, 1H), 7.69 (d, 1H), 7.76 (dd, 1H), 7.81 (d, 1H), 7.88 (d, 1H), 7.95 (dd, 1H), 8.14 (d, 1H), 8.28 (d, 1H), 8.69 (d, 1H).

Example 128

9-Ethyl-3-[1-methyl-5-(1H-1,2,3-triazol-1-yl)-1H-benzimidazole-2-yl]-9H-carbazole

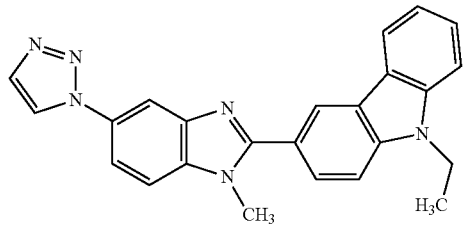 [SMILES: CCn1c2ccccc2c2cc(-c3nc4cc(-n5ccnn5)ccc4n3C)ccc21]

In analogy to Example 4/Variant B, the title compound (20 mg, 5%) was prepared from 157 mg (0.71 mmol) of 9H-carbazole-3-carbaldehyde and 200 mg (1.06 mmol) of $N^1$-methyl-4-(1H-1,2,3-triazol-1-yl)benzene-1,2-diamine.

$^1$H-NMR (400 MHz, DMSO-d6), δ [ppm]=1.37 (t, 3H), 4.05 (s, 3H), 4.54 (q, 2H), 7.24-7.31 (m, 1H), 7.53 (td, 1H), 7.70 (d, 1H), 7.80-7.88 (m, 3H), 7.98-8.03 (m, 2H), 8.19 (t, 1H), 8.34 (d, 1H), 8.73 (d, 1H), 8.89 (d, 1H).

Example 129

2-(9-Ethyl-9H-carbazol-3-yl)-N,1-dimethyl-1H-benzimidazole-5-sulphonamide

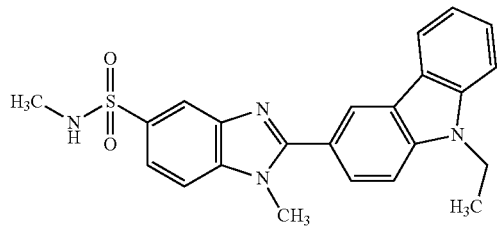 [SMILES: CCn1c2ccccc2c2cc(-c3nc4cc(S(=O)(=O)NC)ccc4n3C)ccc21]

In analogy to Example 4/Variant B, the title compound (150 mg, 36%) was prepared from 138 mg (0.62 mmol) of 9H-carbazole-3-carbaldehyde and 200 mg (0.93 mmol) of 3-amino-N-methyl-4-(methylamino)benzenesulphonamide.

$^1$H-NMR (400 MHz, DMSO-d6), δ [ppm]=1.37 (t, 3H), 2.41 (d, 3H), 4.03 (s, 3H), 4.54 (q, 2H), 7.25-7.30 (m, 1H), 7.39 (q, 1H), 7.53 (ddd, 1H), 7.67-7.74 (m, 2H), 7.85 (dd, 2H), 7.99 (dd, 1H), 8.09 (d, 1H), 8.33 (d, 1H), 8.72 (d, 1H).

Example 130

2-(9-Ethyl-9H-carbazol-3-yl)-1-[2-(trifluoromethoxy)ethyl]-1H-benzimidazole-5-carboxylic acid

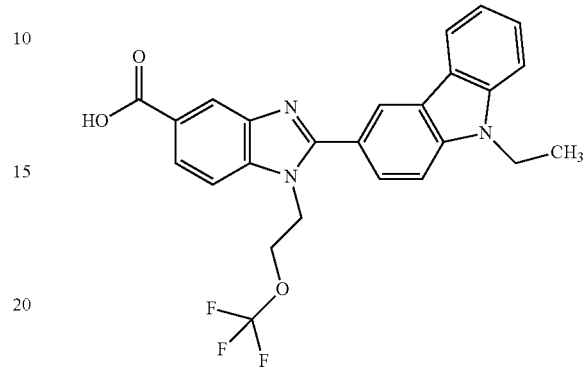

In analogy to the synthesis of Intermediate 29, ethyl 3-amino-4-{[2-(trifluoro-methoxy)ethyl]amino}benzoate was first prepared from 2-(trifluoromethoxy)ethanamine and ethyl 4-chloro-3-nitrobenzoate, which was then reacted analogously to Example 4/Variant B with 9H-carbazole-3-carbaldehyde to give ethyl 2-(9-ethyl-9H-carbazol-3-yl)-1-[2-(trifluoromethoxy)ethyl]-1H-benzimidazole-5-carboxylate. After the hydrolysis of this ester with sodium hydroxide solution, the title compound was obtained analogously to Example 2.

$^1$H-NMR (400 MHz, DMSO-d6), δ [ppm]=1.35-1.41 (m, 3H), 4.40 (t, 2H), 4.54 (q, 2H), 4.80 (t, 2H), 7.27 (t, 1H), 7.53 (td, 1H), 7.69 (d, 1H), 7.79-7.89 (m, 3H), 7.94 (dd, 1H), 8.25-8.30 (m, 2H), 8.60 (d, 1H), COOH not stated.

Example 131

1-(Cyclopropylmethyl)-2-(9-ethyl-1-methyl-9H-beta-carbolin-3-yl)-1H-benzimidazole-5-carboxylic acid

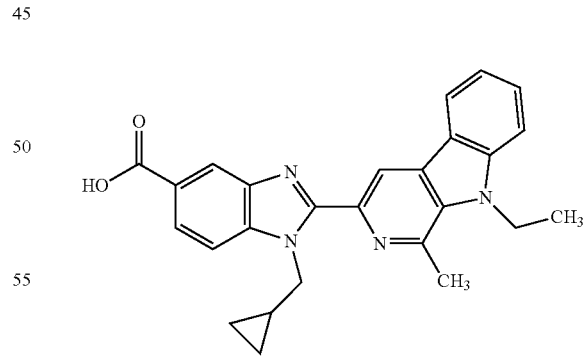

111 mg (0.44 mmol) of 9-ethyl-1-methyl-9H-beta-carbolin-3-carboxylic acid were added to 1 ml of toluene, treated with 0.38 ml (5.24 mmol) of thionyl chloride, heated to reflux for 3 h and then concentrated in vacuo. The residue was taken up in 3.8 ml of acetonitrile, 180 mg (0.87 mmol) of 3-amino-4-[(cyclopropylmethyl)amino]benzoic acid were added and the mixture was heated to 180° C. in a microwave for 30 min. The mixture was concentrated in vacuo and purified by means of preparative HPLC. In this way, 5 mg (3%) of the title compound were obtained.

¹H-NMR (400 MHz, DMSO-d6), δ [ppm]=0.42-0.51 (m, 4H), 1.39-1.46 (m, 3H), 1.47-1.54 (m, 1H), 3.12-3.19 (m, 3H), 4.71-4.79 (m, 2H), 4.93 (d, 2H), 7.36 (t, 1H), 7.64-7.71 (m, 1H), 7.78-7.86 (m, 2H), 7.90-7.97 (m, 1H), 8.29 (d, 1H), 8.46 (d, 1H), 9.02 (s, 1H), COOH not stated.

Example 132

2-(9-Ethyl-9H-carbazol-3-yl)-1-(oxetan-2-ylmethyl)-1H-benzimidazole-5-carboxylic acid

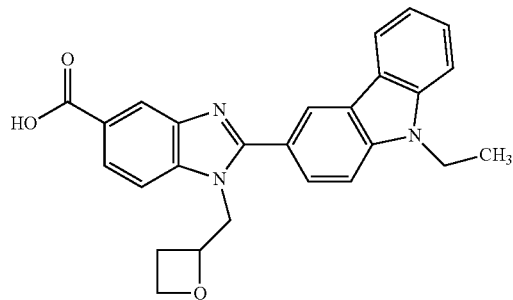 [SMILES: CCn1c2ccccc2c2cc(-c3nc4cc(C(=O)O)ccc4n3CC3CCO3)ccc21]

200 mg (0.54 mmol) of methyl 2-(9-ethyl-9H-carbazol-3-yl)-1H-benzimidazole-5-carboxylate were added to 3 ml DMF, treated with 245 mg (1.62 mmol) of 2-(bromomethyl)oxetane and 530 mg (1.62 mmol) of caesium carbonate and stirred at 60° C. for 2.5 h. After cooling to RT, water was added, the mixture was extracted successively with ethyl acetate and toluene, and the organic phases were dried with sodium sulphate and concentrated in vacuo.

The crude product (0.37 g) thus obtained was taken up in 5 ml of THF and 15 ml of methanol, treated with 170 mg (4.3 mmol) of sodium hydroxide and stirred at 40° C. for 24 h. The mixture was neutralized with 2M hydrochloric acid, and the deposited precipitate was separated, dried and purified by means of preparative HPLC. In this way, 21 mg (6%) of the title compound were obtained.

¹H-NMR (400 MHz, DMSO-d6), δ [ppm]=1.39 (t, 3H), 2.31-2.43 (m, 1H), 2.62-2.73 (m, 1H), 4.40 (dt, 1H), 4.47-4.62 (m, 4H), 4.79 (dd, 1H), 5.15 (qd, 1H), 7.27 (t, 1H), 7.49-7.55 (m, 1H), 7.68 (d, 1H), 7.77-7.82 (m, 2H), 7.90 (dd, 1H), 7.96 (dd, 1H), 8.22-8.27 (m, 2H), 8.71 (d, 1H), COOH not stated.

Example 133

2-(9-Ethyl-9H-carbazol-3-yl)-1-(tetrahydrofuran-2-ylmethyl)-1H-benzimidazole-5-carboxylic acid

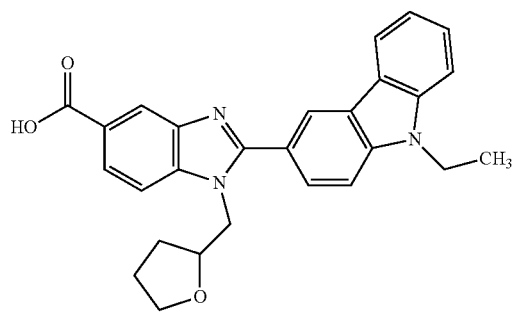 [SMILES: CCn1c2ccccc2c2cc(-c3nc4cc(C(=O)O)ccc4n3CC3CCCO3)ccc21]

Analogously to the procedure of Example 132, starting from 200 mg (0.54 mmol) of methyl 2-(9-ethyl-9H-carbazol-3-yl)-1H-benzimidazole-5-carboxylate and 196 mg (1.62 mmol) of 2-(chloromethyl)tetrahydrofuran, 17 mg of the title compound were obtained.

¹H-NMR (400 MHz, DMSO-d6), δ [ppm]=1.38 (t, 3H), 1.46-1.56 (m, 1H), 1.75 (quin, 2H), 1.88-1.99 (m, 1H), 3.54-3.68 (m, 2H), 4.19-4.28 (m, 1H), 4.39-4.57 (m, 4H), 7.27 (t, 1H), 7.49-7.55 (m, 1H), 7.68 (d, 1H), 7.79 (dd, 2H), 7.87-7.96 (m, 2H), 8.24-8.28 (m, 2H), 8.67 (d, 1H), COOH not stated.

Example 134

2-(9-Ethyl-9H-carbazol-3-yl)-1-[(2R)-2-hydroxy-3-methoxypropyl]-1H-benzimidazole-5-carboxylic acid

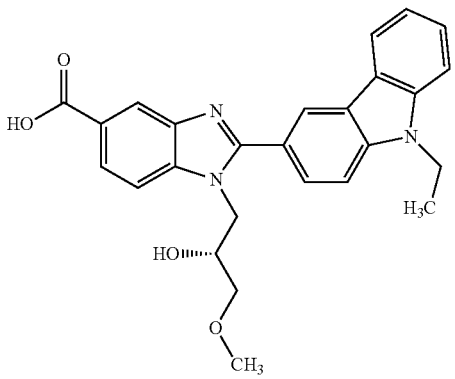 [SMILES: CCn1c2ccccc2c2cc(-c3nc4cc(C(=O)O)ccc4n3C[C@@H](O)COC)ccc21]

Analogously to the procedure of Example 132, starting from 200 mg (0.54 mmol) of methyl-2-(9-ethyl-9H-carbazol-3-yl)-1H-benzimidazole-5-carboxylate and 143 mg (1.62 mmol) of (2R)-2-(methoxymethyl)oxirane, 57 mg of the title compound were obtained.

¹H-NMR (400 MHz, DMSO-d6), δ [ppm]=1.38 (t, 3H), 3.19 (s, 3H), 3.31 (m, 3H), 4.34-4.43 (m, 1H), 4.46-4.57 (m, 3H), 7.26 (t, 1H), 7.49-7.54 (m, 1H), 7.65-7.74 (m, 2H), 7.78 (d, 1H), 7.90 (dd, 1H), 8.03 (dd, 1H), 8.22-8.28 (m, 2H), 8.74 (d, 1H), COOH and OH not stated.

Example 135

2-(9-Ethyl-9H-carbazol-3-yl)-1-[(2S)-2-hydroxy-3-methoxypropyl]-1H-benzimidazole-5-carboxylic acid

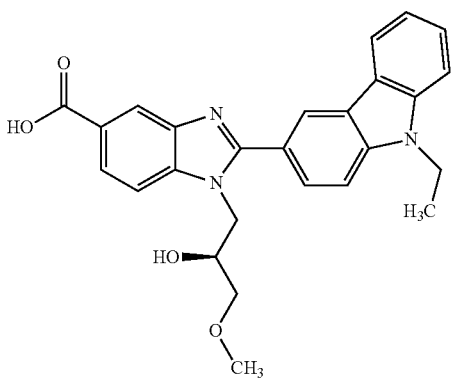 [SMILES: CCn1c2ccccc2c2cc(-c3nc4cc(C(=O)O)ccc4n3C[C@H](O)COC)ccc21]

Analogously to the procedure of Example 132, starting from 200 mg (0.54 mmol) of methyl 2-(9-ethyl-9H-carbazol-3-yl)-1H-benzimidazole-5-carboxylate and 143 mg (1.62 mmol) of (2S)-2-(methoxymethyl)oxirane, 20 mg of the title compound were obtained.

$^1$H-NMR (500 MHz, DMSO-d6), δ [ppm]=1.38 (t, 3H), 3.19 (s, 3H), 3.27-3.35 (m, 3H), 4.35-4.56 (m, 4H), 7.26 (t, 1H), 7.49-7.54 (m, 1H), 7.66-7.73 (m, 2H), 7.78 (d, 1H), 7.90 (dd, 1H), 8.03 (dd, 1H), 8.23-8.27 (m, 2H), 8.74 (d, 1H), COOH and OH not stated.

Example 136

2-(9-Ethyl-9H-carbazol-3-yl)-1-[2-(methylsulphonyl)ethyl]-1H-benzimidazole-5-carboxylic acid

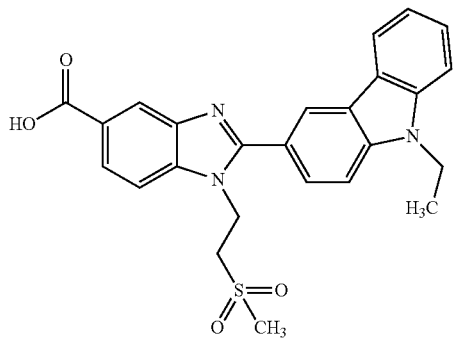 [SMILES: CCn1c2ccccc2c2cc(-c3nc4cc(C(=O)O)ccc4n3CCS(C)(=O)=O)ccc21]

Analogously to the procedure of Example 132, starting from 200 mg (0.54 mmol) of methyl 2-(9-ethyl-9H-carbazol-3-yl)-1H-benzimidazole-5-carboxylate and 304 mg (1.62 mmol) of 1-bromo-2-(methylsulphonyl)ethane, 4 mg of the title compound were obtained.

$^1$H-NMR (500 MHz, DMSO-d6), δ [ppm]=1.39 (t, 3H), 3.00 (s, 3H), 3.81-3.87 (m, 2H), 4.54 (q, 2H), 4.81-4.86 (m, 2H), 7.27 (t, 1H), 7.50-7.55 (m, 1H), 7.69 (d, 1H), 7.79-7.84 (m, 2H), 7.95 (dd, 2H), 8.27 (d, 1H), 8.29-8.34 (m, 1H), 8.64 (d, 1H), COOH not stated.

Example 137

1-(2-Cyclopropyl-2-hydroxyethyl)-2-(9-ethyl-9H-carbazol-3-yl)-1H-benzimidazole-5-carboxylic acid

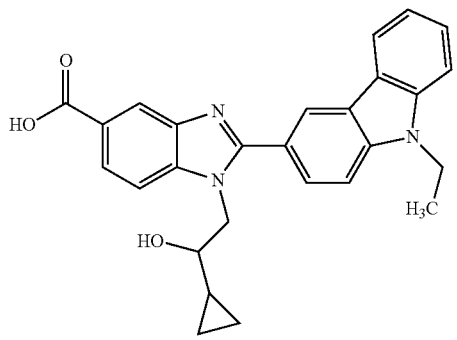 [SMILES: CCn1c2ccccc2c2cc(-c3nc4cc(C(=O)O)ccc4n3CC(O)C3CC3)ccc21]

Analogously to the procedure of Example 132, starting from 200 mg (0.54 mmol) of methyl 2-(9-ethyl-9H-carbazol-3-yl)-1H-benzimidazole-5-carboxylate and 137 mg (1.62 mmol) of 2-cyclopropyloxirane, 10 mg of the title compound were obtained.

$^1$H-NMR (300 MHz, DMSO-d6), δ [ppm]=−0.04 (m, 1H), 0.14-0.33 (m, 3H), 0.67-0.77 (m, 1H), 1.37 (t, 3H), 3.60 (t, 1H), 4.45-4.59 (m, 4H), 5.12 (d, 1H), 7.27 (t, 1H), 7.52 (t, 1H), 7.66-7.82 (m, 3H), 7.89 (dd, 1H), 8.00 (dd, 1H), 8.23-8.30 (m, 2H), 8.73 (d, 1H), COOH not stated.

Example 138

1-[(2S)-2,3-Dihydroxypropyl]-2-(9-ethyl-9H-carbazol-3-yl)-1H-benzimidazole-5-carboxylic acid

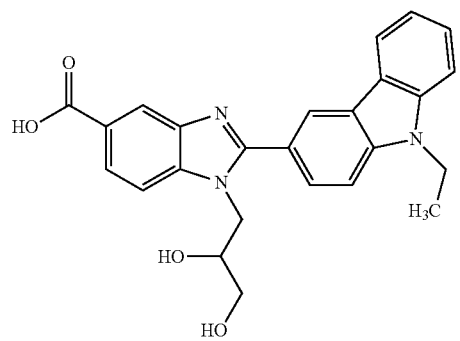 [SMILES: CCn1c2ccccc2c2cc(-c3nc4cc(C(=O)O)ccc4n3CC(O)CO)ccc21]

Analogously to the procedure of Example 132, starting from 200 mg (0.54 mmol) of methyl 2-(9-ethyl-9H-carbazol-3-yl)-1H-benzimidazole-5-carboxylate and 118 mg (1.62 mmol) of (2S)-oxiran-2-ylmethanol, 9 mg of the title compound were obtained.

$^1$H-NMR (400 MHz, DMSO-d6): δ [ppm]=1.38 (t, 3H), 3.34-3.49 (m, 2H), 4.02 (d, 1H), 4.34 (dd, 1H), 4.48-4.57 (m, 3H), 7.26 (t, 1H), 7.51 (t, 1H), 7.67 (d, 1H), 7.75 (dd, 2H), 7.90 (d, 1H), 8.07 (dd, 1H), 8.23-8.28 (m, 2H), 8.78 (s, 1H), COOH and OH not stated.

Examples 139 and 140

1-[(2R)-1,4-Dioxan-2-ylmethyl]-2-(9-ethyl-9H-carbazol-3-yl)-1H-benzimidazole-5-carboxylic acid 1-[(2S)-1,4-Dioxan-2-ylmethyl]-2-(9-ethyl-9H-carbazol-3-yl)-1H-benzimidazole-5-5 carboxylic acid

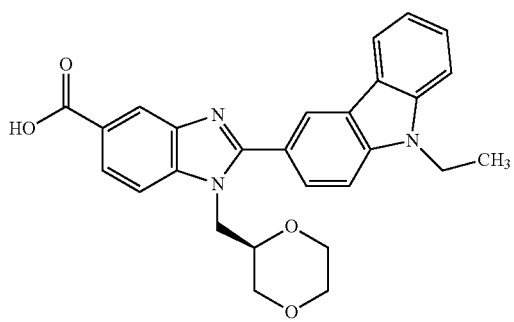

-continued

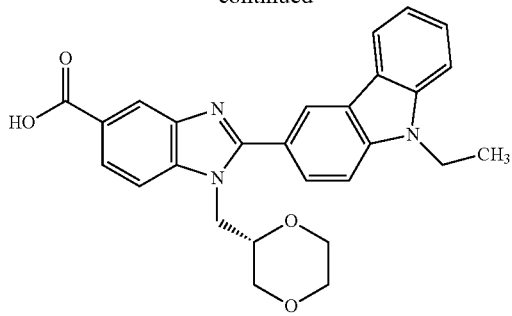

In analogy to the synthesis of Intermediate 29, rac-ethyl 3-amino-4-[(1,4-dioxan-2-ylmethyl)amino]benzoate was first prepared from rac-1-(1,4-dioxan-2-yl)methanamine and ethyl 4-chloro-3-nitrobenzoate, which was then reacted analogously to Example 4/Variant B with 9H-carbazole-3-carbaldehyde to give rac-ethyl-1-(1,4-dioxan-2-ylmethyl)-2-(9-ethyl-9H-carbazol-3-yl)-1H-benzimidazole-5-carboxylate. After the hydrolysis of the ester with sodium hydroxide solution analogously to Example 2, the racemic title compound was obtained. This was separated by means of chiral preparative HPLC into the enantiomers 1 and 2 of the title compound.

Enantiomer 1
$^1$H-NMR (300 MHz, DMSO-d6), δ [ppm]=1.38 (t, 3H), 3.17-3.29 (m, 1H), 3.37-3.49 (m, 2H), 3.62 (dd, 2H), 3.73 (dd, 1H), 3.96 (d, 1H), 4.42-4.59 (m, 4H), 7.28 (t, 1H), 7.48-7.58 (m, 1H), 7.70 (d, 1H), 7.76-7.85 (m, 2H), 7.87-8.02 (m, 2H), 8.22-8.33 (m, 2H), 8.72 (d, 1H), COOH not stated.

Enantiomer 2
$^1$H-NMR (300 MHz, DMSO-d6), δ [ppm]=1.38 (t, 3H), 3.17-3.29 (m, 1H), 3.37-3.49 (m, 2H), 3.62 (dd, 2H), 3.73 (dd, 1H), 3.96 (d, 1H), 4.42-4.59 (m, 4H), 7.28 (t, 1H), 7.48-7.58 (m, 1H), 7.70 (d, 1H), 7.76-7.85 (m, 2H), 7.87-8.02 (m, 2H), 8.22-8.33 (m, 2H), 8.72 (d, 1H), COOH not stated.

Example 141

2-(9-Ethyl-6-methyl-9H-carbazol-3-yl)-1-(2-methoxyethyl)-4-methyl-1H-benzimidazole-5-carboxylic acid

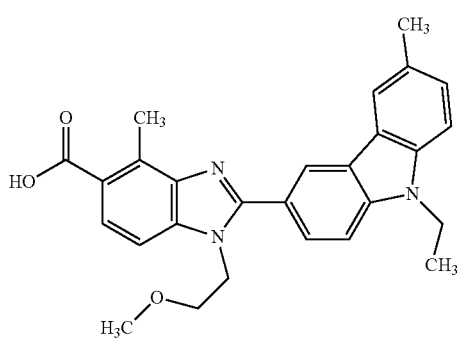 [SMILES: CCn1c2ccc(Cl)cc2c2cc(-c3nc4c(C)c(C(=O)O)ccc4n3CCOC)ccc21]

In analogy to Example 4/Variant B, methyl 2-(9-ethyl-6-methyl-9H-carbazol-3-yl)-1-(2-methoxyethyl)-4-methyl-1H-benzimidazole-5-carboxylate was first prepared from 1.0 g (4.2 mmol) of methyl 3-amino-4-[(2-methoxyethyl)amino]-2-methylbenzoate and 1.0 g (4.2 mmol) of 9-ethyl-6-methyl-9H-carbazole-3-carbaldehyde (CAS No 122060-05-3).

$^1$H-NMR (400 MHz, DMSO-d6), δ [ppm]=1.35 (t, 3H), 2.50 (s, 3H), 2.89 (s, 3H), 3.12 (s, 3H), 3.69 (t, 2H), 3.87 (s, 3H), 4.49 (q, 2H), 4.55 (t, 2H), 7.35 (dd, 1H), 7.58 (t, 2H), 7.75 (d, 1H), 7.83 (d, 1H), 7.90 (dd, 1H), 8.06 (s, 1H), 8.59 (d, 1H).

This was subsequently reacted analogously to Example 2 to give 2-(9-ethyl-6-methyl-9H-carbazol-3-yl)-1-(2-methoxyethyl)-4-methyl-1H-benzimidazole-5-carboxylic acid. (920 mg, 50%).

$^1$H-NMR (300 MHz, DMSO-d6), δ [ppm]=1.35 (t, 3H), 2.49 (s, 3H), 2.89 (s, 3H), 3.12 (s, 3H), 3.69 (t, 2H), 4.43-4.59 (m, 4H), 7.34 (dd, 1H), 7.56 (m, 2H), 7.75 (d, 1H), 7.81-7.93 (m, 2H), 8.07 (s, 1H), 8.59 (d, 1H), 12.25-12.95 (br., 1H).

Example 142

2-(6-Chloro-9-ethyl-9H-carbazol-3-yl)-1-(2-methoxyethyl)-4-methyl-1H-benzimidazole-5-carboxylic acid

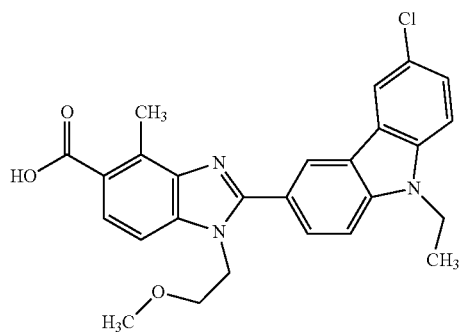

In analogy to Example 4/Variant B, methyl 2-(6-chloro-9-ethyl-9H-carbazol-3-yl)-1-(2-methoxyethyl)-4-methyl-1H-benzimidazole-5-carboxylate (5.3 g, 81%) was first prepared from 3.0 g (12.6 mmol) of methyl 3-amino-4-[(2-methoxyethyl)amino]-2-methylbenzoate and 3.2 g (12.6 mmol) of 6-chloro-9-ethyl-9H-carbazole-3-carbaldehyde.

$^1$H-NMR (300 MHz, DMSO-d6), δ [ppm]=1.36 (t, 3H), 2.88 (s, 3H), 3.09 (s, 3H), 3.66 (t, 2H), 3.86 (s, 3H), 4.48-4.60 (m, 4H), 7.53 (dd, 1H), 7.60 (d, 1H), 7.73 (d, 1H), 7.79-7.87 (m, 2H), 7.96 (dd, 1H), 8.41 (d, 1H), 8.69 (d, 1H).

This was subsequently reacted analogously to Example 2 to give 2-(6-chloro-9-ethyl-9H-carbazol-3-yl)-1-(2-methoxyethyl)-4-methyl-1H-benzimidazole-5-carboxylic acid. (3.4 g, 64%).

$^1$H-NMR (400 MHz, DMSO-d6), δ [ppm]=1.36 (t, 3H), 2.89 (s, 3H), 3.10 (s, 3H), 3.68 (t, 2H), 4.50-4.62 (m, 4H), 7.54 (dd, 1H), 7.63 (d, 1H), 7.74 (d, 1H), 7.82-7.91 (m, 2H), 7.98 (dd, 1H), 8.41 (d, 1H), 8.71 (d, 1H), 12.52-12.80 (br., 1H).

Example 143

2-(8-Chloro-9-ethyl-9H-carbazol-3-yl)-1-(2-methoxyethyl)-4-methyl-1H-benzimidazole-5-carboxylic acid

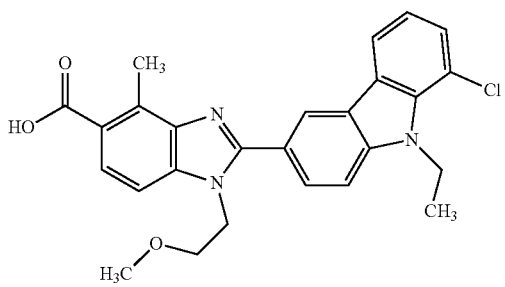 [SMILES: CCn1c2ccc(-c3nc4c(C)c(C(=O)O)ccc4n3CCOC)cc2c2cccc(Cl)c21]

In analogy to Example 4/Variant B, methyl 2-(8-chloro-9-ethyl-9H-carbazol-3-yl)-1-(2-methoxyethyl)-4-methyl-1H-benzimidazole-5-carboxylate (2.12 g, 99%) was first prepared from 1.0 g (4.3 mmol) of methyl 3-amino-4-[(2-methoxyethyl)amino]-2-methylbenzoate and 740 mg (2.9 mmol) of 8-chloro-9-ethyl-9H-carbazole-3-carbaldehyde.

$^1$H-NMR (400 MHz, DMSO-d6), δ [ppm]=1.43 (t, 3H), 2.89 (s, 3H), 3.11 (s, 3H), 3.66-3.70 (m, 2H), 3.87 (s, 3H), 4.55 (t, 2H), 4.83-4.90 (m, 2H), 7.26 (t, 1H), 7.54 (dd, 1H), 7.61 (d, 1H), 7.84 (d, 1H), 7.88 (d, 1H), 7.96-8.01 (m, 1H), 8.30 (dd, 1H), 8.69 (d, 1H).

This was subsequently reacted analogously to Example 2 to give 2-(8-chloro-9-ethyl-9H-carbazol-3-yl)-1-(2-methoxyethyl)-4-methyl-1H-benzimidazole-5-carboxylic acid. (700 mg, 33%).

$^1$H-NMR (300 MHz, DMSO-d6), δ [ppm]=1.43 (t, 3H), 2.89 (s, 3H), 3.11 (s, 3H), 3.69 (t, 2H), 4.54 (t, 2H), 4.86 (q, 2H), 7.26 (t, 1H), 7.51-7.60 (m, 2H), 7.82-7.91 (m, 2H), 7.99 (dd, 1H), 8.27-8.33 (m, 1H), 8.69 (d, 1H), 12.56 (br. s., 1H).

BIOLOGICAL EXAMPLES

1. Syngeneic Mouse Endometriosis Model:

The syngeneic induction of endometriosis in mice is a common animal model for testing the efficacy of substances for the treatment of endometriosis. Endometriosis is induced experimentally by transplantation of murine uterus fragments of a donor mouse of the same strain into the abdominal cavity of the recipient mouse. Female mice of the balb/c strain were used. The cycle of the mouse is determined by means of a vaginal smear. Donor animals which are in oestrus are used exclusively. The donor animals are sacrificed and the uterine horns are removed and subsequently cut open longitudinally. From the uteri, using a punch 2 mm bioptates are punched out, which are subsequently sewn into the recipient animal. The recipient animals are anaesthetised and subjected to a laparotomy. During the intervention, 6 uterus punchings of a donor mouse are sewn onto the parietal peritoneum of the recipient mouse. On the day after this intervention, the 4-week treatment with the substances to be tested begins. After 28 days, the animals are opened up in a final laparotomy and the lesion sizes are determined. The grown lesions are photographically recorded and the area is measured by means of AxioVision Software. Per treatment group, 14 animals are employed.

In the s.c. approach (FIG. 1), the substance according to the invention (Example 4) was tested in 4 different dose schemes and the lesion size was assessed in comparison to the animals treated with vehicle. The following doses were tested: 0.4, 3, 10 and 50 mg/kg/day. The mean lesion sizes (in mm$^2$) per animal are shown (y-axis) in FIG. 2.

2. Flow Cytometry:

For the obtainment of the cells from the peritoneum, 3 ml of cold PBS (phosphate buffered saline) were injected into the peritoneum of the dead animal and removed again after gentle massage of the abdomen. The cells from this peritoneal lavage were spun down at 1400 rpm for 2 min and taken up again in 500 µl of PBS containing 2% FCS (fetal calf serum). 100 µl of this cell suspension were used for each stain with different antibody-fluorochrome conjugate mixes. The cells were spun down for this purpose in 96 hole plates again and resuspended in 50 µl of an antibody solution in the 1:300 diluted anti CD11b-Pacific Blue (eBioscience), 1:200 diluted anti F4/80-PE (eBioscience), 1:200 diluted anti Gr1-APC-Cy7 (BD Pharmigen), 1:400 diluted anti CD11c-PE-Cy7 (BD Pharmigen) and 1:400 diluted anti MHCII-FITC (BD Pharmigen) and stored on ice in the dark for 20 min. Subsequently, 150 µl of PBS containing 2% FCS were added and the cells were once again centrifuged down at 1400 rpm for 2 min. The 200 µl of supernatant were discarded and the cells were washed with 200 µl of PBS containing 2% FCS and once again centrifuged off.

Subsequently, they were taken up in 200 µl of PBS containing 2% FCS and 1:5000 diluted 5 mg/ml DAPI (Sigma) and the fluorescence intensity of the individual fluorochromes per cell was measured with a FACS Canto II flow cytometer. The average intensity of MHCII-FITC on all DAPI-negative F4/80 and CD11b double-positive macrophages per mouse is shown.

3. Detection of the Antagonism of the Human Prostaglandin E2 (Subtype EP$_4$) Receptor Signal 3. 1 Detection Principle Detection of the Antagonism of the hEP4 Signal The binding of the agonist prostaglandin E2 (PGE2) to the EP4 subtype of human hPGE2-R (hEP4-R) induces the activation of membrane-bound adenylate cyclases and thus the formation of cAMP. In the presence of the phosphodiesterase inhibitor IBMX, this cAMP accumulates intracellularly and is employed in a competitive detection procedure after cell lysis. In this procedure, it competes with a fluorescence-labelled cAMP (cAMP-d2) for binding to an Eu cryptate-labelled anti-cAMP antibody. In the absence of cellular cAMP, a complex is formed between the Eu cryptate-labelled anti-cAMP antibody and the cAMP-d2 molecule, which after excitation at 337 nm makes possible an energy transfer based on FRET (fluorescence resonance energy transfer) to the cAMP-d2 tracer and leads to a long-lasting fluorescence signal (emission at 665 and 620 nm). This signal is time-resolved, i.e. measured in a suitable measuring apparatus after decay of the background fluorescence (time resolved; TR-FRET). The wave ratio determination (emission 665 nm/emission 620 nm*10000) moreover makes it possible to standardize individual measurement differences in the added amounts of the detection reagents.

By means of prostaglandin E2 administration and increase in the intracellular cAMP, a lowering of the FRET signal occurs, which in the case of an antagonistic substance action increases again.

3.2. Detection Procedure 3.2.1 Test for Antagonism (Data Per Well of a 384 Hole Plate):

4 µl of a cell suspension (2500 cells/well) expressing hEP4, which moreover already contains the cAMP-D2 tracer, are added to the substance solutions (50 nl; 100% DMSO) introduced into a test plate, After a 20 minute preincubation at room temperature, 2 µl of a 3xPGE2 solution are added and the mixture is incubated in the presence of an EC80 concentration of the agonist (0.4 nM) for a further 60 min at room temperature (volume: ~6 µl), before the overall reaction is subsequently stopped by addition of 2 µl of lysis buffer (volume: ~8 µl). A further 20 min at room temperature later, the cell lysate is measured according to the manufacturer's instructions in a TR-FRET-suitable measuring apparatus (compare cAMP HTRF assay kit: Cisbio International 62AM6PEJ high range)

3.2.2 Test for Antagonism (Data Per Well of a 384-hole Plate):

4 µl of a cell suspension (2500 cells/well) expressing the hEP4, which moreover already contains the cAMP-D2 tracer, are added to the substance solutions (50 nl; 100% DMSO) introduced into a test plate. After a 20-minute preincubation at room temperature, 2 µl of cell medium are added and the mixture is incubated for a further 60 min at room temperature (volume: ~6 µl), before the entire reaction is subsequently stopped by addition of 2 µl of lysis buffer (volume: ~8 µl). A further 20 min at room temperature later, the cell lysate is measured according to the manufacturer's instructions in a TR-FRET-suitable measuring apparatus (cf. cAMP HTRF assay kit: Cisbio International 62AM6PEJ high range)

4. Detection of the Antagonism of the Human Prostaglandin E2 (Subtype EP2) Receptor Signal 4.1 Detection Principle The binding of PGE2 to the EP2 subtype of the human PGE2 receptor induces the activation of membrane-bound adenylate cyclases and leads to the formation of cAMP. In the presence of the phosphodiesterase inhibitor IBMX, the cAMP accumulated on account of this stimulation and released by means of cell lysis is employed in a competitive detection procedure. In this test, the cAMP present in the lysate competes with a fluorescence-labelled cAMP (cAMP-d2) for binding to an Eu cryptate-labelled anti-cAMP antibody.

In the absence of cellular cAMP, a maximum signal results which is to be attributed to the binding of this cAMP-d2 molecule to the antibody. After excitation of the cAMP-d2 molecule at 337 nm, a fluorescence resonance energy transfer (FRET) to the Eu cryptate molecules of the (thus labelled) anti-cAMP antibody occurs, followed by a long-lasting emission signal at 665 nm (and at 620 nM). Both signals are temporally shifted in a suitable measuring apparatus, i.e. measured after decay of the background fluorescence. Any increase in the low FRET signal caused by prostaglandin $E_2$ administration (measured as a well ratio change=$\text{Emission}_{665nm}/\text{Emission}_{620nm}$* 10000) shows the effect of antagonists.

4.2. Detection Procedure 4.2.1. Test for Antagonism (Data Per Well of a 384-hole Plate):

4 µl of a cAMP-d2/cell suspension (625000 cells/ml) were added to a test plate containing the substance solutions already initially introduced (0.05 µl; 100% DMSO, concentration range from 0.8 nM-16.5 µM). After a 20-minute preincubation at room temperature, 2 µl of a 3xPGE2 solution (1.5 nM, in PBS-IBMX) were added and incubated in the presence of the agonist for a further 60 min at room temperature (volume: ~6 µl). Subsequently, the reaction was stopped by addition of 2 µl of lysis buffer and incubated for a further 20 min at room temperature before the actual measurement (volume: ~8 µl).

5. Detection of the Antagonism of the Human Prostaglandin D Receptor Signal 5.1 Detection Principle The binding of prostaglandin D2 to the human PGD receptor induces the activation of membrane-bound adenylate cyclases and leads to the formation of cAMP. In the presence of the phosphodiesterase inhibitor IBMX, the cAMP accumulated on account of this stimulation and released by means of cell lysis is employed in a competitive detection procedure. In this test, the cAMP present in the lysate competes with a fluorescence-labelled cAMP (cAMP-d2) for binding to an Eu cryptate labelled anti-cAMP antibody.

In the absence of cellular cAMP, a maximum signal results, which is to be attributed to the binding of this cAMP-d2 molecule to the antibody. After excitation of the cAMP-d2 molecule at 337 nm, a fluorescence-resonance energy transfer (FRET) occurs to the Eu cryptate molecules of the (thus labelled) anti-cAMP antibody, followed by a long-lasting emission signal at 665 nm (and at 620 nM). Both signals are temporally shifted in a suitable measuring apparatus, i.e. measured after decay of the background fluorescence. Any increase in the low FRET signal caused by prostaglandin E2 administration (measured as a well ratio change=$\text{Emission}_{665nm}/\text{Emission}_{620nm}$* 10000) shows the effect of antagonists.

5.2. Detection Procedure 5.2.1. Test for Antagonism (Details Per Well of a 384-hole Plate):

4 µl of a cAMP-d2/cell suspension (625000 cells/ml) were added to a test plate containing the substance solutions already initially introduced (0.05 µl; 100% DMSO, concentration range from 0.8 nM-16.5 µM). After a 20-minute preincubation at room temperature (RT), 2 µl of a 3xPGD2 solution (6 nM, in PBS-IBMX) were added and incubated in the presence of the agonist for a further 30 min at RT (volume: ~6 µl). Subsequently, the reaction was stopped by addition of 2 µl of lysis buffer and incubated for a further 20 min at RT before the actual measurement (volume: ~8 µl).

FIGURES

FIG. 1: Preventive endometriosis model: s.c. experiment 1

The use of the compound according to the invention (Example 4) after subcutaneous administration in the dose range mentioned led to a significant reduction of the endometrial lesions in the endometriosis model in the mouse. Statistics: 1-way ANOVA followed by Tukey Post-Hoc test,*** $p<0.005$ vs vehicle, * $p<0.05$ vs vehicle; 3 outliers (GRUBBS test) excluded (1 animal of groups 0.4/2/10 in each case).

FIG. 2: Preventive endometriosis model (p.o. experiment)

The use of the compound according to the invention (Example 4) after oral administration in the dose range mentioned led to a significant reduction of the endometrial lesions. Statistics: ** $p<0.01$, unpaired t-test, excluded animals: 1 animal of the control group and 3 animals in the treatment group because of growth of the lesions on the intestine.

FIG. 3: Macrophage activation

The p.o. administration of Example 4 in the endometriosis model in the mouse led to a highly significant reduced number of activated macrophages in the peritoneal fluid in comparison to the vehicle control (detection in FACS) **** $p<0.001$ in the t-test.

TABLE 1

Antagonism of the human EP4 receptor by the compounds according to the invention

| Example | Antagonism hEP4 $IC_{50}$ [M] |
|---|---|
| 1 | 3.1E−6 |
| 2 | 3.12E−7 |
| 3 | 1.75E−7 |
| 4 | 5.59E−9 |
| 5 | 4.04E−7 |
| 6 | 1.44E−8 |
| 7 | 1.43E−6 |
| 8 | 1.97E−8 |
| 9 | 7.12E−8 |
| 10 | 1.03E−8 |
| 11 | 6.36E−9 |
| 12 | 1.02E−8 |
| 13 | 1.8E−8 |
| 14 | 3.34E−8 |
| 15 | 2.38E−8 |
| 16 | 2.86E−8 |
| 17 | 1.47E−8 |
| 18 | 2.28E−8 |
| 19 | 3.22E−8 |
| 20 | 6.83E−7 |
| 21 | 1.03E−7 |
| 22 | 6.57E−8 |
| 23 | 1.43E−7 |
| 24 | 3.38E−7 |
| 25 | 8.63E−8 |
| 26 | 1.76E−7 |
| 27 | 1.17E−7 |
| 28 | 1.22E−7 |
| 29 | 2.19E−7 |
| 30 | 3.01E−8 |
| 31 | 4.28E−8 |
| 32 | 2.74E−8 |
| 33 | 2.87E−8 |
| 34 | 3.94E−8 |
| 35 | 3.38E−8 |
| 36 | 1.31E−8 |
| 37 | 3.78E−6 |
| 38 | 7.42E−7 |
| 39 | 7.68E−7 |
| 40 | 7.83E−8 |
| 41 | 9.67E−8 |
| 42 | 2.39E−7 |
| 43 | 5.46E−8 |
| 44 | 4.21E−7 |
| 45 | 1.34E−8 |
| 46 | 1.24E−8 |
| 47 | 2.56E−8 |
| 48 | 9.95E−8 |
| 49 | 6.15E−8 |
| 50 | 3.36E−8 |
| 51 | 9.55E−8 |
| 52 | 3.59E−8 |
| 53 | 3.53E−8 |
| 54 | 1.76E−8 |
| 55 | 1.17E−7 |
| 56 | 2.38E−7 |
| 57 | 2.39E−7 |
| 58 | 1.74E−7 |
| 59 | 1.69E−8 |
| 60 | 1.98E−8 |
| 61 | 1.67E−7 |
| 62 | 1.86E−7 |
| 63 | 1.17E−7 |
| 64 | 1.38E−7 |
| 65 | 1.33E−7 |
| 66 | 1.61E−8 |
| 67 | 3.69E−8 |
| 68 | 3.63E−8 |
| 69 | 1.55E−7 |
| 70 | 2.46E−6 |
| 71 | 8.72E−7 |
| 72 | 8.25E−8 |
| 73 | 3.82E−7 |
| 74 | 8.72E−8 |
| 75 | 2.14E−8 |
| 76 | 4.13E−8 |
| 77 | 4.92E−8 |
| 78 | 7.43E−8 |
| 79 | 1.06E−7 |
| 80 | 6.83E−8 |
| 81 | 1.23E−7 |
| 82 | 1.34E−7 |
| 83 | 1.22E−7 |
| 84 | 1.43E−7 |
| 85 | 1.86E−6 |
| 86 | 2.45E−7 |
| 87 | 2.09E−7 |
| 88 | 2.1E−6 |
| 89 | 3.64E−6 |
| 90 | 2.86E−6 |
| 91 | 1.13E−7 |
| 92 | 8.0E−6 |
| 93 | 7.33E−7 |
| 94 | 1.95E−7 |
| 95 | 1.03E−6 |
| 96 | 1.65E−8 |
| 97 | 4.12E−7 |
| 98 | 1.12E−7 |
| 99 | 1.71E−6 |
| 100 | 1.58E−7 |
| 101 | 9.89E−7 |
| 102 | 2.83E−6 |
| 103 | 3.11E−6 |
| 104 | 6.44E−8 |
| 105 | 6.43E−8 |
| 106 | 4.37E−8 |
| 107 | 4.33E−7 |
| 108 | 1.19E−7 |
| 109 | 1.78E−7 |
| 110 | 1.18E−6 |
| 111 | 6.12E−7 |
| 112 | 3.46E−8 |
| 113 | 5.95E−8 |
| 114 | 6.42E−9 |
| 115 | 1.16E−8 |
| 116 | 2.22E−8 |
| 117 | 2.21E−8 |
| 118 | 3.62E−8 |
| 119 | 4.37E−8 |
| 120 | 6.3E−8 |
| 121 | 1.0E−7 |
| 122 | 4.64E−7 |
| 123 | 5.15E−8 |
| 124 | 9.43E−8 |
| 125 | 2.57E−7 |
| 126 | 1.18E−7 |
| 127 | 3.05E−7 |
| 128 | 1.11E−7 |
| 129 | 9.44E−7 |
| 130 | 1.43E−8 |
| 131 | 4.8E−7 |
| 132 | 2.45E−8 |
| 133 | 7.0E−9 |
| 134 | 1.36E−7 |
| 135 | 3.4E−7 |
| 136 | 3.25E−7 |
| 137 | 1.86E−8 |
| 138 | 5.67E−7 |
| 139 | 2.52E−7 |
| 140 | 1.76E−7 |
| 141 | 1.53E−8 |
| 142 | 4.16E−9 |
| 143 | 5.19E−9 |

REFERENCES

Giudice L C; Endometriosis; N Engl J Med 2010; 362:2389-98.
Chishima F, Hayakawa S, Sugita K, Kinukawa N, Aleemuzzaman S, Nemoto N, Yamamoto T, Honda M: Increased expression of cyclooxygenase-2 in local lesions of endometriosis patients. Am J Reprod. Immunol 2002; 48:50-56.
Sales K J and Jabbour H N; Cyclooxygenase enzymes and prostaglandins in pathology of the endometrium. Reproduction (2003) 126, 559-567.
Stratton P and Berkley K J; Chronic pelvic pain and endometriosis: translational evidence of the relationship and implications; Human Reproduction Update, Vol. 0, No. 0 pp. 1-21, 2010.
Petraglia F, Hornung D, Seitz C, Faustmann T, Gerlinger C, Luisi S, Lazzeri L, Strowitzki T; Reduced pelvic pain in women with endometriosis: efficacy of long-term dienogest treatment; Arch Gynecol Obstet, 2012 January; 285(1):167-73.

The invention claimed is:
1. A compound of the general formula (I)

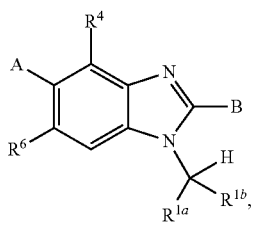

(I)

in which
$R^{1a}$, $R^{1b}$ independently of one another represent H, $C_1$-$C_5$-alkyl, $C_2$-$C_5$-alkenyl, $C_2$-$C_5$-alkynyl, $C_3$-$C_6$-cycloalkyl-$(CH_2)_m$, $C_3$-$C_6$-heterocycloalkyl-$(CH_2)_n$, $C_1$-$C_5$-alkoxy-$C_1$-$C_3$-alkyl, $C_3$-$C_6$-cycloalkoxy-$C_1$-$C_3$-alkyl, amino-$C_1$-$C_3$-alkyl, $C_1$-$C_5$-alkylamino-$C_1$-$C_3$-alkyl, $C_1$-$C_5$-dialkylamino-$C_1$-$C_3$-alkyl or cyano, where the heterocycloalkyl unit is selected from the group consisting of oxetane, tetrahydrofuran, tetrahydropyran, 1,4-dioxane, morpholine, azetidine, pyrrolidine, piperazine and piperidine and where the alkyl, cycloalkyl or heterocycloalkyl unit is optionally mono- or polysubstituted, identically or differently by halogen, $C_1$-$C_5$-alkyl, hydroxyl, carboxyl, carboxy-$C_1$-$C_5$-alkyl, $C_1$-$C_5$-alkoxycarbonyl-$C_1$-$C_5$-alkyl or $C_1$-$C_5$-alkylsulphonyl,
$R^4$ represents H, F, Cl, $C_1$-$C_2$-alkyl, $C_3$-$C_5$-cycloalkyl, $C_1$-$C_2$-alkoxy or $C_3$-$C_4$-cycloalkylmethyl, where the corresponding alkyl or cycloalkyl unit is optionally mono- or polysubstituted, identically or differently by halogen or hydroxyl,
A represents RO—CO$(CH_2)_p$, where R represents H or $C_1$-$C_2$-alkyl,
m is 0, 1, 2 or 3,
n is 0, 1, 2 or 3,
p is 0, and
B is selected from the following structures,

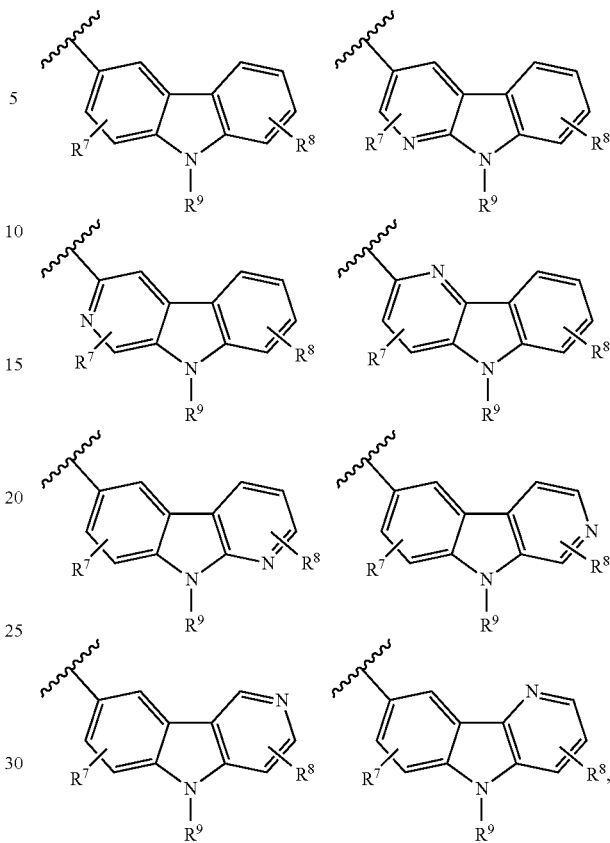

$R^6$ represents H, F, Cl, $CH_3$, $CF_3$, $CH_3O$ or $CF_3O$,
$R^7$, $R^8$ in each case independently of one another represent H, F, Cl, cyano, $SF_5$, $C_1$-$C_3$-alkyl, $C_3$-$C_5$-cycloalkyl, $C_1$-$C_2$-alkoxy or $C_3$-$C_4$-cycloalkylmethyl, where the corresponding alkyl or cycloalkyl unit is optionally mono- or polyhalogenated, and
$R^9$ represents $C_1$-$C_5$-alkyl, $C_2$-$C_5$-alkenyl, $C_2$-$C_5$-alkynyl, $C_3$-$C_6$-cycloalkyl-$(CH_2)_n$, $C_3$-$C_6$-heterocycloalkyl-$(CH_2)_n$, or $C_1$-$C_7$-alkoxy-$C_2$-$C_5$-alkyl, where the heterocycloalkyl unit is selected from the group consisting of oxetane, tetrahydrofuran, tetrahydropyran, morpholine, pyrrolidine and piperidine and where the alkyl, cycloalkyl or heterocycloalkyl units are optionally mono- or polysubstituted, identically or differently by halogen, $C_1$-$C_2$-alkyl, $C_1$-$C_2$-alkoxy or carboxyl,
or an isomer, diastereomer, enantiomer, solvate, salt or cyclodextrin clathrate thereof;
with the proviso that R1a and R1b are not both H at the same time.
2. The compounds of claim 1, wherein
$R^{1a}$ represents H or $C_1$-$C_5$-alkyl,
$R^{1b}$ represents H, $C_1$-$C_5$-alkyl, $C_2$-$C_5$-alkenyl, $C_3$-$C_6$-cycloalkyl-$(CH_2)_m$, $C_3$-$C_6$-heterocycloalkyl-$(CH_2)_n$, $C_1$-$C_5$-alkoxy-$C_1$-$C_3$-alkyl or $C_1$-$C_5$-dialkylamino-$C_1$-$C_3$-alkyl, where the heterocycloalkyl unit is selected from the group consisting of oxetane, tetrahydrofuran, 1,4-dioxane, morpholine and pyrrolidine and where the alkyl- or cycloalkyl unit is optionally mono- or polysubstituted, identically or differently, by $C_1$-$C_5$-alkyl, hydroxyl, or $C_1$-$C_5$-alkylsulphonyl,
$R^4$ represents H, F, Cl, $C_1$-$C_2$-alkyl or $C_1$-$C_2$-alkoxy,
A represents RO—CO$(CH_2)_p$, where R represents H or $C_1$-$C_2$-alkyl, m is 0 or 1,
n is 0 or 1,
p is 0, and
B is selected from the following structures,

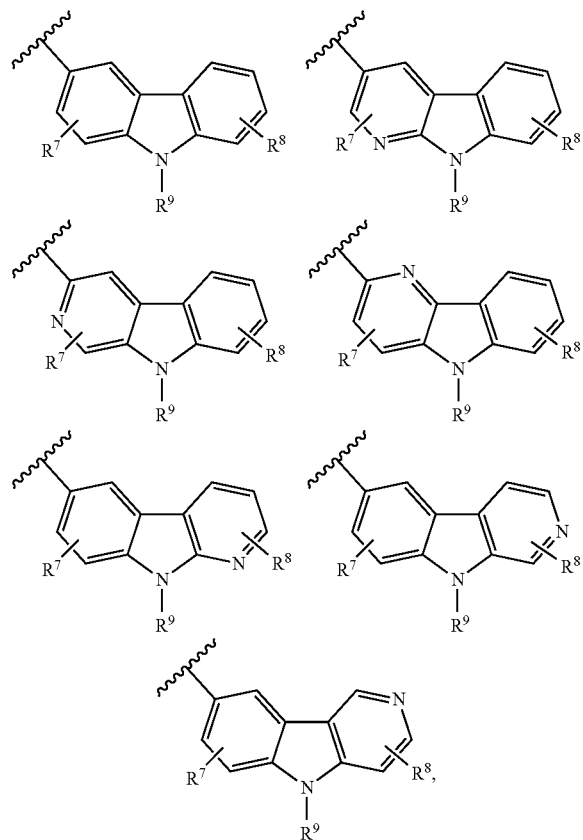

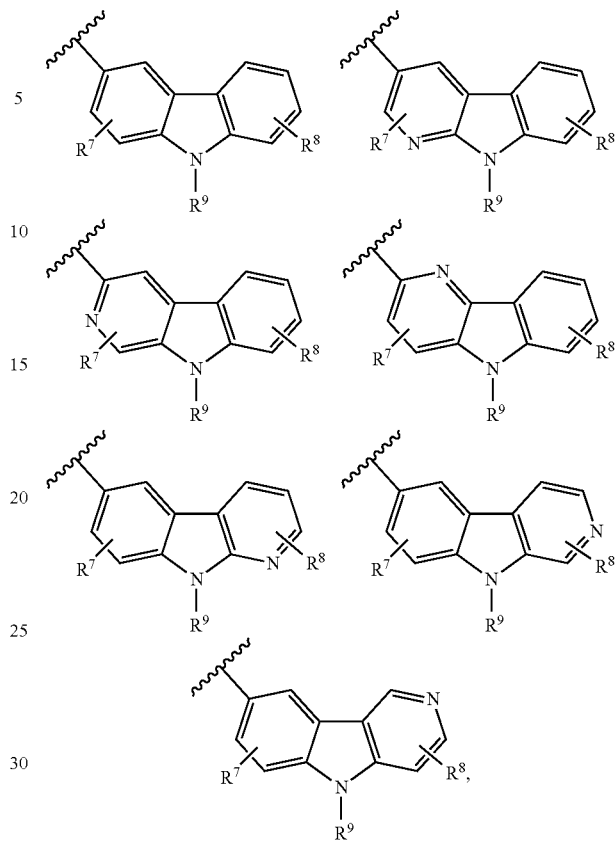

$R^6$ represents H, F, $CH_3$ or $CH_3O$,
$R^7$, $R^8$ in each case independently of one another represents H, F, Cl, $C_1$-$C_3$-alkyl or $C_1$-$C_2$-alkoxy, and
$R^9$ represents $C_1$-$C_5$-alkyl, $C_2$-$C_5$-alkenyl, $C_2$-$C_5$-alkynyl, $C_3$-$C_6$-cycloalkyl-$(CH_2)_n$ or $C_1$-$C_7$-alkoxy-$C_2$-$C_5$-alkyl,
or an isomer, diastereomer, enantiomer, solvate, salt or cyclodextrin clathrate thereof.

3. The compounds of claim 1, wherein
$R^{1a}$ represents H or methyl,
$R^{1b}$ represents H, $C_1$-$C_2$-alkyl, vinyl, cyclopropyl-$(CH_2)_m$, $C_3$-$C_6$-heterocycloalkyl-$(CH_2)_n$, methoxy-$C_1$-$C_2$-alkyl or (N,N-dimethylamino)-methyl, where the heterocycloalkyl unit is selected from the group consisting of oxetane, tetrahydrofuran, 1,4-dioxane, morpholine and pyrrolidine and where the alkyl or cyclopropyl unit is optionally mono- or polysubstituted, identically or differently, by methyl, hydroxyl, or methylsulphonyl,
$R^4$ represents H, F, Cl, methyl or methoxy,
A represents RO—CO$(CH_2)_p$, where R represents H or $C_1$-$C_2$-alkyl,
m is 0 or 1,
n is 0 or 1,
p is 0, and
B is selected from the following structures, $R^6$ represents H, F, $CH_3$ or $CH_3O$,
$R^7$, $R^8$ in each case independently of one another represent H, F, Cl, methyl or methoxy, and
$R^9$ represents $C_1$-$C_3$-alkyl, allyl, propargyl, $C_3$-$C_4$-cycloalkyl-$(CH_2)_n$ or methoxyethyl,
or an isomer, diastereomer, enantiomer, solvate, salt or cyclodextrin clathrate thereof.

4. The compound of claim 1 selected from the group consisting of:
Methyl 1-allyl-2-(9-ethyl-9H-carbazol-3-yl)-1H-benzimidazole-5-carboxylate;
1-Allyl-2-(9-ethyl-9H-carbazol-3-yl)-1H-benzimidazole-5-carboxylic acid;
Methyl 2-(9-ethyl-9H-carbazol-3-yl)-1-(2-methoxyethyl)-1H-benzimidazole-5-carboxylate;
2-(9-Ethyl-9H-carbazol-3-yl)-1-(2-methoxyethyl)-1H-benzimidazole-5-carboxylic acid;
Methyl 1-(cyclopropylmethyl)-2-(9-ethyl-9H-carbazol-3-yl)-1H-benzimidazole-5-carboxylate;
1-(Cyclopropylmethyl)-2-(9-ethyl-9H-carbazol-3-yl)-1H-benzimidazole-5-carboxylic acid;
Methyl 4-chloro-1-(cyclopropylmethyl)-2-(9-ethyl-9H-carbazol-3-yl)-1H-benzimidazole-5-carboxylate;
4-Chloro-1-(cyclopropylmethyl)-2-(9-ethyl-9H-carbazol-3-yl)-1H-benzimidazole-5-carboxylic acid;
1-(Cyclopropylmethyl)-2-(9-ethyl-9H-carbazol-3-yl)-4-methyl-1H-benzimidazole-5-carboxylic acid;
2-(9-Ethyl-7-fluoro-9H-carbazol-3-yl)-1-(2-methoxyethyl)-1H-benzimidazole-5-carboxylic acid;
-2-(9-Ethyl-5-fluoro-9H-carbazol-3-yl)-1-(2-methoxyethyl)-1H-benzimidazole-5-carboxylic acid;
2-(9-Ethyl-8-fluoro-9H-carbazol-3-yl)-1-(2-methoxyethyl)-1H-benzimidazole-5-carboxylic acid;

1-(Cyclopropylmethyl)-2-[9-(2-methoxyethyl)-9H-carbazol-3-yl]-1H-benzimidazole-5-carboxylic acid;
1-(Cyclopropylmethyl)-2-(9-ethyl-9H-pyrido[2,3-b]indol-3-yl)-1H-benzimidazole-5-carboxylic acid;
2-(9-Ethyl-6-methoxy-9H-carbazol-3-yl)-1-(2-methoxyethyl)-1H-benzimidazole-5-carboxylic acid;
2-(9-Allyl-9H-carbazol-3-yl)-1-(cyclopropylmethyl)-1H-benzimidazole-5-carboxylic acid;
1-(Cyclopropylmethyl)-2-(9-methyl-9H-carbazol-3-yl)-1H-benzimidazole-5-carboxylic acid;
1-(Cyclopropylmethyl)-2-[9-(cyclopropylmethyl)-9H-carbazol-3-yl]-1H-benzimidazole-5-carboxylic acid;
2-[9-(Cyclopropylmethyl)-9H-carbazol-3-yl]-1-(2-methoxyethyl)-1H-benzimidazole-5-carboxylic acid;
Ethyl-2-(9-ethyl-9H-carbazol-3-yl)-1-[2-(pyrrolidin-1-yl)ethyl]-1H-benzimidazole-5-carboxylate;
2-(9-Ethyl-9H-carbazol-3-yl)-1-[2-(pyrrolidin-1-yl)ethyl]-1H-benzimidazole-5-carboxylic acid;
2-(5-Ethyl-5H-pyrido [3,2-b]indol-2-yl)-1-(2-methoxyethyl)-1H-benzimidazole-5-carboxylic acid;
1-(Cyclopropylmethyl)-2-(9-ethyl-6-methoxy-9H-carbazol-3-yl)-1H-benzimidazole-5-carboxylic acid;
2-(9-Ethyl-9H-carbazol-3-yl)-1-[2-(morpholin-4-yl)ethyl]-1H-benzimidazole-5-carboxylic acid;
Ethyl-1-[2-(dimethylamino)ethyl]-2-(9-ethyl-9H-carbazol-3-yl)-1H-benzimidazole-5-carboxylate;
1-[2-(Dimethylamino)ethyl]-2-(9-ethyl-9H-carbazol-3-yl)-1H-benzimidazole-5-carboxylic acid;
2-(9-Ethyl-9H-carbazol-3-yl)-1-(2-hydroxyethyl)-1H-benzimidazole-5-carboxylic acid;
Ethyl-2-(9-ethyl-9H-carbazol-3-yl)-1-isopropyl-1H-benzimidazole-5-carboxylate;
2-(9-Ethyl-9H-carbazol-3-yl)-1-isopropyl-1H-benzimidazole-5-carboxylic acid;
Methyl 1-ethyl-2-(9-ethyl-9H-carbazol-3-yl)-1H-benzimidazole-5-carboxylate;
2-(9-Allyl-9H-carbazol-3-yl)-1-(2-methoxyethyl)-1H-benzimidazole-5-carboxylic acid;
Ethyl 1-(2-methoxyethyl)-2-[9-(2-methoxyethyl)-9H-carbazol-3-yl]-1H-benzimidazole-5-carboxylate;
1-(2-Methoxyethyl)-2-[9-(2-methoxyethyl)-9H-carbazol-3-yl]-1H-benzimidazole-5-carboxylic acid;
Ethyl 2-(9-ethyl-9H-carbazol-3-yl)-1-(3-methoxypropyl)-1H-benzimidazole-5-carboxylate;
2-(9-Ethyl-9H-carbazol-3-yl)-1-(3-methoxypropyl)-1H-benzimidazole-5-carboxylic acid;
1-(Cyclopropylmethyl)-2-(9-ethyl-9H-carbazol-3-yl)-6-methoxy-1H-benzimidazole-5-carboxylic acid;
2-(9-Ethyl-9H-carbazol-3-yl)-6-methoxy-1-(2-methoxyethyl)-1H-benzimidazole-5-carboxylic acid;
1-(Cyclopropylmethyl)-2-(9-ethyl-9H-pyrido[2,3-b]indol-3-yl)-4-methyl-1H-benzimidazole-5-carboxylic acid;
1-(Cyclopropylmethyl)-2-(9-ethyl-9H-beta-carbolin-6-yl)-1H-benzimidazole-5-carboxylic acid;
1-(Cyclopropylmethyl)-2-(5-ethyl-5H-pyrido[4,3-b]indol-8-yl)-1H-benzimidazole-5-carboxylic acid;
1-(Cyclopropylmethyl)-2-(9-ethyl-9H-carbazol-3-yl)-6-methyl-1H-benzimidazole-5-carboxylic acid;
2-(9-Ethyl-9H-carbazol-3-yl)-1-(2-methoxyethyl)-6-methyl-1H-benzimidazole-5-carboxylic acid;
2-(9-Ethyl-9H-carbazol-3-yl)-6-fluoro-1-(2-methoxyethyl)-1H-benzimidazole-5-carboxylic acid;
1-(Cyclopropylmethyl)-2-(9-ethyl-9H-carbazol-3-yl)-6-fluoro-1H-benzimidazole-5-carboxylic acid;
2-(9-Ethyl-9H-carbazol-3-yl)-4-fluoro-1-(2-methoxyethyl)-1H-benzimidazole-5-carboxylic acid;
1-(Cyclopropylmethyl)-2-(9-ethyl-9H-carbazol-3-yl)-4-fluoro-1H-benzimidazole-5-carboxylic acid;
1-(Cyclopropylmethyl)-2-(9-ethyl-9H-pyrido[2,3-b]indol-6-yl)-1H-benzimidazole-5-carboxylic acid;
1-(2-Cyclopropylethyl)-2-(9-ethyl-9H-carbazol-3-yl)-1H-benzimidazole-5-carboxylic acid;
1-(2-Methoxyethyl)-2-(9-propyl-9H-carbazol-3-yl)-1H-benzimidazole-5-carboxylic acid;
1-(2-Methoxyethyl)-2-[9-(prop-2-yn-1-yl)-9H-carbazol-3-yl]-1H-benzimidazole-5-carboxylic acid;
1-(Cyclopropylmethyl)-2-(9-propyl-9H-carbazol-3-yl)-1H-benzimidazole-5-carboxylic acid;
1-[(2,2-Dimethylcyclopropyl)methyl]-2-(9-ethyl-9H-carbazol-3-yl)-1H-benzimidazole-5-carboxylic acid;
Ethyl 2-(9-ethyl-9H-carbazol-3-yl)-1-(oxetan-3-ylmethyl)-1H-benzimidazole-5-carboxylate;
2-(9-Ethyl-9H-carbazol-3-yl)-1-(oxetan-3-ylmethyl)-1H-benzimidazole-5-carboxylic acid;
2-[9-(Cyclobutylmethyl)-9H-carbazol-3-yl]-1-(2-methoxyethyl)-1H-benzimidazole-5-carboxylic acid;
2-[9-(Cyclobutylmethyl)-9H-carbazol-3-yl]-1-(cyclopropylmethyl)-1H-benzimidazole-5-carboxylic acid;
2-(9-Ethyl-9H-carbazol-3-yl)-1-[2-(trifluoromethoxy)ethyl]-1H-benzimidazole-5-carboxylic acid;
1-(Cyclopropylmethyl)-2-(9-ethyl-1-methyl-9H-beta-carbolin-3-yl)-1H-benzimidazole-5-carboxylic acid;
2-(9-Ethyl-9H-carbazol-3-yl)-1-(oxetan-2-ylmethyl)-1H-benzimidazole-5-carboxylic acid;
2-(9-Ethyl-9H-carbazol-3-yl)-1-(tetrahydrofuran-2-ylmethyl)-1H-benzimidazole-5-carboxylic acid;
2-(9-Ethyl-9H-carbazol-3-yl)-1-[(2R)-2-hydroxy-3-methoxypropyl]-1H-benzimidazole-5-carboxylic acid;
2-(9-Ethyl-9H-carbazol-3-yl)-1-[(2S)-2-hydroxy-3-methoxypropyl]-1H-benzimidazole-5-carboxylic acid;
2-(9-Ethyl-9H-carbazol-3-yl)-1-[2-(methylsulphonyl)ethyl]-1H-benzimidazole-5-carboxylic acid;
1-(2-Cyclopropyl-2-hydroxyethyl)-2-(9-ethyl-9H-carbazol-3-yl)-1H-benzimidazole-5-carboxylic acid;
1-[(2R)-2,3-Dihydroxypropyl]-2-(9-ethyl-9H-carbazol-3-yl)-1H-benzimidazole-5-carboxylic acid;
1-(1,4-Dioxan-2-ylmethyl)-2R-(9-ethyl-9H-carbazol-3-yl)-1H-benzimidazole-5-carboxylic acid;
1-(1,4-Dioxan-2-ylmethyl)-2S-(9-ethyl-9H-carbazol-3-yl)-1H-benzimidazole-5-carboxylic acid;
2-(9-Ethyl-6-methyl-9H-carbazol-3-yl)-1-(2-methoxyethyl)-4-methyl-1H-benzimidazole-5-carboxylic acid;
2-(6-Chloro-9-ethyl-9H-carbazol-3-yl)-1-(2-methoxyethyl)-4-methyl-1H-benzimidazole-5-carboxylic acid and
2-(8-Chloro-9-ethyl-9H-carbazol-3-yl)-1-(2-methoxyethyl)-4-methyl-1H-benzimidazole-5-carboxylic acid.

5. A method of treatment of edometriosis, comprising administering an effective amount of a compound of claim 1 to a subject in need thereof.

6. A medicament comprising a compound of claim 1 and an active substance selected from the group consisting of a selective oestrogen receptor modulator (SERM), an oestrogen receptor (ER) antagonist, an aromatase inhibitor, a 17β-HSD1 inhibitor, a steroid sulphatase (STS) inhibitor, a GnRH agonist or antagonist, a kisspeptin receptor (KISSR) antagonist, a selective androgen receptor modulator (SARM), an androgen, a 5α-reductase inhibitor, a selective progesterone receptor modulator (SPRM), a gestagen, an antigestagen, an oral contraceptive, an inhibitor of mitogen activated protein (MAP) kinase, an inhibitor of a MAP kinase selected from Mkk3/6, Mek1/2, and Erk1/2, an inhibitor of a protein kinase B selected from PKBα/β/γ; and Akt1/2/3, an inhibitor of a phosphoinositide-3 kinase (PI3K), an inhibitor of cyclin-dependent kinase, an inhibitor of the hypoxia-induced signal pathway selected from an HIF1alpha inhibitor and an activator of prolylhydroxylases, a histone deacetylase (HDAC) inhibitor, a prostaglandin F receptor (FP) (PTGFR) antagonist, a neurokinin 1 receptor antagonist, a selective COX2 inhibitor, and a non-selective COX1/COX2 inhibitor.

7. A medicament comprising a compound of claim 1 and an inert, non-toxic, pharmaceutically suitable excipient.

8. A method of treatment of endometriosis, comprising administering the medicament of claim 7 to a patient in need thereof.

9. The compound of claim 1, wherein
$R^{1a}$ represents H or methyl,
$R^{1b}$ represents H, $C_1$-$C_2$-alkyl, vinyl, cyclopropyl-$(CH_2)_m$, $C_3$-$C_6$-heterocycloalkyl-$(CH_2)_n$, methoxy-$C_1$-$C_2$-alkyl or (N,N-dimethylamino)-methyl, where the heterocycloalkyl unit is selected from the group consisting of oxetane, tetrahydrofuran, 1,4-dioxane, morpholine and pyrrolidine and where the alkyl or cyclopropyl unit is optionally mono- or polysubstituted, identically or differently, by methyl, hydroxyl, or methylsulphonyl,
$R^4$ represents H, F, Cl, methyl or methoxy,
A represents RO—$CO(CH_2)_p$, where R represents H,
m is 0 or 1,
n is 0 or 1,
p is 0, and
B is selected from the following structures,

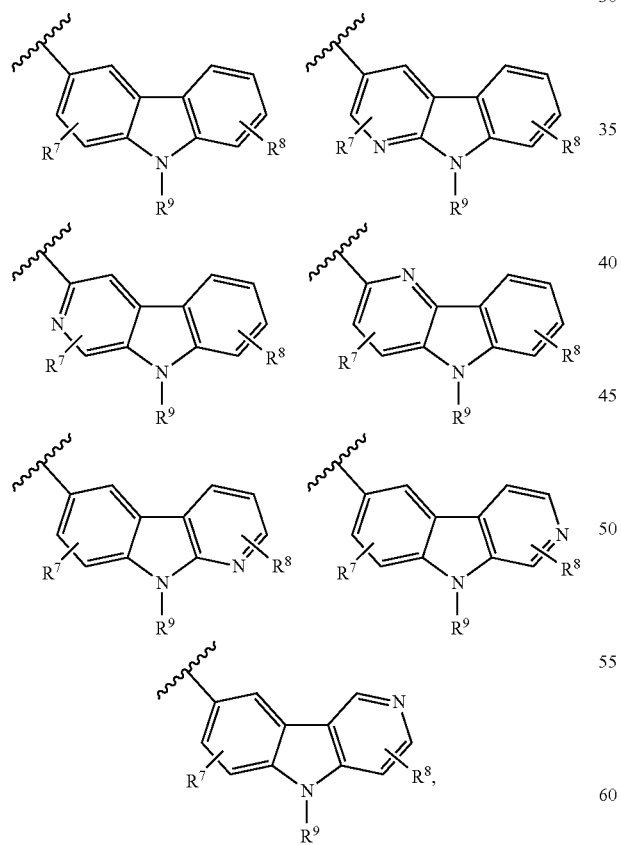

$R^6$ represents H, F, $CH_3$ or $CH_3O$,
$R^7$, $R^8$ in each case independently of one another represent H, F, Cl, methyl or methoxy, and
$R^9$ represents $C_1$-$C_3$-alkyl, allyl, propargyl, $C_3$-$C_4$-cycloalkyl-$(CH_2)_n$ or methoxyethyl,
or an isomer, diastereomer, enantiomer, solvate, salt or cyclodextrin clathrate thereof.

10. The compound of claim 1, wherein
$R^{1a}$ represents H,
$R^{1b}$ represents methoxymethyl,
$R^4$ represents H, F, Cl, methyl or methoxy,
A represents RO—$CO(CH_2)_p$, where R represents H,
p is 0, and
B is selected from the following structures,

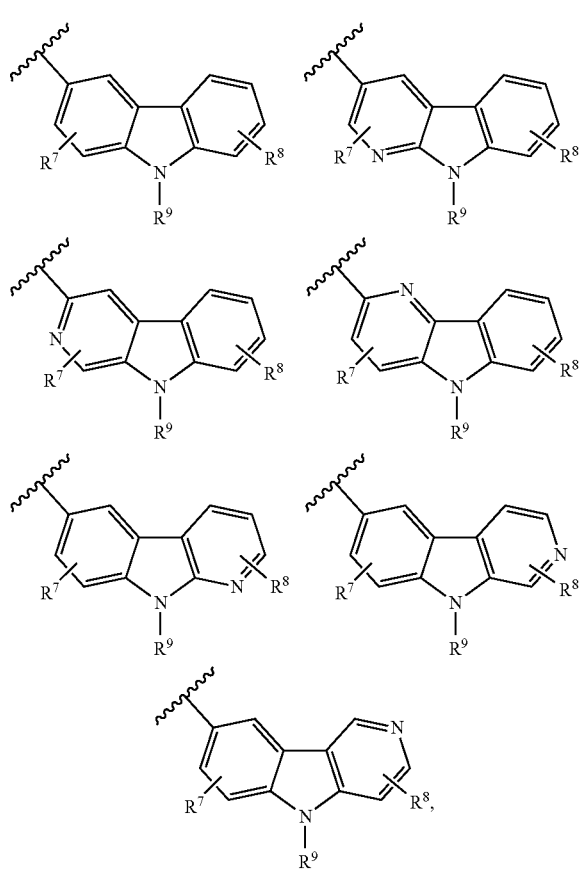

$R^6$ represents H, F, $CH_3$ or $CH_3O$,
$R^7$, $R^8$ in each case independently of one another represents H, F, Cl, methyl or methoxy, and
$R^9$ represents $C_1$-$C_3$-alkyl, allyl, propargyl, $C_3$-$C_4$-cycloalkyl-$(CH_2)_n$ or methoxyethyl,
or an isomer, diastereomer, enantiomer, solvate, salt or cyclodextrin clathrate thereof.

* * * * *